(12) United States Patent
Kano et al.

(10) Patent No.: US 6,310,056 B1
(45) Date of Patent: Oct. 30, 2001

(54) CARBAPENEM DERIVATIVES

(75) Inventors: Yuko Kano; Kazuhiro Aihara; Yumiko Toyooka; Toshiro Sasaki; Hiromasa Takizawa; Kenichi Fushihara; Kazuko Kobayashi; Kunio Atsumi; Katsuyoshi Iwamatsu; Takashi Ida, all of Yokohama (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 09/355,272

(22) PCT Filed: Jan. 28, 1998

(86) PCT No.: PCT/JP98/00347

§ 371 Date: Jul. 28, 1999

§ 102(e) Date: Jul. 28, 1999

(87) PCT Pub. No.: WO98/32760

PCT Pub. Date: Jul. 30, 1998

(30) Foreign Application Priority Data

Jan. 28, 1997 (JP) .................................................. 9-013571
Feb. 19, 1997 (JP) .................................................. 9-034599

(51) Int. Cl.[7] ...................... A61K 31/429; C07D 519/06; C07D 513/04; A61P 31/04; C07F 7/22
(52) U.S. Cl. .................... 514/210.09; 540/302; 540/200; 548/103
(58) Field of Search ..................... 540/302; 514/210.09

(56) References Cited

FOREIGN PATENT DOCUMENTS

| 8-311071 | 11/1996 | (JP) . |
| 95/07912 | 3/1995 | (WO) . |
| 96/11932 | 4/1996 | (WO) . |
| 96/28455 | 9/1996 | (WO) . |

OTHER PUBLICATIONS

Kano, Chem Abstracts 132: 166061 q, Feb, 2000.*

* cited by examiner

Primary Examiner—Mark L. Berch

(57) ABSTRACT

The carbapenem derivatives represented by the following formula (I) is disclosed. These compounds have strong anti-bacterial activities against bacteria including methicillin resistant *Staphylococcus aureus*, penicillin resistant *Streptococcus pneumoniae*, Enterococci, influenza, and β-lactamase producing bacteria, and have high stabilities to DHP-1

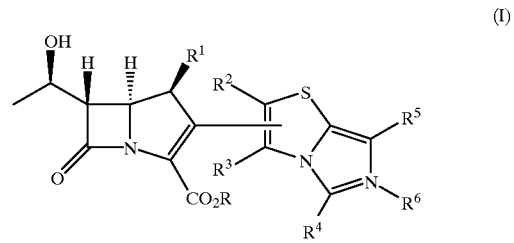

(I)

wherein $R^1$ represents hydrogen or methyl, either one of $R^2$, $R^3$, $R^4$, or $R^5$ represents the bond to the 2-position on the carbapenem ring, and the remaining three respectively represent hydrogen, halogen, nitro, cyano, alkyl, cycloalkyl, alkylthio, alkenyl, formyl, alkylcarbonyl, alkoxycarbonyl, aminosulfonyl, aryl carbonyl, aryl, carbamoyl, N-lower alkylcarbamoyl, N,N-di-lower alkylaminocarbonyl, lower alkoxyiminomethyl, or hydroxyiminomethyl, $R^6$ is not present or represents alkyl, cycloalkyl, or alkenyl, and R is not present, or represents hydrogen or a group which may be metabolically hydrolyzed in the body, provided that when $R^6$ is not present, R represents hydrogen or a group which may be metabolically hydrolyzed in the body, and when $R^6$ is present, R is not present, and the compound forms an inner salt.

29 Claims, No Drawings

CARBAPENEM DERIVATIVES

This application is a 371 application of International Application No. PCT/JP98/00347, filed Jan. 28, 1998.

BACKGROUND OF THE INVENTION

1. Field of the Invention

The present invention relates to a carbapenem compound which has excellent antimicrobial activity and wide range of anti-microbial spectrum, and can be administered not only as an injection but also orally. More particularly, the present invention relates to a novel carbapenem derivative which has a substituted or unsubstituted imidazo[5,1-b]thiazole group or a substituted or unsubstituted imidazo[5,1-b]thiazolium group at the 2-position on the carbapenem ring, or a salt thereof.

2. Background Art

Carbapenem derivatives, by virtue of potent antibacterial activity against a wide spectrum of bacteria, have been energetically studied as a highly useful β-lactam agent, and Imipenem, Panipenem, and Meropenem have been clinically used.

Both Imipenem and Panipenem, however, are used as a mixture due to instability against renal dehydropeptidase-1 ("DHP-1") in the case of Impenem and in order to reduce nephrotoxicity in the case of Panipenem. Meropenem which has recently been marketed has a methyl group at the 1β-position, so that it has increased stability to DHP-1 and thus can be used alone.

However, a need still exists for a drug having higher stability to DHP-1. Furthermore, drugs effective for methicillin resistant *Staphylococcus aureus* ("MRSA"), penicillin resistant *Streptococcus pneumoneae* ("PRSP"), resistant *Pseudomonas aeruginosa* and enterococci which have recently become serious problems as well as influenza have been demanded as well.

Some of the present inventors have previously reported the carbapenem derivatives having a novel heteroaromatic ring imidazo[5,1-b]thiazolium-6-ylmethyl group at the 2-position on the carbapeneni ring in WO 96/028455 and the carbapenem derivatives having an imidazo[5,1-b]thiazole group through a pyrrolidinylthio group at the 2-position of the carbapenem ring in PCT/JP 97/04270.

Further, WO 96/034868 and Japanese Patent Laid-Open Publication No. 273876/1992 disclose the carbapenem derivatives in which a carbon atom on the heteroaromatic ring is bonded to the 2-position of the carbapenem ring. However, there have been described no specific data on the anti-microbial activities or effectiveness for these derivatives. There have been described neither bicyclic heteroaromatic rings nor carbapenem rings having imidazo[5,1-b]thiazole group.

SUMMARY OF THE INVENTION

The present inventors have now found that novel carbapenem derivatives having a substituted or unsubstituted imidazo[5,1-b]thiazole group or a substituted or unsubstituted imidazo[5,1-b]thiazolium group at the 2-position on the carbapenem ring have high anti-microbial activities against MRSA, PRSP, enterococci, influenza and β-lactamase producing bacteria, and high stabilities to DHP-1. The present invention is based on such findings.

Thus, the object of the present invention is to provide novel compounds which have wide range of anti-microbial activities, especially high anti-microbial activities against microorganisms including MRSA, PRSP, enterococci, influenza and β-lactamase producing bacteria, and high stabilities to DHP-1.

Thus, the present invention provides a compound represented by the formula (I), or a pharmacologically acceptable salt thereof:

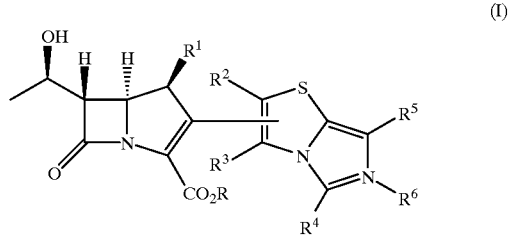

(I)

wherein,
R$^1$ represents hydrogen or methyl,
R$^2$, R$^3$, R$^4$, and R$^5$, either one of which represents the bond to the 2-position on the carbapenem ring, and the remaining three groups, which may be the same or different, respectively represent
hydrogen,
halogen,
nitro,
cyano,
lower alkyl, in which one or more hydrogen atoms on the alkyl may be substituted by a group selected by the group consisting of halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbarnoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, and aryl,
lower cycloalkyl, in which one or more hydrogen atoms on the cycloalkyl may be substituted by a group selected from the group consisting of lower alkyl, halogen, nitro, cyano, lower alkylthio, lower alkoxy, hydroxy, amino, N-lower alkylamino, formyl, lower alkylcarbonyl, arylcarbonyl, carboxyl, lower alko)rycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylainino, aiminosulfonylamino, (N,N-di-lower alkylamino)sulfonylamino, and aryl,
lower alkylthio,
C$_{2-4}$ alkenyl, in which one or more hydrogen atoms on the alkenyl may be substituted by a group selected from the group consisting of lower alkyl, halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, and aryl, formyl,
lower alkylcarbonyl,
lower alkoxycarbonyl,
lower alkylsulfonyl,
arylsulfonyl,
aminosulfonyl,
arylcarbonyl,
aryl, in which one or more hydrogen on the aryl may be substituted by a group selected from the group consisting of lower alkyl, halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, and
(N,N-di-lower alkylamino)sulfonylamino, carbamoyl,
N-lower alkylcarbamoyl,
N,N-di-lower alkylaminocarbonyl,
lower alkoxyiminomethyl, or hydroxyiminomethyl,
$R^6$ is not present, or represents lower alkyl, in which one or more hydrogen atoms on the alkyl may be substituted by a group selected from the group consisting of halogen, nitro, cyano, lower cycloalkyl, lower alkylthio, lower alkoxy, hydroxy, amino, N-lower alkylainino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino) sulfonylamino, aminosulfonylamino, (N,N-di-lower alkylamino)sulfonylamino, and aryl,
lower cycloalkyl, in which one or more hydrogen atoms on the cycloalkyl may be substituted by a group selected from the group consisting of lower alkyl, halogen, nitro, cyano, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, and aryl, or
C2-4 alkenyl, in which one or more hydrogen atoms on the alkenyl may be substituted by a group selected from the group consisting of lower alkyl, halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, and aryl, and
R is not present, or represents hydrogen or a group which may be metabolically hydrolyzed in the body, provided that when R6 is not present, R represents hydrogen or a group which may be metabolically hydrolyzed in the body, and when R6 is present, R is not present, and the compound forms an inner salt.

DETAILED DESCRIPTION OF THE INVENTION

Definition

As used herein, the term "lower alkyl" or "lower alkoxy" as a group or a part of a group means a straight chain or branched chain alkyl or alkyloxy having 1–6 carbon atoms, preferably 1–4 carbon atoms. The examples of the lower alkyl include methyl, ethyl, N-propyl, isopropyl, N-butyl, i-butyl, s-butyl, t-butyl, N-pentyl, N-hexyl, and the like. Further, the lower alkoxy includes by way of example methoxy, ethoxy, N-propoxy, i-propoxy, N-butoxy, i-butoxy, s-butoxy, t-butoxy, and the like.

The term "lower cycloalkyl" means monocyclic alkyl having 3–6 carbon atoms.

The term "halogen" herein means fluorine, chlorine, bromine, or iodine.

Further, the term "aryl" means preferably phenyl or naphthyl.

Compound

In the formul(I), any one of R2, R3, R4, and R5 represents the bond to the 2-position on the carbapenem ring.

The remaining three groups, which may be the same or different, respectively represent hydrogen, halogen, nitro, cyano, lower alkyl which may be substituted, lower cycloalkyl which may be substituted, lower alkylthio, C2–4 alkenyl which may be substituted, formyl, lower alkylcarbonyl, lower alkoxycarbonyl, lower alkylsulfoiny, arylsulfonyl, aminosulionyl, arylcarbonyl, aryl which may be substituted, carbamoyl, N-lower alkylcarbamoyl, N,N-dilower alkylaminocarbonyl, lower alkoxyiminoiiiethyl, or hydroxyiminomethyl. According to the preferred embodiment of the present invention, the remaining three groups is preferably hydrogen, halogen, cyano, lower alkyl which may be substituted, formyl, lower alkylcarbonyl, lower alkoxycarbonyl, aminosulfonyl, carbamoyl, N-lower alkylcarbamoyl, N,N-di-lower alkylaininocarbonyl, lower alkoxyiminomethyl, or hydroxyiminomethyl, more preferably hydrogen, chlorine, cyano, lower alkyl which may be substituted, formyl, lower alkylcarbonyl, lower alkoxycarbonyl, carbamoyl, N-lower alkylcarbamoyl, or N,N-di-lower alkylaminocarbonyl.

In $R^2$, $R^3$, $R^4$, and R5 which represent lower alkyl, one or more hydrogen atoms on the lower alkyl may be substituted by halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino) sulfonyl, (N,N-di-lower alkylamino)sulfonyl, (N-lower alkylamino)sulfonylamino, aminosulfonylamino, (N,N-di-lower alkylamino)sulfonylamino, and aryl. According to the preferred embodiment of the present invention, the substituent includes preferably lower alkoxy, hydroxy, formylamino, and carbamoyl, particularly lower alkoxy, hydroxy, and formylamino. The substituted alkyl includes for example aminomethyl, hydroxymethyl, 2-hydroxyethyl, carbamoylmethyl, 2-carbamoylethyl, 2-fluoroethyl, cyclopropylmethyl, 2-(N-methylcarbamoyl)ethyl, N,N-dimethylcarbamoylmethyl, 2-(N,N-dimethylcarbamoyl) ethyl, 2-aminosulfonylethyl, aminosulfonylaminomethyl, 2-(aminosulfonylamino)ethyl, methoxymethyl, ethoxycarbonylmethyl, formylaminomethyl, methoxyiminomethyl, hydroxyiminomethyl, benzyl.

In $R^2$, $R^3$, $R^4$, and $R^5$ which represent cycloalkyl, one or more hydrogen atoms on the cycloalkyl may be substituted by a group selected from the group consisting of lower alkyl, halogen, nitro, cyano, lower alkylthio, lower alkoxy, hydroxcy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino) sulfonyl, (N,N-di-lower alkylamino)sulfonyl, (N-lower alkylamino)sulfonylamino, aminosulfonylamino, (N,N-di-lower alkylamino)sulfonylamino, and aryl. According to the preferred embodiment of the present invention, the substituent includes for example lower alkoxy, hydroxy, formylamino, and carbamoyl, particularly lower alkoxy, hydroxy, and formylamino.

Furthermore, in $R^2$, $R^3$, $R^4$, and $R^5$ which represent alkenyl, one or more hydrogen atoms on the alkenyl may be substituted, and the substituent includes for example a group selected from the group consisting of lower alkyl, halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamnoyl, N-lower alkylcarbamoyl, N,N-di-lower alkylaminocarbonyl, aminosulfonyl, (N-lower alkylamino) sulfonyl, (N,N-di-lower alkylamino)sulfonyl, (N-lower alkylamino)sulfonylamino, aminosulfonylamino, (N,N-di-lower alkylamino)sulfonylamino, and aryl. According to the preferred embodiment of the present invention, the preferred substituent includes for example lower alkoxy, hydroxy, formylamino, and carbamoyl, particularly lower alkoxy, hydroxy, and formylamino.

The arylcarbonyl represented by $R^2$, $R^3$, $R^4$, and $R^5$ includes preferably phenylcarbonyl or naphthylcarbonyl.

The aryl represented by $R^2$, $R^3$, $R^4$, and $R^5$ includes preferably phenyl or naphthyl. Furthermore, one or more hydrogen atoms on the aryl may be substituted by lower alkyl, halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, and (N,N-di-lower alkylamino)sulfonylamino. According to the preferred embodiment of the present invention, the preferred substituent includes preferably lower alkoxy, hydroxy, formylamino, and carbamoyl, particularly lower alkoxy, hydroxy, and formylamino.

In the formul(I), $R^6$ is not present, or represents lower alkyl, lower cycloalkyl, or $C_{2-4}$ alkenyl, preferably lower alkyl. Further, R is not present, or represents hydrogen or a group which may be metabolically hydrolyzed in the body. In the formul(I), when $R^6$ is not present, R represens hydrogen or a group which may be metabolically hydrolyzed in the body, and when $R^6$ is present, R is not present, and the compound forms an inner salt. The inner salt formed by the presence of $R^6$ and the absence of R means the compound represented by the following formul(II):

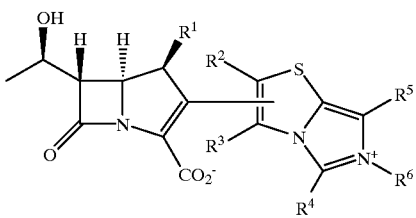

(II)

One or more hydrogen atoms on the lower alkyl represented by $R^6$ may be substituted by a group selected from the group consisting of halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamnoyl, N,N-di-lower alkylaminocarbonyl, aminosulfonyl, (N-lower alkylamino)sulfonyl, (N,N-di-lower alkylamino )sulfonyl, (N-lower alkylamino )sulfonylamino, aminosulfonylamino, (N,N-di-lower alkylamino)sulfonylamino, and aryl.

Further, one or more hydrogen atoms on the lower cycloalkyl represented by $R^6$ may be substituted by a group selected from the group consisting of lower alkyl, halogen, nitro, cyano, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino) sulfonyl, (N,N-di-lower alkylamino)sulfonyl, (N-lower alkylamino)sulfonylamino, aminosulfonylamino, (N,N-di-lower alkylamino)sulfonylamino, and aryl.

One or more hydrogen atoms on the $C_{2-4}$ alkenyl represented by R6 may be substituted, and include a group selected from the group consisting of lower alkyl, halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino) sulfonyl, (N,N-di-lower alkylamino)sulfonyl, (N-lower alkylainino)sulfonylamino, aminosulfonylamino, (N,N-di-lower alkylamino )sulfonylamino, and aryl.

The group represented R which may be metabolically hydrolyzed in the body is preferably ester and includes for example lower alkylcarbonyloxy-lower-alkyl, lower cycloalkylcarbonyloxy-lower-alkyl, lower cycloalkylmethylcarbonyloxy-lower-alkyl, lower alkenylcarbonyloxy-lower-alkyl, arylcarbonyloxy-lower-alkyl, tetrahydrofuranylcarbonyloxymethyl, lower alkoxy-lower-alkyl, lower alkoxy-lower-alkoxy-lower-alkyl, arylmethyloxy-lower-alkyl, arylmethyloxy-lower-alkoxy-lower-alkyl, lower alkyloxycarbonyloxy-lower-alkyl, lower cycloalkyloxycarbonyloxy-lower-alkyl, lower cycloalkylmethoxycarbonyloxy-lower-alkyl, aryloxycarbonyloxy-lower-alkyl, 3-phthalidyl in which the aromatic ring may be substituted, 2-(3-phthalidylidene)ethyl in which the aromatic ring may be substituted, 2-oxotetrahydrofuran-5-yl, 2-oxo-5-lower alkyl-1,3-dioxolen-4-ylmethyl. Preferred example includes lower alkylcarbonyloxy-lower-alkyl, lower cycloalkylcarbonyloxy-lower-alkyl, lower alkyloxycarbonyloxy-lower-alkyl, lower cycloalkyloxycarbonyloxy-lower-alkyl, lower cycloalkylmethoxycarbonyloxy-lower-alkyl, aryloxycarbonyloxy-lower-alkyl, 3-phthalidyl in which the aromatic ring may be substituted, 2-(3-phthalidylidene)ethyl in which the aromatic ring may be substituted, 2-oxotetrahydrofuran-5-yl, and 2-oxo-5-lower alkyl-1,3-dioxolen-4-ylmethyl, more preferably, pivaloyloxymethyl ester, acetoxymethyl ester, 1-(acetoxy)ethyl ester, (1-methylcyclohexan-1-yl)carbonyloxymethyl ester, 1-(ethoxycarbonyloxy) ethyl ester, 1-(isopropoxycarbonyloxy)ethyl ester, 1-(cyclohexyloxycarbonyloxy)ethyl ester, cyclohexyloxycarbonyloxymethyl ester, 3-phthalidyl ester, 5-methyl-2-oxo-1,3-dioxolen-4-ylmethyl ester, 1-[(cyclohexylmethoxy)carbonyloxy]ethyl ester, 1-[(2-methylcyclohexan-1-yl)oxycarbonyloxy]ethyl ester, cyclopentyloxycarbonyloxymethyl ester, (Z)-2-(3-phthalidylidene)ethyl ester, (1R,2S,5R)-(l)-menthyloxycarbonyloxymethyl ester, (1S,2R,5S)-(d)-menthyloxycarbonyloxym ethyl ester, 1-(phenyloxycarbonyloxy)etthyl ester, phenyloxycarbonyloxymethyl ester, and 1-(cyclohexyloxycarbonyloxy)-N-propyl ester.

Further, one or more hydrogen atoms on the lower alkyl, lower cycloalkyl, $C_{2-4}$ alkenyl and aryl as a part of the above ester m oieties may be substituted by, for example, lower alkyl, halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylainino)sulfonyl, (N-lower alkylamino)sulfonylamino, aminosulfonylamino, (N,N-di-lower alkylamino)sulfonylamino, and aryl, preferably lower alkyl, lower alkoxy, hydroxy, formylamino, or carbamoyl.

Furthermore, when the above ester moiety is 3-phthalidyl in which the aromatic ring may be substituted or 2-(3-phthalidylidene)ethyl in which the aromatic ring may be substituted, the substituent includes lower alkyl, halogen, nitro, cyano, lower cycloalkyl, lower alkylthio, lower alkoxy, hydroxy, amino, N-lower alrylamino, formyl, lower alkylcarbonyl, arylcarbonyl, carboxyl, lower alkoxycarbonyl, formylamino, lower alkylcarbonyl amino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, aryl, preferably lower alkoxy, hydroxy, formylamino, and carbamoyl.

The preferred compounds of the formul(I) according to the present invention include those in which $R^6$ is not present, R represents hydrogen or a group which may be metabolically hydrolyzed in the body.

The compounds in which $R^6$ is not present preferably inclouse those in which
  $R^1$ represents hydrogen or methyl,
  $R^2$, $R^3$, $R^4$, and $R^5$, except the one representing the bond to the 2-position on the carbapenem ring, which may be the same or different, respectively represent,
    hydrogen,
    halogen,
    cyano,
    lower alkyl, in which one or more hydrogen atoms on the alkyl may be substituted by a group selected from the group consisting of halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, and aryl, more preferably the alkyl is unsubstituted, or the one substituted with lower alkoxy, hydroxy, or formylamino,
    formyl,
    lower alkylcarbonyl,
    lower alkoxycarbonyl,
    aminosulfonyl,
    carbamoyl,
    N-lower alkylcarbamoyl,
    N,N-di-lower alkylaminocarbonyl,
    lower alkoxyiminomethyl, or
    hydroxyiminomethyl. Among the above compounds, more preferred compounds include those in which R represents lower alkylcarbonyloxy-lower-alkyl, lower cycloalkylcarbonyloxy-lower-alkyl, lower alkyloxycarbonyloxy-lower-alkyl, lower cycloalkyloxycarbonyloxy-lower-alkyl, lower cycloalkylmethoxycarbonyloxy-lower-alkyl, aryloxycarbonyloxy-lower-alkyl, 2-oxo-5-lower alkyl-1,3-dioxolen-4-ylmethyl, 3-phthalidyl in which the aromatic ring may be substituted, or 2-(3-phthalidylidene)ethyl in which the aromatic ring may be substituted is preferred.

Another preferred compounds in which $R^6$ is not present includes those in which
  $R^1$ represents methyl,
  $R^2$ represents the bond to the 2-position on the carbapenem ring,
  $R^3$, $R^4$, and $R^5$, which may be the same or different, respectively represent
    hydrogen,
    halogen
    cyano,
    lower alkyl, in which one or more hydrogen atoms on the alkyl may be substituted by lower alkoxy, hydroxy, or formylamino,
    formyl,
    lower alkylcarbonyl,
    lower alkoxycarbonyl,
    aminosulfonyl,
    carbamoyl,
    N-lower alkylcarbamoyl,
    N,N-di-lower alkylaminocarbonyl,
    lower alkoxyiminomethyl, or
    hydroxyiminomethyl;
those in which
  $R^1$ represents hydrogen,
  $R^2$ represents the bond to the 2-position on the carbapenem ring,
  $R^3$, $R^4$, and $R^5$, which may be the same or different, respectively represent
    hydrogen,
    halogen,
    cyano,
    lower alkyl, in which one or more hydrogen atoms on the alkyl may be substituted by lower alkoxy, hydroxy, or formylamino, formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl;

those in which,
$R^1$ represents methyl,
$R^3$ represents the bond to the 2-position on the carbapenem ring,
$R^2$, $R^4$, and $R^5$, which may be the same or different, respectively represent
hydrogen,
halogen,
cyano,
lower alkyl, in which one or more hydrogen atoms on the alkyl may be substituted by lower alkoxy, hydroxy, or formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl;

those in which
$R^1$ represents hydrogen,
$R^3$ represents the bond to the 2-position on the carbapeneim ring
$R^2$, $R^4$, and $R^5$, which may be the same or different, respectively represent
hydrogen,
halogen
cyano,
lower alkyl, in which one or more hydrogen atoms on the alkyl may be substituted by lower alkoxy, hydroxy, or formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl;

those in which
$R^1$ represents hydrogen or methyl,
$R^4$ represents the bond to the 2-position on the carbapenem ring,
$R^2$, $R^3$, and $R^5$, which may be the same or different, respectively represent
hydrogen,
halogen,
cyano,
lower alkyl, in which one or more hydrogen atoms on the alkyl may be substituted by lower alkoxy, hydroxy, or formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl; and those in which
$R^1$ represents hydrogen or methyl,
$R^5$ represents the bond to the 2-position on the carbapenem ring,
$R^2$, $R^3$, and $R^4$, which may be the same or different, respectively represent
hydrogen,
halogen,
cyano,
lower alkyl, in which one or more hydrogen atoms on the alkyl may be substituted by lower alkoxy, hydroxy, or formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl.

Another preferred compounds of the formul(I) according to the present invention include those in which $R^6$ is present, R is not present, and the compound forms an inner salt.

The compounds in which $R^6$ is present, and the compound forms an inner salt include more preferably those in which
$R^1$ represents hydrogen or methyl,
$R^2$, $R^3$, $R^4$, $R^5$, and $R^6$, except the one representing the bond to the 2-position on the carbapenem ring, which may be the same or different, respectively represent
hydrogen,
halogen,
cyano,
lower alkyl, in which one or more hydrogen atoms on the alkyl may be substituted by halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, and aryl,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl.

Among these compounds, more preferred compounds includes those in which
$R^2$, $R^3$, $R^4$, and $R^5$, except the one representing the bond to the 2-position on the carbapenem ring, represent
hydrogen,
halogen, cyano,
    lower alkyl, in which one or more hydrogen atoms on the alkyl may be substituted by lower alkoxy, hydroxy, and formylamino,
    formyl,
    lower alkylcarbonyl,
    lower alkoxycarbonyl,
    aminosulfonyl,
    carbamoyl,
    N-lower alkylcarbamoyl,
    N,N-di-lower alkylaminocarbonyl,
    lower alkoxyiminomethyl, or
    hydroxyiminomethyl, and
$R^6$ represents lower alkyl which, may be substituted by a group selected from the group consisting of lower alkoxy, hydroxy, formylamino, and carbamoyl.

Another preferred compounds in which $R^6$ is present, and the compound forms an inner salt includes those in which
$R^1$ represents methyl,
$R^2$ represents the bond to the 2-position on the carbapenem ring
$R^3$, $R^4$, and $R^5$, which may be the same or different, respectively represent
    hydrogen,
    halogen,
    cyano,
    lower alkyl, in which one or more hydrogen atoms on the alkyl may be substituted by lower alkoxy, hydroxy, and formylamino,
    formyl,
    lower alkylcarbonyl,
    lower alkoxycarbonyl,
    aminosulfonyl,
    carbamoyl,
    N-lower alkylcarbamoyl,
    N-di-lower alkylaminocarbonyl,
    lower alkoxyiminomethyl, or
    hydroxyiminomethyl, and
$R^6$ represents lower alkyl which may be substituted by a group selected from the group consisting of lower alkoxy, hydroxy, formylamino, and carbamoyl;
those in which
$R^1$ represents hydrogen,
$R^2$ represents the bond to the 2-position on the carbapenem ring,
$R^3$, $R^4$, and $R^5$, which may be the same or different, respectively represent
    hydrogen,
    halogen,
    cyano,
    lower alkyl, in which one or more hydrogen atoms on the alkyl may be substituted by lower alkoxy, hydroxy, and formylamino,
    formyl,
    lower alkylcarbonyl,
    lower alkoxycarbonyl,
    aminosulfonyl,
    carbamoyl,
    N-lower alkylcarbamoyl,
    N,N-di-lower alkylaminocarbonyl,
    lower alkoxyiminomethyl, or
    hydroxyiminomethyl, and
$R^6$ represents lower alkyl which may be substituted by a group selected from the group consisting of lower alkoxy, hydroxy, formylamino, and carbamoyl;
those in which $R^1$ represents methyl,
$R^3$ represents the bond to the 2-position on the carbapenem ring,
$R^2$, $R^4$, and $R^5$, which may be the same or different, respectively represent
    hydrogen,
    halogen,
    cyano,
    lower alkyl, in which one or more hydrogen atoms on the alkyl may be substituted by lower alkoxy, hydroxy, and formylamino,
    formyl,
    lower alkylcarbonyl,
    lower alkoxycarbonyl,
    aminosulfonyl,
    carbamoyl,
    N-lower alkylcarbamoyl,
    N,N-di-lower alkylaminocarbonyl,
    lower alkoxyiminomethyl, or
    hydroxyiminomethyl, and
$R^6$ represents lower alkyl which may be substituted by a group selected from the group consisting of lower alkoxy, hydroxy, formylamino, and carbamoyl;
those in which
$R^1$ represents hydrogen,
$R^3$ represents the bond to the 2-position on the carbapenem ring,
$R^2$, $R^4$, and $R^5$, which may be the same or different, respectively represent
    hydrogen,
    halogen,
    cyano,
    lower alkyl, in which one or more hydrogen atoms on the alkyl may be substituted by a group selected from the group consisting of lower alkoxy, hydroxy, and formylamino,
    formyl,
    lower alkylcarbonyl,
    lower alkoxycarbonyl,
    aminosulfonyl,
    carbamoyl,
    N-lower alkylcarbamoyl,
    N,N-di-lower alkylaminocarbonyl,
    lower alkoxyiminomethyl, or
    hydroxyiminomethyl, and
$R^6$ represents lower alkyl which may be substituted by a group selected from the group consisting of lower alkoxy, hydroxy, formylamino, and carbamoyl;
those in which
$R^1$ represents hydrogen or methyl,
$R^4$ represents the bond to the 2-position on the carbapenem ring,
$R^2$, $R^3$, and $R^5$, which may be the same or different, respectively represent
    hydrogen,
    halogen,
    cyano,
    lower alkyl, in which one or more hydrogen atoms on the alkyl may be substituted by a group selected from the group consisting of lower alkoxy, hydroxy, and formylamino,
    formyl,
    lower alkylcarbonyl,
    lower alkoxycarbonyl,
    aminosulfonyl, carbamoyl,
N-lower alkylcarbamoyl,
N,N-di-lower alkylaminocarbonyl,
lower alkoxyiminomethyl, or
hydroxyiminomethyl, and $R^6$ represents lower alkyl which may be substituted by a group selected from the group consisting of lower alkoxy, hydroxy, formylamino, and carbamoyl; and those in which $R^1$ represents hydrogen or methyl, $R^5$ represents the bond to the 2-position on the carbapenem ring, $R^2$, $R^3$, and $R^4$, which may be the same or different, respectively represent
hydrogen,
halogen,
cyano,
lower alkyl, in which one or more hydrogen atoms on the alkyl may be substituted by a group selected from the group consisting of lower alkoxy, hydroxy, and formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl, and $R^6$ represents lower alkyl which may be substituted by a group selected from the group consisting of lower alkoxy, hydroxy, formylamino, and carbamoyl.

The further preferred compounds of the present invention include those in which $R^2$ or $R^3$ represents the bond to the 2-position on the carbapenem ring.

Furthermore, the another preferred compounds of the present invention include those in which $R^6$ represents alkyl having 1–2 carbon atoms which may be substituted by carbamoyl, fluorine, or hydroxy.

The another preferred compounds of the present invention include those in which $R^2$ represents the bond to the 2-position on the carbapenem ring, all of $R^3$, $R^4$, and $R^5$ represent hydrogen, or both of $R^3$ and $R^4$ represent hydrogen, and $R^5$ represents a group selected from the group consisting of lower alkyl which may be substituted by formylamino or lower alkoxy, chlorine, formyl, lower alkylcarbonyl, cyano, carbamoyl, N-lower alkylcarbamoyl, and N,N-di-lower alkylaminocarbonyl.

The another preferred compounds of the present invention include those in which $R^2$ represents the bond to the 2-position on the carbapenem ring, and $R^3$ represents methyl.

Furthermore, the another preferred compounds of the present invention includes those in which $R^3$ represents the bond to the 2-position on the carbapenem ring, both of $R^2$ and $R^4$ represent a hydrogen atom, and $R^5$ represents hydrogen or cyano.

The compound represented by the formula (I) according to the present invention can exist as a salt, and the preferred salt is a pharmacologically acceptable salt. Such a salt includes for example inorganic salts such as lithium, sodium, potassium, calcium, or magnesium salts, an ammonium salt, salts with organic bases such as triethylamine or diisopropylethylamine, salts with mineral acids such as hydrochloric acid, sulfuric acid, phosphoric acid, or nitric acid, or salts with organic acids such as acetic acid, carbonic acid, citric acid, malic acid, oxalic acid, or methanesulfonic acid, preferably an inner salt, or sodium or potassium salt.

The specific examples of the compounds of the formula (I) according to the present invention include:

1. (1S,5R,6S)-6-((1R)-1-hydroxyethyl)-2-(imidazo[5,1-b]thiazol-2-yl)-1-methyl-1-carbapen-2-em-3-carboxylic acid;
2. Pivaloyloxymethyl (1S,5R,6S)-6-((1R)-1-hydroxyethyl)-2-(imidazo[5,1-b]thiazol-2-yl)-1-methyl-1-carbapen-2-em-3-carboxylate;
3. (1S,5R,6S)-6-((1R)-1-hydroxyethyl)-1-methyl-2-(6-methylimidazo[5,1-b]thiazolium-2-yl)-1-carbapen-2-em-3-carboxylate (inner salt);
4. (1S,5R,6S)-6-((1R)-1-hydroxyethyl)-2-(imidazo[5,1-b]thiazol-3-yl)-1-methyl-1-carbapen-2-em-3-carboxylic acid;
5. Pivaloyloxymethyl (1S,5R,6S)-6-((1R)-1-hydroxyethyl)-2-(imidazo[5,1-b]thiazol-3-yl)-1-methyl-1-carbapen-2-em-3-carboxylate;
6. (1S,5R,6S)-6-((1R)-1-hydroxyethyl)-1-methyl-2-(6-methylimidazo[5,1-b]thiazolium-3-yl)-1-carbapen-2-em-3-carboxylate (inner salt);
7. (5R,6S)-6-((1R)-1-hydroxyethyl)-2-(imidazo[5,1-b]thiazol-2-yl)-1-carbapen-2-em-3-carboxylic acid;
8. (1S,5R,6S)-6-((1R)-1-hydroxyethyl)-1-methyl-2-(3-methylimidazo[5,1-b]thiazol-2-yl)-1-carbapen-2-em-3-carboxylic acid;
9. Pivaloyloxymethyl (1S,5R,6S)-6-((1R)-1-hydroxyethyl)-1-methyl-2-(3-methylimidazo[5,1-b]thiazol-2-yl)-1-carbapen-2-em-3-carboxylate;
10. (1S,5R,6S)2-(3,6-dimethylimidazo[5,1-b]thiazolium-2-yl)-6-((1R)-1-hydroxyethyl)-1-methyl-1-carbapen-2-em-3-carboxylate (inner salt);
11. (5R,6S)-6-((1R)-1-hydroxyethyl)-2-(imidazo[5,1-b]thiazol-3-yl)-1-carbapen-2-em-3-carboxylic acid;
12. Pivaloyloxymethyl (5R,6S)-6-((1R)-1-hydroxyethyl)-2-(imidazo[5,1-b]thiazol-3-yl)-1-carbapen-2-em-3-carboxylate;
13. (5R,6S)-6-((1R)-1-hydroxyethyl)-2-(6-methylimidazo[5,1-b]thiazolium-3-yl)-1-carbapen-2-em-3-carboxylate (inner salt)
14. (5R,6S)-6-((1R)-1-hydroxyethyl)-2-(6-methylimidazo[5,1-b]thiazolium-2-yl)-1-carbapen-2-em-3-carboxylate (inner salt)
15. (1S,5R,6S)-2-(6-carbamoylmethylimidazo[5,-b]thiazolium-2-yl)-6-((1R)-1-hydroxyethyl)-1-methyl-1-carbapen-2-em-3-carboxylate (inner salt);
16. (1S,5R,6S)-6-((1R)-1-hydroxyethyl)-1-methyl-2-(5-methylimidazo[5,1-b]thiazol-2-yl)-1-carbapen-2-em-3-carboxylic acid
17. (1S,5R,6S)-2-(5,6-dimethylimidazo[5,1-b]thiazolium-2-yl)-6-((1R)-1-hydroxyethyl)-1-mnethyl-1-carbapen-2-em-3-carboxylate (inner salt);
18. Pivaloyloxymethyl (1S,5R,6S)-6-((1R)-1-hydroxyethyl)-1-methyl-2-(5-methyirimidazo[5,1-b]thiazol-2-yl)-1-carbapen-2-em-3-carboxylate;
19. (1S,5R,6S)-2-(7-chloroimidazo[5,1-b]thiazol-2-yl)-6-((1R)-1-hydroxyethyl)-1-methyl-1-carbapen-2-em-3-carboxylic acid;
20. (1S,5R,6S)-6-((1R)-1-hydroxyethyl)-1-methyl-2-(2-methylimidazo[5,1-b]thiazol-3-yl)-1-carbapen-2-em-3-carboxylic acid;
21. (5R,6S)-6-((1R)-1-hydroxyethyl)-2-(2-methylimidazo[5,1-b]thiazol-3-yl)-1-carbapen-2-em-3-carboxylic acid;

22. (1S,5R,6S)-2-(7-chloro-6-methylimidazo[5,1-b]thiazolium-2-yl)-6-((1R)-1-hydroxyethyl)-1-methyl-1-carbapen-2-em-3-carboxylate (inner salt);
23. Pivaloyloxymethyl (5R,6S)-6-((1R)-1-hydroxyethyl)-2-(imidazo[5,1-b]thiazol-2-yl)-1-carbapen-2-em-3-carboxylate;
24. (5R,6S)-6-((1R)-1-hydroxyethyl)-2-(5-methylimidazo[5,1-b]thiazol-2-yl)-1-carbapen-2-em-3-carboxylic acid;
25. Pivaloyloxymethyl (5R,6S)-6-((1R)-1-hydroxyethyl)-2-(5-methylimidazo[5,1-b]thiazol-2-yl)-1-carbapen-2-em-3-carboxylate;
26. Sodium (1S,5R,6S)-6-((1R)-1-hydroxyethyl)-1-methyl-2-(7-methylimidazo[5,1-b]thiazol-2-yl)-1-carbapen-2-em-3-carboxylate;
27. Pivaloyloxymethyl (1S,5R,6S)-6-((1R)-1-hydroxyethyl)-1-methyl-2-(7-methylimidazo[5,1-b]thiazol-2-yl)-1-carbapen-2-em-3-carboxylate;
28. (1S,5R,6S)-2-(6,7-dimethylimidazo[5,1-b]thiazolium-2-yl)-6-((1R)-1-hydroxyethyl)-1-methyl-1-carbapen-2-em-3-carboxylate (inner salt);
29. (5R,6S)-2-(5,6-dimethylimidazo[5,1-b]thiazolium-2-yl)-6-((1R)-1-hydroxyethyl)-1-carbapen-2-em-3-carboxylate (inner salt);
30. (1S,5R,6S)-2-(5-formylaminomethyl imidazo[5,1-b]thiazol-2-yl)-6-((1R)-1-hydroxyethyl)-1-methyl-1-carbapen-2-em-3-carboxylic acid;
31. Pivaloyloxymethyl (1S,5R,6S)-2-(5-formylaminomethyl imidazo[5,1-b]thiazol-2-yl)-6-((1R)-1-hydroxyethyl)-1-methyl-1-carbapen-2-em-3-carboxylate;
32. (1S,5R,6S)-2-(5-formylaminomethyl-6-methylimidazo[5,1-b]-thiazolium-2-yl)-6-((1R)- 1-hydroxyethyl)-1-methyl-1-carbapen-2-em-3-carboxylate (inner salt);
33. (1S,5R,6S)-6-((1R)-1-hydroxyethyl)-2-(5-hydroxymethylimidazo[5,1-b]thiazol-2-yl)-1-methyl-1-carbapen-2-em-3-carboxylic acid;
34. Pivaloyloxymethyl (1S,5R,6S)-6-((1R)-1-hydroxyethyl)-2-(5-hydroxymethylimidazo[5,1-b]thiazol-2-yl)-1-methyl-1-carbapen-2-em-3-carboxylate;
35. (1S,5R,6S)-6-((1R)-1-hydroxyethyl)-2-(3-hydroxymethylimidazo[5,1-b]thiazol-2-yl)-1-methyl-1-carbapen-2-em-3-carboxylic acid;
36. (1S,5R,6S)-6-((1R)-1-hydroxyethyl)-1-methyl-2-(7-methylimidazo[5,1-b]thiazol-3-yl)-1-carbapen-2-em-3-carboxylic acid;
37. Sodium (5R,6S)-6-((1R)-1-hydroxyethyl)-2-(7-methylimidazo[5,1-b]thiazol-3-yl)-1-carbapen-2-em-3-carboxylate;
38. Pivaloyloxymethyl (5R,6S)-6-((1R)-1-hydroxyethyl)-2-(7-methylimidazo[5,1-b]thiazol-2-yl)-1-carbapen-2-em-3-carboxylate;
39. Pivaloyloxymethyl (1S,5R,6S)-6-((1R)-1-hydroxyethyl)-1-methyl-2-(7-methylimidazo[5,1-b]thiazol-3-yl)-1-carbapen-2-em-3-carboxylate;
40. (1S,5R,6S)-6-((1R)-1-hydroxyethyl)-2-(5-hydroxymethyl-6-methylimidazo[5,1-b]thiazolium-2-yl)-1-methyl-1-carbapen-2-em-3-carboxylate (inner salt);
41. (5R,6S)-2-(6,7-dimethylimidazo[5,1-b]-thiazolium-2-yl)-6-((1R)-1-hydroxyethyl)-1-carbapen-2-em-3-carboxylate (inner salt);
42. (5R,6S)-6-((1R)-1-hydroxyethyl)-2-(7-methylimidazo[5,1-b]thiazol-3-yl)-1-carbapen-2-em-3-carboxylic acid;
43. Pivaloyloxymethyl (5R,6S)-6-((1R)-1-hydroxyethyl)-2-(7-methylimidazo[5,1-b]thiazol-3-yl)-1-carbapen-2-em-3-carboxylate;
44. (5R,6S)-2-(6,7-dimethylimidazo[5,1-b]thiazolium-3-yl)-6-((1R)-1-hydroxyethyl)-1-carbapen-2-em-3-carboxylate (inner salt)
45. (5R,6S)-6-((1R)-1-hydroxyethyl)-2-(3-methylimidazo[5,1-b]thiazol-2-yl)-1-carbapen-2-em-3-carboxylic acid;
46. Pivaloyloxymethyl (5R,6S)-6-((1R)-1-hydroxyethyl)-2-(3-methylimidazo[5,1-b]thiazol-2-yl)-1-carbapen-2-em-3-carboxylate;
47. Potassium (1S,5R,6S)-6-((1R)-1-hydroxyethyl)-2-(imidazo[5,1-b]thiazol-5-yl)-1-methyl-1-carbapen-2-em-3-carboxylate;
48. (1S,5R,6S)-2-(7-formylaminomethyl-6-methylimidazo[5,1-b]thiazolium-2-yl)-6-((1R)-1-hydroxyethyl)-1-methyl-1-carbapen-2-em-3-carboxylate (inner salt);
49. Pivaloyloxymethyl (1S,5R,6S)-6-((1R)-1-hydroxyethyl)-2-(imidazo[5,1-b]thiazol-5-yl)-1-methyl-1-carbapen-2-em-3-carboxylate;
50. (5R,6S)-2-(3,6-dimethylimidazo[5,1-b]thiazolium-2-yl)-6-((1R)-1-hydroxyethyl)-1-carbapen-2-em-3-carboxylic acid (inner salt);
51 Acetoxymethyl (1S,5R,6S)-6-((1R)-1-hydroxyethyl)-2-(imidazo[5,1-b]thiazol-2-yl)-1-methyl-1-carbapen-2-em-3-carboxylate;
52. 1-(acetoxymethyl (1S,5R,6S)-6-((1R)-1-hydroxyethyl)-2-(imidazo[5,1-b]thiazol-2-yl)-1-methyl-1-carbapen-2-em-3-carboxylate carboxylate (diastereomer mixture);
53. (1-methylcyclohexan-1-yl)carbonyloxymethyl (1S,5R,6S)-6-((1R)-1-hydroxyethyl)-2-(imidazo[5,1-b]thiazol-2-yl)-1-methyl-1-carbapen-2-em-3-carboxylate;
54. 1-(ethoxycarbonyloxy)ethyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture);
55. 1-(isopropoxycarbonyloxy)ethyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture);
56. 1-(cyclohexyloxycarbonyloxy)ethyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture);
57. Cyclohexyloxycarbonyloxy methyl (1S,5R,6S)-6-((1R)-1-hydroxyethyl)-2-(imidazo[5,1-b]thiazol-2-yl)-1-methyl-1-carbapen-2-em-3-carboxylate;
58. Phthalidyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture);
59. (5-methyl-2-oxo-1,3-dioxolen-4-yl)methyl (1S,5R,6S)-6-((1R)-1-hydroxyethyl)-2-(imidazo[5,1-b]thiazol-2-yl)-1-methyl-1-carbapen-2-em-3-carboxylate;
60. 1-[(cyclohexymethoxy)carbonyloxy]ethyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture);
61. 1-[(2-methylcyclohexan-1-yl)oxycarbonyloxy]ethyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture);
62. Cyclopentyloxycarbonyloxymethyl (1S,5R,6S)-6-((1R)-1-hydroxyethyl)-2-(imidazo[5,1-b]thiazol-2-yl)-1-methyl-1-carbapen-2-em-3-carboxylate;
63. (Z)-2-(3-phthlidylidene)ethyl (1S,5R,6S)-6-((1R)-1-hydroxyethyl)-2-(imidazo[5,1-b]thiazol-2-yl)-1-methyl-1-carbapen-2-em-3-carboxylate;
64. (1R,2S,5R)-(1)-menthyloxycarbonyloxymethyl (1S,5R,6S)-6-((1R)-1-hydroxyethyl)-2-(imidazo[5,1-b]thiazol-2-yl)-1-methyl-1-carbapen-2-em-3-carboxylate;
65. (1S,2R,5S)-(d)-menthyloxycarbonyloxymethyl(1S,5R,6S)-6-((1R)-1-hydroxyethyl)-2-(imidazo[5,1-b]thiazol-2-yl)-1-methyl-1-carbapen-2-em-3-carboxylate;
66. 1-(phenyloxycarbonyloxy)ethyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture);

67. phenyloxycarbonyloxymethyl (1S,5R,6S)-6-((1R)-1-hydroxyethyl)-2-(imidazo[5,1-b]thiazol-2-yl)-1-methyl-1-carbapen-2-em-3-carboxylate;
68. 1-(cyclohexyloxycarbonyloxy)-N-propyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture);
69. (1S,5R,6S)-2-(5-carbamoylimidazo[5,1-b]thiazol-2-yl)-6-((1R)-1-hydroxyethyl)-1-methyl-1-carbapen-2-em-3-carboxylic acid
70. Pivaloyloxymethyl (1S,5R,6S)-2-(5-carbamoylimidazo[5,1-b]thiazol-2-yl)-6-((1R)-1-hydroxyethyl)-1-methyl-1-carbapen-2-em-3-carboxylate;
71. Potassium (5R,6S)-6-((1R)-1-hydroxyethyl)-2-(imidazo[5,1-b]thiazol-5-yl)-1-carbapen-2-em-3-carboxylate;
72. Pivaloyloxymethyl (5R,6S)-6-((1R)-1-hydroxyethyl)-2-(imidazo[5,1-b]thiazol-5-yl)-1-carbapen-2-em-3-carboxylate;
73. (1S,5R,6S)-2-(5-formylimidazo[5,1-b]thiazol-2-yl)-6-((1R)-1-hydroxyethyl)-1-methyl-1-carbapen-2-em-3-carboxylic acid;
74. Pivaloyloxymethyl (1S,5R,6S)-2-(5-formylimidazo[5,1-b]thiazol-2-yl)-6-((1R)-1-hydroxyethyl)-1-methyl-1-carbapen-2-em-3-carboxylate;
75. (1S,5R,6S)-6-((1R)-1-hydroxyethyl)-2-(7-hydroxymethylimidazo[5,1-b]thiazol-2-yl)-1-methyl-1-carbapen-2-em-3-carboxylic acid;
76. (1S,5R,6S)-6-((1R)-1-hydroxyethyl)-2-(7-hydroxymethyl-6-methylimidazo[5,1-b]thiazolium-2-yl)-1-methyl-1-carbapen-2-em-3-carboxylate (inner salt);
77. Potassium (1S,5R,6S)-6-((1R)-1-hydroxyethyl)-2-(imidazo[5,1-b]thiazol-7-yl)-1-methyl-1-carbapen-2-em-3-carboxylate;
78. (1S,5R,6S)-6-((1R)-1-hydroxyethyl)-2-(6-methylimidazo[5,1-b]thiazol-7-yl)-1-methyl-1-carbapen-2-em-3-carboxylate (inner salt);
79. Sodium (5R,6S)-2-(7-chloroimidazo[5,1-b]thiazol-2-yl)-6-((1R)-1-hydroxyethyl)-1-carbapen-2-em-3-carboxylate;
80. (5R,6S)-2-(5-carbamoylimidazo[5,1-b]thiazol-2-yl)-6-((1R)-1-hydroxyethyl)-1-carbapen-2-em-3-carboxylic acid;
81. Pivaloyloxymethyl (5R,6S)-2-(5-carbamoylimidazo[5,1-b]thiazol-2-yl)-6-((1R)-1-hydroxyethyl)-1-carbapen-2-em-3-carboxylate;
82. (1S,5R,6S)-2-(5-formyl-6-methylimidazo[5,1-b]thiazolium-2-yl)-6-((1R)-1-hydroxyethyl)-1-methyl-1-carbapen-2-em-3-carboxylate (inner salt);
83. Pivaloyloxyinethyl (1S,5R,6S)-6-((1R)-1-hydroxyethyl)-2-(imidazo[5,1-b]thiazol-7-yl)-1-methyl-carbapen-2-em-3-carboxylate;
84. Pivaloyloxymethyl (1S,5R,6S)-6-((1R)-1-hydroxyethyl)-2-(7-hydroxymethylimidazo[5,1-b]thiazol-2-yl)-1-methyl-1-carbapen-2-em-3-carboxylate;
85. (5R,6S)-2-(7-chloro-6-methylimidazo[5,1-b]thiazolium-2-yl)-6-((1R)-1-hydroxyethyl)-1-carbapen-2-em-3-carboxylate (inner salt);
86. Pivaloyloxymethyl (5R,6S)-2-(7-chloroimidazo[5,1-b]thiazol-2-yl)-6-((1R)-1-hydroxyethyl)-1-carbapen-2-em-3-carboxylate;
87. (5R,6S)-2-(6-carbamoylmethylimidazo[5,1-b]thiazolium-2-yl)-6-((1R)-1-hydroxyethyl)-1-carbapen-2-em-3-carboxylate (inner salt);
88. Sodium (1S,5R,6S)-2-(5,7-dimethylimidazo[5,1-b]thiazol-2-yl)-6-((1R)-1-hydroxyethyl)-1-methyl-1-carbapen-2-em-3-carboxylate;
89. Sodium (1S,5R,6S)-2-(7-formylaminomethylimidazo[5,1-b]thiazol-2-yl)-6-((1R)-1-hydroxyethyl)-1-methyl-1-carbapen-2-em-3-carboxylate;
90. Acetoxymethyl (5R,6S)-6-((1R)-1-hydroxyethyl)-2-(imidazo[5,1-b]thiazol-3-yl)-1-carbapen-2-em-3-carboxylate;
91. 1-(acetoxy)ethyl (5R,6S)-2-(imidazo[5,1-b]thiazol-3-yl)-6-((1R)-1-hydroxyethyl)-1-carbapen-2-em-3-carboxylate (diastereomer mixture);
92. (1-methylcyclohexan-1-yl)carbonyloxymethyl (5R,6S)-6-(1R)-1-hydroxyethyl)-2-(imidazo[5,1-b]-thiazol-3-yl)-1-carbapen-2-em-3-carboxylate;
93. 1-(ethoxycarbonyloxy)ethyl (5R,6S)-6-((1R)-1-hydroxyethyl)-2-(imidazo[5,1-b]-thiazol-3-yl)-1-carbapen-2-em-3-carboxylate (diastereomer mixture);
94. 1-(isopropoxycarbonyloxy)ethyl (5R,6S)-6-((1R)-1-hydroxyethyl)-2-(imidazo[5,1-b]-thiazol-3-yl)-1-carbapen-2-em-3-carboxylate (diastereomer mixture);
95. 1-(cyclohexyloxycarbonyloxy)ethyl (5R,6S)-6-((1R)-1-hydroxyethyl)-2-(imidazo[5,1-b]-thiazol-3-yl)-1-carbapen-2-em-3-carboxylate (diastereomer mixture);
96. cyclohexyloxycarbonyloxymethyl (5R,6S)-6-((1R)-1-hydroxyethyl)-2-(imidazo[5,1-b]-thiazol-3-yl)-1-carbapen-2-em-3-carboxylate;
97. 3-phthalidyl (5R,6S)-6-((1R)-1-hydroxyethyl)-2-(imidazo[5,1-b]-thiazol-3-yl)-1-carbapen-2-em-3-carboxylate (diastereomer mixture);
98. (5-methyl-2-oxo-1,3-dioxolen-4-yl)methyl (5R,6S)-6-(((1R)-1-hydroxyethyl)-2-(imidazo[5,1-b]-thiazol-3-yl)-1-carbapen-2-em-3-carboxylate;
99. Pivaloyloxymethyl (1S,5R,6S)-2-(7-formylaminomethylimidazo[5,1-b]thiazol-2-yl)-6-((1R)-1-hydroxyethyl)-1-methyl-1-carbapen-2-em-3-carboxylate;
100. Sodium (5R,6S)-2-(7-formylaminomethyl imidazo[5,1-b]thiazol-3-yl)-6-((1R)-1-hydroxyethyl)-1-carbapen-2-em-3-carboxylate
101. Pivaloyloxymethyl (5R,6S)-2-(7-formylamino methylimidazo[5,1-b]thiazol-3-yl)-6-((1R)-1-hydroxyethyl)-1-carbapen-2-em-3-carboxylate;
102. (5R,6S)-2-(7-carbamoylimidazo[5,1-b]thiazol-3-yl)-6-((1R)-1-hydroxyethyl)-1-carbapen-2-em-3-carboxylic acid;
103. Pivaloyloxymethyl (5R,6S)-2-(7-carbamoylimidazo[5,1-b]thiazol-3-yl)-6-((1R)-1-hydroxyethyl)-1-carbapen-2-em-3-carboxylate;
104. (1S,5R,6S)-6-((1R)-1-hydroxyethy)-1-methyl-2-(5,6,7-methylimidazo[5,1-b]thiazolium-2-yl)-1-carbapen-2-em-3-carboxylate (inner salt);
105. Sodium (5R,6S)-6-((1R)-1-hydroxyethyl)-2-(7-hydroxymethylimidazo[5,1-b]thiazol-3-yl)-1-carbapen-2-em-3-carboxylate;
106. Sodium (1S,5R,6S)-2-(7-formylimidazo[5,1-b]thiazol-2-yl)-6-((1R)-1-hydroxyethyl)-1-methyl-1-carbapen-2-em-3-carboxylate;
107. Pivaloyloxpymethyl (1S,5R,6S)-2-(7-formylimidazo[5,1-b]thiazol-2-yl)-6-((1R)-1-hydroxyethyl)-1-methyl-1-carbapen-2-em-3-carboxylate;
108. (1S,5R,6S)-2-(7-carbamoylimidazo[5,1-b]thiazol-2-yl)-6-((1R)-1-hydroxyethyl)-1-methyl-1-carbapen-2-em-3-carboxylic acid;
109. Pivaloyloxymethyl (1S,5R,6S)-2-(7-carbamoylimidazo[5,1-b]thiazol-2-yl)-6-((1R)-1-hydroxyethyl)-1-methyl-1-carbapen-2-em-3-carboxylate;
110. Sodium (1S,5R,6S)-6-((1R)-1-hydroxyethyl)-2-(7-methoxymethylimidazo[5,1-b]thiazol-2-yl)-1-methyl-carbapen-2-em-3-carboxylate;
111. Pivaloyloxymethyl (1S,5R,6S)-6-((1R)-1-hydroxyethyl)-2-(7-methoxymethylimidazo[5,1-b]thiazol-2-yl)-1-methyl-carbapen-2-em-3-carboxylate;

112. Sodium (5R,6S)-6-((1R)-1-hydroxyethyl)-2-(7-methoxymethylimidazo[5,1-b]thiazol-3-yl)-1-carbapen-2-em-3-carboxylate;
113. Pivaloyloxymethyl (5R,6S)-6-((1R)-1-hydroxyethyl)-2-(7-methoxymethylimidazo[5,1-b]-thiazol-3-yl)-1-carbapen-2-em-3-carboxylate;
114. Pivaloyloxymethyl (5R,6S)-6-((1R)-1-hydroxyethyl)-2-(7-hydroxymethylimidazo[5,1-b]-thiazol-3-yl)-1-carbapen-2-em-3-carboxylate;
115. (1S,5R,6S)-2-(7-cyanoimidazo[5,1-b]-thiazol-2-yl)-6-((1R)-1-hydroxyethyl)-1-methyl-1-carbapen-2-em-3-carboxylic acid;
116. Pivaloyloxymethyl (1S,5R,6S)-2-(7-cyanoimidazo[5,1-b]thiazol-2-yl)-6-((1R)-1-hydroxyethyl)- 1-methyl-1-carbapen-2-em-3-carboxylate;
117. (1S,5R,6S)-2-(7-ethylimidazo[5,1-b]thiazol-2-yl)-6-((1R)-1-hydroxyethyl)-1-methyl-1-carbapen-2-em-3-carboxylic acid;
118. Pivaloyloxymethyl (1S,5R,6S)-2-(7-ethylimidazo[5,1-b]-thiazol-2-yl)-6-((1R)-1-hydroxyethyl)-1-methyl-1-carbapen-2-em-3-carboxylate;
119. (5R,6S)-2-(5-carbamoy3imidazo[5,1-b]thiazol-3-yl)-6-((1R)-1-hydroxyethyl)-1-carbapen-2-em-3-carboxylic acid;
120. (5R,6S)-2-(7-ethylimidazo[5,1-b]thiazol-2-yl)-6-((1R)-1-hydroxyethyl)-1-carbapen-2-em-3-carboxylic acid;
121. Pivaloyloxymethyl (5R,6S)-2-(7-ethylimidazo[5,1-b]thiazol-2-yl)-6-((1R)-1-hydroxyethyl)-1-carbapen-2-em-3-carboxylate;
122. (5R,6S)-2-(7-ethylimidazo[5,1-b]thiazol-3-yl)-6-((1R)-1-hydroxyethyl)-1-carbapen-2-em-3-carboxylic acid;
123. Pivaloyloxymethyl (5R,6S)-2-(7-ethylimidazo[5,1-b]thiazol-3-yl)-6-((1R)-1-hydroxyethyl)-1-carbapen-2-em-3-carboxylate;
124. (5R,6S)-2-(7-cyanoimidazo[5,1-b]thiazol-2-yl)-6-((1R)-1-hydroxyethyl)-1-carbapen-2-em-3-carboxylic acid;
125. Pivaloyloxymethyl (5R,6S)-2-(7-cyanoimidazo[5,1-b]thiazol-2-yl)-6-((1R)-1-hydroxyethyl)-1-carbapen-2-em-3-carboxylate;
126. (1S,5R,6S)-2-(7-ethyl-6-methylimidazo[5,1-b]thiazolium-2-yl)-6-((1R)-1-hydroxyethyl)-1-methyl-1-carbapen-2-em-3-carboxylate (inner salt);
127. (5R,6S)-2-(5,7-dimethylimidazo[5,1-b]thiazol-2-yl)-6-((1R)-1-hydroxyethyl)-1-carbapen-2-em-3-carboxylic acid;
128. Pivaloyloxymethyl (5R,6S)-2-(5,7-dimethylimidazo[5,1-b]thiazol-2-yl)-6-((1R)-1-hydroxyethyl)-1-carbapen-2-em-3-carboxylate;
129. (5R,6S)-2-(7-formylimidazo[5,1-b]thiazol-3-yl)-6-((1R)-1-hydroxyethyl)-1-carbapen-2-em-3-carboxylic acid;
130. Pivaloyloxymethyl (5R,6S)-2-(7-formylimidazo[5,1-b]thiazol-3-yl)-6-((1R)- 1-hydroxyethyl)-1-carbapen-2-em-3-carboxylate;
131. (5R,6S)-2-(7-ethyl-6-methylimidazo[5,1-b]thiazoliuin-3-yl)-6-((1R)-1-hydroxyethyl)-1-carbapen-2-em-3-carboxylate (inner salt);
132. (5R,6S)-6-((1R)-1-hydroxyethyl)-2-(5,6,7-trimethylimidazo[5,1-b]thiazoliunm-2-yl)-1-carbapen-2-em-3-carboxylate (inner salt);
133. Sodium (1S,5R,6S)-2-(7-acetylimidazo[5,1-b]thiazol-2-yl)-6-((1R)-1-hydroxyethyl)-1-methyl-1-carbapen-2-em-3-carboxylate;
134. Pivaloyloxymethyl (1S,5R,6S)-2-(7-acetylimidazo[5,1-b]thiazol-2-yl)-6-((1R)-1-hydroxyethyl)-1-methyl-1-carbapen-2-em-3-carboxylate;
135. (5R,6S)-2-(7-acetylimidazo[5,1-b]thiazol-3-yl)-6-((1R)-1-hydroxyethyl)-1-carbapen-2-em-3-carboxylic acid;
136. (1S,5R,6S)-6-((1R)-1-hydroxyethyl)-2-(7-methoxyiminomethylimidazo[5,1-b]thiazol-2-yl)-1-methyl-1-carbapen-2-em-3-carboxylic acid (geometrical isomer derived from a high polar oxime isomer as a raw material);
137. (1S,5R,6S)-6-((1R)-1-hydroxyethyl)-1-methyl-2-[7-(N-methylcarbamoyl)imidazo[5,1-b]thiazol-2-yl]-1-carbapen-2-em-3-carboxylic acid;
138. Pivaloyloxymethyl (1S,5R,6S)-6-((1R)-1-hydroxyethyl)-1-methyl-2-[7-(N-methylcarbamoyl)imidazo[5,1-b]thiazol-2-yl]-1-carbapen-2-em-3-carboxylate;
139. Sodium (1S,5R,6S)-2-[7-(N,N-dimethylcarbamoyl)imidazo[5,1-b]thiazol-2-yl]-6-((1R)-1hydroxyethyl)-1-methyl-1-carbapen-2-em-3-carboxylate;
140. Pivaloyloxymethyl (1S,5R,6S)-2-[7-(N,N-dimethylcarbamoyl)imidazo[5,1-b]thiazol-2-yl]-6-((1R)-1-hydroxyethyl)-1-methyl-1-carbapen-2-em-3-carboxylate;
141. Sodium (1S,5R,6S)-2-[7-(N,N -dimethylcarbamoyl)imidazo[5,1-b]thiazol-3-yl]-6-((1R)-1-hydroxyethyl)-1-methyl-1-carbapen-2-em-3-carhoxylate;
142. Pivaloyloxymethyl (1S,5R,6S)-2-[7-(N,N-dimethylcarbamoyl)imidazo[5,1-b]thiazol-3-yl]-6-((1R)-1-hydroxyethyl)-1-methyl-1-carbapen-2-em-3-carboxylate;
143. (5R,6S)-2-(7-cyanoimidazo[5,1-b]thiazol-3-yl)-6-((1R)-1-hydroxyethyl)-1-carbapen-2-em-3-carboxylic acid;
144. Pivaloyloxymethyl (5R,6S)-2-(7-cyanoimidazo[5,1-b]-thiazol-3-yl)-6-((1R)-1-hydroxyethyl)-1-carbapen-2-em-3-carboxylate;
145. (5R,6S)-6-((1R)-1-hydroxyethyl)-2-[7-(N-methylcarbamoyl)imidazo[5,1-b]thiazol-2-yl]-1-carbapen-2-em-3-carboxylic acid;
146. Pivaloyloxymethyl (5R,6S)-6-((1R)-1-hydroxyethyl)-2-[7-(N-methylcarbamoyl)imidazo[5,1-b]-thiazol-2-yl]-1-carbapen-2-em-3-carboxylate;
147. Sodium (1S,5R,6S)-6-((1R)-1-hydroxyethyl)-2-(7-methoxyiminomethylimidazo[5,1-b]thiazol-2-yl)-1-methyl-1-carbapen-2-em-3-carboxylate (geometrical isomer derived from a high polar oxime isomer as a raw material);
148. Pivaloyloxymethyl (1S,5R,6S)-6-((1R)-1-hydroxyethyl)-2-(7-methooxyiminomethylimidazo[5,1-b]thiazol-2-yl)-1-methyl-1-carbapen-2-em-3-carboxylate (geometrical isomer derived from a high polar oxime isomer as a raw material).

Preparation of the Compounds

The compounds according to the present invention can be prepared by a variety of methods. The preferred preparation methods are shown below.

Process (1)

Fisrt, the compound of the formula (I) according to the present invention can be prepared according to the following reaction scheme.

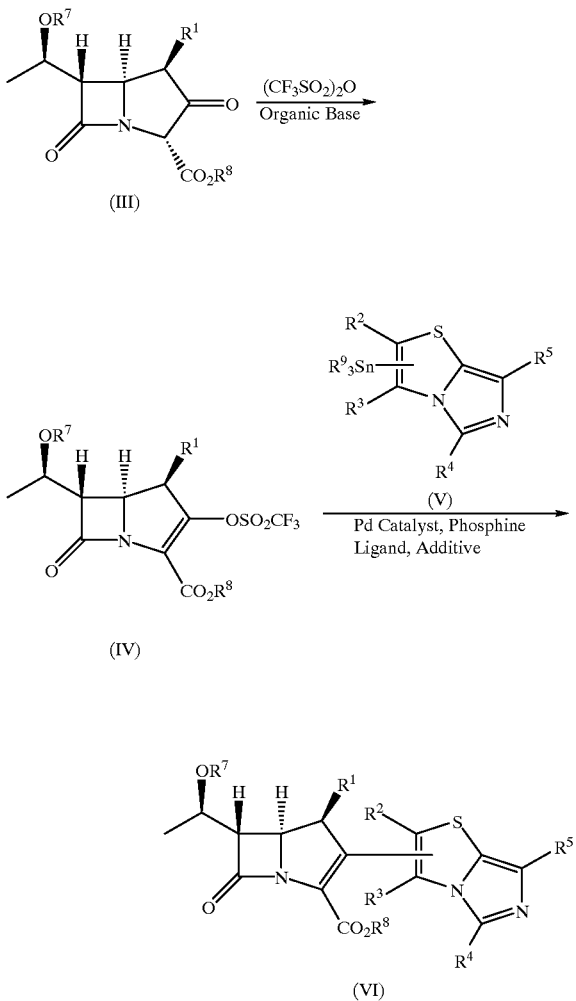

(III)

(IV)

(VI)

wherein $R^1$, $R^2$, $R^3$, $R^4$ and $R^5$ have the same meaning as defined in the formula (I), $R^7$ represents hydrogen or a hydroxyl protecting group such as t-butyldimethylsilyl, trimethylsilyl, triethylsilyl, 4-nitrobenzyloicycarbonyl, 4-methoxybenzyloxycarbonyl, $R^8$ represents a carboxyl protecting group such as 4-nitrobenzyl, 4-methoxybenzyl, diphenylmethyl, t-butyldimethylsilyl, $R^9$ represents lower alkyl, preferably n-butyl and methyl.

The compound of the formula (III) can be prepared by the ordinary method, and the tin compound of the formula (V) can be prepared by a method described below.

In the first step, the compound of the formula (III) can be converted into the compound of the formula (IV) by the following method. The compound (IV) can be prepared by reacting the compound of the the formula (III) with one (1) equivalent or an excessive amount of anhydrous trifluoromethanesulfonic acid in the presence of an organic base, preferably diisopropylethylamine in an amount of one (1) equivalent or an excessive amount to anhydrous trifluoromethanesulfonic acid in an inert solvent such as acetonitrile, tetrahydrofuran, dichloromethane, and toluene, and the mixed solvent thereof at a temperature of −50° C.−+50° C. for 10 minutes−24 hours, and then subjecting the reaction mixture to the usual purification procedure.

In the second step, the compound of the formula (IV) can be converted into the compound of the formula (VI) by the following method. The compound of the formula (VI) can be prepared by reacting the compound of the formula (IV) with one (1) equivalent or an excessive amount of the compound of the formula (V) in the presence of 0.001–1 equivalent of a palladium catalyst such as tetrakis(triphenylphosphine)palladium(0), tris(dibenzylideneacetone)-dipalladium(0), or tris(dibenzylideneacetone)dipalladium(0)-chloroform adduct, 0.01–1 equivalent of a phosphine ligand such as triphenylphosphine, tri-2-furylphosphine, or tri-2-thienylphosphine, tris(2,4,6-trimethoxyphenyl)phosphine, and 1–10 equivalents of an additive such as zinc chloride, lithium chloride, or cesium fluoride alone or in combination thereof in an inert solvent such as tetrahydrofuran, dimethoxyethane, dioxane, acetonitrile, acetone, ethanol, dimethylsulfoxide, sulfolane, N,N-dimethylformamide, N,N-dimethylacetamide, N-methylpyrrolidinone, or hexamethylphosphoric triamide, or a mixed solvent thereof at 0–100° C. for 10 minutes–7 days, and then subjecting the reaction mixture to the ordinary post-treatment.

Then, the protective groups $R^7$ and $R^8$ in the compound of the formula (VI) can be removed by the deprotection reaction in one step or plural steps depending on the kinds of the protective groups to obtain the compound of the formula (I) according to the present invention. The deprotection reactions, which depend on the kinds of the protective groups $R^7$ and $R^8$ used, can be carried out according to the usual methods generally known in the art. When either one or both of the protective groups can be removed under the acidic condition, a mineral acid such as hydrochloric acid, an organic acid such as oxalic acid, acetic acid or citric acid, or a Lewis acid such as aluminium chloride is used. When the protective groups is removed under a reducing condition, catalytic reduction with a variety of catalysts, or a metallic reducing agent such as zinc or iron is used. When $R^7$ is a silyl type protective group such as a t-butyldiinethylsilyl group, a trimethylsilyl group or a triethylsilyl group, it can be easily removed with use of a fluorine ion reagent such as tetrabutylammonium fluoride. When $R^7$ is an allyoxycarbonyl group and $R^8$ is an allyl group, the protective groups can be easily removed with use of a variety of palladium complexes such as tetrakis(triphenylphosphine)palladium(0).

Process (2)

The compound of the formula (I) according to the present invention, in which $R^6$ is not present, can be also prepared according to the following reaction.

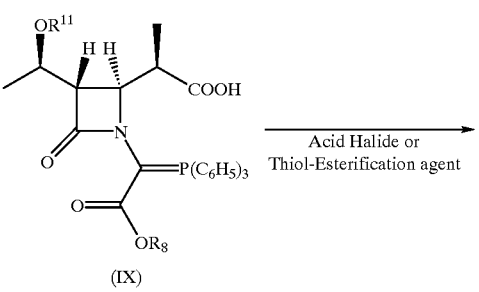

(IX)

-continued

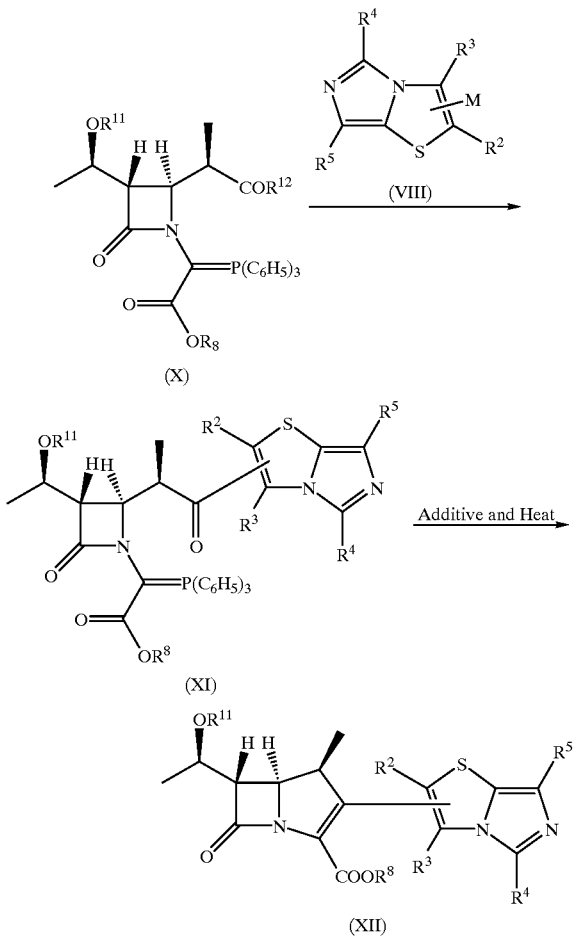

in which
R¹, R², R³, R⁴ and R⁵ have the same meanings as defined in the formula (I),
R⁸ has the same meaning as defined above,
R¹¹ represents a hydroxyl protecting group such as t-butyldimethylsilyl, trimethylsilyl, triethylsily or 4-nitrobenzyloxycarbonyl,
R¹² represents lower alkylcarbonyloxy such as t-butylcarbonyloxy, sec-butylcarbonyloxy, isopropylcarbonyloxy, arylcarbonyloxy such as benzenecarbonyloxy, 2-chlorobenzenecarbonyloxcy, arylthio, preferably 2-pyridylthio,
M represents Li, MgCl, MgBr or MgI.

The compound of the formula (VIII) in the scheme can be prepared by the method described in PCT/JP97/04270.

In the first step, the compound of the formula (IX) can be converted into the compound of the formula (X) by the following method. When the reactant used is an acid halide such as pivaloyl chloride or 2-chlorobenzoyl chloride, the compound of the formula (IX) can be reacted with one (1) equivalent or an excessive amount of the acid halide in the presence of an organic base such as triethylamine, diisopropylethylamine, pyridine, 2,6-lutidine, diazabicyclo[2,2,2]undecene in a proportion of one (1) equivalent or an excessive amount to the acid halide in an inert solvent such as acetonitrile, THF, dichloromethane or toluene, or a mixed solvent thereof at a temperature of −50° C.−+50° C. for 10 minutes–24 hours, and then subjected to the ordinary post-treatment to give the compound of the formula (X).

When the reactant used is a thiol-esterification agent, preferably 2,2'-dipyridyl disulfide, the compound of the formula (IX) can be reacted with one (1) equivalent or an excessive amount of the thiol-esterification agent in the presence of a phosphine compound such as triphenylphosphine or tributyl phosphine in a proportion of one (1) equivalent or an excessive amount to the thiol-esterification agent in an inert solvent such as acetonitrile, THF, dichloromethane or toluene, or a mixed solvent thereof at a temperature of −50° C.−+50° C. for 10 minutes–24 hours, and then subjected to the ordinary post-treatment to give the compound of the formula (X).

In the second step, the compound of the formula (X) can be converted into the compound of the formula (XI) by the following method. The compound of the formula (XI) can be prepared by adding one (1) equivalent or an excessive amount of a solution of the compound of the formula (X) in an inert solvent such as diethyl ether or THF to the compound of the formula (VIII) dissolved or suspended in an inert solvent such as diethyl ether or THF, or by adding the compound of the formula (VIII) in an amount of less than one (1) equivalent dissolved or suspended in an inert solvent such as diethyl ether or THF to the compound of the formula (X) dissolved in an inert solvent such as diethyl ether or THF, reacting the mixture at a temperature of −50° C.−+50° C. for 10 minutes–24 hours, and subjecting to the ordinary post-treatment.

Then, in the third step, the compound of the formula (XI) can be converted into the compound of the formula (XII) for example by the following method. The compound of the formula (XII) can be prepared by reacting the compound of the formula (XI) dissolved in an inert solvent such as benzene, toluene, xylene, THF or dioxane with a catalytic amount of an additive, preferably hydroquinone at a temperature of room temperature to refluxing temperature for 10 minutes–24 hours, and subjected to the ordinary post-treatment.

The protective groups R⁸ and R¹¹ in the compound of the formula (VI) can be removed by the deprotection reaction in one or more steps depending on the kinds of the protective groups to obtain the compound of the formula (I) according to the present invention. The deprotection reactions, which depend on the kinds of the protective groups R⁸ and R¹¹ used, can be carried out according to the usual methods generally known in the art. When either one or both of the protective groups can be removed under the acidic condition, a mineral acid such as hydrochloric acid, an organic acid such as oxalic acid, acetic acid or citric acid, or a Lewis acid such as aluminium chloride is used. When the protective groups is removed under a reducing condition, catalytic reduction with a variety of catalysts, or a metallic reducing agent such as zinc or iron is used. When R¹¹ is a silyl type protective group such as a t-butyldimethylsilyl group, a trimethylsilyl group or a triethylsilyl group, it can be easily removed with use of a fluorine ion reagent such as tetrabutylammonium fluoride. When R¹¹ is an allyoxycarbonyl group and R⁸ is an allyl group, the protective groups can be easily removed with use of a variety of palladium complexes such as tetrakis(triphenylphosphine)palladium (0).

The compound of the formula (I) thus obtained can be isolated and purified by crystallization or by chromatography with a nonionic macro-high porous resin, gel filtration with Sephadex or the like, or reverse phase silica gel column chromatography.

Process (3)

The compounds of the formula (I) in which R represents an ester hydrolizable in organisms can be prepared by converting the compounds represented by the formula (I) into the ester derivatives.

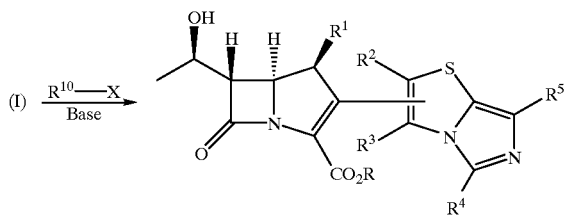

in which
R$^1$, R$^2$, R$^3$, R$^4$, R$^5$, and R have the same meanings as defined in the formula (I),
X represents a leaving group such as Cl, Br, I, —OSO$_2$CF$_3$, —OSO$_2$CH$_3$, or —OSO$_2$PhCH$_3$.

The ester derivatives can be prepared by reacting the compound of the formula (I) with an alkyl halide R10-X in the presence of one (1) equivalent or an excessive amount of a base at a temperature of −70–+50° C., preferably −30° C.–+20° C. for 10 minutes–24 hours.

The base usable in the reaction includes for example organic bases such as diisopropylethylamine, diazabicyclo[2,2,2]undecene and 2,6-lutidine, and inorganic bases such as sodium hydroxide, potassium hydroxide, sodium hydrogen carbonate, potassium hydrogen carbonate, sodium carbonate, potassium carbonate and cesium carbonate.

The alkyl halide R$^{10}$-X includes for example pivaloyloxymethyl iodide, 1-(pivaloyloxy)ethyl iodide, isobutyryloxymethyl iodide, 1-(isobutyryloxy)ethyl iodide, acetoxymethyl iodide, 1-(acetoxy)ethyl iodide, (1-methyl cyclohexan-1-yl)carbonyloxy methyl iodide, 1-(cyclohexyloxycarbonyloxy)ethyl iodide, 1-[(cyclohexylmethoxy)carbonyloxy]ethyl iodide, 1-(ethoxycarbonyloxy)ethyl iodide, cyclohexyloxycarbonyloxymethyl iodide, 1-[(2-methylcyclohexan-1-yl) oxycarbonyloxy]ethyl iodide, cyclopentyloxycarbonyloxymethyl iodide, 1-(isopropyloxycarbonyloxy)ethyl iodide, (1R, 2S,5R)-(1)-menthyloxycarbonyloxymethyl iodide, (1S,2R,5S)-(d)-menthyloxycarbonyloxymethyl iodide, 1-(phenyloxycarbonyloxy)ethyl iodide, phenyloxycarbonyloxymethyl iodide, 1-(cyclohexyloxycarbonyloxy)-N-propyl iodide, (5-methyl-2-oxo-1,3-dioxolen-4-yl)methyl bromide, 3-phthalidyl bromide, (Z)-2-(3-phthalidylidne) ethyl bromide, and the like.

The inert solvent usable in the reaction includes N,N-dimethylforamide, N,N-dimethylacetamide, N,N-diethylformamide, N,N-diethylacetamide, N-methylpyrrolidinone, N,N-dimethylimidazolidinoen, dimethylsulfoxide, sulfolane, acetonitrile, acetone, ethyl acetate, tetrahydrofuran, 1,4-dioxane, diethyl ether, anisole, dichloromethane, 1,2-dichloroethane, chloroform, toluene, benzene, hexamethylphosphoric triamide, methanol, and ethanol.

The ester derivatives thus obtained can be isolated and purified by precipitation, crystallization, gel filtration with Sephadex, or silica gel chromatography.

Process (4)

The compound represented by the formula (I) in which R6 is present can be prepared preferably by the following reaction.

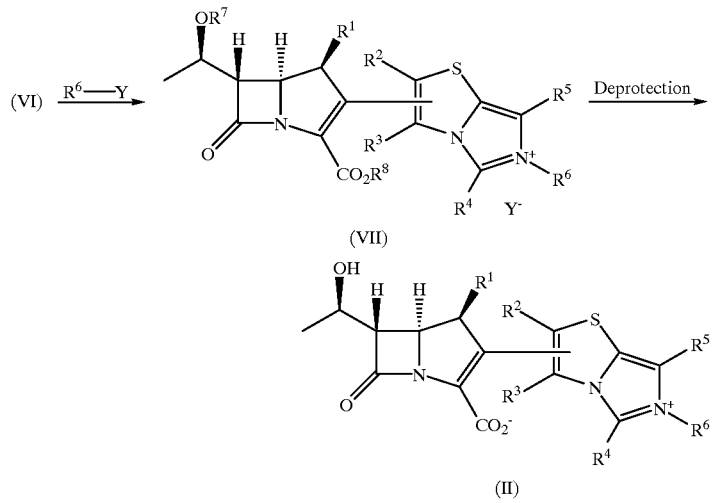

in which
R$^1$, R$^2$, R$^3$, R$^4$, R$^5$, and R$^6$ have the same meanings as defined in the formula (I),
R$^7$ and R$^8$ have the same meanings as defined above,
Y represents a leaving group such as Cl, Br, I, —OSO$_2$CF$_3$, —OSO$_2$CH$_3$ or —OSO$_2$PhCH$_3$.

The compound of the formula (VI) can be prepared according to the method described above.

In the first step, the compound of the formula (VI) can be converted into the compound of the formula (VII) by the following method. The compound of the formula (VII) can be prepared by reacting the compound of the formula (VI) with one (1) equivalent or an excessive amount of the compound R$^6$-Y in the absence or presence of an inert solvent such as acetonitrile, acetone, tetrahydrofuran, dichloromethane, toluene, N,N-dimethylformamide, N,N-dimethylacetamide or dimethylsulfoxide alone or in combination thereof at −80° C.–+60° C. for 15 minutes–1 week, and subjected to the usual post-treatment. The compound of the formula R$^6$-Y includes for example methyl iodide, carbamoulmethyl iodide, 2-fluoroethyl tri fluoro methanesulfonate, 2-hydroxyethyl trifluoromethanesulfonate, cyclopropylmethyl bromide, and methoxymethyl iodide.

Then, the protective groups $R^7$ and $R^8$ in the compound of the formula (VII) can be removed by the deprotection reaction in one step or plural steps depending on the kinds of the protective groups to obtain the compound of the formula (I) according to the present invention. The deprotection reactions, which depend on the kinds of the protective groups $R^7$ and $R^8$ used, can be carried out according to the usual methods generally known in the art. When either one or both of the protective groups can be removed under the acidic condition, a mineral acid such as hydrochloric acid, an organic acid such as oxalic acid, acetic acid or citric acid, or a Lewis acid such as aluminium chloride is used. When the protective groups is removed under a reducing condition, catalytic reduction with a variety of catalysts, or a metallic reducing agent such as zinc or iron can be used. When $R^7$ is a silyl type protective group such as t-butyldimethylsilyl, trimethylsilyl or triethylsilyl, it can be easily removed with use of a fluorine ion reagent such as tetrabutylammonium fluoride. When $R^7$ is allyoxycarbonyl and $R^8$ is allyl, the protective groups can be easily removed with use of a variety of palladium complexes such as tetrakis(triphenylphosphine)palladium(0).

The compound of the formula (I) thus obtained can be isolated and purified by crystallization or by chromatography with a nonionic macro-high porous resin, gel filtration with Sephadex or the like, or reverse phase silica gel column chromatography.

Process (5)

The compound of the formula (V) used in the above described reaction can be prepared by the following method.

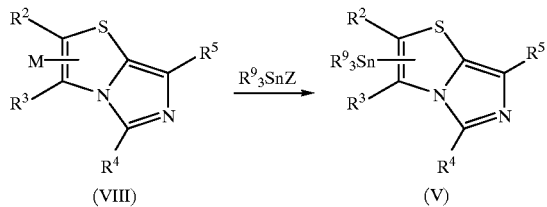

in which
  $R^2$, $R^3$, $R^4$, and $R^5$, either one of which is M or $R^9{}_3SN$, and the remaining three, which may be the same or different, have the same meanings as defined in the formula (I), that is, respectively represent hydrogen, halogen, nitro, cyano, lower alkyl, lower cycloalkyl, lower alkylthio, $C_{2-4}$ alkenyl, formyl, lower alkylcarbonyl, arylcarbonyl, aryl,
  $R^9$ represents lower alkyl, preferably N-butyl or methyl,
  M represents Li, MgCl, MgBr or MgI, and
  Z represents Cl, Br, I or $-OSO_2CF_3$.

The compound of the formula (VIII) used can be prepared according to the method described in Japanese Patent Application No. 313922/1996.

The compound of the formula (VIII) can be converted into the compound of the formula (V) by the following method. The compound of the formula (V) can be prepared by reacting the compound of the formula (VIII) in an inert solvent such as tetrahydrofuran, diethyl ether, 1,4-dioxane, anisole, dimethoxyethane, dichloromethane or toluene solely or in combination thereof with $R^9{}_3SNZ$ in a proportion of one (1) equivalent or an excessive amount to the compound of the formula (VIII) at a temperature of $-100°$ C.$-+5°$ C. for 15 minutes–24 hours, and then subjected to the usual post-treatment.

The compound of the formula (I) thus obtained can be isolated and purified by crystallization or by chromatography with a nonionic macro-high porous resin, gel filtration with Sephadex or the like, or reverse phase silica gel column chromatography.

Applications of the Compound/Pharmaceutical Composition

The compound according to the present invention has wide and strong anti-microbial activities against Gram-positive and Gram-negative bacteria, and exhibits strong anti-microbial activities against MRSA, PRSP, enterococci, influenza and β-lactamase producing bacteria as well. Furthermore, it has low toxicity and stable to DHP-1. Thus, the compound according to the present invention can be used for the treatment of infections caused by various pathogenic bacteria in animals including human beings.

The compound of the formula (I) in which R represents a group hydrolyzable in organisms above all can be advantageously administered orally because of its excellent oral absorption property.

The pharmaceutical composition comprising the compound according to the present invention and a pharmacologically acceptable salt and ester thereof as an effective ingredient can be administered orally or parenterally by the administration routes including intravenous injection, intramuscular injection, or subcutaneous, rectal or percutaneous administration to human begins and the other animals. Thus, the pharmaceutical composition comprising the compound according to the present invention as an effective ingredient can be formed into appropriate dosage forms depending on its administration routes, and specifically prepared primarily into any one of the preparation forms including injections such as intravenous injection and intramuscular injection, preparations for oral administration such as capsules, tablets, granules, powder, pills, particulates, troches, preparations for rectal administration, and fatty suppositories. These preparations can be prepared by the usual methods with ordinarily used excipients, fillers, binding agents, humidifiers, disintegrants, surface active agents, lubricants, dispersants, buffers, storing agents, dissolution aids, preservatives, flavoring agents, analgesic agents, stabilizing agents, and the like. Such non-toxic additives which can be used include for example lactose, fructose, glucose, starch, gelatin, magnesium carbonate, synthetic magnesium silicate, talc, magnesium stearate, methylcellulose or a salt thereof, gum arabic, polyethylene glycol, syrup, petrolatum, glycerol, ethanol, propylene glycol, citric acid, sodium chloride, sodium sulfite, sodium phosphate, and the like. The dosage amount is appropriately determined in consideration of the dosage route, and the age, sex and condition of a patient, and the preparation may be administered for the treatment of infections usually in an amount of about 25 mg–2000 mg, preferably 50 mg–1000 mg per day for adult in one or several portions.

EXAMPLE

The present invention is now described with reference to Examples and Synthetic Examples, but it is not limited thereto.

Preparation 1

3-(tri-n-butylstannyl)imidazo[5,1-b]thiazole and 2-(-tri-n-butylstannyl)imidazo[5,1-b]thiazole A solution of imidazo[5,1-b]thiazole (248 mg) in anhydrous THF (4 ml) was cooled to $-78°$ C. under the atmosphere of argon. A 1.6 N solution of n-butyl lithium in n-hexane (1.31 ml) was added dropwise at an internal temperature of −60° C.−−55° C. The reaction was stirred at the same temperature for 1 hour, and it was further stirred for 40 minutes during which the mixture was allowed to be warmed to room temperature. The reaction mixture was diluted with 50 ml of a semi-saturated aqueous ammonium chloride solution, and extracted with 50 ml of diethyl ether. The organic layer was dried over anhydrous magnesium sulfate, and the solvent was removed under reduced pressure. The residue thus obtained was purified by column chromatography on silica gel (toluene:ethyl acetate=1:1).

3-(tri-n-butylstannyl)imidazo[5,1-b]thiazole was obtained in an amount of 221 mg from the fraction having Rf=0.7.

NMR (CDCl$_3$) δ: 0.90 (9H, t, J=7.1 Hz), 1.22 (6H, m), 1.34 (6H, m), 1.59 (6H, m), 6.63 (1H, s), 7.10 (1H, s), 7.92 (1H, s).

2-(tri-n-butylstannyl)imidazo[5,1-b]thiazole was obtained in an amount of 270 mg from the fraction having Rf=0.5.

NMR (CDCl$_3$) δ: 0.92 (3H, t, 3=7.3 Hz), 1.16 (2H, m), 1.35 (2H, m), 1.58 (2H, m), 7.02 (1H, s), 7.17 (1H, s), 7.95 (1H, s).

Preparation 2

2-(tri-n-butylstannyl)-3-methylimidazo[5,1-b] thiazole

A solution of 3-methylimidazo[5,1-b]thiazole (513.2 mg) in anhydrous THF (8 ml) was cooled to −78° C. under the atmosphere of argon, and a 1.6 N solution of n-butyl lithium in n-hexane (2.47 ml) was added dropwise. After the reaction was stirred at the same temperature for 1 hour, 1.06 ml of tri-n-butylstannyl chloride was added, and the mixture was further stirred at the same temperature for 1 hour and then for 30 minutes during which the mixture was allowed to be warmed to room temperature. The reaction mixture was diluted with 50 ml of a semi-saturated aqueous ammonium chloride solution, and extracted with 50 ml of diethyl ether. The organic layer was dried over anhydrous magnesium sulfate, and the solvent was then removed under reduced pressure. The residue thus obtained was purified by column chromatography on silica gel (hexane:ethyl acetate=1:1) to give 2-(tri-n-butylstannyl)-3-methylimidazo[5,1-b]thiazole in a yield of 1.44 g.

NMR (CDCl$_3$) δ: 0.84 (9H, t, J=7.3 Hz), 1.10 (6H, m), 1.28 (6H, m), 1.50 (6H, m), 2.31 (3H, s), 6.96 (1H, s), 7.75 (1H, s). MS (PB(CH$_4$-CI)): 429 (M$^+$+H).

Preparation 3

5-methyl-2-(tri-n-butylstannyl)imidazo[5,1-b] thiazole

A solution of 5-methylimidazo[5,1-b]thiazole (1.10 g) in THF (16 ml) was cooled to −78° C. under the atmosphere of argon, and a 1.6 N solution of n-butyl lithium in n-hexane (5.24 ml) was added dropwise thereto at an internal temperature of −70−−65° C. After the mixture was stirred at the same temperature for 1 hour, 2.40 ml of ri-n-butylstannyl chloride was added, and the mixture was stirred at the same temperature for 1 hour, then for further two hours during which the mixture was allowed to be warmed to −40° C. The reaction mixture was diluted with 100 ml of a semi-saturated aqueous ammonium chloride solution and extracted with 100 ml of diethyl ether. The organic layer was dried over anhydrous magnesium sulfate, and the solvent was then removed under reduced pressure. The residue thus obtained was purified by column chromatography on silica gel (toluene:ethyl acetate=1:1) to give the title compound in a yield of 2.23 g.

NMR (CDCl$_3$) δ: 0.92 (9H, t, J=7.2 Hz), 1.15(6H, m), 1.36(6H, m), 1.57(6H, m), 2.57(3H, s), 6.88(1H, s), 6.93 (1H, s).

Preparation 4

7-chloro-3-(tri-n-butylstannyl)imidazo[5,1-b] thiazole and 7-chloro-2-(tri-n-butylstannyl)imidazo [5,1-b]thiazole a) 5,7-dichloroimidazo[5,1-b]thiazole, 5-chloroimidazo[5,1-b]thiazole and 7-chloroimidazo[5,1-b]thiazole To a solution of imidazo[5,1-b]thiazole (18.624 g) in dichloroethane (450 ml) was added 20.030 g of N-chlorosuccinimide, the mixture was heated in a bath at a temperature of 60–65° C. for 1 hour. After air cooling, insolubles were removed by filtration, and the solvent was removed under reduced pressure. The residue thus obtained was dissolved in 3.0 l of ethyl acetate, and washed three times with 3.0 l of distilled water. After the organic layer was dried over anhydrous magnesium sulfate and the magnesium sulfate was removed by filtration, the solvent was removed under reduced pressure. The solid product thus obtained was purified by column chromatography on silica gel (ethyl acetate) to give 2.020 g of 5,7-dichloroimidazo[5,1-b] thiazole as a pale brown powder from the fraction of Rf=0.85.

NMR (CDCl$_3$) δ: 6.91 (1H, d, J=4.3 Hz), 7.28 (1H, d, J=4.3 Hz); MS (TSP): 195 (M$^+$+3H), 193 (M$^+$+H).

Further, 5-chloroimidazo[5,1-b]thiazole was obtained as a pale brown powder (2.550 g) from the fraction of Rf=0.7.

NMR (CDCl$_3$) δ: 6.87 (1H, d, J=4.3 Hz), 7.02 (1H, s), 7.29 (1H, d, J=4.3 Hz). MS (TSP): 161 (M$^+$+3H), 159 (M$^+$+H).

Furthermore, 7-chloroimidazo[5,1-b]thiazole was obtained as a yellowish white plate (13.384 g) from the fraction of Rf=0.5.

NMR (CDCl$_3$) δ: 6.87 (1H, d, J=4.2 Hz), 7.38(1H, d, J=4.2 Hz), 7.87 (1H, s). MS (TSP): 161 (M$^+$+3H), 159(M$^+$+H).

b) 7-chloro-3-(tri-n-butylstannyl)imidazo[5,1-b]thiazole and 7-chloro-2-(tri-n-butylstannyl)imidazo[5,1-b]thiazole To 40 ml of THF was added 6.25 ml of a 1.6 N solution of n-butyl lithium in n-hexane, and the mixture was cooled to −78° C. A solution of 7-chloroimidazo[5,1-b]thiazole (1.59 g) in THF (40 ml) was added dropwise at an internal temperature of −40° C. After the reaction mixture was stirred for 1 hour during which the temperature was raised up to 0° C., 3.43 ml of tri-n-butylstannyl chloride was added, and the mixture was stirred for 2 hours during which the temperature was raised up to room temperature. The reaction mixture was diluted with 300 ml of a semi-saturated aqueous ammonium chloride solution and extracted with 300 ml of diethyl ether. The organic layer was dried over anhydrous magnesium sulfate, and the solvent was removed under reduced pressure. The residue thus obtained was purified by column chromatography on silica gel (hexane:ethyl acetate= 20:1–10:1–5:1–3:1).

As a low polar component, 7-chloro-3-(tri-n-butylstannyl)imidazo[5,1-b]thiazole was obtained in a yield of 362 mg.

NMR (CDCl$_3$) δ: 0.90 (9H, t, J=7.3 Hz), 1.22 (6H, m), 1.34 (6H, m), 1.54 (6H, m), 6.63 (1H, s), 7.77 (1H, s).

Further, as a high polar component, 7-chloro-2-(tri-n-butyl-stannyl)imidazo[5,1-b]thiazole was obtained in a yield of 2.78 g.

NMR (CDCl$_3$) δ: 0.92 (9H, t, J=7.4 Hz), 1.16 (6H, m), 1.35 (6H, m), 1.58 (6H, m), 7.11 (1H, s), 7.80 (1H, s).

Preparation 5

2-methyl-3-(tri-n-butylstannyl)imidazo[5,1-b]thiazole

The title compound was obtained in an amount of 2.67 g from 2.20 g of 2-methylimidazo[5,1-b]thiazole in the same manner as in Preparation 3.

NMR (CDCl$_3$) δ: 0.90 (9H, t, J=7.2 Hz), 1.24 (6H, m), 1.35 (6H, m), 1.54 (6H, m), 2.35 (3H, s), 7.00 (1H, s), 7.83 (1H, s).

Preparation 6

5-formylaminomethyl-2-(tri-n-butylstannyl)imidazo[5,1-b]thiazole

A solution of 9 06 mg of 5-formylaminomethyl imidazo[5,1-b]-thiazole in a mixed solvent of 30 ml of THF and 6 ml of HMPA was cooled to −78° C. under the atmosphere of argon, and 10.9 ml of a 1.6 N solution of n-butyl lithium/n-hexane was added dropwise at an internal temperature of −70−−65° C. After the reaction mixture was stirred at the same temperature for 1 hour, 1.63 ml of tri-n-butylstannyl chloride was added, and the mixture was further stirred at the same temperature for 1 hour and for 2 hours during which the temperature was raised up to 0° C. 100 ml of a semi-saturated aqueous ammonium chloride solution was added to the reaction mixture, and extracted with 100 ml of diethyl ether. The organic layer was dried over anhydrous magnesium sulfate, and the solvent was removed under reduced pressure. The residue thus obtained was purified by column chromatography on silica gel (hexane:ethyl acetate=1:2) to give the title compound in an amount of 1.59 g.

NMR (CDCl$_3$) δ: 0.92 (9H, t, J=7.4 Hz), 1.16 (6H, m), 1.35 (6H, m), 1.57 (6H, m), 4.74 (2H, d, J=6.1 Hz), 6.90 (1H, s), 7.22 (1H, br. s), 7.37 (1H, s), 8.28 (1H, s).

Preparation 7

3-(t-butyldimethylsilyloxy)methyl-2-(tri-n-butylstannyl)imidazo[5,1-b]thiazole a) 3-(t-butyldimethylsilyloxy)methylimidazo[5,1-b]thiazole To an ice-cooled solution of 3.39 g of 3-hydroxymethylimidazo[5,1-b]thiazole in 22 ml of DMF were added 1.95 g of imidazole and 3.81 g of t-butyldimethylsilyl chloride. After the reaction mixture was reacted at room temperature for 6 hours, it was diluted with 150 ml of ethyl acetate, and washed three times with saline. The organic layer was dried over anhydrous magnesium sulfate, the solvent was removed under reduced pressure to give 5.83 g of 3-(t-butyldi methylsilyloxy)methylimidazo[5,1-b]thiazole.

NMR (CDCl$_3$) δ: 0.09 (6H, s), 0.88 (9H, s), 4.76 (2H, s), 6.60 (1H, s), 7.07 (1H, s), 8.02 (1H, s).

b) 3-(t-butyldimethylsilyloxy)methyl-2-(tri-n-butylstannyl)imidazo[5,1-b]thiazole The title compound was obtained in an amount of 1.01 g from 548 mg of 3-(t-butyldimethylsilyloxy)methylimidazo[5,1-b]thiazole in the same manner as in Preparation 3.

NMR (CDCl$_3$) δ: 0.15 (6H, s), 0.91 (9H, t, J=7.4 Hz), 0.93 (9H, s), 1.16 (6H, m), 1.34 (6H, m), 1.56 (6H, m), 4.68 (2H, s), 7.01 (1H, s), 8.02 (1H, s).

Preparation 8

5-(t-butyldimethylsilyloxy)methyl-2-(tri-n-butylstannyl)imidazo[5,1-b]thiazole a) 5-(t-butyldimethylsilyloxy)methylimidazo[5,1-b]thiazole 5-(t-butyldimethylsilyloxy)methylimidazo[5,1-b]thiazole was obtained in an amount of 2.71 g from 1.54 g of 5-hydroxymethylimidazo[5,1-b]thiazole in the same manner as in Preparation 7-a).

NMR (CDCl$_3$) δ: 0.06 (6H, s), 0.89 (9H, s), 4.97 (2H, s), 6.79 (1H, d, J=4.3 Hz), 6.97 (1H, s), 7.55 (1H, d, J=4.3 Hz).

b) 5-(t-butyldimethylsilyloxy)methyl-2-(tri-n-butylstannyl)imidazo[5,1-b]thiazole The title compound was obtained in an amount of 2.60 g from 1.34 g of 5-(t-butyldimethylsilyloxy)methylimidazo[5,1-b]thiazole in the same manner as in Preparation 3.

NMR (CDCl$_3$) δ: 0.05 (6H, s), 0.89 (9H, s), 0.91 (9H, t, J=7.1 Hz), 1.14 (6H, m), 1.35 (6H, m), 1.57 (6H, m), 4.96 (2H, s), 6.90 (1H, s), 7.32 (1H, s).

Preparation 9

5-carbamoyl-3-(tri-n-butylstannyl)imidazo[5,1-b]thiazole and 5-carbamoyl-2-(tri-n-butylstannyl)imidazo[5,1-b]thiazole 5-carbamoyl-3-(tri-n-butylstannyl)imidazo[5,1-b]thiazole was obtained as a low polar component in an amount of 114 mg from 167 mg of 5-carbamoylimidazo[5,1-b]thiazole in the same manner as Preparation 6.

NMR (CDCl$_3$) δ: 0.87 (9H, t, J=7.4 Hz), 1.12 (6H, m), 1.32 (6H, m), 1.53 (6H, m), 5.23 (1H, br. s), 6.88 (1H, s), 6.95 (1H, br. s), 7.19 (1H, s).

Further, 5-carbamoyl-2-(tri-n-butylstannyl)imidazo[5,1-b]-thiazole was obtained as a high polar component in an amount of 211 mg.

NMR (CDCl$_3$) δ: 0.91 (9H, t, J=7.4 Hz), 1.18 (6H, m), 1.35 (6H, m), 1.57 (6H, m), 5.40 (1H, br. s), 6.90 (1H, br. s), 7.12 (1H, s), 8.12 (1H, s).

Preparation 10

7-carbamoyl-3-(tri-n-butylstannyl)imidazo[5,1-b]thiazole and 7-carbamoyl-2-(tri-n-butylstannyl)imidazo[5,1-b]thiazole a) 7-carboxylimidazo[5,1-b]thiazole To an ice-cooled solution of 5.00 g of 7-iodoimidazo[5,1-b]-thiazole in 150 ml of THF under the atmosphere of argon was added dropwise 20 ml of a 1.0 N solution of N-ethylmagnesium bromide in THF. After the reaction mixture stirred at room temperature for 30 minutes, it was further stirred under bubbling carbon dioxide gas at room temperature for 20 hours. The reaction mixture was concentrated under reduced pressure, diluted with 100 ml of water, and adjusted to pH 6.5 with 1 N HCl. It was purified with DIAION HP-20 (5–10% methanolic water) to give 3.31 g of 7-carboxylimidazo[5,1-b]thiazole.

NMR (DMSO-d$_6$) δ: 7.25 (1H, d, J=4.1 Hz), 7.86 (1H, d, J=4.1 Hz), 8.09 (1H, s).

b) 7-carbamoylimidazo[5,1-b]thiazole

To a solution of 2.46 g of 7-carboxylimidazo[5,1-b]thiazole in 100 ml of DMF were added 5.62 g of 1-hydroxybenzo-triazole and 5.62 g of 1-(3-dimethylaminopropyl)-3-ethylcarbodiimide hydrochloride, and the mixture was stirred at room temperature for 1.5 hours, diluted with 15 ml of a 3.5 N ammonia solution in ethanol, and further stirred at room temperature for 20 hours. The reaction mixture was concentrated under reduced pressure, diluted with 200 ml of an aqueous potassium carbonate solution to adjust pH to 10.4, and extracted ten times with dichloromethane. The organic layer was dried over anhydrous magnesium sulfate, and the solvent was removed under reduced pressure. The residue thus obtained was purified by column chromatography on silica gel (dichloromethane:methanol=30:1) to give 7-carbamoylimidazo[5,1-b]thiazole in a yield of 1.83 g.

NMR (CDCl$_3$) δ: 5.36 (1H, br. s), 6.77 (1H, br. s), 7.04 (1H, d, J=4.1 Hz), 7.50 (1H, d, J=4.1 Hz), 7.94 (1H, s).

c) 7-carbamoyl-3-(tri-n-butylstannyl)imidazo[5,1-b]thiazole and 7-carbamoyl-2-(tri-n-butylstannyl)imidazo[5,1-b]thiazole 7-carbamoyl-3-(tri-n-butylstannyl)imidazo[5,1-b]thiazole was obtained as a low polar component in an amount of 360 mg from 1.23 g of 7-carbamoylimidazo[5,1-b]thiazole in the same manner as Preparation 6.

NMR (CDCl$_3$) δ: 0.90 (9H, t, J=7.3 Hz), 1.24 (6H, m), 1.35 (6H, m), 1.55 (6H, m), 5.38 (1H, br. s), 6.78 (1H, brs. s), 6.82 (1H, s), 7.83(1H, s).

Further, 7-carbamoyl-2-(tri-n-butylstannyl)imidazo[5,1-b]thiazole was obtained as a high polar component in an amount of 420 mg.

NMR (CDCl$_3$) δ: 0.91 (9H, t, J=7.2 Hz), 1.17 (6H, m), 1.35 (6H, m), 1.58 (6H, m), 5.35 (1H, br. s), 6.75(1H, br. s), 7.23(1H, s), 7.88(1H, s).

Preparation 11

7-cyano-2-(tri-n-butylstannyl)imidazo[5,1-b]thiazole a) 7-cyanoimidazo[5,1-b]thiazole To a suspension of 997 mg of 7-carbamoylimidazo[5,1-b]-thiazole in 80 ml of dichloromethane were add under ice-cooling 7.28 ml of N,N-diisopopylethylamine and 2.23 ml of phosphorus oxychloride. After the reaction mixture was stirred at the same temperature, it was poured onto ice-water, adjusted pH to 7.5 with aqueous sodium hydrogen carbonate, and extracted three times with dichloromethane. The organic layer was dried over anhydrous magnesium sulfate, and the solvent was removed under reduced pressure. The residue thus obtained was purified by column chromatography on silica gel (dichloromethane:methanol=15:1) to give 871 mg of 7-cyanoimidazo[5,1-b]thiazole.

NMR (CDCl$_3$) δ: 7.08 (1H, d, J=4.2 Hz), 7.56 (1H, d, J=4.2 Hz), 8.01 (1H, s).

b) 7-cyano-2-(tri-n-butylstannyl)imidazo[5,1-b]thiazole

A solution of 903 mg of 7-cyanoimidazo[5,1-b]thiazole in 35 ml of THF was cooled to −78° C. under the atmosphere of argon, and 6.36 ml of a 1.0 N solution of lithium bistrimethylsilylamide in THF was added dropwise at an internal temperature of −70—65° C. After the reaction mixture was stirred at the same temperature for 1 hour, 1.81 ml of tri-n-butylstannyl chloride was added, and the mixture was stirred at the same temperature for 1 hour. The reaction mixture was diluted with 100 ml of a semi-saturated aqueous ammonium chloride solution and extracted with 100 ml of ethyl acetate. The organic layer was dried over anhydrous magnesium sulfate, and the solvent was removed under reduced pressure. The residue thus obtained was purified by column chromatography on silica gel (hexane:ethyl acetate=3:1) to give the title compound in a yield of 795 mg.

NMR (CDCl$_3$) δ: 0.92 (9H, t, J=7.3 Hz), 1.19 (6H, m), 1.36 (6H, m), 1.58 (6H, m), 7.26 (1H, s), 7.93 (1H, s).

Preparation 12

7-ethyl-3-(tri-n-butylstannyl)imidazo[5,1-b]thiazole and 7-ethyl-2-(tri-n-butylstannyl)imidazo[5,1-b]thiazole a) 7-vinylimidazo[5,1-b]thiazole To a solution of 5.0 g of 7-iodoimidazo[5,1-b]thiazole in 40 ml of NMP were added under the atmosphere of argon 550 mg of tris(dibenzilideneacetone) dipalladium, 558 mg of tri-2-furyl phosphine, and 6.42 ml of tri-n-butylvinyltin, and the mixture was reacted at 70° C. for 1.5 hours, and at 80° C. for 2 hours. The reaction mixture was poured into a mixture of 50 ml of a saturated aqueous sodium hydrogen carbonate solution and 50 ml of a saturated saline, and extracted two times with 200 ml of ethyl acetate. The organic layers were combined, washed three times with 200 ml of saline, dried over anhydrous magnesium sulfate, and the solvent was removed under reduced pressure. The residue thus obtained was purified by column chromatography on silica gel (dichloromethane:ethyl acetate=15:1) to give 7-vinylimidazo[5,1-b]thiazole in an amount of 1.99 g.

NMR (CDCl$_3$) δ: 5.27 (1H, d), 5.41 (1H, d), 6.80 (1H, dd), 6.91 (1H, d), 7.42 (1H, d), 7.98 (1H, s).

b) 7-ethylimidazo[5,1-b]thiazole

To a solution of 5.0 g of 7-vinylimidazo[5,1-b]thiazole in 40 ml of ethanol and 8 ml of water was added 2.0 g of 10% Pd-C, and the mixture was stirred under the atmosphere of hydrogen at room temperature overnight. The catalyst was removed by filtration, and the filtrate was concentrated to a small volume. The concentrate was diluted with 10 ml of a saturated aqueous sodium hydrogen carbonate solution, and extracted with 100 ml of ethyl acetate. The organic layer was washed with aqueous saline and dried over anhydrous magnesium sulfate, and the solvent was removed under reduced pressure. The residue thus obtained was purified by column chromatography on silica gel (dichloromethane:ethyl acetate=3:2) to give 1.27 g of 7-ethylimidazo[5,1-b]thiazole.

NMR (CDCl$_3$) δ: 1.33 (3H, t), 2.76 (2H, q), 6.76 (1H, d), 7.32 (1H, d), 7.91 (1H, s).

c) 7-ethyl-3-(tri-n-butylstannyl)imidazo[5,1-b]thiazole and 7-ethyl-2-(tri-n-butylstannyl)imidazo[5,1-b]thiazole In the same manner as in Preparation 3, 1.50 g of 7-ethyl-3-(tri-n-butylstannyl)imidazo[5,1-b]thiazole as a low polar component from 1.27 g of 7-ethylimidazo[5,1-b]thiazole.

NMR (CDCl$_3$) δ: 0.90 (9H, t), 1.1–1.5 (15H, m), 1.5–1.7 (6H, m), 2.76 (2H, q), 6.57 (1H, s), 7.82 (1H, s).

Further, 1.32 g of 7-ethyl-2-(tri-n-butylstannyl)imidazo[5,1-b]-thiazole was obtained as a high polar component.

NMR (CDCl$_3$) δ: 0.92 (9H, t), 1.1–1.5 (15H, m), 1.5–1.7 (6H, m), 2.75 (2H, q), 7.09 (1H, s), 7.86 (1H, s).

Preparation 13

7-(1-t-butyldimethylsilyloxy)ethyl-3-(tri-n-butyl-stannyl)imidazo[5,1-b]thiazole and 7-(1-t-butyldimethylsilyloxy)ethyl-2-(tri-n-butyl-stannyl)imidazo[5,1-b]thiazole a) 7-(1-hydroxy)ethylimidazo[5,1-b]thiazole A solution of 3.043 g of 7-formyl[5,1-b]thiazole in 60 ml of of dry THF was cooled to −58° C. under the atmosphere of argon. To this solution was added dropwise 23 ml of a 0.92 M methylmagnesium bromide solution in THF under stirring at a temperature of −60—55° C. over 10 minutes, the mixture was further stirred at the same temperature for 10 minutes, then directly warmed slowly to room temperature with stirring for further 2 days. The reaction mixture was diluted with 50 ml of a saturated aqueous ammonium chloride-solution, subjected to salting out, and extracted four times with 150 ml of ethyl acetate. The combined organic layer was dried over anhydrous sodium sulfate, filtered, and the solvent was removed under reduced pressure. The yellow oil thus obtained was purified by column chromatography on silica gel (dichloromethane:methanol=95:5) to give 7-(1-hydroxy)ethylimidazo[5,1-b]thiazole as light yellow crystals in a yield of 2.164 g.

NMR (CDCl₃) δ: 1.62 (3H, d, J=6.5 Hz), 2.95 (1H, br. s), 5.08 (1H, q, J=6.5 Hz), 6.82 (1H, d, J=4.3 Hz), 7.37 (1H, d, J=4.3 Hz), 7.94 (1H, s). MS (TSP): 169(M⁺+H).

b) 7-(1-t-butyldimethyloxy)ethylimidazo[5,1-b]thiazole

To a solution of 2.086 g of 7-(1-hydroxy)ethylimidazo[5,1-b]thiazole in 12.4 ml of dry DMF were added under ice-cooling 1.098 g of imidazole and 2.150 g of t-butyldimethylsilyl chloride, and the mixture was immediately stirred under the atmosphere of argon for 1 hour. The reaction mixture was diluted with 100 ml of ethyl acetate, and washed three times with 50 ml of semi-saturated aqueous saline. The organic layer was dried over anhydrous magnesium sulfate, filtered, and the solvent was removed under reduced pressure. The yellow oil thus obtained was purified by column chromatography on silica gel (dichloromethane alone—dichloromethane:methanol=96:4) to give 3.440 g of 7-(1-t-butyldimethyloxy)ethylimidazo[5,1-b]thiazole as milk white crystals in a yield of 3.440 g.

NMR (CDCl₃) δ: 0.09 (3H, s), 0.12 (3H, s), 0.95 (9H, s), 1.52 (3H, d, J=6.3 Hz), 5.10 (1H, q, J=6.3 Hz), 6.77 (1H, d, J=4.3 Hz), 7.33 (1H, d, J=4.3 Hz), 7.90 (1H, s). MS (TSP): 283(M⁺+H).

c) 7-(1-t-butyldimethylsilyloxy)ethyl- 3-(tri-n-butylstannyl)imidazo[5,1-b]thiazole and 7-(1-t-butyldimethylsilyloxy)ethyl-2-(tri-n-butylstannyl)imidazo[5,1-b]thiazole In the same manner as in Preparation 3,7-(1-t-butyldimethylsilyloxy)ethyl-3-(tri-n-butylstannyl)imidazo[5,1-b]thiazole was obtained as a low polar component in a yield of 1.38 g from 1.67 g of 7-(1-t-butyldimethylsilyloxy)ethylimidazo[5,1-b]thiazole.

NMR (CDCl₃) δ: 0.08 (3H, s), 0.12 (3H, s), 0.89 (9H, t, J=7.3 Hz), 0.95 (9H, s), 1.20 (6H, m), 1.34 (6H, m), 1.54 (9H, m), 5.10 (1H, q, J=6.3 Hz), 6.59 (1H, s), 7.82 (1H, s).

Further, 7-(1-t-butyldimethylsilyloxy)ethyl-2-(tri-n-butyl-stannyl)imidazo[5,1-b]thiazole was obtained as a high polar component in a yield of 812 mg.

NMR (CDCl₃) δ: 0.09 (3H, s), 0.12 (3H, s), 0.91 (9H, t, J=7.4 Hz), 0.95 (9H, s), 1.13 (6H, m), 1.34 (6H, m), 1.55 (9H, m), 5.08 (1H, q, J=6.3 Hz), 7.09 (1H, s), 7.85 (1H, s).

Preparation 14

7-cyano-3-(tri-n-butylstannyl)imidazo[5,1-b]thiazole, 7-methoxyiminomethyl-3-(tri-n-butylstannyl)imidazo[5,1-b]thiazole (geometrical isomer derived from a raw material which is a high polar oxime isomer), 7-cyano-2-(tri-n-butylstannyl)imidazo[5,1-b]thiazole, and 7-methoxyiminomethyl-2-(tri-n-butylstannyl)imidazo[5,1-b]thiazole (geometrical isomer derived from a raw material which is a high polar oxime isomer)

a) 5-formylimidazo[5,1-b]thiazole and 7-formylimidazo[5,1-b]thiazole

To the mixture of 15.48 ml of DMF and 80 ml of dichloromethane was added dropwise a solution of 18.32 ml of phosphorus oxychloride in 80 ml of dichloromethane under ice-cooling. The mixture was reacted at room temperature for 30 minutes, and a solution of imidazo[5,1-b]thiazole in 40 ml of chloromethane was added dropwise. After heating under reflux for 2.5 hours, the reaction mixture was poured onto ice, adjusted to pH 9.8 with a 5 N aqueous sodium hydroxide solution, extracted five times with 200 ml of dichloromethane, dried over anhydrous magnesium sulfate, and the solvent was removed under reduced pressure. The residue thus obtained was purified by column chromatography on silica gel (dichloromethane:ethyl acetate=5:1-ethyl acetate alone—dichloromethane:methanol=10:1). As a low polar component, 5-formylimidazo[5,1-b]thiazole was obtained in a yield of 495 mg.

NMR (CDCl₃) δ: 7.18 (1H, d, J=4.1 Hz), 7.46 (1H, s), 8.46 (1H, d, J=4.1 Hz), 9.76 (1H, s).

Further, as a high polar component, 7-formylimidazo[5,1-b]thiazole was obtained in a yield of 2.37 g.

NMR (CDCl₃) δ: 7.17 (1H, d, J=4.1 Hz), 7.60 (1H, d, J=4.1 Hz), 8.07 (1H, s), 9.93 (1H, s).

b) 7-methoxyiminomethylimidazo[5,1-b]thiazole (high polar geometrical isomer) and 7-methoxyiminomethylimidazo[5,1-b]thiazole (low polar geometrical isomer)

To a suspension of 249 mg of 7-formylimidazo[5,1-b]thiazole in 10 ml of ethanol were added 219 mg of o-methylhydroxylamine hydrochloride and 2.67 ml of a 1N sodium hydroxide solution. The reaction mixture was stirred at room temperature for 20 hours, concentrated, then diluted with 50 ml of water, and extracted with dichloromethane. The organic layer was dried over anhydrous magnesium sulfate, and the solvent was removed under reduced pressure. The residue thus obtained was purified by column chromatography on silica gel (dichloromethane:ethyl acetate=1:1) to give 7-methoxyiminomethylimidazo[5,1-b]thiazole (low polar geometrical isomer) in a yield of 164 mg from the low polarity fraction.

NMR (CDCl₃) δ: 3.96 (3H, s), 7.01 (1H, d, J=4.1 Hz), 7.48 (1H, d, J=4.1 Hz), 8.02 (1H, s), 8.24 (1H, s).

Further, 7-methoxyiminomethylimidazo[5,1-b]thiazole (high polar geometrical isomer) was obtained in a yield of 71 mg from the low polar fraction.

NMR (CDCl₃) δ: 4.40 (3H, s), 6.90 (1H, d, J=4.4 Hz), 7.43 (1H, d, J=4.4 Hz), 7.46 (1H, s), 7.94 (1H, s).

c) 7-cyano-3-(tri-n-butylstannyl)imidazo[5,1-b]thiazole, 7-methoxyiminomethyl-3-(tri-n-butylstannyl)imidazo[5,1-b]thiazole (geometrical isomer derived from a raw material which is a high polar oxime isomer), 7-cyano-2-(tri-n-butylstannyl)imidazo[5,1-b]thiazole, and 7-methoxyiminomethyl-2-(tri-n-butylstannyl)imidazo[5,1-b]-tiazole (geometrical isomer derived from a raw material which is a high polar oxime isomer)

In the same manner as in Preparation 3, 7-cyano-3-(tri-n-butylstannyl)imidazo[5,1-b]thiazole was obtained in an amount of 67 mg from the fraction having Rf=0.8 (n-hexane:ethyl acetate=3:1) starting from 1.17 g of 7-methoxyiminomethylimidazo[5,1-b]thiazole (high polar geometrical isomer).

NMR (CDCl₃) δ: 0.90 (9H, t, J=7.2 Hz), 1.26 (6H, m), 1.35 (6H, m), 1.57 (6H, m), 6.80 (1H, s), 7.87 (1H, s).

Further, 7-methoxyiminomethyl-3-(tri-n-butylstannyl)imidazo[5,1-b]thiazole (geometrical isomer derived from a raw material which is a high polar oxime isomer) was obtained in a yield of 1.26 g from the fraction having Rf=0.6 (n-hexane:ethyl acetate=3:1).

NMR (CDCl₃) δ: 0.90 (9H, t, J=7.4 Hz), 1.22 (6H, m), 1.34 (6H, m), 1.56 (6H, m), 3.98 (3H, s), 6.71 (1H, s), 7.46 (1H, s), 7.84 (1H, s).

Furthermore, 7-cyano-2-(tri-n-butylstannyl)imidazo[5,1-b]thiazole was obtained in a yield of 150 mg from the fraction having Rf=0.4 (n-hexane:ethyl acetate=3:1).

The NMR data of this compound were well agreed with those obtained in Preparation 11.

Furthermore, 7-methoxyiminomethyl-2-(tri-n-butylstannyl)imidazo[5,1-b]thiazole (geometrical isomer derived from a raw material which is a high polar oxime isomer) was obtained in a yield of 980 mg from the fraction having Rf=0.2 (n-hexane:ethyl acetate=3:1).

NMR (CDCl₃) δ: 0.92 (9H, t, J=7.3 Hz), 1.16 (6H, m), 1.36 (6H, m), 1.58 (6H, m), 4.00 (3H, s), 7.18 (1H, s), 7.45 (1H, s), 7.89 (1H, s).

Preparation 15

7-cyano-3-(tri-n-butylstannyl)imidazo[5,1-b]
thiazole, 7-methoxyimino-methyl-3-(tri-n-
butylstannyl)imidazo[5,1-b]thiazole (stereoisomer
derived from a raw material which is a low polar
oxime isomer), 7-cyano-2-(tri-n-butylstannyl)
imidazo[5,1-b]thiazole, and 7-methoxyiminomethyl-
2-(tri-n-butylstannyl)imidazo[5,1-b]thiazole
(stereoisomer derived from a raw material which is
a low polar oxime isomer)

In the same manner as in Preparation 3, 7-cyano-3-(tri-n-butylstannyl)imidazo[5,1-b]thiazole was obtained in a yield of 288 mg from the fraction having Rf=0.8 (n-hexane:ethyl acetate=3:1) starting from 1.47 g of 7-methoxyiminomethylimidazo[5,1-b]thiazole (low polar geometrical isomer) described in Preparation 14-b).

The NMR data of this compound were well agreed with those obtained in Preparation 14.

Further, 7-methoxyiminomethyl-3-(tri-n-butylstannyl)imidazo[5,1-b]thiazole (geometrical isomer derived from a raw material which is a low polar oxime isomer) was obtained in a yield of 1.68 g from the fraction having Rf=0.7 (n-hexane:ethyl acetate=3:1).

NMR (CDCl$_3$) δ: 0.90 (9H, t, J=7.4 Hz), 1.24 (6H, m), 1.35 (6H, m), 1.55 (6H, m), 3.96 (3H, s), 6.81 (1H, s), 7.92 (1H, s), 8.25 (1H, s).

Furthermore, 7-cyano-2-(tri-n-butylstannyl)imidazo[5,1-b]thiazole was obtained in a yield of 353 mg from the fraction having Rf=0.4 (n-hexane:ethyl acetate=3:1).

The NMR data of this compound were well agreed with those obtained in Preparation 11.

Furthermore, 7-methoxyiminomethyl-2-(tri-n-butylstannyl)imidazo[5,1b]thiazole (geometrical isomer derived from a raw material which is a low polar oxime isomer) was obtained in a yield of 704 mg from the fraction having Rf=0.3 (n-hexane:ethyl acetate=3:1).

NMR (CDCl$_3$) δ: 0.92 (9H, t, J=7.3 Hz), 1.18 (6H, m), 1.35 (6H, m), 1.57 (6H, m), 3.97 (3H, s), 7.22 (1H, s), 7.96 (1H, s), 8.23 (1H, s).

Preparation 16

7-formylaminomethyl-3-(tri-n-butylstannyl)imidazo
[5,1-b]thiazole and 7-formylaminomethyl-2-(tri-n-
butylstannyl)imidazo[5,1-b]thiazole Using 0.72 g of 7-formylaminomethyl imidazo[5,1-b]thiazole, 7-formylaminomethyl-3-(tri-n-butylstannyl)imidazo[5,1-b]thiazole was obtained in a yield of 0.99 g as a low polar component, and 7-formylaminomethyl-2-(tri-n-butylstannyl)imidazo[5,1-b]thiazole in a yield of 0.64 g as a high polar component in the same manner as in Preparation 1.

7-formylaminomethyl-3-(tri-n-butylstannyl)imidazo[5,1-b]thiazole

NMR (CDCl$_3$) δ: 0.90 (9H, t, J=7.1 Hz), 1.22 (6H, m), 1.34 (6H, m), 1.55 (6H, m), 4.58 (2H, d, J=5.6 Hz), 6.32 (1H, br s), 6.63 (1H, s), 7.85 (1H, s), 8.27 (1H, s).

7-formylaminomethyl-2-(tri-n-butylstannyl)imidazo[5,1-b]thiazole

NMR (CDCl$_3$) δ: 0.92 (9H, t, J=7.3 Hz), 1.16 (6H, m), 1.35 (6H, m), 1.58 (6H, m), 4.56 (2H, d, J=6.4 Hz), 6.51 (1H, br s), 7.13 (1H, s), 7.89 (1H, s), 8.38 (1H, s).

Preparation 17

7-(t-butyldimethylsilyloxy)methyl-3-(tri-n-
butylstannyl)imidazo[5,1-b]thiazole and 7-(t-
butyldimethylsilyloxy)methyl-2-(tri-n-butyl-stannyl)
imidazo[5,1-b]thiazole a) 7-(t-butyldimethylsilyloxy)methylimidazo[5,1-b]thiazole To a solution of 2.42 mg of 7-hydroxymethylimidazo[5,1-b]thiazole in 15 ml of DMF were added under ice-cooling 1.4 g of imidazole and 2.73 g of t-butyldimethylsilylchloride, and the mixture was stirred at the same temperature for 2 hours. DMF was removed under reduced pressure, and the residue was extracted two times with ethyl acetate. The organic layer was washed two times with a saturated aqueous sodium chloride solution, dried over anhydrous magnesium sulfate, and removed under reduced pressure to give 7-(t-butyldimethylsilyloxy) methylimidazo[5,1-b]thiazole in a yield of 4.02 g.

NMR (CDCl$_3$) δ: 0.13 (6H, s), 0.97 (9H, s), 4.88 (2H, s), 6.78 (1H, d, J=4.1 Hz), 7.34 (1H, d, J=4.1 Hz), 7.92 (1H, s).

b) 7-(t-butyldimethylsilyloxy)methyl-3-(tri-n-butylstannyl)imidazo[5,1-b]thiazole and 7-(-t-butyldimethylsilyloxy)methyl-2-(tri-n-butyl-stannyl)imidazo[5,1-b]thiazole A solution of 2.25 g of 7-(t-butyldimethylsilyloxy)methylimidazo[5,1-b]thiazole in 5 ml of THF was cooled to −78° C. under the atmosphere of argon, and 5.3 ml of a 1.6 N solution of n-butyl lithium in n-hexane was added dropwise at the same temperature. After the reaction mixture was stirred for 2 hours, 2.24 ml of tri-n-butyl-stannyl chloride was added, and the resulting mixture was stirred at the same temperature for 1 hour, and for 3 hours during which the temperature was raised up to 0° C. The reaction mixture was diluted with a saturated sodium chloride solution, and extracted two times with ethyl acetate. The organic layer was dried over anhydrous magnesium sulfate, and the solvent was removed under reduced pressure. The residue thus obtained was purified by column chromatography on silica gel (hexane:ethyl acetate=2:1).

7-(t-butyldimethylsilyloxy)methyl-3-(tri-n-butylstannyl)imidazo[5,1-b]thiazole was obtained in a yield of 1.54 g from the fraction having Rf=0.6 (hexane:ethyl acetate=1:1).

NMR (CDCl$_3$) δ: 0.01 (6H, s), 0.76 (9H, t, J=7.1 Hz), 0.83 (9H, s), 1.04–1.26 (12H, m), 1.38–1.49 (6H, m), 4.74 (2H, s), 6.47 (1H, s), 7.71 (1H, s). MS (TSP): 559(M$^+$+3H), 557(M$^+$+H).

Further, 7-(t-butyldimethylsilyloxy)methyl-2-(tri-n-butyl-stannyl)imidazo[5,1-b]thiazole was obtained in a yield of 1.67 g from the fraction having Rf=0.3.

NMR (CDCl$_3$) δ: 0.01 (6H, s), 0.78 (9H, t, J=7.1 Hz), 0.83 (9H, s), 1.00–1.07 (6H, m), 1.18–1.30 (6H, m), 1.40–1.50 (6H, m), 4.73 (2H, s), 6.97 (1H, s), 7.73 (1H, s). MS (TSP): 559(M$^+$+3H), 557(M$^+$+H).

Preparation 18

7-(N-methylcarbamoyl)-3-(tri-n-butylstannyl)
imidazo[5,1-b]thiazole and 7-(N-methylcarbamoyl)-
2-(tri-n-butylstannyl)imidazo[5,1-b]thiazole a) 7-(N-methylcarbamoyl)imidazo[5,1-b]thiazole To a solution of 2.06 g of 7-carboxylimidazo[5,1-b]thiazole in 90 ml of DMF were added 4.98 g of 1-hydroxybenzotriazole and 4.72 g of 1-(3-dimethylaminopropyl)-3-ethylcarbodiimide hydrochloride, and the mixture was stirred at room temperature for 10 minutes. Then, 18.5 ml of a 2N solution of methylamine in THF was added, and the mixture was stirred at the same temperature 18 hours. The reaction mixture was diluted with water and adjusted to pH=9.6 with powdery potassium carbonate, and extracted five times with dichloromethane and five times with ethyl acetate. The combined organic layer was dried over anhydrous magnesium sulfate, and the solvent was removed under reduced pressure. The residue thus obtained was purified by column chromatography on silica gel (dichloromethane:methanol=10:1) followed by Sephadex LH-20 (dichloromethane:methanol=1:1) to give 0.80 g of 7-(N-methylcarbamoyl)imidazo[5,1-b]thiazole.

NMR (CDCl$_3$) δ: 3.01 (3H, d, J=5.0 Hz), 6.90 (1H, br, s), 7.00 (1H, d, J=4.1 Hz), 7.48 (1H, d, J=4.1 Hz), 7.92 (1H, s). MS (EI): 181 (M$^+$).

b) 7-(N-methylcarbamoyl)-3-(tri-n-butylstannyl)imidazo[5,1-b]thiazole and 7-(N-methylcarbamoyl)-2-(tri-n-butylstannyl)imidazo[5,1-b]thiazole A solution of 716 mg of 7-(N-methylcarbamoyl)imidazo[5,1-b]thiazole in 35 ml of THF was cooled to −78° C. under the atmosphere of argon, and 6.0 ml of a 1.6 N solution of n-butyl lithium in n-hexane was added dropwise at the same temperature. After the reaction mixture was stirred for 1.5 hours, 1.40 ml of tri-n-butylstannyl chloride was added, and the mixture was stirred for 5 hours during which the temperature was raised up to −40° C. The reaction mixture was diluted with water, and extracted two times with ethyl acetate. The organic layer was washed with a saturated aqueous sodium chloride solution, dried over anhydrous magnesium sulfate, and the solvent was removed under reduced pressure. The residue thus obtained was purified by column chromatography o)n) silica gel (hexane:ethyl acetate=3:1).

7-(N-methylcarbamoyl)-3-(tri-n-butylstannyl)imidazo[5,1-b]thiazole was obtained in a yield of 441 mg from the fraction having Rf=0.5(hexane:ethyl acetate=1:1).

NMR (CDCl$_3$) δ: 0.83 (9H, t, J=7.3 Hz), 1.16–1.32 (12H, m), 1.44–1.61 (6H, m), 2.94 (3H, d, J=5.0 Hz), 6.72 (1H, s), 6.70–6.80 (1H, m), 7.73 (1H, s).

Further, 702 mg of 7-(N-methylcarbamoyl)-2-(tri-n-butylstannyl)imidazo[5,1-b]thiazole was obtained from the fraction having Rf=0.4.

NMR (CDCl$_3$) δ: 0.91 (9H, t, J=7.3 Hz), 1.15–1.40 (12H, m), 1.55–1.60 (6H, m), 3.00 (3H, d, J=5.2 Hz), 6.80–6.88 (1H, m), 7.21 (1H, s), 7.85 (1H, s). MS (APCI): 472 (M$^+$+3H), 470 (M$^+$+H).

Preparation 19

7-methyl-3-(tri-n-butylstannyl)imidazo[5,1-b]thiazole and 7-methyl-2-(tri-n-butylstannyl)imidazo[5,1-b]thiazole A 1.66 N solution of n-butyl lithium/n-hexane (15.8 ml) dissolved in dry THF (75 ml) cooled to −69° C. under the atmosphere of argon, and a solution of 3.455 g of 7-methylimidazo[5,1-b]thiazole in 50 ml of THF was added dropwise under stirring at −69—66° C. over 20 minutes. The reaction mixture was further stirred at the same temperature 10 minutes, and 7.8 ml of tri-n-butylstannyl chlorideat was added dropwise at the same temperature over the period of 10 minutes. Then, The reaction mixture was gradually warmed to room temperature, and stirred for 15 hours. The reaction mixture was diluted with 100 ml of a semi-saturated aqueous saline, and extracted with 250 ml of ethyl acetate. The organic layer was dried over anhydrous magnesium sulfate, filtered, and the solvent was removed by distillation. The oil thus obtained was purified by column chromatography on silica gel (n-hexane:ethyl acetate=2:1–1:1).

7-methyl-3-(tri-n-butylstannyl)imidazo[5,1-b]thiazole was obtained as a yellow oil in a yield of 4.760 g from the fraction having Rf=0.5 (n-hexane:ethyl acetate=2:1).

NMR (CDCl$_3$) δ: 0.89 (9H, t, J=7.2 Hz), 1.17–1.23 (6H, m), 1.27–1.40 (6H, m), 1.50–1.65 (6H, m), 2.36 (3H, s), 6.57 (1H, s), 7.83 (1H, s). MS(TS): 429(M$^+$+3H), 427(M$^+$+H).

Further, 7-methyl-2-(tri-n-butylstannyl)imidazo[5,1-b]thiazole was obtained as a yellow oil in a yield of 3.653 g from the fraction having Rf=0.2 (n-hexane:ethyl acetate=2:1).

NMR (CDCl$_3$) δ: 0.91 (9H, t, J=7.2 Hz), 1.11–1.17 (6H, m), 1.19–1.41 (6H, m), 1.53–1.63 (6H, m), 2.34 (3H, s), 7.08 (1H, s), 7.85 (1H, s). MS(TS): 429(M$^+$+3H), 427(M$^+$+H).

Preparation 20

5,7-dimethyl-2-(tri-n-butylstannyl)imidazo[5,1-b]thiazole a) 2-(1-acetylamino)ethylthiazole To a solution of 3.40 g of 2-(1-amino)ethylthiazole in 53 ml of THF was added 2.6 ml of dry pyridine, and the mixture was cooled to −70° C. under the atmosphere of argon. To the mixture was added dripwise 2.6 ml of acetic anhydride over a period of 5 minutes, and further stirred on an ice bath for 1 day. The reaction mixture was diluted with 40 ml of 5% aqueous sodium hydrogen carbonate, and extracted once with 200 ml and thrice with 100 ml of dichloromethane. The combined organic layer was dried over anhydrous sodium sulfate, filtered, and the solvent was removed under reduced pressure. The solid residue thus obtained was purified by column chromatography on silica gel (ethyl acetate alone—ethyl acetate:methanol=96:4) to give 2-(1-acetyl-amino)ethylthiazole as a milk white powder in a yield of 3.456 g.

NMR (CDCl$_3$) δ: 1.62 (3H, d, J=6.9 Hz), 2.05 (3H, s), 5.44 (1H, quintet, J=6.9 Hz), 6.43 (1H, br. s), 7.28 (1H, d, J=3.3 Hz), 7.71 (1H, d, J=3.3 Hz). MS (TSP): 171(M$^+$+H).

b) 5,7-dimethylimidazo[5,1-b]thiazole

To 3.392 g of 2-(1-acetylamino)ethylthiazole were added 17 ml of dry toluene and 9 ml of phosphorus oxychloride, and the mixture was stirred at a bath temperature of 90° C. for 75 minutes. The reaction mixture was cooled to room temperature, diluted with 30 ml of distilled water and 100 ml of dichloromethane, neutralized under stirring with potassium carbonate, salted out, and the organic layer was separated. The aqueous layer was further extracted with 50 ml of dichloromethane. The combined organic layer was dried over anhydrous potassium carbonate. The crude fine crystalline product thus obtained was purified by column chromatography on silica gel (dichloromethane:methanol=98:2) to give 5,7-dimethylimidazo[5,1-b]thiazole as milk white crystals in a yield of 2.787 g.

NMR (CDCl$_3$) δ: 2.30 (3H, s), 2.53 (3H, s), 6.71 (1H, d, J=4.2 Hz), 7.12 (1H, d, J=4.2 Hz). MS (TSP): 153(M$^+$+H).

c) 5,7-dimethyl-2-(tri-n-butylstannyl)imidazo[5,1-b]thiazole

To 50 ml of anhydrous THF cooled to −65° C. under the atmosphere of argon was added 10.9 ml of a 1.63 N n-butyl lithium/n-hexane solution, and a solution of 2.564 g of 5,7-dimethylimidazo[5,1-b]thiazole in 17 ml of anhydrous THF was further added dropwise at −64—60° C. over a period of 15 minutes. The reaction mixture was then stirred at the same temperature for 80 minutes. After 5.0 ml of tri-n-butylstannyl chloride was added dropwise to the mixture at a temperature of −63—58° C. over a period of 10 minutes, it was warmed to −30° C., and further stirred for 110 minutes. The reaction mixture was diluted with 100 ml of semi-saturated aqueous saline, extracted with 150 ml of ethyl acetate. The organic layer was dried over anhydrous sodium sulfate, filtered, and the solvent was removed under reduced pressure. The oil thus obtained was purified by column chromatography on silica gel (n-hexane:ethyl acetate=1:1—1:2) to give the title compound as a light orange oil in a yield of 6.164 g.

NMR (CDCl$_3$) δ: 0.92 (9H, t, J=7.2 Hz), 1.10–1.17 (6H, m), 1.30–1.42 (6H, m), 1.53–1.65 (6H, m), 2.29 (3H, s), 2.53 (3H, s), 6.85 (1H, s). MS (TSP): 443, 441, 439.

Preparation 21

7-methoxymethyl-3-(tri-n-butylstannyl)imidazo[5,1-b]thiazole and 7-methoxymethyl-2-(tri-n-butylstannyl)imidazo[5,1-b]thiazole a) 7-methoxymethylimidazo[5,1-b]thiazole

To a solution of 2.0 g of 7-hydroxymethylimidazo[5,1b]thiazole in 25 ml of DMF was added under ice-cooling 600 mg of sodium hydride (60% in oil) under the atmosphere of argon. White insolubles were produced in a short time. When stirring becomes difficult, DMF was added. After 30 minutes, 2.0 g of iodomethane was added to dissolve the precipitate. After additional stirring for 1 hour, 200 ml of ethyl acetate and 100 ml of semi-saturated aqueous saline were added, and the mixture was stirred and separated. The organic layer was washed three times with 100 ml of semi-saturated aqueous saline, dried over anhydrous magnesium sulfate, and purified by column chromatography on silica gel and on Sephadex LH-20 to give 1.41 g of 7-methoxymethylimidazo[5,1-b]thiazole.

NMR (CDCl$_3$) δ: 3.43 (3H, s), 4.59 (2H, s), 6.83 (1H, d, J=4.2 Hz), 7.38 (1H, d, J=4.2 Hz), 7.96 (1H, s).

b) 7-methoxymethyl-3-(tri-n-butylstannyl)imidazo[5,1-b]thiazole and 7-methoxymethyl-2-(tri-n-butylstannyl)imidazo[5,1-b]thiazole A solution of 925 mg of 7-methoxymethylimidazo[5,1-b]thiazole in anhydrous THF was cooled to −70° C. under the atmosphere of argon and 3.54 ml of a 1.6 N n-butyl lithium/n-hexane solution was slowly added, and the mixture was stirred for 1 hour. To the reaction mixture was slowly added a solution of 1.88 g of tri-n-butylstannyl chloride in 2 ml of anhydrous THF, and the mixture was stirred for further 1.5 hours. After the addition of 100 ml of ethyl acetate, the solvent was removed by distillation to concentrate the mixture to a total volume of about 1 ml. Purification by silica gel chromatography gave 896 mg of 7-methoxymethyl-3-(tri-n-butylstannyl)imidazo[5,1-b]thiazole from a low polar fraction eluted with dichloromethane:ethyl acetate=4:1.

NMR (CDCl$_3$) δ: 0.80–1.80 (27H, m), 3.42 (3H, s), 4.58 (2H, s), 6.63 (1H, s), 7.87 (1H, s).

Further, purification by column chromatography on silica gel gave 712 mg of 7-methoxymethyl-2-(tri-n-butylstannyl)imidazo[5,1-b]thiazole from a high polar fraction eluted with dichloromethane:ethyl acetate 1:1–1:4.

NMR (CDCl$_3$) δ: 0.80–1.80 (27H, m), 3.42 (3H, s), 4.57 (2H, s), 7.13 (1H, s), 7.90 (1H, s).

Preparation 22

7-(N,N-dimethylcarbamoyl)-3-(tri-n-butylstannyl)imidazothiazole and 7-(N,N-dimethylcarbamoyl)-2-(tri-n-butylstannyl)imidazothiazole (approximately 1:1 mixture)

a) 7-(N,N-dimethylcarbamoyl)imidazo[5,1-b]thiazole

To a solution of 1.71 g of 7-carboxylimidazo[5,1-b]thiazole in 34 ml of DMF was added 5.45 g of 1-hydroxybenzotriazole and 6.80 g of 1-(3-dimethylaminopropyl)-3-ethylcarbodiimide hydrochloride at room temperature under the atmosphere of argon, and the mixture was stirred for 1 hour. To the reaction mixture was added under ice-cooling 20 ml of a saturated dimethylamine solution in THF, and the mixture was stirred at room temperature overnight. The reaction mixture was diluted with 300 ml of dichloromethane and 180 ml of water, stirred vigorously and separated. The organic layer was dried over anhydrous magnesium sulfate, and the solvent was removed under reduced pressure. The residue thus obtained was purified by column chromatography on silica gel (dichloromethane:methanol=94:6–90:10) to give 663 mg of 7-(N,N-dimethyl-carbamoyl)imidazo[5,1-b]thiazole.

NMR (CDCl$_3$) δ: 3.0–3.8 (6H, m), 6.99 (1H, d, J=4.2 Hz), 7.47 (1H, d, J=4.2 Hz), 7.93 (1H, s).

b) 7-(N,N-dimethylcarbamoyl)-3-(tri-n-butylstannyl)imidazothiazole and 7-(N,N-dimethylcarbamoyl)-2-(tri-n-butyl-tannyl)imidazothiazole (mixture)

A solution of 660 mg of 7-(N,N-dimethylcarbamoyl)imidazo[5,1-b]thiazole in 30 ml of anhydrous THF was cooled to −55° C. under the atmosphere of argon. 2.4 ml of a 1.6 N solution of n-butyl lithium/n-hexane was slowly added, and the mixture was stirred for 1 hour. A solution of 1.30 g of tri-n-butylstannyl chloride in 10 ml of anhydrous THF was slowly added, and the reaction mixture was stirred for 1 hour. The reaction mixture was diluted with 120 ml of ethyl acetate and 30 ml of water, stirred and separated. The organic layer was dried over anhydrous magnesium sulfate, and the solvent was removed to concentrate the organic layer to a total volume of about 1 ml. The residue thus obtained was purified by chromatography on silica gel (hexane:ethyl acetate=1:1) to give 980 mg of the title compound as an approximately 1:1 mixture.

NMR (CDCl$_3$) δ: 0.7–1.7 (27H, m), 2.9–3.9 (6H, br. s), 6.81 (0.5H, s, 3-stannyl derivative), 7.21 (0.5H, s, 2-stannyl derivative), 7.84 (0.5H, s, 3-stannyl derivative), 7.88 (0.5H, s, 2-stannyl derivative).

Example 1

(1S,5R,6S)-6-((1R)-1-hydroxyethyl)-2-(imidazo[5,1-b]thiazol-2-yl)-1-methyl-1-carbapen-2-em-3-carboxylic Acid a) 4-nitrobenzyl (1S,5R,6S)-6-((1R)-1-hydroxyethyl)-2-(imidazo[5,1-b]thiazol-2-yl)-1-methyl-1-carbapen-2-em-3-carboxylate To a solution of 7.24 g of 4-nitrobenzyl (1R,3R,5R,6S)-6-((1R)-1-hydroxyethyl)-1-methyl-2-oxo-1-carbapenam-3-carboxylate in 150 ml of dry acetonitrile was added dripwise 6.97 ml of N,N-diisopropylethylamine, followed by 3.70 ml of anhydrous trifluo-methanesulfonic acid under the atmosphere of argon at −15° C. After the reaction mixture was stirred at the same temperature for 30 minutes, it was diluted with 500 ml of ethyl acetate, and washed sequentially with semi-saturated aqueous saline, a mixture of semi-saturated aqueous saline and 1N hydrochloric acid (pH 1.1), a mixture of semi-saturated aqueous saline and saturated aqueous sodium hydrogen carbonate (pH 8.9), and saturated aqueous saline. After drying over anhydrous magnesium sulfate, the reaction mixture was filtered, diluted with 40 ml of dry N-methylpyrrolidine, and ethyl acetate and acetonitrile was removed under reduced pressure. The residue was mixed with a solution of 553 mg of tris(dibenzylideneacetone)dipalladium (0), 558 mg of tri-2-furylphosphine, 9.14 g of 2-(tri-n-butylstannyl)imidazo[5,1-b]thiazole in 10 ml of dry N-methylpyrrolidinone, and 5.47 g of zinc chloride, and the mixture was stirred under the atmosphere of argon at 50° C. for 1 hour. The solvent was evaporated under reduced pressure, the concentrate was diluted with 150 ml of diethyl ether, and the supernatant was separated. The procedure was repeated two more times, and the residue thus obtained was diluted with 400 ml of ethyl acetate and 80 ml of water. The insolubles were collected by filtration, and washed with ethyl acetate and water (insolubles 1). The organic layer was separated from the filtrate, dried over anhydrous magnesium sulfate, and the solvent was removed under reduced pressure. The residue was diluted with 100 ml of diethyl ether and 100 ml of ethyl acetate, and the insolubles were collected by filtration (insolubles 2). Insolubles 1 described above was diluted with 1000 ml of ethyl acetate, 500 ml of methanol, and 500 ml of acetone, and the mixture was stirred for 45 minutes at room temperature. After the insolubles were collected by filtration and the solvent was removed under reduced pressure, the residue was diluted with 30 ml of diethyl ether and 15 ml of ethyl acetate, and the insolubles were collected by filtration (insolubles 3). Insolubles 2 and insolubles 3 were combined, dissolved in 100 ml of acetone, diluted with 900 ml of ethyl acetate and 400 ml of semi-saturated aqueous sodium hydrogen carbonate, and the mixture was stirred at room temperature for 30 minutes. The insolubles were removed by filtration, and the organic layer was separated from the filtrate, washed three times with 500 ml of semi-saturated aqueousesaline, dried over anhydrous magnesium sulfate, and evaporated under reduced pressure to give 5.71 g of 4-nitrobenzyl (1S,5R,6S)-6-((1R)-1-hydroxyethyl)-2-(imidazo[5,1-b]thiazol-2-yl)-1-methyl-1-carbapen-2-em-3-carboxylate.

NMR (CDCl$_3$) δ: 1.31 (3H, d, J=7.4 Hz), 1.40 (3H, d, J=6.3 Hz), 3.37 (1H, dd, J$_1$=6.6 Hz, J$_2$=2.8 Hz), 3.47 (1H, m), 4.34 (1H, m), 4.38 (1H, dd, J$_1$=9.4 Hz, J$_2$=2.8 Hz), 5.28 (1H, d, J=13.7 Hz), 5.53 (1H, d, J=13.7 Hz), 7.08 (1H, s), 7.68 (2H, d, J=8.5 Hz), 8.03 (1H, s), 8.24 (2H, d, J=8.5 Hz), 8.34 (1H, s).

b) (1S,5R,6S)-6-((1R)-1-hydroxyethyl)-2-(imidazo[5,1-b]thiazol-2-yl)-1-methyl-1-carbapen-2-em-3-carboxylic Acid To a solution of 4.70 g of 4-nitro-benzyl (1S,5R,6S)-6-((1R)-1-hydroxyethyl)-2-(imidazo[5,1-b]thiazol-2-yl)-1-methyl-1-carbapen-2-em-3-carboxylate in 90 ml of THF and 50 ml of 1/15 M phosphate buffer (pH 6.8) was added 7.0 g of 10% Pd-C. The reactor was purged with hydrogen, and the reaction mixture was stirred at room temperature for 4 hours. The catalyst was removed by filtration with Celite, and washed with 300 ml of water and 50 ml of THF. The filtrate was diluted with 200 ml of ethyl acetate and washed with water. The aqueous layer was separated from the filtrate, and concentrated under reduced pressure to a volume of about 300 ml, which was purified by column chromatography on DIAION HP-20. The fraction containing the aimed product was concentrated under reduced pressure, crystallized from 12 ml of water to give 656 mg of the title compound.

NMR (DMSO-d$_6$) δ: 1.18 (3H, d, J=6.1 Hz), 1.19 (3H, d, J=7.1 Hz), 3.32 (1H, dd, J$_1$=6.3 Hz, J$_2$=2.8 Hz), 3.60 (1H, m), 4.00 (1H, m), 4.25 (1H, dd, J$_1$=9.6 Hz, J$_2$=2.8 Hz), 5.10 (1H, br), 7.02 (1H, s), 8.22 (1H, s), 8.37 (1H, s). MS (TS): 334 (M$^+$+H).

Example 2

(1S,5R,6S)-6-((1R)-1-hydroxyethyl-2-(imidazo[5,1-b]thiazol-2-yl)-1-methyl-1-carbapen-2-em-3-carboxylic Acid a) 4-nitrobenzyl (1S,5R,6S)-6-[(1R)-1-(t-butyldimethylsilyloxy)ethyl]-2-(imidazo[5,1-b]thiazol-2-yl)-1-methyl-1-carbapen-2-em-3-carboxylate A solution of 292 mg of 4-nitro-benzyl (1R,3R,5R,6S)-6-[(1R)-1-(t-butyldimethyl-silyloxy)ethyl]-1-methyl-2-oxo-1-carbapenam-3-carboxylate in 8 ml of dry acetonitrile was ice-cooled under the atmosphere of argon, and 0.267 ml of N,N-diisopropylethylamine was added dropwise, followed by 0.103 ml of anhydrous trifluoromethanesulfonic acid. After the reaction mixture was stirred at the same temperature for 30 minutes, it was diluted with ethyl acetate, a mixture of semi-saturated aqueous saline saturated aqueous sodium hydrogen carbonate (pH 8.9), and semi-saturated aqueous saline in this sequence. The organic layer was dried over anhydrous magnesium sulfate, filtered, mixed with 3 ml of N-methylpyrrolidinone, and the ethyl acetate was removed under reduced pressure. The residue was mixed with 17 mg of tris(dibenzylideneacetone)dipalladium (0), 17 mg of tri-2-furylphosphine, 376 mg of 2-(tri-n-butylstannyl)imidazo[5,1-b]thiazole in 1 ml of dry N-methylpyrrolidinone, and 167 mg of zinc chloride, and the mixture was stirred under the atmosphere of argon at 50° C. for 4 hours. The reaction mixture was diluted with ethyl acetate, and washed with semi-saturated aqueous saline. The organic layer was dried over anhydrous magnesium sulfate, and the solvent was removed under reduced pressure. The residue thus obtained was purified by column chromatography on silica gel (ethyl acetate) and on Sephadex LH-20 (chloroform:methanol=1:1) in this sequence to give 111 mg of 4-nitrobenzyl (1S,5R,6S)-6-[(1R)-1-(t-butyldimethylsilyloxy)ethyl]-2-(imidazo[5,1-b]thiazol-2-yl)-1-methyl-1-carbapen-2-em-3-carboxylate.

NMR (CDCl$_3$) δ: 0.08 (3H, s), 0.10 (3H, s), 0.86 (9H, s), 1.26 (3H, d, J=6.3 Hz), 1.28 (3H, d, J=7.7 Hz), 3.33 (1H, dd, J$_1$=4.7 Hz, J$_2$=2.8 Hz), 3.41 (1H, m), 4.31 (1H, m), 4.37 (1H, dd, J$_1$=9.6 Hz, J$_2$=2.8 Hz), 5.26 (1H, d, J=13.7 Hz), 5.49 (1H, d, J=13.7 Hz), 7.26 (1H, s), 7.67 (2H, d, J=8.3 Hz), 8.03 (1H, s), 8.23 (2H, d, J=8.3 Hz), 8.33 (1H, s).

b) 4-nitrobenzyl (1S,5R,6S)-6-((1R)-1-hydroxyethyl)-2-(imidazo[5,1-b]thiazol-2-yl)-1-methyl-1-carbapen-2-em-3-carboxylate To a solution of 111 mg of 4-nitrobenzyl (1S,5R,6S)-6-[(1R)-1-(t-butyldimethylsilyloxy)ethyl]-2-(imidazo[5,1-b]thiazol-2-yl)-1-methyl-1-carbapen-2-em-3-carboxylate in 3 ml of anhydrous THF were added 0.164 ml of acetic acid and 0.954 ml of a 1 M solution of tetra-n-butylammonium fluoride/THF, and the mixture was stirred at room temperature under the atmosphere of argon at 20 hours. The reaction mixture was diluted with ethyl acetate, and washed with a mixed solvent of semi-saturated aqueous saline and saturated aqueous sodium hydrogen carbonate (pH 8.0), and semi-saturated aqueous saline in this sequence. The organic layer was dried over anhydrous magnesium sulfate, filtered, and the solvent was removed by distillation. The residue thus obtained was purified by column chromatography on Sephadex LH-20 (chloroform:methanol=1:1) to give 57.3 mg of 4-nitrobenzyl (1S,5R,6S)-6-((1R)-1-hydroxyethyl)-2-(imidazo[5,1-b]thiazol-2-yl)-1-methyl-1-carbapen-2-em-3-carboxylate.

The NMR data was well agreed with those in Example 1-a).

c) (1S,5R,6S)-6-((1R)-1-hydroxyethyl)-2-(imidazo[5,1-b]thiazol-2-yl)-1-methyl-1-carbapen-2-em-3-carboxylic Acid In the same manner as in Example 1-b), (1S,5R,6S)-6-((1R)-1-hydroxyethyl)-2-(imidazo[5,1-b]thiazol-2-yl)-1-methyl-1-carbapen-2-em-3-carboxylic acid was obtained from 4-nitrobenzyl (1S,5R,6S)-6-((1R)-1-hydroxyethyl)-2-(imidazo[5,1-b]thiazol-2-yl)-1-methyl-1-carbapen-2-em-3-carboxylate.

The NMR data was well agreed with those in Example 1-a).

Example 3

Pivaloyloxymethyl (1S,5R,6S)-6-((1R)-1-hydroxyethyl)-2-(imidazo[5,1-b]thiazol-2-yl)-1-methyl-1-carbapen-2-em-3-carboxylate To a suspension of 947 mg of (1S,5R,6S)-6-((1R)-1-hydroxyethyl)-2-(imidazo[5,1-b]thiazol-2-yl)-1-methyl-1-carbapen-2-em-3-carboxylic acid in 180 ml of water was added 7.8 ml of 0.1 N aqueous sodium hydrogen carbonate, and the mixture was stirred at room temperature for 2 hours to form a solution, which was then frozen. The frozen solution was dissolved in 12 ml of dry DMF, mixed with 0.36 ml of iodomethyl pivalate under the atmosphere of argon at −30° C., and stirred for 1.5 hours during which the temperature was raised up to −10° C. The reaction mixture was diluted with 100 ml of ethyl acetate, and washed with 100 ml of semi-saturated aqueous saline. The organic layer was dried over anhydrous magnesium sulfate, filtered, and concentrated under reduced pressure to a total volume of 5 ml. The residue thus obtained was purified by column chromatography on silica gel (chloroform:methanol 10:1) and on Sephadex LH-20 (chloroform:methanol=1:1) in this sequence to give 576 mg of the title compound.

NMR (CDCl$_3$) δ: 1.20 (9H, s), 1.29 (3H, d, J=7.2 Hz), 1.36 (3H, d, J=6.2 Hz), 3.33 (1H, dd, J$_1$=6.5 Hz, J$_2$=2.8 Hz), 3.45 (1H, m), 4.29 (1H, m), 4.35 (1H, dd, J$_1$=9.7 Hz, J$_2$=2.8 Hz), 5.88 (1H, d, J=5.6 Hz), 5.98 (1H, d, J=5.6 Hz), 7.07 (1H, s), 8.06 (1H, s), 8.34 (1H, s). MS(TS): 448(M$^+$+H).

Example 4

(1S,5R,6S)-6-((1R)-1-hydroxyethyl)-1-methyl-2-(6-methylimidazo[5,1-b]thiazolium-2-yl)-1-carbapen-2-em-3-carboxylate (inner salt)

a) 4-Nitrobenzyl (1S,5R,6S)-6-((1R)-1-hydroxyethyl)-1-methyl-2-(6-methylimidazo[5,1-b]thiazolium-2-yl)-1-carbapen-2-em-3-carboxylate Iodide To a solution of 64.7 mg of 4-nitrobenzyl (1S,5R, 6S)-6-((1R)-1-hydroxyethyl)-2-(imidazo[5,1-b]thiazol-2-yl)-1-methyl-1-carbapen-2-em-3-carboxylate in 1 ml of dry dichloromethane was added 0.86 ml of iodomethane, and the mixture was stirred under the atmosphere of argon in darkness at room temperature for 21 hours. Evaporation of the unreacted reagent under reduced pressure gave 4-nitrobenzyl (1S,5R,6S)-6-((1R)-1-hydroxyethyl)-1-methyl-2-(6-methylimidazo[5,1-b]thiazolium-2-yl)-1-carbapen-2-em-3-carboxylate.

NMR (DMSO-d$_6$) δ: 1.18 (3H, d, J=6.6 Hz), 1.22 (3H, d, J=7.4 Hz), 3.49 (1H, dd), 3.73 (1H, m), 4.05 (1H, m), 4.07 (3H, s), 4.39 (1H, dd), 5.18 (1H, d), 5.39 (1H, d, J=14.3 Hz), 5.51 (1H, d, J=14.3 Hz), 7.72 (2H, d, J=8.8 Hz), 7.80 (1H, s), 8.22 (2H, d, J=8.8 Hz), 8.61 (1H, s), 9.51 (1H, s).

b) (1S,5R,6S)-6-((1R)-1-hydroxyethyl)-1-methyl-2-(6-methylimidazo[5,1-b]thiazolium-2-yl)-1-carbapen-2-em-3-carboxylate (inner salt)

The total volume of 4-nitrobenzyl (1S,5R,6S)-6-((1R)-1-hydroxyethyl)-1-methyl-2-(6-methylimidazo[5,1-b]thiazolium-2-yl)-1-carbapen-2-em-3-carboxylate iodide was dissolved in a mixture of 2 ml of THF and 2 ml of 1/15 M phosphate buffer (pH 6.8), 77 mg of 10% Pd-C was added. The reactor was purged with hydrogen, and the reaction mixture was stirred at room temperature for 5 hours. The catalyst was collected by filtration with Celite and washed with water. The filtrate was washed with 20 ml of ethyl acetate, and purified by column chromatography on DIAION HP-20 to give 14.1 mg of the title compound.

NMR (D$_2$O) δ(HOD=4.80 ppm): 1.23 (3H, d, J=7.1 Hz), 1.30 (3H, d, J=6.3 Hz), 3.53 (1H, dd, J$_1$=6.1 Hz, J$_2$=2.5 Hz), 4.06 (3H, s), 4.28 (2H, m), 7.47 (1H, s), 8.05 (1H, s), 9.10 (1H, s).

Example 5

(1S,5R,6S)-6-((1R)-1-hydroxyethyl)-2-(imidazo[5,1-b]thiazol-3-yl)-1-methyl-1-carbapen-2-em-3-carboxylic Acid a) 4-nitrobenzyl (1S,5R,6S)-6-((1R)-1-hydroxyethyl)-2-(imidazo[5,1-b]thiazol-3-yl)-1-methyl-1-carbapen-2-em-3-carboxylate To a solution of 491 mg of 4-nitrobenzyl (1R,3R,5R,6S)-6-((1R)-1-hydroxyethyl)-1-methyl-2-oxo-1-carbapenam-3-carboxylate in 12 ml of dry acetonitrile was added dropwise 0.59 ml of N,N-diisopropylethylamine followed by 0.227 ml of anhydrous trifluoromethanesulfonic acid under the atmosphere of argon at −15° C. After the reaction mixture was stirred at the same temperature for 30 minutes, it was diluted with 40 ml of ethyl acetate and washed sequentially with semi-saturated aqueous saline, a mixed solvent of semi-saturated aqueous saline and 1N aqueous hydrochloric acid (pH 1.1), a mixed solvent of semi-saturated aqueous saline and saturated aqueous sodium hydrogen carbonate(pH 8.9), and semi-saturated aqueous saline. The organic layer was dried over anhydrous magnesium sulfate, filtered, and the solvent was removed under reduced pressure. The residue thus obtained was dissolved in 4 ml of dry N-methylpyrrolidinone, mixed with 37 mg of tri-2-furylphosphine, 370 mg of zinc chloride, 37 mg of tris (dibenzylideneacetone)dipalladium (0), and a solution of 765 mg of 3-(tri-n-butylstannyl)imidazo[5,1-b]thiazole in 2 ml of dry N-methylpyrrolidinone, and the mixture was stirred under the atmosphere of argon at 50° C. for 40 minutes. The reaction mixture was diluted with 200 ml of ethyl acetate and 200 ml of water, and the organic layer was separated. The organic layer was diluted with 100 ml semi-saturated aqueous sodium hydrogen carbonate and stirred for 30 minutes to remove insolubles by filtration. The organic layer of the filtrate was separated, washed three times with 200 ml of semi-saturated aqueous saline, dried over anhydrous magnesium sulfate, and the solvent was removed under reduced pressure. The residue thus obtained was purified by column chromatography on silica gel (chloroform:methanol=30:1) to give 225 mg of 4-nitrobenzyl (1S,5R,6S)-6-((1R)-1-hydroxyethyl)-2-(imidazo[5,1-b]thiazol-3-yl)-1-methyl-1-carbapen-2-em-3-carboxylate.

NMR (CDCl$_3$) δ: 1.16 (3H, d, J=7.2 Hz), 1.36 (3H, d, J=6.3 Hz), 3.48 (1H, dd, J$_1$=5.9 Hz, =3.2 Hz), 3.65 (1H, m), 4.34 (1H, m), 4.55 (1H, dd, J$_1$=10.4 Hz, J$_2$=3.2 Hz), 5.12 (1H, d, J=13.4 Hz), 5.30 (1H, d, J=13.4 Hz), 6.98 (1H, s), 7.06 (1H, s), 7.35 (2H, d, J=8.9 Hz), 7.89 (1H, s), 8.12 (2H, d, J=8.9 Hz).

b) (1S,5R,6S)-6-((1R)-1-hydroxyethyl)-2-(imidazo[5,1-b]thiazol-3-yl)-1-methyl-1-carbapen-2-em-3-carboxylic Acid To a solution of 4.70 g of 4-nitrobenzyl (1S,5R,6S)-6-((1R)-1-hydroxyethyl)-2-(imidazo[5,1-b]thiazol-3-yl)-1-methyl-1-carbapen-2-em-3-carboxylate in 10 ml of THF and 10 ml of 1/15 M phosphate buffer was added 240 mg of 10% Pd-C. The reactor was purged with hydrogen, and the reaction mixture was stirred at room temperature for 3 hours. The catalyst was collected by filtration and washed with water. The filtrate was washed with ethyl acetate, and the aqueous layer was purified by column chromatography on DIAION HP-20 to give 27.5 mg of the title compound.

NMR (D$_2$O) δ (HOD=4.80 ppm): 1.16 (3H, d, J=7.1 Hz), 1.32 (3H, d, J=6.3 Hz), 3.50–3.65 (2H, m), 4.25–4.48 (2H, m), 7.42 (1H, s), 7.45 (1H, s), 8.70 (1H, s).

Example 6

Pivaloyloxymethyl (1S,5R,6S)-6-((1R)-1-hydroxyethyl)-2-(imidazo[5,1-b]thiazol-3-yl)-1-methyl-1-carbapen-2-em-3-carboxylate To a suspension of 32.5 mg of (1S,5R,6S)-6-((1R)-1-hydroxyethyl)-2-(imidazo[5,1-b]thiazol-3-yl)-1-methyl-1-carbapen-2-em-3-carboxylic acid in a mixture of 10 ml of water and 8 ml of methanol was added 7.8 mg of sodium hydrogen carbonate, and the mixture was stirred at room temperature for 10 minutes to form a solution. Methanol was removed under reduced pressure, and the residue was lyophilized. The lyophilized product was dissolved in 2 ml of dry DMF, 0.03 ml of iodomethyl pivalate was added under the atmosphere of argon at −30° C., and the mixture was stirred for 2 hours during which the temperature was raised up to −10° C. Ethyl acetate was added to the reaction mixture, and the mixture was washed with semi-saturated aqueous saline. The organic layer was dried over anhydrous magnesium sulfate, filtered, and concentrated under reduced pressure to a total volume of 3 ml. The residue thus obtained was purified by column chromatography on silica gel (chloroform:methanol=30:1–10:1) to give 26.6 mg of the title compound.

NMR (CDCl$_3$) δ: 1.14 (3H, d, J=7.4 Hz), 1.17 (9H, s), 1.37 (3H, d, J=6.3 Hz), 3.43 (1H, dd, J$_1$=6.3 Hz, J$_2$=3.1 Hz), 3.70 (1H, m), 4.32 (1H, m), 4.48 (1H, dd, J$_1$=10.4 Hz, J$_2$=3.1 Hz), 5.74 (1H, d, J=5.5 Hz), 5.87 (1H, d, J=5.5 Hz), 7.07 (1H, s), 7.13 (1H, s), 7.85 (1H, s).

Example 7

(1S,5R,6S)-6-((1R)-1-hydroxyethyl)-1-methyl-2-(6-methylimidazo[5,1-b]thiazolium-3-yl)-1-carbapen-2-em-3-carboxylate(inner salt)

a) 4-Nitrobenxyl (1S,5R,6S)-6-((1R)-1-hydroxyethyl)-1-methyl-2-(6-methylimidazo[5,1-b]thiazolium-3-yl)-1-carbapen-2-em-3-carboxylate Iodide To a suspension of 102 mg of 4-nitrobenzyl (1S,5R,6S)-6-((1R)-1-hydroxyethyl)-2-(imidazo[5,1-b]thiazol-3-yl)-1-methyl-1-carbapen-2-em-3-carboxylate 1.5 ml of dry dichloromethane was added 2.7 ml of iodomethane, and the mixture was stirred under the atmosphere of argon in the darkness at room temperature for 3 days. Unreacted reagent was removed under reduced pressure to give 122 mg of 4-nitrobenzyl (1S,5R,6S)-6-((1R)-1-hydroxyethyl)-1-methyl-2-(6-methylimidazo[5,1-b]thiazolium-3-yl)-1-carbapen-2-em-3-carboxylate iodide.

NMR (DMSO-d$_6$) δ: 1.06 (3H, d, J=7.6 Hz), 1.17 (3H, d, J=6.3 Hz), 3.55 (1H, dd, J$_1$=5.5 Hz, J$_2$=3.2 Hz), 3.66 (1H, m), 3.94 (1H, m), 3.98 (3H, s), 4.44 (1H, dd, J$_1$=10.5 Hz, J$_2$=3.2 Hz), 5.19 (1H, d, J=13.4 Hz), 5.28 (1H, d, J=13.4 Hz), 7.49 (2H, d, J=8.8 Hz), 7.72 (1H, s), 7.82 (1H, s), 8.19 (2H, d, J=8.8 Hz), 9.73 (1H, s).

b) (1S,5R,6S)-6-((1R)-1-hydroxyethyl)-1-methyl-2-(6-methylimidazo[5,1-b]thiazolium-3-yl)-1-carbapen-2-em-3-carboxylate (inner salt)

To a solution of 60.5 mg of 4-nitrobenzyl (1S,5R,6S)-6-((1R)-1-hydroxyethyl)-1-methyl-2-(6-methylimidazo[5,1-b]thiazolium-3-yl)-1-carbapen-2-em-3-carboxylate in 1.8 ml of THF and 1.8 ml of ⅟₁₅ M phosphate buffer (pH 6.8) was added 71 mg of 10% Pd-C. The reactor was purged with hydrogen, and the reaction mixture was stirred at room temperature for 3.5 hours. The catalyst was collected by filtration through Celite, and washed with water. The filtrate was washed with 20 ml of ethyl acetate, and purified by column chromatography on DIAION HP-20 and on COSMOSEAL40C18-PREP (water:methanol=20:1) to give 8.3 mg of the title compound.

NMR (D$_2$O) δ (HOD=4.80 ppm): 1.14 (3H, d, J=7.4 Hz), 1.31 (3H, d, J=6.3 Hz), 3.55 (1H, m), 3.62 (1H, dd, J$_1$=5.8 Hz, J$_2$=2.9 Hz), 4.06 (3H, s), 4.30 (1H, m), 4.43 (1H, dd, J$_1$=9.9 Hz, J$_2$=2.9 Hz), 7.52 (1H, s), 7.61 (1H, s), 9.06 (1H, s).

Example 8

(5R,6S)-6-((1R)-1-hydroxyethyl)-2-(imidazo[5,1-b]thiazol-2-yl)-1-carbapen-2-em-3-carboxylic Acid a) 4-Nitrobenzoyl (5R,6S)-6-((1R)-1-hydroxyethyl)-2-(imidazo[5,1-b]thiazol-2-yl)-1-carbapen-2-em-3-carboxylate To ice-cooled solution of 149 mg of 4-nitrobenzyl (3R,5R,6S)-6-((1R)-1-hydroxyethyl)-2-oxo-1-carbapenam-3-carboxylate in 4 ml of dry acetonitrile was added dropwise 0.187 ml of N,N-diisopropylethylamine, followed by 0.071 ml of anhydrous trifluoro-methanesulfonic acid under the atmosphere of argon. The solution was stirred at the same temperature for 30 minutes, diluted with ethyl acetate, and washed sequentially with a mixed solvent of semi-saturated aqueous saline and saturated aqueous sodium hydrogen carbonate (pH 8.9), and semi-saturated aqueous saline. The organic layer was dried over anhydrous magnesium sulfate, filtered, and the solvent was removed under reduced pressure. The residue thus obtained was dissolved in 2 ml of dry N-methylpyrrolidinone, added with 12 mg of tri-2-furylphosphine, 116 mg of zinc chloride, 12 mg of tris (dibenzylideneacetone)dipalladium (0), and a solution of 306 mg of 2-(tri-n-butylstannyl)imidazo[5,1-b]thiazole in 1 ml of dry N-methylpyrrolidinone, and the mixture was stirred under the atmosphere of argon at 50° C. for 2 hours. The reaction mixture was diluted with 50 ml of ethyl acetate and 50 ml water, and insolubles were removed by filtration, and washed with ethyl acetate. The organic layer of the filtrate was separated, dried over anhydrous magnesium sulfate, and the solvent was removed under reduced pressure. The residue thus obtained was purified by column chromatography on Sephadex LH-20 (chloroform:methanol=1:1). The fraction containing the aimed product was concentrated under reduced pressure, and triturated with 13 ml of diethyl ether to collect insolubles and thus to give 38.5 mg of 4-nitrobenzyl (5R,6S)-6-((1R)-1-hydroxyethyl)-2-(imidazo[5,1-b]thiazol-2-yl)-1-carbapen-2-em-3-carboxylate.

NMR (DMSO-d$_6$) δ: 1.17 (3H, d, J=6.2 Hz), 3.31 (1H, m), 3.40–3.55 (3H, m), 4.01 (1H, m), 4.24 (1H, m), 5.15 (1H, d, J=4.9 Hz), 5.41 (1H, d, J=14.0 Hz), 5.53 (1H, d, J=14.0 Hz), 7.04 (1H, s), 7.75 (2H, d, J=8.9 Hz), 8.24 (2H, d, J=8.9 Hz), 8.28 (1H, s), 8.37 (1H, s).

b) (5R,6S)-6-((1R)-1-hydroxyethyl)-2-(imidazo[5,1-b]thiazol-2-yl)-1-carbapen-2-em-3-carboxylic Acid To a solution of 41 mg of 4-nitrobenzyl (5R,6S)-6-((1R)-1-hydroxyethyl)-2-(imidazo[5,1-b]thiazol-2-yl)-1-carbapen-2-em-3-carboxylate in 2 ml of THF and 2 ml of ⅟₁₅ M phosphate buffer (pH 6.8) was added 61 mg of 10% Pd-C. The reactor was purged with hydrogen, and the reaction mixture was stirred at room temperature for 2 hours. The catalyst was removed by filtration on Celite and washed with water. The filtrate was washed with ethyl acetate, and the aqueous layer was purified by column chromatography on DIAION HP-20 to give 5.7 mg of the title compound.

NMR (D$_2$O) δ (HOD=4.80 ppm): 1.31 (3H, d, J=6.3 Hz), 3.30 (2H, m), 3.53 (1H, dd, J$_1$=5.9 Hz, J$_2$=3.0 Hz), 4.26 (2H, m), 7.37 (1H, s), 7.89 (1H, s), 8.88 (1H, s).

Example 9

(1S,5R,6S)-6-((1R)-1-hydroxyethyl)-1-methyl-2-(3-methylimidazo[5,1-b]thiazol-2-yl)-1-carbapen-2-em-3-carboxylic Acid a) 4-nitrobenzyl (1S,5R,6S)-6-((1R)-1-hydroxyethyl)-1-methyl-2-(3-methylimidazo[5,1-b]thiazol-2-yl)-1-carbapen-2-em-3-carboxylate To a solution of 353.2 mg of 4-nitrobenzyl (1R,3R,5R,6S)-6-((1R)-1-hydroxyethyl)-1-methyl-2-oxo-1-carbapenam-3-carboxylate in 7 ml of dry acetonitrile was added dropwise 0.34 ml of N,N-diisopropylethylamine, followed by 0.18 ml of anhydrous trifluoromethanesulfonic acid under the atmosphere of argon at −15° C. After the reaction mixture was stirred at the same temperature 30 minutes, it was diluted with 10 ml of ethyl acetate, washed sequentially with semi-saturated aqueous saline, a mixed solution of semi-saturated aqueous saline and 1 N hydrochloric acid, a mixed solution of semi-saturated aqueous saline and saturated aqueous sodium hydrogen carbonate, and semi-saturated aqueous saline. The organic layer was dried over anhydrous magnesium sulfate, filtered, mixed with 2 ml of dry N-methylpyrrolidinone, and ethyl acetate was removed under reduced pressure. To the residue were added a solution of 26.8 mg of tris(dibenzylideneacetone)dipalladium(0), 27.2 mg of tri-2-furylphosphine and 470 mg of 3-methyl-2-(tri-n-butyl-stannyl)imidazo[5,1-b]thiazole in 0.5 ml of dry N-methylpyrrolidinone 0.5 ml, and 266 mg of zinc chloride, and the mixture was stirred under the atmosphere of argon at 50° C. for 1 hour. The solvent was concentrated under reduced pressure, diluted with 20 ml of ethyl acetate and 80 ml of water, and adjusted weak alkaline with saturated aqueous sodium hydrogen carbonate. The insolubles were collected by filtration, the residue was dissolved in acetone, and the solubles were concentrated. Further, the organic layer of the filtrate was separated, washed once with 20 ml of saturated aqueous saline, combined with the acetone solubles, dried over anhydrous magnesium sulfate, and the solvent was removed under reduced pressure. The residue was purified by column chromatography on silica gel (ethyl acetate:methanol=95:5) to give 5.71 g of 4-Nitrobenzyl (1S,5R,6S)-6-((1R)-1-hydroxyethyl)-1-methyl-2-(3-methylimidazo[5,1-b]thiazol-2-yl)-1-carbapen-2-em-3-carboxylate.

NMR (CDCl$_3$) δ: 1.11 (3H, d, J=7.3 Hz), 1.30 (3H, d, J=6.3 Hz), 2.14 (3H, s), 3.31–3.41 (2H, m), 4.26 (1H, m), 4.39 (1H, dd, J$_1$=0.2 Hz, J$_2$=3.6 Hz), 5.13 (1H, d, J=13.7 Hz), 5.33 (1H, d, J=13.7 Hz), 7.02 (1H, s), 7.43 (2H, d, J=8.5 Hz), 7.80 (1H, s), 8.05 (2H, d, J=8.5 Hz). MS (FAB$^+$): 483 (M$^+$+H).

b) (1S,5R,6S)-6-((1R)-1-hydroxyethyl)-1-methyl-2-(3-methylimidazo[5,1-b]thiazol-2-yl)-1-carbapen-2-em-3-carboxylic Acid To a solution of 157.3 mg of 4-nitrobenzyl (1S,5R,6S)-6-((1R)-1-hydroxyethyl)-1-methyl-2-(3-methylimidazo[5,1-b]thiazol-2-yl)-1-carbapen-2-em-3-carboxylate in 3 ml of THF and 3 ml of 1/15 M phosphate buffer (pH 6.8) was added 0.24 g of 100 Pd-C. The reactor was purged with hydrogen, the reaction mixture was stirred at room temperature for 1 hour. The catalyst was collected by filtration, and washed with 50 ml of water. The filtrate was diluted with 20 ml of ethyl acetate, separated, and the organic layer was further washed with water. The combined aqueous layer was concentrated under reduced pressure to a volume of about 30 ml. The residual concentrate was purified by column chromatography on DIAION HP-20. The fraction containing the aimed product was lyophilized to give 63.5 mg of the title compound.

NMR (D$_2$O) δ (HOD=4.80 ppm): 1.16 (3H, d, J=7.1 Hz), 1.30 (3H, d, J=6.3 Hz), 2.38 (3H, s), 3.40(1H, m), 3.57 (1H, m), 4.28 (1H, m), 4.38 (1H, dd, J$_1$=9.7 Hz, J$_2$=3.0 Hz), 7.50 (1H, s), 9.00 (1H, s). MS(FAB$^+$)-: 348(M$^+$+H).

Example 10

Pivaloyloxymethyl (1S,5R,6S)-6-((1R)-1-hydroxyethyl)-1-methyl-2-(3-methylimidazo[5,1-b]thiazol-2-yl)-1-carbapen-2-em-3-carboxylate To a solution of 29.4 mg of sodium (1S,5R,6S)-6-((1R)-1-hydroxyethyl)-1-methyl-2-(3-methylimidazo[5,1-b]thiazol-2-yl)-1-carbapen-2-em-3-carboxylate in 0.8 ml of dry DMF was added 0.017 ml of iodomethyl pivalate under the atmosphere of argon at −30° C., and the mixture was stirred for 4 hours during which the temperature was raised up to 10° C. The reaction mixture was diluted with 10 ml of ethyl acetate, separated, and the aqueous layer was extracted twice with ethyl acetate, while the organic layer was washed with 10 ml of semi-saturated aqueous saline. The combined organic layer was dried over anhydrous magnesium sulfate, filtered, and concentrated under reduced pressure to a volume of 1 ml. The residue thus obtained was purified by column chromatography on silica gel (chloroform:methanol=20:1) and on Sephadex LH-20 (dichloromethane:methanol=1:1) in this sequence to give 7.9 mg of the title compound.

NMR (CDCl$_3$) δ: 1.02(9H, S), 1.09(3H, d, J=7.4 Hz), 1.29(3H, d, J=6.3 Hz), 3.27–3.34(2H, m), 4.24(1H, m), 4.33(1H, dd, J$_1$=9.7 Hz, J$_2$=2.8 Hz), 5.69(1H, d, J=5.5 Hz), 5.82(1H, d, J=5.5 Hz), 7.02(1H, s), 7.88(1H, s).

Example 11

(1S,5R,6S)-2-(3,6-methylimidazo[5,1-b]thiazolium-2-yl)-6-((1R)-1-hydroxyethyl)-1-methyl-1-carbapen-2-em-3-carboxylate (inner salt)

a) 4-nitrobenzyl (1S,5R,6S)-2-(3,6-dimethylimidazo[5,1-b]thiazolium-2-yl)-6-((1R)-1-hydroxyethyl)-1-methyl-1-carbapen-2-em-3-carboxylate Iodide To a solution of 73.6 mg of 4-nitrobenzyl (1S,5R, 6S)-6-((1R)-1-hydroxyethyl)-1-methyl-2-(3-methylimidazo[5,1-b]thiazol-2-yl)-1-carbapen-2-em-3-carboxylate in 0.5 ml of dry dichloromethane was added 0.95 ml of iodomethane, and the mixture was stirred under the atmosphere of argon in the darkness at room temperature for 18 hours. Unreacted reagent was removed under reduced pressure to give 89.1 mg of 4-nitrobenzyl (1S,5R,6S)-2-(3,6-dimethylimidazo[5,1-b]thiazolium-2-yl)-6-((1R)-1-hydroxyethyl)-1-methyl-1-carbapen-2-em-3-carboxylate iodide.

NMR (CD$_3$OD) δ: 0.99(3H, d, J=7.4 Hz), 1.09(3H, d, J=6.0 Hz), 2.10(3H, s), 3.10(1H, m), 3.92(3H, s), 3.98(1H, m), 4.29(1H, dd, J$_1$=10.5 Hz, J$_2$=3.0 Hz), 5.02(1H, d, J=13.1 Hz), 5.15(1H, d, J=13.1 Hz), 7.34(2H, d, J=8.5 Hz), 7.54 (1H, s), 7.89(2H, d, J=8.5 Hz), 9.26(1H, s).

b) (1S,5R,6S)-2-(3,6-dimethylimidazo[5,1-b]thiazolium-2-yl)-6-((1R)-1-hydroxyethyl)-1-methyl-1-carbapen-2-em-3-carboxylate (inner salt)

To a solution of 89.1 mg of 4-nitrobenzyl (1S,5R,6S)-2-(3,6-dimethylimidazo[5,1-b]thiazolium-2-yl)-6-((1R)-1-hydroxyethyl)-1-methyl-1-carbapen-2-em-3-carboxylate iodide in 2 ml of THF and 2 ml of 1/15 M phosphate buffer (pH 6.8) was added 102.7 mg of 10% Pd-C. The reactor was purged with hydrogen, the reaction mixture was stirred at room temperature for 5 hours. The catalyst was collected by filtration, and washed with water. The filtrate was diluted with 20 ml of ethyl acetate 20 ml, separated, and the organic layer was further washed with water. The combined aqueous layer was concentrated under reduced pressure to a volume of about 30 ml. The concentrate was purified by column chromatography on DIAION HP-20 to give 17.0 mg of the title compound.

NMR (D$_2$O) δ (HOD=4.80 ppm): 1.16(3H, d, J=7.2 Hz), 1.30(3H, d, J=6.3 Hz), 2.37(3H, s), 3.40(1H, m), 3.58(1H, m), 4.09(3H, s), 4.28(1H, m), 4.39(1H, dd, J$_1$=9.8 Hz, J$_2$=2.2 Hz), 7.58(1H, s), 9.22(1H, s).

Example 12

(5R,6S)-6-((1R)-1-hydroxyethyl)-2-(imidazo[5,1-b]thiazol-3-yl)-1-carbapen-2-em-3-carboxylic Acid a) 4-nitrobenzyl (5R,6S)-6-((1R)-1-hydroxyethyl)-2-(imidazo[5,1-b]thiazol-3-yl)-1-carbapen-2-em-3-carboxylate To an ice-cooled solution of 493 mg of 4-nitrobenzyl (3R,5R,6S)-6-((1R)-1-hydroxyethyl)-2-oxo-1-carbapenam-3-carboxylate in 13 ml of dry acetonitrile 13 ml was added dropwise 0.619 ml of N,N-diisopropylethylamine, followed by 0.235 ml of anhydrous trifluoro-methanesulfonic acid under the atmosphere of argon. After the reaction mixture was stirred at the same temperature for 30 minutes, it was diluted with ethyl acetate, and washed with semi-saturated aqueous saline, a mixed solution of semi-saturated aqueous saline and 1 N hydrochloric acid (pH 1.1), a mixed solution of semi-saturated aqueous saline and saturated aqueous sodium hydrogen carbonate (pH 8.9), and semi-saturated aqueous saline in this sequence.-The organic layer was dried over anhydrous magnesium sulfate, filtered, and the solvent was removed under reduced pressure. The residue thus obtained was dissolved in 5 ml of dry N-methylpyrrolidinone, mixed with 40 mg of tri-2-furylphosphine, 384 mg of zinc chloride, 40 mg of tris (dibenzylideneacetone)dipalladium (0), and 950 mg of 3-(tri-n-butylstannyl)imidazo[5,1-b]thiazole in 2 ml of dry N-methyl-pyrrolidinone, and the mixture was stirred under the atmosphere of argon at 50° C. for 1.5 hours. The reaction mixture was diluted with 50 ml of ethyl acetate and 50 ml of semi-saturated aqueous sodium hydrogen carbonate, the insolubles was removed by filtration, and the filtrate was washed with ethyl acetate. The organic layer of the filtrate was separated, dried over anhydrous magnesium sulfate, and the solvent was removed under reduced pressure. The residue thus obtained was purified by column chromatography on silica gel (chloroform:methanol=15:1) to give 303 mg of 4-nitrobenzyl (5R,6S)-6-((1R)-1-hydroxyethyl)-2-(imidazo[5,1-b]thiazol-3-yl)-1-carbapen-2-em-3-carboxylate.

NMR (CDCl$_3$) δ: 1.40(3H, d, J=6.3 Hz), 3.38(3H, m), 4.33(1H, m), 4.44(1H, m), 5.22(1H, d, J=13.2 Hz), 5.36(1H, d, J=13.2 Hz), 7.06(1H, s), 7.09(1H, s), 7.43(2H, d, J=8.9 Hz), 7.75(1H, s), 8.18(2H, d, J=8.9 Hz).

b) (5R,6S)-6-((1R)-1-hydroxyethyl)-2-(imidazo[5,1-b]thiazol-3-yl)-1-carbapen-2-em-3-carboxylic Acid To a solution of 203 mg of 4-nitrobenzyl (5R,6S)-6-((1R)-1-hydroxyethyl)-2-(imidazo[5,1-b]thiazol-3-yl)-1-carbapen-2-em-3-carboxylate in 4 ml of THF and 4 ml of 1/15 M phosphate buffer (pH 6.8) was added 152 mg of 10% Pd-C. The reactor was purged with hydrogen, the reaction mixture was stirred at room temperature for 1 hour. The catalyst was collected by filtration on Celite, and washed with water. The filtrate was washed with ethyl acetate, and then the aqueous layer was purified by column chromatography on DIAION HP-20, followed by crystallization form 1 ml of water to give 32.8 mg of the title compound.

NMR (DMSO-d$_6$) δ: 1.17(3H, d, J=6.3 Hz), 3.20(1H, m), 3.55(2H, m), 3.99(1H, m), 4.28(1H, m), 5.14(1H, m), 7.06 (1H, s), 7.34(1H, s), 7.99(1H, s).

Example 13 pivaloyloxymethyl (5R,6S)-6-((1R)-1-hydroxyethyl)-2-(imidazo[5,1-b]thiazol-3-yl)-1-carbapen-2-em-3-carboxylate To a suspension of 42.1 mg of (5R,6S)-6-((1R)-1-hydroxyethyl)-2-(imidazo[5,1-b]thiazol-3-yl)-1-carbapen-2-em-3-carboxylic acid 10 ml of water was added 1.3 ml of a 0.1 N aqueous sodium hydrogen carbonate solution, and the mixture was stirred at room temperature for 1 hour to form a solution, which was then lyophilized. The lyophilized product was dissolved in 1 ml of dry DMF, 0.034 ml of iodomethyl pivalate was added under the atmosphere of argon at −30° C., and the mixture was stirred for 1.5 hours during which the temperature was raised up to −10° C. The reaction mixture was diluted with 20 ml of ethyl acetate, and washed with semi-saturated aqueous saline. The organic layer was dried over anhydrous magnesium sulfate, filtered, and concentrated under reduced pressure to a volume of 3 ml, The residue thus obtained was purified by column chromatography on silica gel (chloroform:methanol=15:1) and on Sephadex LH-20 (chloroform:methanol=1:1) in this sequence to give 27.2 mg of the title compound.

NMR (CDCl$_3$) δ: 1.19(9H, s), 1.38(3H, d, J=6.2 Hz), 3.37(3H, m), 4.29(1H, m), 4.42(1H, m), 5.78(1H, d, J=5.5 Hz), 5.88(1H, d, J=5.5 Hz), 7.13(2H, s), 7.80(1H, s).

Example 14

(5R,6S)-6-((1R)-1-hydroxyethyl)-2-(6-methylimidazo[5,1-b]thiazolium-3-yl)-1-carbapen-2-em-3-carboxylate (inner salt)

To a suspension of 100 mg of 4-nitrobenzyl (5R, 6S)-6-((1R)-1-hydroxyethyl)-2-(imidazo[5,1-b]thiazol-3-yl)-1-carbapen-2-em-3-carboxylate in 1.5 ml of dry dichloromethane was added 1.37 ml of iodomethane, and the mixture was stirred under the atmosphere of argon in the darkness at room temperature for 24 hours. Unreacted reagent was removed under reduced pressure. The residue thus obtained was dissolved in 4 ml of THF and 4 ml of 1/15 M phosphate buffer (pH 6.8), and 160 mg of 10% Pd-C was added. The reactor was purged with hydrogen, the reaction mixture was stirred at room temperature for 3.5 hours. The catalyst was collected by filtration on Celite and washed with water. The filtrate was washed with ethyl acetate, and purified by column chromatography on DIAION HP-20 and COSMOSEAL 40C18-PREP (water:methanol=20:1) to give 4.8 mg of the title compound.

NMR (D$_2$O) δ (HOD=4.80 ppm): 1.31(3H, d, J=6.5 Hz), 3.25(1H, m), 3.45(1H, m), 3.60(1H, dd, J$_1$=6.0 Hz, J$_2$=3.2 Hz), 4.08(3H, s), 4.28(1H, m), 4.39(1H, m), 7.49(1H, s), 7.62(1H, s), 8.93(1H, s).

Example 15

(5R,6S)-6-((1R)-1-hydroxyethyl)-2-(6-methylimidazo[5,1-b]thiazolium-2-yl)-1-carbapen-2-em-3-carboxylate (inner salt)

a) 4-nitrobenzyl (5R,6S)-6-((1R)-1-hydroxyethyl)-2-(6-methylimidazo[5,1-b]thiazolium-2-yl)-1-carbapen-2-em-3-carboxylate Iodide To 51.6 mg of 4-nitrobenzyl (5R,6S)-6-((1R)-1-hydroxyethyl)-2-(imidazo[5,1-b]thiazol-2-yl)-1-carbapen-2-em-3-carboxylate was added 1.5 ml of iodomethane, and the mixture was stirred under the atmosphere of argon in the darkness at room temperature for 2 days. Unreacted reagent was removed under reduced pressure to give 59.5 mg of 4-nitrobenzyl (5R,6S)-6-((1R)-1-hydroxyethyl)-2-(6-methylimidazo[5,1-b]thiazolium-2-yl)-1-carbapen-2-em-3-carboxylate.

NMR (DMSO-d$_6$) δ: 1.18(3H, d, J=6.2 Hz), 3.45(2H, m), 3.58(1H, dd, J$_1$=5.8 Hz, J$_2$=3.1 Hz), 4.05(1H, m), 4.07(3H, s), 4.31(1H, m), 5.44(1H, d, J=13.5 Hz), 5.55(1H, d, J=13.5 Hz), 7.75(2H, d, J=8.8 Hz), 7.81(1H, s), 8.25(2H, d, J=8.8 Hz), 8.59(1H, s), 9.53(1H, s).

b) (5R,6S)-6-((1R)-1-hydroxyethyl)-2-(6-methylimidazo[5,1-b]thiazolium-2-yl)-1-carbapen-2-em-3-carboxylate (inner salt)

To a solution of 58 mg of 4-nitrobenzyl (5R,6S)-6-((1R)-1-hydroxyethyl)-2-(6-methylimidazo[5,1-b]thiazolium-2-yl)-1-carbapen-2-em-3-carboxylate iodide in 2 ml of THF and 2 ml of 1/15 M phosphate buffer (pH 6.8) was added 68 mg of 10% Pd-C. The reactor was purged with hydrogen, and the reaction mixture was stirred at room temperature for 4 hours. The catalyst was collected by filtration on Celite, and washed with water. The filtrate was washed with ethyl acetate, the aqueous layer was purified by column chromatography on DIAION HP-20 to give 5.4 mg of the title compound.

NMR (D$_2$O) δ (HOD=4.80 ppm): 1.29(3H, d, J=6.5 Hz), 3.31(2H, m), 3.53(1H, dd, J$_1$=5.8 Hz, J$_2$=3.0 Hz), 4.05(3H, s), 4.25(2H, m), 7.47(1H, s), 7.90(1H, s), 9.09(1H, s).

Example 16

(1S,5R,6S)-2-(6-carbamoylmethylimidazo[5,1-b]thiazolium-2 yl)-6-((1R)-1-hydroxyethyl)-1-methyl-1-carbapen-2-em-3-carboxylate (inner salt)

a) 4-nitrobenzyl (1S,5R,6S)-2-(6-carbamoylmethylimidazo[5,1-b]thiazolium-2-yl)-6-((1R)-1-hydroxyethyl)-1-methyl-1-carbapen-2-em-3-carboxylate In the same manner as in Example 88-a) described below, 4-nitrobenzyl (1S,5R,6S)-2-(6-carbamoylmethylimidazo[5,1-b]thiazolium-2-yl)-6-((1R)-1-hydroxyethyl)-1-methyl-1-carbapen-2-em-3-carboxylate iodide was obtained from 64.3 mg of 4-nitrobenzyl (1S,5R,6S)-6-((1R)-1-hydroxyethyl)-2-(imidazo[5,1-b]thiazol-2-yl)-1-methyl-1-carbapen-2-em-3-carboxylate.

NMR (DMSO-d$_6$) δ: 1.18(3H, d, J=6.3 Hz), 1.22(3H, d, J=7.2 Hz), 3.50(1H, dd, J$_1$=5.7 Hz, J$_2$=3.0 Hz), 3.72(1H, m), 4.05(1H, m), 4.38(1H, m), 5.18(2H, s), 5.40(1H, d, J=13.8 Hz), 5.51(1H, d, J=13.8 Hz), 7.59(1H, s), 7.71(2H, d, J=9.0 Hz), 7.83(2H, m), 8.22(2H, d, J=9.0 Hz), 8.64(1H, s), 9.54(1H, s).

b) (1S,5R,6S)-2-(6-carbamoylmethylimidazo[5,1-b]thiazolium-2-yl)-6-((1R)-1-hydroxyethyl)-1-methyl-1-carbapen-2-em-3-carboxylate (inner salt)

In the same manner as in Example 4-b), 58.6 mg of the title compound was obtained from the total amount of 4-nitrobenzyl (1S,5R,6S)-2-(6-carbamoylmethylimidazo[5,1-b]thiazolium-2-yl)-6-((1R)-1-hydroxyethyl)-1-methyl-1-carbapen-2-em-3-carboxylate iodide obtained above.

NMR (D$_2$O) δ (HOD=4.80 ppm): 1.26(3H, d, J=7.2 Hz), 1.31(3H, d, J=6.4 Hz), 3.57(1H, dd, J$_1$=6.1 Hz, J$_2$=2.8 Hz), 3.66(1H, m), 4.28(1H, m), 4.36(1H, dd, J$_1$=9.3 Hz, J$_2$=2.8 Hz), 5.25(2H, s), 7.57(1H, s), 8.13(1H, s), 9.25(1H, s).

Example 17

(1S,5R,6S)-6-((1R)-1-hydroxyethyl)-1-methyl-2-(5-methylimidazo[5,1-b]thiazol-2-yl)-1-carbapen-2-em-3-carboxylic Acid a) 4-nitrobenzyl (1S,5R,6S)-6-((1R)-1-hydroxyethyl)-1-methyl-2-(5-methylimidazo[5,1-b]thiazol-2-yl)-1-carbapen-2-em-3-carboxylate In the same manner as in Example 5-a), 433 mg of 4-nitro-benzyl (1S,5R,6S)-6-((1R)-1-hydroxyethyl)-1-methyl-2-(5-methylimidazo[5,1-b]thiazol-2-yl)-1-carbapen-2-em-3-carboxylate was obtained from 724 mg of 4-nitrobenzyl (1R,3R,5R,6S)-6-((1R)-1-hydroxyethyl)-1-methyl-2-oxo-1-carbapenam-3-carboxylate and 1.04 g of 5-methyl-2-(tri-n-butylstannyl)imidazo[5,1-b]thiazole.

NMR (CDCl$_3$) δ: 1.30(3H, d, J=7.4 Hz), 1.39(3H, d, J=6.3 Hz), 2.59(3H, s), 3.36(1H, dd, J$_1$=6.5 Hz, J$_2$=2.8 Hz), 3.46(1H, m), 4.32(1H, m), 4.37(1H, dd, J$_1$=9.6 Hz, J$_2$=2.8 Hz), 5.27(1H, d, J=13.8 Hz), 5.53(1H, d, J=13.8 Hz), 6.92(1H, s), 7.67(2H, d, J=8.7 Hz), 8.19(1H, s), 8.22(2H, d, J=8.5 Hz).

b) (1S,5R,6S)-6-((1R)-1-hydroxyethyl)-1-methyl-2-(5-methylimidazo[5,1-b]thiazol-2-yl)-1-carbapen-2-em-3-carboxylic Acid In the same manner as Example 5-b), 98.5 mg of the title compound was obtained from 326 mg of 4-nitrobenzyl (1S,5R,6S)-6-((1R)-1-hydroxyethyl)-1-methyl-2-(5-methylimidazo[5,1-b]thiazol-2-yl)-1-carbapen-2-em-3-carboxylate.

NMR (D$_2$O) δ (HOD=4.80 ppm): 1.21(3H, d, J=7.1 Hz), 1.29(3H, d, J=6.4 Hz), 2.77(3H, s), 3.51(1H, dd, J$_1$=6.0 Hz, J$_2$=2.7 Hz), 3.60(1H, m), 4.27(2H, m), 7.25(1H, s), 7.92(1H, s).

Example 18

(1S,5R,6S)-2-(5,6-dimethylimidazo[5,1-b]thiazolium-2-yl)-6-((1R)-1-hydroxyethyl)-1-methyl-1-carbapen-$^2$-em-3-carboxylate (inner salt)

In the same manner as in Example 14 except that purification was carried out by column chromatography on DIAION HP-20, 19.1 mg of the title compound was obtained from 107 mg of 4-nitrobenzyl (1S,5R,6S)-6-((1R)-1-hydroxyethyl)-1-methyl-2-(5-methylimidazo[5,1-b]thiazol-2 yl)-1-carbapen-2-em-3-carboxylate.

NMR (D$_2$O) δ (HOD=4.80 ppm): 1.26(3H, d, J=7.1 Hz), 1.31(3H, d, J=6.4 Hz), 2.78(3H, s), 3.55(1H, dd, J$_1$=6.1 Hz, J$_2$=2.8 Hz), 3.64(1H, m), 3.92(3H, s), 4.28(1H, m), 4.33(1H, dd, J$_1$=9.3 Hz, J$_2$=2.8 Hz), 7.37(1H, s), 7.97(1H, s).

Example 19 pivaloyloxymethyl (1S,5R,6S)-6-((1R)-1-hydroxyethyl)-1-methyl-2-(5-methylimidazo[5,1-b]thiazol-2-yl)-1-carbapen-2-em-3-carboxylate To a solution of 46.8 mg of (1S,5R,6S)-6-((1R)-1-hydroxyethyl)-1-methyl-2-(5-methylimidazo[5,1-b]thiazol-2-yl)-1-carbapen-2-em-3-carboxylic acid 5 ml of water was added 134 ml of a 0.1 N aqueous sodium hydrogen carbonate solution. The mixture was lyophilized, dissolved in 1 ml of DMF, added with 0.034 ml of pivaloyloxymethyl iodide under the atmosphere of argon at −30° C., and stirred at the same temperature for 1.5 hours. The reaction mixture was diluted with 50 ml of ethyl acetate, and washed with 50 ml of semi-saturated aqueous saline. The organic layer was dried over anhydrous magnesium sulfate, filtered, and concentrated under reduced pressure to a volume of 1 ml. The residue thus obtained was purified by column chromatography on silica gel (dichloromethane:methanol=20:1) and on Sephadex LH-20(chloroform:methanol=1:1) in this sequence to give 44.5 mg of the title compound.

NMR (CDCl$_3$) δ: 1.21(9H, s), 1.28(3H, d, J=7.1 Hz), 1.37(3H, d, J=6.3 Hz), 2.63(3H, s), 3.32(1H, dd, J$_1$=6.7 Hz, J$_2$=2.8 Hz), 3.44(1H, m), 4.31(2H, m), 5.87(1H, d, J=5.6 Hz), 5.99(1H, d, J=5.6 Hz), 6.92(1H, s), 8.16(1H, s).

Example 20

(1S,5R,6S)-2-(7-chloroimidazo[5,1-b]thiazol-2-yl)-6-((1R)-1-hydroxyethyl)-1-methyl-1-carbapen-2-em-3-carboxylic Acid a) 4-nitrobenzyl (1S,5R,6S)-2-(7-chloroimidazo[5,1-b]thiazol-2-yl)-6-((1R)-1-hydroxyethyl)-1-methyl-1-carbapen-2-em-3-carboxylate In the same manner as in Example 5-a), 183 mg of 4-nitrobenzyl(1S,5R,6S)-2-(7-chloroimidazo[5,1-b]thiazol-2-yl)-6-((1R)-1-hydroxyethyl)-1-methyl-1-carbapen-2-em-3-carboxylate was obtained from 724 mg of 4-nitrobenzyl (1R,3R,5R,6S)-6-((1R)-1-hydroxyethyl)-1-methyl-2-oxo-1-carbapenam-3-carboxylate and 1.07 g of 7-chloro-2-(tri-n-butylstannyl)imidazo[5,1-b]thiazole.

NMR (CDCl$_3$) δ: 1.31(3H, d, J=7.4 Hz), 1.40(3H, d, J=6.3 Hz), 3.37(1H, dd, J$_1$=6.5 Hz, J$_2$=2.7 Hz), 3.46(1H, m), 4.35(2H, m), 5.28(1H, d, J=13.5 Hz), 5.52(1H, d, J=13.5 Hz), 7.68(2H, d, J=8.9 Hz), 7.89(1H, s), 8.24(2H, d, J=8.9 Hz)), 8.27(1H, s).

b) (1S,5R,6S)-2-(7-chloroimidazo[5,1-b]thiazol-2-yl)-6-((1R)-1-hydroxyethyl)-1-methyl-1-carbapen-2-em-3-carboxylic Acid In the same manner as in Example 5-b), 8.2 mg of the title compound was obtained from 134 mg of 4-nitrobenzyl (1S,5R,6S)-2-(7-chloroimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.22(3H, d, J=7.1 Hz), 1.32(3H, d, J=6.3 Hz), 3.53(2H, m), 4.29(2H, m), 7.81(1H, s), 7.98(1H, s).

Example 21

(1S,5R,6S)-6-((1R)-1-hydroxyethyl)-1-methyl-2-(2-methylimidazo[5,1-b]thiazol-3-yl)-1-carbapen-2-em-3-carboxylic Acid a) 4-nitrobenzyl (1S,5R,6S)-6-((1R)-1-hydroxyethyl)-1-methyl-2-(2-methylimidazo[5,1-b]thiazol-3-yl)-1-carbapen-2-em-3-carboxylate In the same manner as in Example 5-a), 40.4 mg of 4-nitrobenzyl (1S,5R,6S)-6-((1R)-1-hydroxyethyl)-1-methyl-2-(2-methylimidazo[5,1-b]thiazol-3-yl)-1-carbapen-2-em-3-carboxylate from 190 mg of 4-nitrobenzyl (1R,3R,5R,6S)-6-((1R)-1-hydroxyethyl)-1-methyl-2-oxo-1-carbapenam-3-carboxylate and 272 mg of 2-methyl-3-(tri-n-butylstannyl)imidazo[5,1-b]thiazole.

NMR (DMSO-d$_6$) δ: 1.00(3H, m), 1.17(3H, d, J=6.1 Hz), 2.14(3H, s), 3.56(1H, m), 3.78(1H, m), 4.06(1H, m), 4.55 (1H, m), 5.10–5.40(3H, m), 7.00(1H, m), 7.50–7.70(2H, m), 8.12–8.28(3H, m).

b) (1S,5R,6S)-6-((1R)-1-hydroxyethyl)-1-methyl-2-(2-methylimidazo[5,1-b]thiazol-3-yl)-1-carbapen-2-em-3-carboxylic Acid In the same manner as in Example 5-b), 11.9 mg of the title compound was obtained from 40.4 mgo of 4-nitrobenzyl (1S,5R,6S)-6-((1R)-1-hydroxyethyl)-1-methyl-2-(2-methylimidazo[5,1-b]thiazol-3-yl)-1-carbapen-2-em-3-carboxylate.

NMR (D$_2$O) δ (HOD=4.80 ppm): 1.06(3H, d, J=7.1 Hz), 1.32(3H, d, J=6.4 Hz), 2.42(3H, s), 3.62(2H, m), 4.31(1H, m), 4.46(1H, dd, J$_1$=9.9 Hz, J$_2$=2.8 Hz), 7.52(1H, s), 8.98 (1H, s).

Example 22

(5R,6S)-6-((1R)-1-hydroxyethyl)-2-(2-methylimidazo[5,1-b]thiazol-3-yl)-1-carbapen-2-em-3-carboxylic Acid a) 4-nitrobenzyl (5R,6S)-6-((1R)-1-hydroxyethyl)-2-(2-methylimidazo[5,1-b]thiazol-3-yl)-1-carbapen-2-em-3-carboxylate In the same manner as in Example 5-a), 123 mg of 4-nitrobenzyl (5R,6S)-6-((1R)-1-hydroxyethyl)-2-(2-methylimidazo[5,1-b]thiazol-3-yl)-1-carbapen-2-em-3-carboxylate was obtained from 270 mg of 4-nitrobenzyl (3R,5R,6S)-6-((1R)-1-hydroxyethyl)-2-oxo-1-carbapenam-3-carboxylate and 406 mg of 2-methyl-3-(tri-n-butyl-stannyl)imidazo[5,1-b]thiazole.

NMR (CDCl$_3$) δ: 1.37(3H, d, J=6.2 Hz), 2.18(3H, s), 3.27(2H, br.s), 3.44(1H, dd, J$_1$=5.7 Hz, J$_2$=2.5 Hz), 4.31(1H, m), 4.51(1H, m), 5.15(1H, d, J=13.4 Hz), 5.30(1H, d, J=13.4 Hz), 6.99(1H, s), 7.33(2H, d, J=8.7 Hz), 7.78(1H, s), 8.11 (2H, d, J=8.7 Hz).

b) (5R,6S)-6-((1R)-1-hydroxyethyl)-2-(2-methylimidazo[5,1-b]thiazol-3-yl)-1-carbapen-2-em-3-carboxylic Acid In the same manner as in Example 5-b), 12.9 mg of the title compound was obtained from 73 mg of 4-nitrobenzyl (5R,6S)-6-((1R)-1-hydroxyethyl)-2-(2-methylimidazo[5,1-b]thiazol-3-yl)-1-carbapen-2-em-3-carboxylate.

NMR (D$_2$O) δ (HOD=4.80 ppm): 1.30(3H, d, J=6.4 Hz), 2.36(3H, s), 3.14(1H, dd, J$_1$=17.7 Hz, J$_2$=10.1 Hz), 3.38(1H, dd, J$_1$=17.7 Hz, J$_2$=8.6 Hz), 3.61(1H, dd, J$_1$=5.9 Hz, J$_2$=2.9 Hz), 4.28(1H, m), 4.42(1H, m), 7.47(1H, s), 8.80(1H, s).

Example 23

(1S,5R,6S)-2-(7-chloro-6-methylimidazo[5,1-b] thiazolium-2-yl)-6-((1R)-1-hydroxyethyl)-1-methyl-1-carbapen-2-em-3-carboxylate (inner salt)

a) 4-nitrobenzyl (1S,5R,6S)-2-(7-chloro-6-methylimidazo [5,1-b]thiazolium-2-yl)-6-((1R)- 1-hydroxyethyl)-1-methyl-1-carbapen-2-em-3-carboxylate Iodide In the same manner as in Example 4-a) except that the reaction was carried out for 4 days, 4-nitrobenzyl (1S,5R,6S)-2-(7-chloro-6-methylimidazo[5,1-b]thiazolium-2-yl)-6-((1R)-1-hydroxyethyl)-1-methyl-1-carbapen-2-em-3-carboxylate iodide was obtained from 49 mg of 4-nitrobenzyl (1S,5R,6S)-2-(7-chloroimidazo[5,1-b]thiazol-2-yl)-6-((1R)-1-hydroxyethyl)-1-methyl-1-carbapen-2-em-3-carboxylate.

NMR (DMSO-d$_6$) δ: 1.18(3H, d, J=6.2 Hz), 1.22(3H, d, J=7.4 Hz), 3.50(1H, dd, J$_1$=5.9 Hz, J$_2$=2.8 Hz), 3.25(1H, m), 4.01(3H, s), 4.03(1H, m), 4.40(1H, dd, J$_1$=10.3 Hz, J$_2$=2.8 Hz), 5.41(1H, d, J=13.9 Hz), 5.53(1H, d, J=13.9 Hz), 7.74(2H, d, J=8.9 Hz), 8.24(2H, d, J=8.9 Hz), 8.71(1H, s), 9.69(1H, s).

b) (1S,5R,6S)-2-(7-chloro-6-methylimidazo[5,1-b] thiazolium-2-yl)-6-((1R)-1-hydroxyethyl)-1-methyl-1-carbapen-2-em-3-carboxylate (inner salt)

In the same manner as in Example 4-b), 12.1 mg of the title compound was obtained from the whole amount of 4-nitrobenzyl (1S,5R,6S)-2-(7-chloro-6-methyliazo[5,1-b]thiazolium-2-yl)-6-((1R)-1-hydroxyethyl)-1-methyl-1-carbapen-2-em-3-carboxylate iodide obtained above.

NMR (D$_2$O) δ (HOD=4.80 ppm): 1.24(3H, d, J=7.1 Hz), 1.31(3H, d, J=6.4 Hz), 3.54(1H, dd, J$_1$=6.1 Hz, J$_2$=2.9 Hz), 3.63(1H, m), 4.01(3H, s), 4.27(1H, m), 4.32(1H, dd, J$_1$=9.4 Hz, J$_2$=2.9 Hz), 8.11(1H, s), 9.26(1H, s).

Example 24

Pivaloyloxymethyl (5R,6S)-6-((1R)-1-hydroxyethyl)-2-(imidazo[5,1-b]thiazol-2-yl)-1-carbapen-2-em-3-carboxylate In the same manner as in Example 19, 14.6 mg of the title compound was obtained from 30.6 mg of (5R,6S)-6-((1R)-1-hydroxyethyl)-2-(imidazo[5,1-b]thiazol-2-yl)-1-carbapen-2-em-3-carboxylic acid.

NMR (CDCl$_3$) δ: 1.23(9H, s), 1.37(3H, d, J=6.2 Hz), 3.30(3H, m), 4.30(2H, m), 5.91(1H, d, J=5.5 Hz), 6.01(1H, d, J=5.5 Hz), 7.07(1H, s), 8.05(1H, s), 8.31(1H, s).

Example 25

(5R,6S)-6-((1R)-1-hydroxyethyl)-2-(5-methylimidazo[5,1-b]thiazol-2-yl)-1-carbapen-2-em-3-carboxylic Acid a) 4-nitrobenzyl (5R,6S)-6-((1R)-1-hydroxyethyl)-2-(5-methylimidazo[5,1-b]thiazol-2-yl)-1-carbapen-2-em-3-carboxylate In the same manner as in Example 5-a), 218 mg of 4-nitrobenzyl (5R,6S)-6-((1R)-1-hydroxyethyl)-2-(5-methylimidazo[5,1-b]thiazol-2-yl)-1-carbapen-2-em-3-carboxylate was obtained from 730 mg of 4-nitrobenzyl (3R,5R,6S)-6-((1R)-1-hydroxyethyl)-2-oxo-1-carbapenam-3-carboxylate and 730 mg of 5-methyl-2-(tri-n-butylstannyl)imidazo[5,1-b]thiazole.

NMR (CDCl$_3$) δ: 1.40(3H, d, J=6.4 Hz), 2.59(3H, s), 3.32(3H, m), 4.32(2H, m), 5.31(1H, d, J=13.8 Hz), 5.56(1H, d, J=13.8 Hz), 6.91(1H, s), 7.70(2H, d, J=8.9 Hz), 8.11(1H, s), 8.25(2H, d, J=8.9 Hz).

b) (5R,6S)-6-((1R)-1-hydroxyethyl)-2-(5-methylimidazo[5,1-b]thiazol-2-yl)-1-carbapen-2-em-3-carboxylic Acid In the same manner as in Example 5-b), 46.5 mg of the title compound was obtained from 161 mg of 4-nitrobenzyl (5R,6S)-6-((1R)-1-hydroxyethyl)-2-(5-methylimidazo[5,1-b]thiazol-2-yl)-1-carbapen-2-em-3-carboxylate.

NMR (D$_2$O) δ (HOD=4.80 ppm): 1.30(3H, d, J=6.4 Hz), 2.72(3H, s), 3.23(2H, m), 3.50(1H, dd, J$_1$=5.8 Hz, J$_2$=3.0 Hz), 4.24(2H, m), 7.23(1H, s), 7.72(1H, s).

Example 26

Pivaloyloxymethyl (5R,6S)-6-((1R)-1-hydroxyethyl)-2-(5-methylimidazo[5,1-b]thiazol-2-yl)-1-carbapen-2-em-3-carboxylate In the same manner as in Example 19, 20.0 mg of the title compound was obtained from 40.2 mg of (5R,6S)-6-((1R)-1-hydroxyethyl)-2-(5-methylimidazo[5,1-b]thiazol-2-yl)-1-carbapen-2-em-3-carboxylic acid.

NMR (CDCl$_3$) δ: 1.23(9H, s), 1.36(3H, d, J=6.2 Hz), 2.61(3H, s), 3.26(1H, dd, J$_1$=6.6 Hz, J$_2$=2.8 Hz), 3.33(2H, m), 4.30(2H, m), 5.90(1H, d, J=5.5 Hz), 6.01(1H, d, J=5.5 Hz), 6.91(1H, s), 8.12(1H, s).

Example 27

Sodium (1S,5R,6S)-6-((1R)-1-hydroxyethyl)-1-methyl-2-(7-methylimidazo[5,1-b]thiazol-2-yl)-1-carbapen-2-em-3-carboxylate a) 4-nitrobenzyl (1S,5R,6S)-6-((1R)-1-hydroxyethyl)-1-methyl-2-(7-methylimidazo[5,1-b]thiazol-2-yl)-1-carbapen-2-em-3-carboxylate In the same manner as in Example 5-a), 110 mg of 4-nitro-benzyl (1S,5R,6S)-6-((1R)-1-hydroxyethyl)-1-methyl-2-(7-methylimidazo[5,1-b]thiazol-2-yl)-1-carbapen-2-em-3-carboxylate was prepared as a yellow solid from 725 mg 4-nitrobenzyl (1R,3R,5R,6S)-6-((1R)-1-hydroxyethyl)-1-methyl-2-oxo-1-carbapen-2-em-3-carboxyate and 1.04 g of 7-methyl-2-(tri-n-butylstannyl)imidazo[5,1-b]thiazole.

NMR (CDCl$_3$) δ: 1.30(3H, d, J=7.2 Hz), 1.40(3H, d, J=6.2 Hz), 2.34(3H, s), 3.34–3.49(2H, m), 4.28–4.39(2H, m), 5.27(1H, d, J=13.7 Hz), 5.52(1H, d, J=13.7 Hz), 7.67(2H, d, J=6.9 Hz), 7.95(1H, s), 8.23(2H, d, J=6.9 Hz), 8.24(1H, s). MS (TSP): 483 (M$^+$+H).

b) Sodium (1S,5R,6S)-6-((1R)-1-hydroxyethyl)-1-methyl-2-(7-methylimidazo[5,1-b]thiazol-2-yl)-1-carbapen-2-em-3-carboxylate 1.5 mg of the title compound was obtained in the same manner as in Example 134-d) described below except that the reaction was carried out with 90 mg of 4-nitrobenzyl (1S,5R,6S)-6-((1R)-1-hydroxyethyl)-1-methyl-2-(7-methylimidazo[5,1-b]thiazol-2-yl)-1-carbapen-2-em-3-carboxylate, and purification was carried out with CHP-20P (3% THF in water).

NMR (D$_2$O) δ (HOD=4.80 ppm): 1.24(3H, d, J=7.1 Hz), 1.31(3H, d, 6.3 Hz), 2.34(3H, s), 3.48–3.59(2H, m), 4.21–4.32(2H, m), 7.78(1H, s), 8.01(1H, s). MS(FAB$^+$): 392 (M$^+$+Na), 370 (M$^+$+H).

Example 28

Pivaloyloxymethyl (1S,5R,6S)-6-((1R)-1-hydroxyethyl)-1-methyl-2-(7-methylimidazo[5,1-b]thiazol-2-yl)-1-carbapen-2-em-3-carboxylate In the same manner as in Example 135 described below, 28 mg of the title compound was obtained from 42.8 mg of sodium (1S,5R,6S)-6-((1R)-1-hydroxyethyl)-1-methyl-2-(7-methylimidazo[5,1-b]thiazol-2-yl)-1-carbapen-2-em-3-carboxylate.

NMR (CDCl$_3$) δ: 1.21(9H, s), 1.29(3H, d, J=7.4 Hz), 1.37(3H, d, J=6.2 Hz), 2.34(3H, s), 3.32(1H, dd, J$_1$=7.0 Hz, J$_2$=2.9 Hz), 3.40–3.48(1H, m), 4.25–4.35(2H, m), 5.88(1H, d, J=5.6 Hz), 5.99(1H, d, J=5.6 Hz), 7.96(1H, s), 8.25(1H, s). MS (TSP): 462 (M$^+$+H).

Example 29

(1S,5R,6S)-2-(6,7-dimethylimidazo[5,1-b]thiazolium-2-yl)-6-((1R)-1-hydroxyethyl)-1-methyl-1-carbapen-2-em-3-carboxylate (inner salt)

a) 4-nitrobenzyl (1S,5R,6S)-2-(6,7-dimethylimidazo[5,1-b]thiazolium-2-yl)-6-((1R)-1-hydroxyethyl)-1-methyl-1-carbapen-2-em-3-carboxylate Iodide In the same manner as in Example 4-a), 18.8 mg of 4-nitrobenzyl (1S,5R,6S)-2-(6,7-dimethylimidazo[5,1-b]thiazolium-2-yl)-6-((1R)-1-hydroxyethyl)-1-methyl-1-carbapen-2-em-3-carboxylate iodide was obtained as a yellowish orange oil by using 18.5 mg of 4-nitrobenzyl (1S,5R,6S)-6-((1R)-1-hydroxyethyl)-1-methyl-2-(7-methylimidazo[5,1-b]thiazol-2-yl)-1-carbapen-2-em-3-carboxylate and 0.5 ml of methyl iodide.

NMR (Acetone-d$_6$) δ: 1.31(3H, d, J=6.3 Hz), 1.36(3H, d, J=7.2 Hz), 2.63(3H, s), 3.55(1H, dd, J$_1$=6.3 Hz, J$_2$=3.0 Hz), 3.82–3.92(1H, m), 4.22(3H, s), 4.35–4.45(1H, br.s), 4.55 (1H, dd, J$_1$=9.9 Hz, J$_2$=3.0 Hz), 5.44(1H, d, J=13.8 Hz), 5.62(1H, d, J=13.8 Hz), 7.83(2H, d, J=6.9 Hz), 8, 25(2H, d, J=6.9 Hz), 9.01(1H, s), 9.85(1H, s). MS (TSI): 497 (M$^+$).

b) (1S,5R,6S)-2-(6,7-dimethylimidazo[5,1-b]thiazolium-2-yl)-6-((1R)-1-hydroxyethyl)-1-methyl-1-carbapen-2-em-3-carboxylate (inner salt)

In the same manner as in Example 4-b) except that 18.8 mg of 4-nitrobenzyl (1S,5R,6S)-2-(6,7-dimethylimidazo[5,1-b]thiazolium-2-yl)-6-((1R)-1-hydroxyethyl)-1-methyl-1-carbapen-2-em-3-carboxylate iodide was used and purification was carried out on CHP-20P (2% THF in water), 9.3 mg of the title compound was obtained as a yellow amorphous product.

NMR (D$_2$O) δ (HOD=4.80 ppm): 1.25(3H, d, J=7.1 Hz), 1.31(3H, d, 6.3 Hz), 2.41(3H, s), 3.53–3.65(2H, m), 3.93 (3H, s), 4.22–4.36(2H, m), 8.01(1H, s), 9.05(0.5H, s, partially exchanged with D$_2$O). MS (FAB$^+$): 362 (M$^+$+H).

Example 30

(5R,6S-dimethylimidazo[5,1-b]thiazolium-2-yl)-6-((1R)-1-hydroxyethyl)-1-carbapen-2-em-3-carboxylate (inner salt)

a) 4-nitrobenzyl (5R,6S)-2-(5,6-dimethylimidazo[5,1-b]thiazolium-2-yl)-6-((1R)-1-hydroxyethyl)-1-carbapen-2-em3-carboxylate Iodide In the same manner as in Example 4-a) except that the reaction was carried out for 3 days, 4-nitrobenzyl (5R,6S)-2-(5,6-dimethylimidazo[5,1-b]thiazolium-2-yl)-6-((1R)-1- hydroxyethyl)-1-carbapen-2-em-3-carboxylate iodide was obtained from 57 mg of 4-nitrobenzyl (5R,6S)-6-((1R)-1-hydroxyethyl)-2-(5-methylimidazo[5,1-b]thiazol-2-yl)-1-carbapen-2-em-3-carboxylic acid.

NMR (DMSO-$d_6$) δ: 1.17(3H, d, J=6.2 Hz), 2.82(3H, s), 3.48(2H, m), 3.59(1H, dd, $J_1$=5.5 Hz, $J_2$=3.1 Hz), 3.92(3H, s), 4.04(1H, m), 4.33(1H, m), 5.44(1H, d, J=13.7 Hz), 5.55(1H, d, J=13.7 Hz), 7.71(1H, s), 7.76(2H, d, J=8.8 Hz), 8.25(2H, d, J=8.8 Hz), 8.58(1H, s).

b) (5R,6S)-2-(5,6-dimethylimidazo[5,1-b]thiazolium-2-yl)-6-((1R)-1-hydroxyethyl)-1-carbapen-2-em-3-carboxylate (inner salt)

In the same manner as in Example 4-b), 14.2 mg of the title compound was obtained from the whole amount of 4-nitrobenzyl (5R,6S)-2-(5,6-dimethylimidazo[5,1-b]thiazolium-2-yl)-6-((1R)-1-hydroxyethyl)-1-carbapen-2-em-3-carboxylate iodide obtained above.

NMR ($D_2O$) δ (HOD=4.80 ppm): 1.31(3H, d, J=6.4 Hz), 2.77(3H, s), 3.32(2H, m), 3.55(1H, dd, $J_1$=6.2 Hz, $J_2$=3.0 Hz), 3.91(3H, s), 4.28(2H, m), 7.37(1H, s), 7.83(1H, s).

Example 31

(1S,5R,6S)-2-(5-formylaminomethyl imidazo[5,1-b]thiazol-2-yl)-6-((1R)-1-hydroxyethyl)-1-methyl-1-carbapen-2-em-3-carboxylic Acid a) 4-nitrobenzyl (1S,5R,6S)-2-(5-formylaminomethyl imidazo[5,1-b]thiazol-2-yl)-6-((1R)-1-hydroxyethyl)-1-methyl-1-carbapen-2-em-3-carboxylate In the same manner as in Example 5-a), 40.4 mg of 4-nitrobenzyl(1S,5R,6S)-2-(5-formylaminomethyl imidazo[5,1-b]thiazol-2-yl)-6-((1R)-1-hydroxyethyl)-1-methyl-1-carbapen-2-em-3-carboxylate was obtained from 305 mg of 4-nitrobenzyl (1R,3R,5R,6S)-6-((1R)-1-hydroxyethyl)-1-methyl-2-oxo-1-carbapenam-3-carboxylate and 473 mg of 5-formylaminomethyl-2-(tri-n-butylstannyl)imidazo[5,1-b]thiazole.

NMR (CDCl$_3$) δ: 1.33(3H, d, J=7.2 Hz), 1.38(3H, d, J=6.3 Hz), 3.37(1H, dd, $J_1$=6.1 Hz, $J_2$=2.8 Hz), 3.57(1H, m), 4.34(2H, m), 4.73(2H, d, J=6.3 Hz), 5.29(1H, d, J=13.7 Hz), 5.53(1H, d, J=13.7 Hz), 6.94(1H, s), 6.96(1H, br.s), 7.66(2H, d, J=8.8 Hz), 8.21(2H, d, J=8.8 Hz), 8.26(1H, s), 8.33(1H, s).

b) (1S,5R,6S)-2-(5-formylaminomethyl imidazo[5,1-b]thiazol-2-yl)-6-((1R)-1-hydroxyethyl)-1-methyl-1-carbapen-2-em-3-carboxylic Acid In the same manner as in Example 5-b), 44.3 mg of the title compound. was obtained from 160 mg of 4-nitrobenzyl (1S,5R,6S)-2-(5-formylaminomethyl imidazo[5,1-b]thiazol-2-yl)-6-((1R)-1-hydroxyethyl)-1-methyl-1-carbapen-2-em-3-carboxylate.

NMR ($D_2O$) δ (HOD=4.80 ppm): 1.25(3H, d, J=7.2 Hz), 1.31(3H, d, J=6.4 Hz), 3.55(1H, dd, $J_1$=6.0 Hz, $J_2$=2.7 Hz), 3.64(1H, m), 4.27(1H, m), 4.34(1H, dd, $J_1$=9.3 Hz, $J_2$=2.7 Hz), 4.92(2H, d, J=2.7 Hz), 7.37(1H, s), 8.07(1H, s), 8.25(1H, s).

Example 32

Pivaloylmethy (1S,5R,6S)-2-(5formylaminomethyl imidazo[5,1-b]thiazol-2-yl)-6-((1R)-1-hydroxyethyl)-1-methyl-1-carbapen-2-em-3-carboxylate In the same manner as in Example 19, 31.2 mg of the title compound was obtained from 34.7 mg of (1S,5R,6S)-2-(5-formylamino-methylimidazo[5,1-b]thiazol-2-yl)-6-((1R)-1-hydroxyethyl)-1-methyl-1-carbapen-2-em-3-carboxylic acid.

NMR (CDCl$_3$) δ: 1.19(9H, s), 1.31(3H, d, J=7.3 Hz), 1.35(3H, d, J=6.2 Hz), 3.34(1H, dd, $J_1$=6.0 Hz, $J_2$=2.9 Hz), 3.56(1H, m), 4.32(2H, m), 4.77(2H, m), 5.86(1H, d, J=5.6 Hz), 5.97(1H, d, J=5.6 Hz), 6.94(1H, s), 7.08(1H, br.s), 8.26(1H, s), 8.28(1H, s).

Example 33

(1S,5R,6S)-2-(5-formylaminomethyl-6-methylimidazo[5,1-b]thiazolium-2-yl)-6-((1R)-1-hydroxyethyl)-1-methyl-1-carbapen-2-em-3-carboxylate (inner salt)

a) 4-nitrobenzyl (1S,5R,6S)-2-(5-formylaminomethyl-6-methylimidazo[5,1-b]thiazolium-2-yl)-6-((1R)-1-hydroxyethyl)-1-methyl-1-carbapen-2-em-3-carboxylate Iodide In the same manner as in Example 4-a), 4-nitrobenzyl (1S,5R,6S)-2-(5-formylaminomethyl-6-methylimidazo[5,1-b]thiazolium-2-yl)-6-((1R)-1-hydroxyethyl)-1-methyl-1-carbapen-2-em-3-carboxylate iodide was obtained from 50.4 mg of 4-nitrobenzyl (1S,5R,6S)-2-(5-formylaminomethyl imidazo[5,1-b]thiazol-2-yl)-6-((1R)-1-hydroxyethyl)-1-methyl-1-carbapen-2-em-3-carboxylate.

NMR (DMSO-$d_6$) δ: 1.18(3H, d, J=6.1 Hz), 1.26(3H, d, J=7.1 Hz), 3.50(1H, dd, $J_1$=5.2 Hz, $J_2$=3.0 Hz), 3.76(1H, m), 4.05(3H, s), 4.07(1H, m), 4.41(1H, dd, $J_1$=10.0 Hz, $J_2$=3.0 Hz), 4.88(2H, m), 5.19(1H, d, J=4.9 Hz), 5.41(1H, d, J=13.8 Hz), 5.52(1H, d, J=13.8 Hz), 7.73(2H, d, J=8.9 Hz), 7.79(iH, s), 8.14(1H, s), 8.22(2H, d, J=8.9 Hz), 8.64(1H, s), 8.83(1H, m).

b) (1S,5R,6S)-2-(5-formylaminomethyl-6-methylimidazo[5,1-b]thiazolium-2-yl)-6-((1R)-1-hydroxyethyl)-1-methyl-1-carbapen-2-em-3-carboxylate (inner salt)

In the same manner as in Example 4-b), 22.2 mg of the title compound was obtained from the whole amount of 4-nitrobenzyl (1S,5R,6S)-2-(5-formylaminomethyl-6-methylimidazo[5,1-b]thiazolium-2-yl)-6-((1R)-1-hydroxyethyl)-1-methyl-1-carbapen-2-em-3-carboxylate iodide.

NMR ($D_2O$) δ (HOD=4.80 ppm): 1.28(3H, d, J=7.2 Hz), 1.31(3H, d, J=6.4 Hz), 3.56(1H, m), 3.67(1H, m). 4.05(3H, s), 4.28(1H, m), 4.34(1H, m), 4.95(2H, d, J=3.8 Hz), 7.50(1H, s), 8.16(1H, s), 8.20(1H, s).

Example 34

(1S,5R,6S)-6-((1R)-1-hydroxyethyl)-2-(5-hydroxymethylimidazo[5,1-b]thiazol-2-yl)-1-methyl-1-carbapen-2-em-3-carboxylic Acid a) 4-nitrobenzyl (1S,5R,6S)-2-(5-t-butyldimethylsilyloxymethylimidazo[5,1-b]thiazol-2-yl)-6-((1R)-1-hydroxyethyl)-1-methyl-1-carbapen-2-em-3-carboxylate In the same manner as in Example 5-a), 799 mg of 4-nitrobenzyl (1S,5R,6)-2-(5-t-butyldimethylsilyloxymethylimidazo[5,1-b]thiazol-2-yl)-6-((1R)-1-hydroxyethyl)-1-methyl-1-carbapen-2-em-3-carboxylate was obtained from 724 mg of 4-nitrobenzyl (1R,3R,5R,6S)-6-((1R)-1-hydroxyethyl)-1-methyl-2-oxo-1-carbapenam-3-carboxylate and 1.34 g of 5-(t-butyldimethylsilyloxy) methyl-2-(tri-n-butylstannyl) imidazo[5,1-b]thiazole.

NMR (CDCl$_3$) δ: 0.08(3H, s), 0.09(3H, s), 0.89(9H, s), 1.31(3H, d, J=7.4 Hz), 1.40(3H, d, J=6.3 Hz), 3.36(1H, dd, $J_1$=6.6 Hz, $J_2$=2.7 Hz), 3.49(1H, m), 4.34(2H, m), 4.97(2H, s), 5.26(1H, d, J=13.7 Hz), 5.51(1H, d, J=13.7 Hz), 6.94(1H, s), 7.67(2H, d, J=8.8 Hz), 8.23(2H, d, J=8.8 Hz), 8.35(1H, s).

b) 4-nitrobenzyl (1S,5R,6S)-6-((1R)-1-hydroxyethyl)-2-(5-hydroxymethylimidazo[5,1-b]thiazol-2-yl)-1-methyl-1-carbapen-2-em-3-carboxylate To a solution of 799 mg of 4-nitrobenzyl (1S,5R,6S)-2-(5-t-butyldimethylsilyloxymethylimidazo[5,1-b]thiazol-2-yl)-6-((1R)-1-hydroxyethyl)-1-methyl-1-carbapen-2-em-3-carboxylate in 20 ml of THF were added 1.1 ml of acetic acid and 6.5 ml of 1 M solution of tetra-n-butylammonium fluoride in THF under the atmosphere of argon, and the mixture was stirred at room temperature for 30 minutes. The reaction mixture was concentrated under reduced pressure, and diluted with 100 ml of ethyl acetate, 100 ml of aqueous saline and a saturated aqueous sodium hydrogen carbonate solution to adjust pH to 7.8. The organic layer was separated, washed with aqueous saline, dried over anhydrous magnesium sulfate, and the solvent was removed under reduced pressure. The residue thus obtained was purified by column chromatography on Sephadex LH-20 (chloroform:methanol=1:1) to give 619 mg of 4-nitrobenzyl (1S,5R,6S)-6-((1R)-1-hydroxyethyl)-2-(5-hydroxymethylimidazo[5,1-b]thiazol-2-yl)-1-methyl-1-carbapen-2-em-3-carboxylate.

NMR (DMSO-$d_6$) δ: 1.19(3H, d, J=6.3 Hz), 2.23(3H, d, J=7.2 Hz), 3.40(1H, dd, J1=5.8 Hz, J2=2.7 Hz), 3.69(1H, m), 4.04(1H, m), 4.33(1H, dd, J1=9.7 Hz, J2=2.8 Hz), 4.68(2H, d, J=5.8 Hz), 5.14(1H, d, J=5.2 Hz), 5.38(1H, d, J=14.3 Hz), 5.49(1H, t, J=5.8 Hz), 5.51(1H, d, J=14.3 Hz), 6.92(1H, s), 7.73(2H, d, J=8.5 Hz), 8.21(2H, d, J=8.5 Hz), 8.36(1H, s).

c) (1S,5R,6S)-6-((1R)-1-hydroxyethyl)-2-(5-hydroxymethylimidazo[5,1-b]thiazol-2-yl)-1-methyl-1-carbapen-2-em-3-carboxylic Acid In the same manner as in Example 5-b), 57.8 mg of the title compound was obtained from 200 mg of 4-nitrobenzyl (1S,5R,6S)-6-((1R)-1-hydroxyethyl)-2-(5-hydroxymethylimidazo[5,1-b]thiazol-2-yl)-1-methyl-1-carbapen-2-em-3-carboxylate.

NMR ($D_2O$) δ (HOD=4.80 ppm): 1.26(3H, $d_7$ J=7.6 Hz), 1.32(3H, d, J=6.1 Hz), 3.54(1H, m), 3.63(1H, m), 4.30(2H, m), 4.97(2H, m), 7.18(1H, s), 7.98(1H, s).

Example 35

Pivaloyloxymethyl (1S,5R,6S)-6-((1R)-1-hydroxyethyl)-2-(5-hydroxymethylimidazo[5,1-b]thiazol-2-yl)-1-methyl-1-carbapen-2-em-3-carboxylate In the same manner as in Example 19, 20.3 mg of the title compound was obtained from 39.6 mg of (1S,5R,6S)-6-((1R)-1-hydroxyethyl)-2-(5-hydroxymethylimidazo[5,1-b]thiazol-2-yl)-1-methyl-1-carbapen-2-em-3-carboxylic acid.

NMR (CDCl$_3$) δ: 1.18(9H, s), 1.28(3H, d, J=7.4 Hz), 1.36(3H, d, J=6.3 Hz), 3.33(1H, dd, J$_1$=6.5 Hz, J$_2$=2.7 Hz), 3.47(1H, m), 4.31(2H, m), 4.95(2H, s), 5.87(1H, d, J=5.6 Hz), 5.97(1H, d, J=5.6 Hz), 6.96(1H, s), 8.26(1H, s).

Example 36

(1S,5R,6S)-6-((1R)-1-hydroxyethyl)-2-(3-hydroxymethylimidazo[5,1-b]thiazol-2-yl)-1-methyl-1-carbapen-2-em-3-carboxylic Acid a) 4-nitrobenzyl (1S,5R,6S)-2-(3-t-butyldimethylsilyloxymethylimidazo[5,1-b]thiazol-2-yl)-6-((1R)-1-hydroxyethyl)-1-methyl-1-carbapen-2-em-3-carboxylate In the same manner as in Example 5-a), 146 mg of 4-nitrobenzyl (1S,5R,6S)-2-(3-t-butyldimethylsilyloxymethylimidazo[5,1-b]thiazol-2-yl)-6-((1R)-1-hydroxyethyl)-1-methyl-1-carbapen-2-em-3-carboxylate was obtained from 256 mg of 4-nitrobenzyl (1R,3R,5R,6S)-6-((1R)-1-hydroxyethyl)-1-methyl-2-oxo-1-carbapenam-3-carboxylate and 346 mg of 3-(t-butyldimethylsilyloxy)methyl-2-(tri-n-butylstannyl)imidazo[5,1-b]thiazole.

NMR (CDCl$_3$) δ: 0.01(3H, s), 0.06(3H, s), 0.85(9H, s), 1.22(3H, d, J=7.4 Hz), 1.39(3H, d, J=6.2 Hz), 3.40(1H, m), 4.34(1H, m), 4.44(1H, m), 4.45(1H, d, J=13.4 Hz), 4.59(1H, d, J=13.4 Hz), 5.19(1H, d, J=13.7 Hz), 5.40(1H, d, J=13.7 Hz), 7.08(1H, s), 7.52(2H, d J=8.9 Hz), 8.09(1H, s), 8.15(2H, d, J=8.9 Hz).

b) 4-nitrobenzyl (1S,5R,6S)-6-((1R)-1-hydroxyethyl)-2-(3-hydroxymethylimidazo[5,1-b]thiazol-2-yl)-1-methyl-1-carbapen-2-em-3-carboxylate In the same manner as in Example 34-b), 75.9 mg of 4-nitrobenzyl (1S,5R,6S)-6-((1R)-1-hydroxyethyl)-2-(3-hydroxymethylimidazo[5,1-b]thiazol-2-yl)-1-methyl-1-carbapen-2-em-3-carboxylate was obtained from 200 mg of 4-nitrobenzyl (1S,5R,6S)-2-(3-t-butyldimethylsilyloxymethylimidazo[5,1-b]thiazol-2-yl)-6-((1R)-1-hydroxyethyl)-1-methyl-1-carbapen-2-em-3-carboxylate.

NMR(CDCl3) δ: 1.16(3H, d, J=7.4 Hz), 1.37(3H, d, J=6.3 Hz), 3.42(2H, m), 4.32(1H, m), 4.46(1H, dd, J$_1$=10.4 Hz, J$_2$=3.1 Hz), 4.54(1H, d, J=13.6 Hz), 4.61(1H, d, J=13.6 Hz), 5.22(1H, d, J=13.4 Hz), 5.44(1H, d, J=13.4 Hz), 7.07(1H, s), 7.56(2H, d, J=8.5 Hz), 8.18(2H, d, J=8.5 Hz), 8.20(1H, s).

c) (1S,5R,6S)-6-((1R)-1-hydroxyethyl)-2-(3-hydroxymethylimidazo[5,1-b]thiazol-2-yl)-1-methyl-1-carbapen-2-em-3-carboxylic Acid In the same manner as in Example 5-b), 11.4 mg of the title compound was obtained from 5.9 mg of 4-nitrobenzyl (1S,5R,6S)-6-((1R)-1-hydroxyethyl)-2-(3-hydroxymethylimidazo[5,1-b]thiazol-2-yl)-1-methyl-1-carbapen-2-em-3-carboxylate.

NMR ($D_2O$) δ (HOD=4.80 ppm): 1.18(3H, d, J=6.9 Hz), 1.32(3H, d, J=6.4 Hz), 3.44(1H, m), 3.61(1H, m), 4.30(1H, m), 4.42(1H, m), 7.61(1H, s), 9.19(1H, s).

Example 37

(1S,5R,6S)-6-((1R)-1-hydroxyethyl)-1-methyl-2-(7-methylimidazo[5,1-b]thiazol-3-yl)-1-carbapen-2-em-3-carboxylic Acid a) 4-nitrobenzyl (1S,5R,6S)-6-((1R)-1-hydroxyethyl)-1-methyl-2-(7-methylimidazo[5,1-b]thiazol-3-yl)-1-carbapen-2-em-3-carboxylate In the same manner as in Example 5-a), 406 mg of 4-nitrobenzyl (1S,5R,6S)-6-((1R)-1-hydroxyethyl)-1-methyl-2-(7-methylimidazo[5,1-b]thiazol-3-yl)-1-carbapen-2-em-3-carboxylate was obtained from 543 mg of 4-nitrobenzyl (1R,3R,5R,6S)-6-((1R)-1-hydroxyethyl)-1-methyl-2-oxo-1-carbapenam-3-carboxylate and 780 mg of 7-methyl-3-(tri-n-butylstannyl)imidazo[5,1-b]thiazole.

NMR (CDCl$_3$) δ: 1.16(3H, d, J=7.4 Hz), 1.37(3H, d, J=6.3 Hz), 2.29(3H, s), 3.46(1H, dd, J$_1$=6.0 Hz, J$_2$=3.2 Hz), 3.63(1H, m), 4.33(1H, m), 4.51(1H, dd, J$_1$=10.4 Hz, J$_2$=3.2 Hz), 5.13(1H, d, J=13.4 Hz), 5.31(1H, d, J=13.4 Hz), 6.92(1H, s), 7.36(2H, d, J=8.5 Hz), 7.75(1H, s), 8.14(2H, d, J=8.5 Hz).

b) (1S,5R,6S)-6-((1R)-1-hydroxyethyl)-1-methyl-2-(7-methylimidazo[5,1-b]thiazol-3-yl)-1-carbapen-2-em-3-carboxylic Acid In the same manner as in Example 5-b), 79.1 mg of the title compound was obtained from 200 mg of 4-nitrobenzyl (1S,5R,6S)-6-((1R)-1-hydroxyethyl)-1-methyl-2-(7-methylimidazo[5,1-b]thiazol-3-yl)-1-carbapen-2-em-3-carboxylate.

NMR (D₂O) δ (HOD=4.80 ppm): 1.14(3H, d, J=7.4 Hz), 1.31(3H, d, J=6.4 Hz), 2.42(3H, s), 3.55(1H, m), 3.60(1H, dd, J$_1$=5.9 Hz, J$_2$=3.0 Hz), 4.30(1H, m), 4.42(1H, dd, J$_1$=10.0 Hz, J$_2$=3.0 Hz), 7.37(1H, s), 8.60(1H, s).

Example 38

Sodium (5R,6S)-6-((1R)-1-hydroxyethyl)-2-(7-methylimidazo[5,1-b]thiazol-2-yl)-1-carbapen-2-em-3-carboxylate a) 4-nitrobenzyl (5R,6S)-6-((1R)-1-hydroxyethyl)-2-(7-methylimidazo[5,1-b]thiazol-2-yl)-1-carbapen-2-em-3-carboxylate In the same manner as in Example 5-a), 758 mg of 4-nitro-benzyl (5R,6S)-6-((1R)-1-hydroxyethyl)-2-(7-methylimidazo[5,1-b]thiazol-2-yl)-1-carbapen-2-em-3-carboxylate was obtained as an orange amorphous from 934 mg of 4-nitrobenzyl (3R,5R,6S)-6-((1R)-1-hydroxyethyl)-2-oxo-1-carbapen-2-em-3-carboxylate and 1.375 g of 7-methyl-2-(tri-n-butylstannyl)imidazo[5,1-b]thiazole.

NMR (CDCl₃) δ: 1.40(3H, d, J=6.3 Hz), 2.1(1H, br.s), 2.33(3H, s), 3.29–3.36(3H, m), 4.25–4.38(2H, m), 5.31(1H, d, J=13.7 Hz), 5.54(1H, d, J=13.7 Hz), 7.69(2H, d, J=6.9 Hz), 7.93(1H, s), 8.14(1H, s), 8.24(2H, d, J=6.9 Hz). MS (TSP): 469 (M$^+$+H).

b) Sodium (5R,6S)-6-((1R)-1-hydroxyethyl)-2-(7-methylimidazo[5,1-b]thiazol-2-yl)-1-carbapen-2-em-3-carboxylate In the same manner as in Example 134-d) described below except that 328 mg of 4-nitrobenzyl (5R,6S)-6-((1R)-1-hydroxyethyl)-2-(7-methylimidazo[5,1-b]thiazol-2-yl)-1-carbapen-2-em-3-carboxylate, and purification was carried out with CHP-20P (2% THF in water), 111.4 mg of the title compound was obtained.

NMR (D₂O) δ (HOD=4.80 ppm): 1.30(3H, d, J=6.3 Hz), 2.37(3H, s), 3.31–3.34(2H, br.s, t), 3.53–3.55(1H, m), 4.22–4.35(2H, m), 7.82(1H, s), 8.70(1H, s). MS (TSP): 356 (M$^+$+Na), 334 (M$^+$+H).

Example 39

Pivaloyloxymethyl (5R,6S)-6-((1R)-1-hydroxyethyl)-2-(7-methylimidazo[5,1-b]thiazol-2-yl)-1-carbapen-2-em-3-carboxylate In the same manner as in Example 135 described below, 29.1 mg of the title compound was obtained as a yellow powder from 51.4 mg of sodium (5R,6S)-6-((1R)-1-hydroxyethyl)-2-(7-methylimidazo[5,1-b]thiazol-2-yl)-1-carbapen-2-em-3-carboxylate.

NMR (CDCl₃) δ: 1.22(9H, s), 2.33(3H, s), 3.22–3.34(3H, m), 4.24–4.35(2H, m), 5.90(1H, d, J=5.6 Hz), 6.00(1H, d, J=5.6 Hz), 7.94(1H, s), 8.18(1H, s). MS (TSP): 448 (M$^+$+H).

Example 40

Pivaloylmethyl (1S,5R,6S)-6-((1R)-1-hydroxyethyl)-1-methyl-2-(7-methylimidazo[5,1-b]thiazol-3-yl)-1-carbapen-2-em-3-carboxylate In the same manner as in Example 19, 28.3 mg of the title compound was obtained from 39.5 mg of (1S,5R,6S)-6-((1R)-1-hydroxyethyl)-1-methyl-2-(7-methylimidazo[5,1-b]thiazol-3-yl)-1-carbapen-2-em-3-carboxylic acid.

NMR (CDCl₃) δ: 1.12(3H, d, J=7.2 Hz), 1.16(9H, s), 1.36(3H, d, J=6.2 Hz), 2.34(3H, s), 3.41(1H, dd, J$_1$=6.5 Hz, J$_2$=3.2 Hz), 3.70(1H, m), 4.31(1H, m), 4.47(1H, dd, J$_1$=10.4 Hz, J$_2$=3.2 Hz), 5.73(1H, d, J=5.5 Hz), 5.86(1H, d, J=5.5 Hz), 7.03(1H, s), 7.78(1H, s).

Example 41

(1S,5R,6S)-6-((1R)-1-hydroxyethyl)-2-(5-hydroxymethyl-6-methylimidazo[5,1-b]thiazolium-2-yl)-1-methyl-1-carbapen-2-em-3-carboxylate (inner salt)

In the same manner as in Example 14 except that the reaction was carried out for 3 days, 19.3 mg of the title compound was obtained from 100 mg of 4-nitrobenzyl (1S,5R,6S)-6-((1R)-1-hydroxyethyl)-2-(5-hydroxymethylimidazo[5,1-b]thiazol-2-yl)-1-methyl-1-carbapen-2-em-3-carboxylate.

NMR (D₂O) δ (HOD=4.80 ppm): 1.26(3H, d, J=6.9 Hz), 1.32(3H, d, J=6.1 Hz), 3.56(1H, m), 3.66(1H, m), 4.05(3H, s), 4.30(2H, m), 5.13(2H, s), 7.51(1H, s), 8.14(1H, s).

Example 42

(5R,6S)-2-(6,7-dimethylimidazo[5,1-b]thiazolium-2-yl)-6-((1R)-1-hydroxyethyl)-1-carbapen-2-em-3-carboxylate (inner salt)

a) 4-nitrobenzyl (5R,6S)-2-(6,7-dimethylimidazo[5,1-b]thiazolium-2-yl)-6-((1R)-1-hydroxyethyl)-1-carbapen-2-em-3-carboxylate Iodide In the same manner as in Example 4-a), 64.0 mg of 4-nitrobenzyl (5R,6S)-2-(6,7-dimethylimidazo[5,1-b]thiazolium-2-yl)-6-((1R)-1-hydroxyethyl)-1-carbapen-2-em-3-carboxylate iodide was prepared as a yellowish orange oil by using 93.7 mg of 4-nitrobenzyl (5R,6S)-6-((1R)-1-hydroxyethyl)-2-(7-methylimidazo[5,1-b]thiazol-2-yl)-1-carbapen-2-em-3-carboxylate.

NMR (CD₃OD) δ: 1.31(3H, d, J=6.3 Hz), 2.49(3H, s), 3.45–3.55(3H, m), 4.01(3H, s), 4.10–4.25(1H, m), 4.30–4.40(1H, m), 5.40(1H, d, J=13.5 Hz), 5.55(1H, d, J=13.5 Hz), 7.76(2H, d, J=9 Hz), 8.24(2H, d, J=9.0 Hz), 8.38(1H, s), 9.25(0.2H, s, exchanged with CD₃OD). MS (TSP): 483 (M$^+$).

b) (5R,6S)-2-(6,7-dimethylimidazo[5,1-b]thiazolium-2-yl)-6-((1R)-1-hydroxyethyl)-1-carbapen-2-em-3-carboxylate (inner salt)

The title compound was obtained in a yield of 7.2 mg as a yellow amorphous from 61.0 mg of 4-nitrobenzyl (5R,6S)-2-(6,7-dimethylimidazo[5,1-b]thiazolium-2-yl)-6-((1R)-1-hydroxyethyl)-1-carbapen-2-em-3-carboxylate in the same manner as in Example 4-b) except that purification was carried out on CHP-20P (2% THF in water) and COSMOSEAL 40C18-PREP (water:methanol=20:1–10:1).

NMR (D₂O) δ (HOD=4.80 ppm): 1.30(3H, d, J=6.3 Hz), 2.41(3H, s), 3.24–3.40(2H, m), 3.51–3.55(1H, m), 3.92(3H, s), 4.22–4.28(2H, m), 7.86(1H, m), 9.04(0.5H, s, exchanged with D₂O). MS( ).

Example 43

(5R,6S)-6-((1R)-1-hydroxyethyl)-2-(7-methylimidazo[5,1-b]thiazol-3-yl)-1-carbapen-2-em-3-carboxylic Acid a) 4-nitrobenzyl (5R,6S)-6-((1R)-1-hydroxyethyl)-2-(7-methylimidazo[5,1-b]thiazol-3-yl)-1-carbapen-2-em-3-carboxylate In the same manner as in Example 5-a), 608 mg of 4-nitrobenzyl (5R,6S)-6-((1R)-1-hydroxyethyl)-2-(7-methylimidazo[5,1-b]thiazol-3-yl)-1-carbapen-2-em-3-carboxylate was obtained from 696 mg of 4-nitrobenzyl (3R,5R,6S)-6-((1R)-1-hydroxyethyl)-2-oxo-1-carbapenam-3-carboxylate and 1.05 g of 7-methyl-3-(tri-n-butylstannyl)imidazo[5,1-b]thiazole.

NMR (CDCl₃) δ: 1.39(3H, d, J=6.3 Hz), 2.30(3H, s), 3.35(3H, m), 4.31(1H, m), 4.43(1H, m), 5.21(1H, d, J=13.3 Hz), 5.34(1H, d, J=13.3 Hz), 7.01(1H, s), 7.42(2H, d, J=8.9 Hz), 7.67(1H, s), 8.16(2H, d, J=8.9 Hz).

b) (5R,6S)-6-((1R)-1-hydroxyethyl)-2-(7-methylimidazo[5,1-b]thiazol-3-yl)-1-carbapen-2-em-3-carboxylic Acid In the same manner as in Example 5-b), the title compound was obtained in a yield of 45.5 mg from 306 mg of 4-nitrobenzyl (5R,6S)-6-((1R)-1-hydroxyethyl)-2-(7-methylimidazo[5,1-b]thiazol-3-yl)-1-carbapen-2-em-3-carboxylate.

NMR (D₂O) δ (HOD=4.80 ppm): 1.32(3H, d, J=6.1 Hz), 2.48(3H, s), 3.25(1H, dd, J₁=17.2 Hz, J₂=10.0 Hz), 3.47(1H, dd, J₁=17.2 Hz, J₂=8.4 Hz), 3.61(1H, m), 4.29(1H, m), 4.40(1H, m), 7.47(1H, s), 8.73(1H, s).

Example 44

Pivaloyloxymethyl (5R,6S)-6-((1R)-1-hydroxyethyl)-2-(7-methylimidazo[5,1-b]thiazol-3-yl)-1-carbapen-2-em-3-carboxylate In the same manner as in Example 19, the title compound was obtained in a yield of 37.8 mg from 62.6 mg of (5R,6S)-6-((1R)-1-hydroxyethyl)-2-(7-methylimidazo[5,1-b]thiazol-3-yl)-1-carbapen-2-em-3-carboxylic acid.

NMR (CDCl₃) δ: 1.19(9H, s), 1.38(3H, d, J=6.2 Hz), 2.34(3H, s), 3.35(3H, m), 4.28(1H, m), 4.40(1H, m), 5.78(1H, d, J=5.5 Hz), 5.88(1H, d, J=5.5 Hz), 7.09(1H, s), 7.71(1H, s).

Example 45

(5R,6S)-2-(6,7-dimethylimidazo[5,1-b]thiazolium-3-yl)-6-((1R)-1-hydroxyethyl)-1-carbapen-2-em-3-carboxylate (inner salt)

a) 4-nitrobenzyl (5R,6S)-2-(6,7-dimethylimidazo[5,1-b]thiazolium-3-yl)-6-((1R)-1-hydroxyethyl)-1-carbapen-2-em-3-carboxylate Iodide In the same manner as in Example 4-a), 4-nitrobenzyl (5R,6S)-2-(6,7-dimethylimidazo[5,1-b]thiazolium-3-yl)-6-((1R)-1-hydroxyethyl)-1-carbapen-2-em-3-carboxylate iodide was obtained from 103 mg of 4-nitrobenzyl (5R,6S)-6-((1R)-1-hydroxyethyl)-2-(7-methylimidazo[5,1-b]thiazol-3-yl)-1-carbapen-2-em-3-carboxylate.

NMR (DMSO-d₆) δ: 1.18(3H, d, J=6.2 Hz), 2.39(3H, s), 3.30(2H, m), 3.55(1H, m), 3.88(3H, s), 4.04(1H, m), 4.33(1H, m), 5.22(1H, d, J=13.7 Hz), 5.31(1H, d, J=13.7 Hz), 7.53(2H, d, J=8.7 Hz), 7.84(1H, s), 8.20(2H, d, J=8.7 Hz), 9.57(1H, s).

b) (5R,6S)-2-(6,7-dimethylimidazo[5,1-b]thiazolium-3-yl)-6-((1R)-1-hydroxyethyl)-1-carbapen-2-em-3-carboxylate (inner salt)

In the same manner as in Example 4-b), the title compound was obtained in a yield of 24.9 mg from the whole amount of 4-nitrobenzyl (5R,6S)-2-(6,7-dimethylimidazo[5,1-b]thiazolium-3-yl)-6-((1R)-1-hydroxyethyl)-1-carbapen-2-em-3-carboxylate iodide obtained above.

NMR (D₂O) δ (HOD=4.80 ppm): 1.30(3H, d, J=6.5 Hz), 2.45(3H, s), 3.22(1H, dd, J₁=17.6 Hz, J₂=10.2 Hz), 3.44(1H, dd, J₁=17.6 Hz, J₂=8.8 Hz), 3.58(1H, dd, J₁=5.8 Hz, J₂=2.8 Hz), 3.94(3H, s), 4.26(1H, m), 4.37(1H, m), 7.44(1H, s), 8.85(1H, s).

Example 46

(5R,6S)-6-((1R)-1-hydroxyethyl)-2-(3-methylimidazo[5,1-b]thiazol-2-yl)-1-carbapen-2-em-3-carboxylic Acid a) 4-nitrobenzyl (5R,6S)-6-((1R)-1-hydroxyethyl)-2-(3-methylimidazo[5,1-b]thiazol-2-yl)-1-carbapen-2-em-3-carboxylate In the same manner as in Example 5-a), 4-nitrobenzyl (5R,6S)-6-((1R)-1-hydroxyethyl)-2-(3-methylimidazo[5,1-b]thiazol-2-yl)-1-carbapen-2-em-3-carboxylate was obtained in a yield of 622 mg from 696 mg of 4-nitrobenzyl (3R,5R,6S)-6-((1R)-1-hydroxyethyl)-2-oxo-1-carbapenam-3-carboxylate and 1.14 g of 3-methyl-2-(tri-n-butyl-stannyl)imidazo[5,1-b]thiazole.

NMR (CDCl₃) δ: 1.39(3H, d, J=6.3 Hz), 2.20(3H, s), 3.20(2H, m), 3.35(1H, dd, J₁=6.4 Hz, J₂=2.9 Hz), 4.31(1H, m), 4.40(1H, m), 5.24(1H, d, J=13.7 Hz), 5.42(1H, d, J=13.7 Hz), 7.09(1H, s), 7.54(2H, d, J=8.4 Hz), 7.86(1H, s), 8.15(2H, d, J=8.4 Hz).

b) (5R,6S)-6-((1R)-1-hydroxyethyl)-2-(3-methylimidazo[5,1-b]thiazol-2-yl)-1-carbapen-2-em-3-carboxylic Acid In the same manner as in Example 5-b), the title compound was obtained in a yield of 94.6 mg from 329 mg of 4-nitrobenzyl (5R,6S)-6-((1R)-1-hydroxyethyl)-2-(3-methylimidazo[5,1-b]thiazol-2-yl)-1-carbapen-2-em-3-carboxylate.

NMR (D₂O) δ (HOD=4.80 ppm): 1.30(3H, d, J=6.5 Hz), 2.37(3H, s), 3.15(1H, dd, J₁=17.3 Hz, J₂=10.2 Hz), 3.32(1H, dd, J₁=17.3 Hz, J₂=8.3 Hz), 3.58(1H, dd, J₁=5.8 Hz, J₂=3.0 Hz), 4.26(1H, m), 4.37(1H, m), 7.52(1H, s), 9.06(1H, s).

Example 47

Pivaloyloxymethyl (5R,6S)-6-((1R)-1-hydroxyethyl)-2-(3-methylimidazo[5,1-b]thiazol-2-yl)-1-carbapen-2-em-3-carboxylate In the same manner as in Example 19, 38.6 mg of the title compound was obtained from 61.4 mg of (5R,6S)-6-((1R)-1-hydroxyethyl)-2-(3-methylimidazo[5,1-b]thiazol-2-yl)-1-carbapen-2-em-3-carboxylic acid.

NMR (CDCl₃) δ: 1.11(9H, s), 1.37(3H, d, J=6.3 Hz), 2.30(3H, s), 3.19(2H, m), 3.31(1H, dd, J₁=6.5 Hz, J₂=2.9 Hz), 4.28(1H, m), 4.36(1H, m), 5.80(1H, d, J=5.5 Hz), 5.90(1H, d, J=5.5 Hz), 7.08(1H, s), 7.93(1H, s).

Example 48

Potassium (1S,5R,6S)-6-((1R)-1-hydroxyethyl)-2-(imidazo[5,1-b]thiazol-5-yl)-1-methyl-1-carbapen-2-em-3-carboxylate a) (3S,4R)-1-[(allyloxycarbonyl)(triphenylphosphoranylidine)methyl]-3-((1R)-1-t-butyldimethylsilyloxyethyl)-4-[(1R)-1-[(pyridine-2-yl)thiocarbonyl]ethyl]azetidin-2-one To the ice-cooled mixture of 6.6 g of (3S,4R)-1-[(allyoxycarbonyl)(triphenylphosphoranylidine)methyl]-3-((1R)-1-t-butyldimethylsilyloxyethyl)-4-[(1R)-1-(carboxy)ethyl]azetidin-2-one and 2.75 g of triphenylphosphine in 30 ml of acetonitrile was added 2.31 g of 2,2'-dipyridyl disulfide under the atmosphere of argon, and the mixture was stirred at room temperature for 2 hours. The reaction mixture was concentrated under reduced pressure, and purified by column chromatography on silica gel (hexane:ethyl acetate=3:1) to give 5.2 g of (3S,4R)-1-[(allyloxycarbonyl)(triphenylphosphoranylidine)methyl]-3-((1R)-1-t-butyldimethylsilyloxyethyl)-4-[(1R)-1-[(pyridine-2-yl)thiocarbonyl]ethyl]azetidin-2-one.

NMR (CDCl₃) δ: −0.15(3H, s), −0.07(3H, s), 0.80(9H, s), 0.97(3H, d, J=6.1 Hz), 1.13(3H, d, J=7.1 Hz), 2.25–2.35(1H, m), 2.60–2.67(2H, m), 3.16(1H, m), 4.15–4.30(1H, m), 4.60–4.75(2H, m), 5.10–5.22(1H, m), 7.50–7.80(19H, m).

b) Ally (1S,5R,6S)-6-((1R)-1-t-butyldimethylsilyloxyethyl)-2-(imidazo[5,1-b]thiazol-5-yl)-1-methyl-1-carbapen-2-em-3-carboxylate To an ice-cooled solution of 0.61 g of 5-bromoimidazo[5,1-b]thiazole in 6 ml of THF was added 3.2 ml of 1 M solution of ethyl magnesium bromide in THF. After stirring at room temperature for 2 hours, the mixture was cooled to −50° C., and a solution of 2.23 g of (3S,4R)-1-[(allyloxycarbonyl)(triphenylphosphoranylidene)methyl]-3-((1R)-1-t-butyldimethylsilyloxyethyl)-4-[(1R)-1-[(pyridin-2-yl)thiocarbonyl]ethyl]azetidin-2-one in 6 ml of THF was added. The mixture was stirred for 1 hour during which the temperature was raised up to 10° C. The reaction mixture was diluted with 12 ml of a saturated aqueous ammonium chloride solution, extracted with dichloromethane, and the organic layer was dried over anhydrous magnesium sulfate. The solvent was removed under reduced pressure, and the residue thus obtained was purified by column chromatography on silica gel (hexane:ethyl acetate=3:2) to give 0.67 g of crude product. A 0.63 g portion of the crude product and a solution of 4.5 mg of hydroquinone in 7 ml of xylene were stirred under heating at 140° C. for 6 hours. The reaction mixture was diluted with 30 ml of ethyl acetate, washed with saturated aqueous sodium hydrogen carbonate, and saturated aqueous saline in this sequence, and dried over anhydrous magnesium sulfate. The solvent was removed under reduced pressure, and the residue thus obtained was purified by column chromatography on silica gel (hexane:ethyl acetate=2:1) to give 0.35 g of allyl (1S,5R,6S)-6-((1R)-1-t-butyldimethylsilyloxyethyl)-2-(imidazo[5,1-b]thiazol-5-yl)-1-methyl-1-carbapen-2-em-3-carboxylate.

NMR (CDCl$_3$) δ: 0.12(6H, s), 0.90(9H, s), 1.12(3H, d, J=7.4 Hz), 1.29(3H, d, J=6.1 Hz), 3.32(1H, dd, J=2.9, 6.4 Hz), 3.81–3.91(1H, m), 4.23–4.35(2H, m), 4.62–4.78(2H, m), 5.18–5.38(2H, m), 5.79–5.93(1H, m), 6.90(1H, d, J=4.2 Hz), 7.17(1H, d, J=4.2 Hz), 7.31(1H, s).

c) Allyl (1S,5R,6S)-6-((1R)-1-hydroxyethyl)-2-(imidazo[5,1-b]thiazol-5-yl)-1-methyl-1-carbapen-2-em-3-carboxylate To a solution of 0.35 g of allyl (1S,5R,6S)-6-((1R)-1-t-butyldimethylsilyloxyethyl)-2-(imidazo[5,1-b]thiazole-5-yl)-1-methyl-1-carbapen-2-em-3-carboxylate in 12 ml of THF was added under ice-cooling 0.66 ml of acetic acid and 2.9 ml of a 1 M solution of tetra-n-butyl-ammonium fluoride in THF, and the mixture was stirred at room temperature for 36 hours. The reaction mixture was diluted with 50 ml of ethyl acetate, washed with saturated aqueous sodium hydrogen carbonate and saturated aqueous saline in this sequence, and dried over anhydrous magnesium sulfate. The solvent was removed under reduced pressure, and the residue thus obtained was purified by column chromatography on silica gel (ethyl acetate) to give 0.16 g of allyl (1S,5R,6S)-6-((1R)-1-hydroxyethyl)-2-(imidazo[5,1-b]thiazol-5-yl)-1-methyl-1-carbapen-2-em-3-carboxylate.

NMR (CDCl$_3$) δ: 1.17(3H, d, J=7.4 Hz), 1.37(3H, d, J=6.3 Hz), 3.38(1H, dd, J=2.9, 6.6 Hz), 3.82–3.92(1H, m), 4.25–4.35(1H, m), 4.39(1H, dd, J=2.9, 10.0 Hz), 4.60–4.78 (1H, m), 5.18–5.34(2H, m), 5.77–5.90(1H, m), 6.91(1H, d, J=4.3 Hz), 7.15(1H, d, J=4.3 Hz), 7.31(1H, s).

d) Potassium (1S,5R,6S)-6-((1R)-1-hydroxyethyl)-2-(imidazo[5,1-b]thiazol-5-yl)-1-methyl-1-carbapen-2-em-3-carboxylate To a solution of 40 mg of allyl (1S,5R,6S)-6-((1R)-1-hydroxyethyl)-2-(imidazo[5,1-b]thiazol-5-yl)-1-methyl-1-carbapen-2-em-3-carboxylate in 0.8 ml of dichloromethane and 0.8 ml of ethyl acetate were added under the atmosphere of argon 3.4 mg of triphenylphosphine, 29 mg of potassium 2-ethylhexanoate, 6.4 mg of tetrakis-triphenylphosphine palladium (0), and the mixture was stirred at room temperature for 1 hour. The reaction mixture was poured into diethyl ether, and the resulting precipitate was collected by filtration, and purified by column chromatography on COSMOSEAL 40C18-PREP (water:methanol=20:1) to give 13 mg of the title compound.

NMR (D$_2$O) δ (HOD=4.80 ppm): 1.10(3H, d, J=7.2 Hz), 1.31(3H, d, J=6.4 Hz), 3.50–3.65(2H, m), 4.25–4.37(2H, m), 7.10(1H, d, J=4.3 Hz), 7.22(1H, s), 7.38(1H, d, J=4.3 Hz).

Example 49

(1S,5R,6S)-2-(7-formylaminomethyl-6-methylimidazo[5,1-b]thiazolium-2-yl)-6-((1R)-1-hydroxyethyl)-1-methyl-1-carbapen-2-em-3-carboxylate (inner salt)

To a solution of 134 mg of 4-nitrobenzyl (1S,5R,6S)-2-(7-formylaminomethyl imidazo[5,1-b]thiazol-2-yl)-6-((1R)-1-hydroxyethyl)-1-methyl-1-carbapen-2-em-3-carboxylate in 2 ml of DMF was added 1.6 ml of methyl iodide, and the mixture was stirred at room temperature for 12 hours. The solvent was removed under reduced pressure. The residue thus obtained was dissolved in 5 ml of THF and 5 ml of 0.1 M sodium phosphate buffer (pH 6.8), and 150 mg of 10% Pd-C. The reactor was purged with hydrogen, the reaction mixture was stirred at room temperature for 1 hour. The catalyst was collected by filtration, and washed with a mixed solution of 2 ml of 0.1 M sodium phosphate buffer (pH 6.8) and 2 ml of THF. The filtrate was washed with 10 ml of ethyl acetate, and the aqueous layer obtained was purified by column chromatography on COSMOSEAL 40C18-PREP (water:methanol=20:1). The fraction containing the aimed product was concentrated under reduced pressure, and then lyophilized to give 58 mg of the title compound.

NMR (D$_2$O) δ (HOD=4.80 ppm): 1.24(3H, d, J=7.2 Hz), 1.30(3H, d, J=6.4 Hz), 3.52–3.68(2H, m), 4.01(3H, s), 4.23–4.35(2H, m), 4.68(2H, s), 8.09(1H, s), 8.26(1H, s), 9.15(1H, s).

Example 50

Pivaloyloxymethyl (1S,5R,6S)-6-((1R)-1-hydroxyethyl)-2-(imidazo[5,1-b]thiazol-5-yl)-1-methyl-1-carbapen-2-em-3-carboxylate To a solution of 40 mg of potassium (1S,5R,6S)-6-((1R)-1-hydroxyethyl)-2-(imidazo[5,1-b]thiazol-5-yl)-1-methyl-1-carbapen-2-em-3-carboxylate in 0.8 ml of DMF was added at −30° C. 30 mg of pivaloyloxymethyl iodide, and the mixture was stirred for 1 hour during which the temperature was raised up to room temperature. The reaction mixture was diluted with 30 ml of dichloromethane, washed with semi-saturated aqueous saline, and dried over anhydrous magnesium sulfate. The solvent was removed under reduced pressure, and the residue thus obtained was purified by column chromatography on silica gel (ethyl acetate:methanol=4:1) to give 54 mg of the title compound.

NMR (CDCl$_3$) δ: 1.17(3H, d, J=7.0 Hz), 1.20(9H, s), 1.37(3H, d, J=6.3 Hz), 3.38(1H, dd, J=2.9, 6.6 Hz), 3.85–3.95(1H, m), 4.25–4.33(1H, m), 4.38(1H, dd, J=2.9, 10.0 Hz), 5.78(1H, d, J=5.5 Hz), 5.96(1H, d, J=5.5 Hz), 6.95(1H, d, J=4.2 Hz), 7.15(1H, d, J=4.2 Hz), 7.34(1H, s).

Example 51

(5R,6S)-2-(3,6-dimethylimidazo[5,1-b]thiazolium-2-yl)-6-((1R)-1-hydroxyethyl)-1-carbapen-2-em-3-carboxylate (inner salt)

In the same manner as in Example 14, 4.6 mg of the title compound was obtained from 109 mg of 4-nitrobenzyl (5R,6S)-6-((1R)-1-hydroxyethyl)-2-(3-methylimidazo[5,1-b]thiazol-2-yl)-1-carbapen-2-em-3-carboxylate.

NMR (D$_2$O) δ (HOD=4.80 ppm): 1.31(3H, d, J=6.5 Hz), 2.36(3H, s), 3.15(1H, dd, J$_1$=17.1 Hz, J$_2$=9.8 Hz), 3.32(1H, dd, J$_1$=17.1 Hz, J$_2$=8.3 Hz), 3.59(1H, m), 4.09(3H, s), 4.28(1H, m), 4.38(1H, m), 7.57(1H, s), 9.20(1H, s).

Example 52

Acetoxymethyl (1S,5R,6S)-6-((1R)-1-hydroxyethyl)-2-(imidazo[5,1-b]thiazol-2-yl)-1-methyl-1-carbapen-2-em-3-carboxylate To a solution of 49 mg of sodium (1S,5R,6S)-6-((1R)-1-hydroxyethyl)-2-(imidazo[5,1-b]thiazol-2-yl)-1-methyl-1-carbapen-2-em-3-carboxylate in 1 ml of DMF was added 32 mg of acetoxymethyl bromide under the atmosphere of argon at −20° C., and the mixture was stirred for 3 hours during which the temperature was raised up to −10° C. The reaction mixture was extracted twice with 20 ml of ethyl acetate, and the organic layer was washed twice with 10 ml of semi-saturated aqueous saline, dried over anhydrous magnesium sulfate, filtered and concentrated under reduced pressure to a volume of 2 ml. The residue thus obtained was purified by column chromatography on silica gel (chloroform:methanol=9:1) and on Sephadex LH-20 (dichloromethane:methanol=1:1) in this sequence to give 11 mg of the title compound.

NMR (CDCl$_3$) δ: 1.29(3H, d, J=7.4 Hz), 1.37(3H, d, J=6.3 Hz), 2.13(3H, s), 3.31–3.51(2H, m), 4.27–4.39(2H, m), 5.88, 5.96(2H, AB, J=5.7 Hz), 7.08(1H, s), 8.06(1H, s), 8.38(1H, s). MS (TSP): 406 (M$^+$+H).

Example 53

1-(acetoxy)ethyl (1S,5R,6S)-6-((1R)-1-hydroxyethyl)-2-(imidazo[5,1-b]thiazol-2-yl)-1-methyl-1-carbapen-2-em-3-carboxylate (diastereomer-mixture)

In the same manner as in Example 52, 11 mg of the title compound was obtained from 49 mg of sodium (1S,5R,6S)-6-((1R)-1-hydroxyethyl)-2-(imidazo[5,1-b]thiazol-2-yl)-1-methyl-1-carbapen-2-em-3-carboxylate and 45 mg of 1-(acetoxy)ethyl iodide.

NMR (CDCl$_3$) δ: 1.27, 1.28(total 3H, d each, J=7.1 Hz), 1.37, 1.38(total 3H, d each, J=6.0 Hz), 1.56, 1.61(total 3H, d each, J=5.5 Hz), 2.06, 2.13(total 3H, s each), 3.09–3.49 (2H, m), 4.26–4.42(2H, m), 7.01–7.07(2H, m), 8.05(1H, s), 8.41(1H, s).

Example 54

(1-methylcyclohexan-1-yl)carbonyloxymethyl (1S,5R,6S)-6-((1R)-1-hydroxyethyl)-2-(imidazo[5,1-b]thiazol-2-yl)-1-methyl-1-carbapen-2-em-3-carboxylate In the same manner as in Example 52, 42 mg of the title compound was obtained from 49 mg of sodium (1S,5R,6S)-6-((1R)-1-hydroxyethyl)-2-(imidazo[5,1-b]thiazol-2-yl)-1-methyl-1-carbapen-2-em-3-carboxylate and 39 mg of (1-methylcyclohexan-1-yl)carbonyloxymethyl iodide.

NMR (CDCl$_3$) δ: 1.14(3H, s), 1.28(3H, d, J=7.1 Hz), 1.36(3H, d, J=6.1 Hz), 1.17–1.60(8H, m), 1.95–2.05(2H, m), 3.29–3.50(2H, m), 4.25–4.40(2H, m), 5.92, 5.97(2H, AB, J=5.5 Hz), 7.07(1H, s), 8.07(1H, s), 8.33(1H, s).

Example 55

1-(ethoxycarbonyloxy)ethyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture)

In the same manner as in Example 52, 39 mg of the title compound was obtained from 49 mg of sodium (1S,5R,6S)-6-((1R)-1-hydroxyethyl)-2-(imidazo[5,1-b]thiazol-2-yl)-1-methyl-1-carbapen-2-em-3-carboxylate and 68 mg of 1-(ethoxycarbonyloxy)ethyl iodide.

NMR (CDCl$_3$) δ: 1.27–1.39(9H, m), 1.59, 1.65(total 3H, d each, J=5.5 Hz), 3.30–3.49(2H, m), 4.15–4.45(4H, m), 6.91–7.00(1H, m), 7.07(1H, s), 8.04(1H, s), 8.41, 8.42(total 1H, s each). MS (TSP): 450 (M$^+$+H).

Example 56

1-(isopropoxycarbonyloxy)ethyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture)

In the same manner as in Example 52, 30 mg of the title compound was obtained from 49 mg of sodium (1S,5R,6S)-6-((1R)-1-hydroxyethyl)-2-(imidazo[5,1-b]thiazol-2-yl)-1-methyl-1-carbapen-2-em-3-carboxylate Sodium and 71 mg of 1-(isopropoxycarbonyloxy)ethyl iodide.

NMR (CDCl$_3$) δ: 1.26–1.39(12H, m), 1.59, 1.65(total 3H, d each, J=5.5 Hz), 3.29–3.49(2H, m), 4.26–4.35(2H, m), 4.84–5.00(1H, m), 6.91–6.98(1H, m), 7.07(1H, m), 8.03(1H, s), 8.43(1H, s). MS (TSP): 464 (M$^+$+H).

Example 57

1-(cyclohexyloxycarbonyloxy)ethyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture)

In the same manner as in Example 52, 30 mg of the title compound was obtained from 49 mg of sodium (1S,5R,6S)-6-((1R)-1-hydroxyethyl)-2-(imidazo[5,1-b]thiazol-2-yl)-1-methyl-1-carbapen-2-em-3-carboxylate and 62 mg of 1-(cyclohexyloxycarbonyloxy)ethyl iodide.

NMR (CDCl$_3$) δ: 1.28, 1.29(total 3H, d each, J=7.4 Hz), 1.36, 1.38(total 3H, d each, J=6.4 Hz), 1.59, 1.65(total 3H, d each, J=5.4 Hz), 1.15–2.05(8H, m), 3.29–3.49(2H, m), 4.26–4.35(2H, m), 4.57–4.75(1H, m), 6.92–6.98(1H, m), 7.07(1H, s), 8.03(1H, s), 8.42, 8.43(total 1H, s each). MS (TSP): 504(M$^+$+H).

Example 58

Cyclohexyloxycarbonyloxy methyl (1S,5R,6S)-6-((1R)-1-hydroxyethyl)-2-(imidazo[5,1-b]thiazol-2-yl)-1-methyl-1-carbapen-2-em-3-carboxylate In the same manner as in Example 52, 46 mg of the title compound was obtained from 49 mg of sodium (1S,5R,6S)-6-((1R)-1-hydroxyethyl)-2-(imidazo[5,1-b]thiazol-2-yl)-1-methyl-1-carbapen-2-em-3-carboxylate and 59 mg of cyclohexyloxycarbonyloxymethyl iodide.

NMR (CDCl$_3$) δ: 1.28(3H, d, J=7.4 Hz), 1.37, (3H, d, J=6.2 Hz), 1.20–1.60(4H, m), 1.68–1.80(2H, m), 1.82–1.98 (2H, m), 3.30–3.50(2H, m), 4.25–4.40(2H, m), 4.61–4.70 (1H, m), 5.90, 5.96(2H, AB, J=5.8 Hz), 7.08(1H, s), 8.05 (1H, s), 8.41(1H, s).

Example 59

3-phthalidyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture)

In the same manner as in Example 52, 38 mg of the title compound was obtained from 44 mg of sodium (1S,5R,6S)-

6-((1R)-1-hydroxyethyl)-2-(imidazo[5,1-b]thiazol-2-yl)-1-methyl-1-carbapen-2-em-3-carboxylate and 32 mg of 3-phthalidyl bromide.

NMR (CDCl$_3$) δ: 1.25–1.40(6H, m), 3.30–3.60(2H, m), 4.21–4.35(2H, m), 7.07, 7.10(total 1H, s each), 7.46, 7.47 (total 1H, s each), 7.62–7.86(4H, m), 8.01, 8.06(total 1H, s each), 8.25, 8.51(total 1H, s each). MS (TSP): 466 (M$^+$+H).

Example 60

(5-methyl-2-oxo-1,3-dioxolen-4-yl)methyl (1S,5R,6S)-6-((1R)-1-hydroxyethyl)-2-(imidazo[5,1-b]thiazol-2-yl)-1-methyl-1-carbapen-2-em-3-carboxylate In the same manner as in Example 52, 37 mg of the title compound was obtained from 49 mg of sodium (1S,5R,6S)-6-((1R)-1-hydroxyethyl)-2-(imidazo[5,1-b]thiazol-2-yl)-1-methyl-1-carbapen-2-em-3-carboxylate and 53 mg of (5-methyl-2-oxo-1,3-dioxolen-4-yl)methyl bromide.

NMR (CDCl$_3$) δ: 1.29(3H, d, J=7.4 Hz), 1.37(3H, d, J=6.3 Hz), 2.22(3H, s), 3.32–3.52(2H, m), 4.25–4.45(2H, m), 5.01, 5.08(2H, AB, J=14.0 Hz), 7.08(1H, s), 8.07(1H, s), 8.26(1H, s).

Example 61

1-[(cyclohexylmethoxy)carbonyloxy]ethyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture)

In the same manner as in Example 52, the title compound was obtained in a yield of 42.1 mg from 44.8 mg of sodium (1S,5R,6S)-6-((1R)-1-hydroxyethyl)-2-(imidazo[5,1-b]thiazol-2-yl)-1-methyl-1-carbapen-2-em-3-carboxylate and 89.0 mg of 1-[(cyclohexylmethoxy)carbonyloxy]ethyl iodide.

NMR (CDCl3) δ: 0.85–1.00(2H, m), 1.10–1.20(2H, m), 1.20, 1.21(total 3H, d each, J=7.2 Hz), 1.28, 1.31(total 3H, d each, J=6.2 Hz), 1.53(3H, d, J=5.5 Hz), 1.58(3H, d, J=5.5 Hz), 1.60–1.75(4H, m), 1.98–2.10(4H, m), 3.25–3.28(1H, m), 3.34–3.42(1H, m), 3.88–3.96(2H, m), 4.78–4.30(2H, m), 6.83–6.90(1H, m), 7.02(1H, s), 8.02(1H, s), 8.35–8.36(1H, m). MS (TSP): 518 (M$^+$+H).

Example 62

1-[(2-methylcyclohexan-1-yl)oxycarbonyloxy]ethyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture)

In the same manner as in Example 52, 59.6 mg of the title compound was obtained from 61.7 mg of sodium (1S,5R,6S)-6-((1R)-1-hydroxyethyl)-2-(imidazo[5,1-b]thiazol-2-yl)-1-methyl-1-carbapen-2-em-3-carboxylate and 89.0 mg of 1-[(2-methylcyclohex-1-yl)oxycarbonyloxy]ethyl iodide.

NMR (CDCl$_3$) δ: 0.80–0.93(4H, m), 1.20, 1.21(total 3H, d each, J=7.4 Hz), 1.28, 1.30(total 3H, d each, J=6.3 Hz), 1.52, 1.58(total 3H, d each, J=5.5 Hz), 1.58(3H, d, J=5.5 Hz), 1.62–1.73(2H, m), 1.90–2.15(4H, m), 3.23–3.28(1H, m), 3.35–3.42(1H, m), 3.42(3H, s), 4.18–4.30(3H, m), 6.83–6.92(1H, m), 7.01(1H, s), 8.01(1H, s), 8.32–8.37(1H, m). MS (TSP): 518 (M$^+$+H).

Example 63

Cyclopentyloxycarbonyloxymethyl (1S,5R,6S)-6-((1R)-1-hydroxyethyl)-2-(imidazo[5,1-b]thiazol-2-yl)-1-methyl-1-carbapen-2-em-3-carboxylate In the same manner as in Example 52, 54.4 mg of the title compound was obtained from 61.6 mg of sodium (1S,5R,6S)-6-((1R)-1-hydroxyethyl)-2-(imidazo[5,1-b]thiazol-2-yl)-1-methyl-1-carbapen-2-em-3-carboxylate and 69.7 mg of cyclopentyloxycarbonyloxymethyl iodide.

NMR (CDCl$_3$) δ: 1.21(3H, d, J=7.1 Hz), 1.29(3H, d, J=6.1 Hz), 1.48–1.58(2H, m), 1.63–1.85(5H, m), 3.25–3.30(1H, m), 3.35–3.42(1H, m), 4.20–4.38(4H, m), 5.00–5.08(1H, m), 5.82(1H, d, J=5.7 Hz), 5.88(1H, d, J=5.7 Hz), 7.00(1H, s), 7.99(1H, s), 8.32(1H, s). MS (TSP): 476 (M$^+$+H).

Example 64

(Z)-2-(3-phthalidylidene)ethyl (1S,5R,6S)-6-((1R)-1-hydroxyethyl)-2-(imidazo[5,1-b]thiazol-2-yl)-1-methyl-1-carbapen-2-em-3-carboxylate In the same manner as in Example 52, 36.8 mg of the title compound was obtained from 58.0 mg of sodium (1S,5R,6S)-6-((1R)-1-hydroxyethyl)-2-(imidazo[5,1-b]thiazol-2-yl)-1-methyl-1-carbapen-2-em-3-carboxylate and 81.2 mg of (Z)-3-(2-bromoethylidene)phthalide.

NMR (CDCl$_3$) δ: 1.30(3H, d, J=7.3 Hz), 1.38(3H, d, J=6.2 Hz), 3.33–3.50(3H, m), 4.29–4.38(2H, m), 5.18–5.30(2H, m), 5.80–5.85(1H, m), 7.08(1H, s), 7.21–7.26(2H, m), 7.91–7.95(1H, m), 8.06(1H, s), 8.39(1H, s). MS (TSP): 492 (M$^+$+H).

Example 65

(1R,2S,5R)-(1)-menthyloxycarbonyloxymethyl (1S,5R,6S)-6-((1R)-1-hydroxyethyl)-2-(imidazo[5,1-b]thiazol-2-yl)-1-methyl-1-carbapen-2-em-3-carboxylate In the same manner as in Example 52, 80.4 mg of the title compound was obtained from 64.4 mg of sodium (1S,5R,6S)-6-((1R)-1-hydroxyethyl)-2-(imidazo[5,1-b]thiazol-2-yl)-1-methyl-1-carbapen-2-em-3-carboxylate and 92.5 mg of (1R,2S,5R)-(1)-menthyloxycarbonyloxymethyl iodide.

NMR (CDCl$_3$) δ: 0.67(3H, d, J=6.9 Hz), 0.79(3H, d, J=6.9 Hz), 0.84(3H, d, J=6.6 Hz), 0.90–1.05(2H, m), 1.22(3H, d, J=7.5 Hz), 1.30(3H, d, J=6.3 Hz), 1.38–1.45(1H, m), 1.56–1.65(2H, m), 1.80–1.93(3H, m), 2.00–2.08(1H, m), 3.22–3.28(1H, m), 3.33–3.45(1H, m), 4.19–4.30(2H, m), 4.42–4.51(1H, m), 5.83(1H, d, J=5.8 Hz), 5.90(1H, d, J=5.8 Hz), 7.00(1H, s), 7.98(1H, s), 8.33(1H, s). MS (APCI): 546 (M$^+$+H).

Example 66

(1S,2R,5S)-(d)-menthyloxycarbonyloxymethyl (1S,5R,6S)-6-((1R)-1-hydroxyethyl)-2-(imidazo[5,1-b]thiazol-2-yl)-1-methyl-1-carbapen-2-em-3-carboxylate In the same manner as in Example 52, 89.2 mg of the title compound was obtained from 61.7 mg of sodium (1S,5R,6S)-6-((1R)-1-hydroxyethyl)-2-(imidazo[5,1-b]thiazol-2-yl)-1-methyl-1-carbapen-2-em-3-carboxylate and 90.0 mg of (1S,2R,5S)-(d)-menthyloxycarbonyloxynethyl iodide.

NMR (CDCl$_3$) δ: 0.70(3H, d, J=7.1 Hz), 0.81(3H, d, J=7.2 Hz), 0.83(3H, d, J=7.1 Hz), 0.90–1.05(2H, m), 1.21(3H, d, J=7.1 Hz), 1.29(3H, d, J=6.0 Hz), 1.32–1.43(1H, m), 1.55–1.62(2H, m), 1.80–2.03(4H, m), 3.23–3.28(1H, m), 3.36–3.42(1H, m), 4.18–4.30(2H, m), 4.41–4.52(1H, m), 5.83(1H, d, J=5.8 Hz), 5.90(1H, d, J=5.8 Hz), 7.00(1H, s), 7.98(1H, s), 8.33(1H, s). MS (APCI): 546 (M$^+$+H).

Example 67

1-(phenyloxycarbonyloxy)ethyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture)

In the same manner as in Example 52, 43.3 mg of the title compound was obtained from 63.8 mg of sodium (1S,5R, 6S)-6-((1R)-1-hydroxyethyl)-2-(imidazo[5,1-b]thiazol-2-yl)-1-methyl-1-carbapen-2-em-3-carboxylate and 268.6 mg of 1-(phenyloxycarbonyloxy)ethyl iodide.

NMR (CDCl$_3$) δ: 1.25–1.35(3H, m), 1.38–1.45(3H, m), 1.67, 1.73(total 3H, d each, J=5.5 Hz), (5H, m), 3.32–3.50 (1H, m), 4.25–4.40(2H, m), 7.00–7.06(1H, m), 7.07(1H, s), 7.18–7.42(5H, m), 8.04(1H, s), 8.41(1H, s). MS (TSP): 498 (M$^+$+H).

Example 68

Phenyloxycarbonyloxymethyl (1S,5R,6S)-6-((1R)-1-hydroxyethyl)-2-(imidazo[5,1-b]thiazol-2-yl)-1-methyl-1-carbapen-2-em-3-carboxylate In the same manner as in Example 52, 79.0 mg of the title compound was obtained from 63.5 mg of sodium (1S,5R,6S)-6-((1R)-1-hydroxyethyl)-2-(imidazo[5,1-b]thiazol-2-yl)-1-methyl-1-carbapen-2-em-3-carboxylate and 101.9 mg of phenyloxycarbonyloxymethyl iodide.

NMR (CDCl$_3$) δ: 1.24(3H, d, J=7.1 Hz), 1.34(3H, d, J=6.3 Hz), 3.31–3.45(3H, m), 4.28–4.40(2H, m), 5.95(1H, d, J=5.8 Hz), 6.10(1H, d, J=5.8 Hz), 7.05(1H, s), 7.25–7.40(5H, m), 8.04(1H, s), 8.31(1H, s). MS (TSP): 484 (M$^+$+H).

Example 69

1-(cyclohexyloxycarbonyloxy)-n-propyl (1S,5R,6S)-6-((1R)-1-hydroxyethyl)-2-(imidazo[5,1-b]thiazol-2-yl)-1-methyl-1-carbapen-2-em-3-carboxylate (diastereomer mixture)

In the same manner as in Example 52, 60.0 mg of the title compound was obtained from 61.3 mg of sodium (1S,5R,6S)-6-((1R)-1-hydroxyethyl)-2-(imidazo[5,1-b]thiazol-2-yl)-1-methyl-1-carbapen-2-em-3-carboxylate and 100.8 mg of 1-(cyclohexyloxycarbonyloxy)-n-propyl iodide. NMR (CDCl$_3$) δ: 1.01, 1.08(total 3H, t each, J=7.4 Hz), 1.28, 1.30(total 3H, d each, J=7.1 Hz), 1.36, 1.39(total 3H, d each, J=6.6 Hz), 1.42–1.80(6H, m), 1.85–2.05(4H, m), 3.30–3.46 (2H, m), 4.25–4.35(2H, m), 4.60–4.72(1H, m), 6.78–6.84 (1H, m), 7.08(1H, s), 8.03(1H, s), 8.44, 8.46(total 1H, s each). MS (TSP): 518 (M$^+$+H).

Example 70

(1S,5R,6S)-2-(5-carbamoylimidazo[5,1-b]thiazol-2-yl)-6-((1R)-1-hydroxyethyl)-1-methyl-1-carbapen-2-em-3-carboxylic Acid a) 4-nitrobenzyl (1S,5R,6S)-2-(5-carbamoylimidazo[5,1-b]thiazol-2-yl)-6-((1R)-1-hydroxyethyl)-1-methyl-1-carbapen-2-em-3-carboxylate In the same manner as in Example 5-a), 92 mg of 4-nitrobenzyle (1S,5R,6S)-2-(5-carbamoylimidazo[5,1-b]thiazol-2-yl)-6-((1R)-1-hydroxyethyl)-1-methyl-1-carbapen-2-em-3-carboxylate was obtained from 251 mg of 4-nitrobenzyl (1R,3R,5R,6S)-6-((1R)-1-hydroxyethyl)-1-methyl-2-oxo-1-carbapenam-3-carboxylate and 364 mg of 5-carbamoyl-2-(tri-n-butylstannyl)imidazo[5,1-b]thiazole.

NMR (DMSO-d$_6$) δ: 1.17(3H, d, J=7.0 Hz), 1.20(3H, d, J=6.3 Hz), 3.42(1H, m), 3.72(1H, m), 4.04(1H, m), 4.34(1H, m), 5.14(1H, d, J=4.7 Hz), 5.37(1H, d, J=13.8 Hz), 5.49(1H, d, J=13.8 Hz), 7.23(1H, s), 7.52(1H, br.s), 7.70(2H, d, J=8.2 Hz), 7.81(1H, br.s), 8.19(2H, d, J=8.2 Hz), 8.71(1H, s).

b) (1S,5R,6S)-2-(5-carbamoylimidazo[5,1-b]thiazol-2-yl)-6-((1R)-1-hydroxyethyl)-1-methyl-1-carbapen-2-em-3-carboxylic Acid In the same manner as in Example 5-b), 23.9 mg of the title compound was obtained from 92 mg of 4-nitrobenzyl (1S,5R,6S)-2-(5-carbamoylimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.24(3H, d, J=7.1 Hz), 1.33(3H, d, J=6.3 Hz), 3.50(1H, m), 3.58(1H, m), 4.30(2H, m), 7.10(1H, s), 8.21(1H, s).

Example 71

Pivaloyloxymethyl (1S,5R,6S)-2-(5-carbamoylimidazo[5,1-b]thiazol-2-yl)-6-((1R)-1-hydroxyethyl)-1-methyl-1-carbapen-2-em-3-carboxylate In the same manner as in Example 19, 9.8 mg of the title compound was obtained from 15.7 mg of (1S,5R,6S)-2-(5-carbamoylimidazo[5,1-b]thiazol-2-yl)-6-((1R)-1-hydroxyethyl)-1-methyl-1-carbapen-2-em-3-carboxylate.

NMR (CDCl$_3$) δ: 1.22(9H, s), 1.33(3H, d, J=7.2 Hz), 1.37(3H, d, J=6.3 Hz), 3.35(1H, dd, J$_1$=6.3 Hz, J$_2$=2.7 Hz), 3.66(1H, m), 4.30(1H, m), 4.37(1H, dd, j$_1$=9.5 Hz, J$_2$=2.7 Hz), 5.58(1H, br.s), 5.89(1H, d, J=5.5 Hz), 5.99(1H, d, J=5.5 Hz), 7.00(1H, br.s), 7.15(1H, s), 8.73(1H, s).

Example 72

Potassium (5R,6S)-6-((1R)-1-hydroxyethyl)-2-(imidazo[5,1-b]thiazol-5-yl)-1-carbapen-2-em-3-carboxylate a) (3S,4R)-1-[(allyloxycarbonyl)(triphenylphosphoranylidene)methyl]-3-[(1R)-1-(t-butyldimethyl-ilyloxy)ethyl]-4-[(pivaloyloxycarbonyl)methyl]azetidine-2-one To a solution of 0.65 g of (3S,4R)-1-[(allyloxycarbonyl)(triphenylphosphoranylidene)methyl]-3-[(1R)-1-(t-butyldimethylsilyloxy)ethyl]-4-(carboxymethyl)azetidine-2-one in 4 ml of toluene were added under ice-cooling 0.14 ml of triethylamine and 0.12 ml of pivaloyl chloride, and the mixture was stirred at room temperature. The resulting precipitate was collected by filtration, and the filtrate was purified by column chromatography on silica gel (hexane:ethyl acetate=2:1) to give 0.60 g of (3S,4R)-1-[(allyloxycarbonyl)(triphenylphosphoranylidene)methyl]-3-[(1R)-1-(t-butyldimethylsilyloxy)ethyl]-4-[(pivaloyloxycarbonyl)methyl]azetidine-2-one.

NMR (CDCl$_3$) δ: −0.13(3H, s), −0.05(3H, s), 0.80(9H, s), 1.06(3H, d, J=6.0 Hz), 2.52–2.62(1H, m), 2.73–2.95(2H, m), 4.03–4.20(1H, m), 4.40–4.67(2H, m), 5.10–5.35(2H, m), 5.87–5.98(1H, m), 7.43–7.85(15H, m).

b ) Allyl (5R,6S)-6-[(R)-1-(t-butyldimethylsilyloxy)ethyl]-2-(imidazo[5,1-b]thiazol-5-yl)-1-carbapen-2-em-3-carboxylate In the same manner as in Example 48-b), 0.31 g of allyl (5R,6S)-6-[(1R)-1-(t-butyldimethylsilyloxy)ethyl]-2-(imidazo[5,1-b]thiazol-5-yl)-1-carbapen-2-em-3-carboxylate was obtained from -1.52 g of (3S,4R)-1-[(allyloxycarbonyl)(triphenylphosphoranylidene)methyl]-3-[(R)-1-(t-butyldimethylsilyloxy)ethyl]-4-[(pivaloyloxycarbonyl)methyl]azetidine-2-one.

NMR (CDCl$_3$) δ: 0.10(6H, s), 0.90(9H, s), 1.28(3H, d, J=6.0 Hz), 3.22(1H, dd, J=2.9, 6.2 Hz), 3.35(1H, dd, J=8.8, 18.6 Hz), 3.60(1H, dd, J=10.0, 18.6 Hz), 4.22–4.32(2H, m), 4.70–4.75(2H, m), 5.20–5.38(2H, m), 5.80–5.94(1H, m), 6.91(1H, d, J=4.2 Hz), 7.12(1H, d, J=4.2 Hz), 7.30(1H, s).

c) Allyl (5R,6S)-6-((1R)-1-hydroxyethyl)-2-(imidazo[5,1-b]thiazol-5-yl)-1-carbapen-2-em-3-carboxylate In the same manner as in Example 48-c), 72 mg of allyl (5R,6S)-6-((1R)-1-hydroxyethyl)-2-(imidazo[5,1-b]thiazol- 5-yl)-1-carbapen-2-em-3-carboxylate was obtained from 0.31 g of allyl (5R,6S)-6-[(1R)-1-(t-butyldimethylsilyloxy) ethyl]-2-(imidazo[5,1-b]thiazol-5-yl)-1-carbapen-2-em-3-carboxylate.

NMR (CDCl$_3$) δ: 1.40(3H, d, J=6.3 Hz), 3.30(1H, dd, J=3.0, 6.6 Hz), 3.40(1H, dd, J=12.0, 18.7 Hz), 3.60(1H, dd, J=10.0, 18.7 Hz), 4.24–4.36(2H, m), 4.64–4.82(2H, m), 5.20–5.36(2H, m), 5.81–5.94(1H, m), 6.92(1H, d, J=4.2 Hz), 7.10(1H, d, J=4.2 Hz), 7.31(1H, s).

d) Potassium (5R,6S)-6-((1R)-1-hydroxyethyl)-2-(imidazo [5,1-b]thiazol-5-yl)-1-carbapen-2-em-3-carboxylate In the same manner as in Example 48-d), 49 mg of the title compound was obtained from 172 mg of allyl (5R,6S)-6-((1R)-1-hydroxyethyl)-2-(imidazo[5,1-b]thiazol-5-yl)-1-carbapen-2-em-3-carboxylate.

NMR (D$_2$O) δ (HOD=4.80 ppm): 1.32(3H, d, J=6.5 Hz), 3.22(1H, dd, J=10.1, 17.8 Hz), 3.48(1H, dd, J=9.0, 17.8 Hz), 3.56(1H, dd, J=2.8, 5.8 Hz), 4.25–4.44(2H, m), 7.11(1H, d, J=4.1 Hz), 7.19(1H, s), 7.27(1H, d, J=4.1 Hz).

Example 73

Pivaloyloxymethyl (5R,6S)-6-((1R)-1-hydroxyethyl)-2-(imidazo[5,1-b]thiazol-5-yl)-1-carbapen-2-em-3-carboxylate In the same manner as in Example 50, 20 mg of the title compound was obtained from potassium (5R,6S)-6-((1R)-1-hydroxyethyl)-2-(imidazo[5,1-b]thiazol-5-yl)-1-carbapen-2-em-3-carboxylate.

NMR (CDCl$_3$) δ: 1.20(9H, s), 1.38(3H, d, J=6.4 Hz), 3.38(1H, dd, J=9.1, 19.8 Hz), 3.60(1H, dd, J=9.9, 19.8 Hz), 4.23–4.48(2H, m), 5.84(1H, d, J=5.5 Hz), 5.95(1H, d, J=5.5 Hz), 6.96(1H, d, J=4.3 Hz), 7.13(1H, d, J=4.3 Hz), 7.33(1H, s).

Example 74

(1S,5R,6S)-2-(5-fromylimidazo[5,1-b]thiazol-2-yl)-6-((1R)-1-hydroxyethyl)-1-methyl-1-carbapen-2-em-3-carboxylic Acid a) 4-nitrobenzyl (1S,5R,6S)-2-(5-formylimidazo[5,1-b]thiazol-2-yl)-6-((1R)-1-hydroxyethyl)-1-methyl-1-carbapen-2-em-3-carboxylate To a suspension of 292 mg of (1S,5R,6S)-6-((1R)-1-hydroxyethyl)-2-(5-hydroxymethylimidazo[5,1-b]thiazol-2-yl)-1-methyl-1-carbapen-2-em-3-carboxylate in 20 ml of dichloromethane was added 936 mg of manganese dioxide, and the mixture was stirred at room temperature for 2 days. The manganese dioxide was removed by filtration, and the filtrate was purified by column chromatography on silica gel (dichloromethane:methanol=20:1) to give 148 mg of 4-nitrobenzyl (1S,5R,6S)-2-(5-formylimidazo[5,1-b]thiazol-2-yl)-6-((1R)-1-hydroxyethyl)-1-methyl-1-carbapen-2-em-3-carboxylate.

NMR (CDCl$_3$) δ: 1.36(3H, d, J=7.4 Hz), 1.40(3H, d, J=6.2 Hz), 3.40(1H, dd, J$_1$=6.4 Hz, J$_2$=2.9 Hz), 3.67(1H, m), 4.32(1H, m), 4.41(1H, dd, J$_1$=9.3 Hz, J$_2$=2.9 Hz), 5.31(1H, d, J=13.4 Hz), 5.55(1H, d, J=13.4 Hz), 7.41(1H, s), 7.68(2H, d, J=8.8 Hz), 8.24(2H, d, J=8.8 Hz), 8.82(1H, s), 9.75(1H, s).

b) (1S,5R,6S)-2-(5-formylimidazo[5,1-b]thiazol-2-yl)-6-((1R)-1-hydroxyethyl)-1-methyl-1-carbapen-2-em-3-carboxylic Acid In the same manner as in Example 5-b), 34.7 mg of the title compound was obtained from 115 mg of 4-nitrobenzyl (1S,5R,6S)-2-(5-formylimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.23(3H, d, J=6.9 Hz), 1.34(3H, d, J=6.3 Hz), 3.51(1H, m), 3.59(1H, m), 4.30(2H, m), 7.37(1H, s), 8.32(1H, s), 9.40(1H, s).

Example 75

Pivaloyloxymethyl (1S,5R,6S)-2-(5-formylimidazo [5,1-b]thiazol-2-yl)-6-((1R)-1-hydroxyethyl)-1-methyl-1-carbapen-2-em-3-carboxylate In the same manner as in Example 19, 33.2 mg of the title compound was obtained from 40.0 mg of (1S,5R,6S)-2-(5-formylimidazo[5,1-b]thiazol-2-yl)-6-((1R)-1-hydroxyethyl)-1-methyl-1-carbapen-2-em-3-carboxylic acid.

NMR (CDCl$_3$) δ: 1.22(9H, s), 1.34(3H, d, J=7.4 Hz), 1.37(3H, d, J=6.2 Hz), 3.37(1H, dd, J$_1$=6.4 Hz, J$_2$=2.9 Hz), 3.67(1H, m), 4.30(1H, m), 4.39(1H, dd, J$_1$=9.6 Hz, J$_2$=2.9 Hz), 5.90(1H, d, J=5.6 Hz), 6.00(1H, d, J=5.6 Hz), 7.42(1H, s), 8.80(1H, s), 9.76(1H, s).

Example 76

(1S,5R,6S)-6-((1R)-1-hydroxyethyl)-2-(7-hydroxymethylimidazo[5,1-b]thiazol-2-yl)-1-methyl-1-carbapen-2-em-3-carboxylic Acid a) 4-nitrobenzyl (1S,5R,6S)-2-(7-t-butyldimethylsilyloxymethylimidazo[5,1-b]thiazol-2-yl)-6-((1R)-1-hydroxyethyl)-1-methyl-1-carbapen-2-em-3-carboxylate In the same manner as in Example 5-a), 392.6 mg of 4-nitrobenzy (1S,5R,6S)-2-(7-t-butyldimethylsilyloxymethylimidazo[5,1-b]thiazol-2-yl)-6-((1R)-1-hydroxyethyl)-1-methyl-1-carbapen-2-em-3-carboxylate was obtained from 598.9 mg of 4-nitrobenzyl (1R,3R,5R,6S)-6-((1R)-1-hydroxyethyl)-1-methyl-2-oxo-1-carbapenam-3-carboxylate and 1.03 g of 7-t-butyldimethylsilyloxymethyl-2-(tri-n-butylstannyl)imidazo [5,1-b]thiazole.

NMR (CDCl$_3$) δ: 0.14, 0.16(total 6H, s each), 0.97, 1.09(total 9H, s each), 1.30(3H, d, J=7.2 Hz), 1.40(3H, d, J=6.2 Hz), 3.35–3.39(1H, m), 3.43–3.51(1H, m), 4.28–4.40 (2H, m), 4.88, 4.89(total 2H, s each), 5.27(1H, d, J=14.0 Hz), 5.52(1H, d, J=14.0 Hz), 7.51(1H, s), 7.68(2H, d, J=8.9 Hz), 7.95(1H, s), 8.24(2H, d, J=8.9 Hz), 8.33(1H, s).

b) 4-nitrobenzyl (1S,5R,6S)-6-((1R)-1-hydroxyethyl)-2-(7-hydroxymethylimidazo[5,1-b]thiazol-2-yl)-1-methyl-1-carbapen-2-em-3-carboxylate To a solution of 334.6 mg of 4-nitrobenzyl (1S,5R,6S)-2-(7-t-butyldimethylsilyloxymethylimidazo[5,1-b]thiazol-2-yl)-6-((1R)-1-hydroxyethyl)-1-methyl-1-carbapen-2-em-3-carboxylate in 10 ml of THF were added 0.28 ml of acetic acid and 1.64 ml of a 1 M solution of tetra-n-butylammonium fluoride in THF, and the mixture was stirred at room temperature for 2.5 hours. After the reaction mixture was adjusted to pH 8.2 with a saturated aqueous sodium hydrogen carbonate solution, it was extracted twice with ethyl acetate, and semi-saturated aqueous saline. The organic layer was dried over anhydrous magnesium sulfate, and the solvent was removed under reduced pressure. The residue thus obtained was purified by column chromatography on silica gel (ethyl acetate:methanol=9:1) to give 183 mg of 4-nitrobenzyl (1S,5R,6S)-6-((1R)-1-hydroxyethyl)-2-(7-hydroxylmethylimidazo[5,1-b]thiazol-2-yl)-1-methyl-1-carbapen-2-em-3-carboxylate.

NMR (CDCl$_3$) δ: 1.29(3H, d, J=6.8 Hz), 1.39(3H, d, J=6.2 Hz), 2.92–3.00(1H, m), 3.36(1H, dd, J$_1$=6.6 Hz, J$_2$=2.7 Hz), 3.38–3.50(1H, m), 4.29–4.39(2H, m), 4.77(2H, s), 5.27(1H, d, J=13.8 Hz), 5.52(1H, d, J=13.8 Hz), 7.67(2H, d, J=8.9 Hz), 7.98(1H, s), 8.23(2H, d, J=8.9 Hz), 8.31(1H, s).

c) (1S,5R,6S)-6-((1R)-1-hydroxyethyl)-2-(7-hydroxymethylimidazo[5,1-b]thiazol-$^2$-yl)-1-methyl-1-carbapen-2-em-3-carboxylic Acid In the same manner as in Example 5-b), 87.7 mg of the title compound was obtained from 139.9 mg of 4-nitrobenzyl (1S,5R,6S)-6-((1R)-1-hydroxyethyl)-2-(7-hydroxymethylimidazo[5,1-b]thiazol-2-yl)-1-methyl-1-carbapen-2-em-3-carboxylate.

NMR (D$_2$O) δ (HOD=4.80 ppm): 1.25(3H, d, J=7.1 Hz), 1.31(3H, d, J=6.3 Hz), 3.50–3.61(2H, m), 4.24–4.32(2H, m), 4.66(2H, s), 7.89(1H, s), 8.11(1H, s).

Example 77

(1S,5R,6S)-6-((1R)-1-hydroxyethyl)-2-(7-hydroxymethyl-6-methylimidazo[5,1-b]thiazolium-2-yl)-1-methyl-1-carbapen-2-em-3-carboxylate
(inner salt)

a) 4-nitrobenzyl (1S,5R,6S)-6-((1R)-1-hydroxyethyl)-2-(7-hydroxymethyl-6-methylimidazo[5,1-b]thiazolium-2-yl)-1-methyl-1-carbapen-2-em-3-carboxylate Iodide In the same manner as in Example 4-a), 68.1 mg of 4-nitrobenzyl (1S,5R,6S)-6-((1R)-1-hydroxyethyl)-2-(7-hydroxymethyl-6-methylimidazo[5,1-b]thiazolium-2-yl)-1-methyl-1-carbapen-2-em-3-carboxate iodide was obtained from 54.5 mg of 4-nitrobenzyl (1S,5R,6S)-6-((1R)-1-hydroxyethyl)-2-(7-hydroxymethylimidazo[5,1-b]thiazol-2-yl)-1-methyl-1-carbapen-2-em-3-carboxylate.

NMR (CD$_3$OD) δ: 1.22(3H, d, J=6.3 Hz), 1.26(3H, d, J=7.4 Hz), 3.24(3H, s), 3.60–3.68(1H, m), 3.96(2H, s), 4.03–4.12(1H, m), 4.31–4.36(1H, m), 5.25(1H, d, J=13.7 Hz), 5.42(1H, d, J=13.7 Hz), 7.63(2H, d, J=8.8 Hz), 8.11 (2H, d, J=8.8 Hz), 8.42(1H, s), 9.29(1H, s).

b) (1S,5R,6S)-6-((1R)-1-hydroxyethyl)-2-(7-hydroxymethyl-6-methylimidazo[5,1-b]thiazolium-2-yl)-methyl-1-carbapen-2-em-3-carboxylate (inner salt)

In the same manner as in Example 4-b), 16.9 mg of the title compound was obtained from 68.1 mg of 4-nitrobenzyl (1S,5R,6S)-6-((1R)-1-hydroxyethyl)-2-(7-hydroxymethyl-6-methylimidazo[5,1-b]thiazolium-2-yl)-1-methyl-1-carbapen-2-em-3-carboxylate.

NMR (D$_2$O) δ (HOD=4.80 ppm): 1.24(3H, d, J=7.2 Hz), 1.30(3H, d, J=6.3 Hz), 3.51–3.67(3H, m), 4.01(2H, s), 4.21–4.33(3H, m), 4.86(2H, s), 8.06(1H, s), 9.14(1H, s).

Example 78

Potassium (1S,5R,6S)-6-((1R)-1-hydroxyethyl)-2-(imidazo[5,1-b]thiazol-7-yl)-1-methyl-1-carbapen-2-em-3-carboxylate a) (3S,4R)-1-(allyloxycarbonyl)(triphenylphosphoranylidene)methyl-3-((1R)-1-t-butyldimethylsilyloxyethyl)-4-[(1R)-1-(imidazo[5,1-b]thiazol-7-ylcarbonyl)ethyl]-azetidine-2-one To a solution of 540 mg of 7-iodoimidazo[5,1-b]thiazole in 16 ml of THF was added 2.4 ml of a 1 M solution of ethylmagnesium bromide in THF under ice-cooling under the atmosphere of argon, and the mixture was stirred at room temperature for 30 minutes. After confirming the exhaustion of the starting materials, the reaction mixture was cooled to −35−−40° C., and a solution of 1.64 g of 3S,4R)-1-(allyloxycarbonyl)(triphenylphosphoranylidene)methyl-3-((1R)-1-t-butyldimethylsilyloxyethyl)-4-[(1R)-1-(pivaloyloxycarbonyl)ethyl]-azetidine-2-one in 10 ml of THF was slowly added to the reaction mixture. After 15 minutes, the reaction mixture was placed in an ice bath, and stirred for 3 hours. It was diluted with 25 ml of a saturated ammonium, and extracted four times with 25 ml of ethyl acetate. The organic layer was washed twice with 30 ml of saturated aqueous saline, dried over anhydrous magnesium sulfate, and the solvent was removed under reduced pressure. The residue thus obtained was purified by column chromatography on silica gel (hexane:ethyl acetate=1:4—ethyl acetate) to give 570 mg of (3S,4R)-1-(allyloxycarbonyl)(triphenylphosphoranylidene)methyl-3-((1R)-1-t-butyldimethylsilyloxyethyl)-4-[(1R)-1-(imidazo[5,1-b]thiazol-7-yl-1-carbonyl)ethyl]-azetidine-2-one.

NMR (CDCl$_3$) δ: −0.2–0.0(6H, m), 0.6–0.8(9H, m), 0.8–1.5(6H, m), 2.7–3.4(3H, m), 4.0–4.7(3H, m), 5.0–5.4 (2H, m), 5.8–6.0(1H, m), 7–8(18H, m).

b) Allyl (1S,5R,6S)-6-((1R)-1-t-butyldimethylsilyloxyethyl)-2-(imidazo[5,1-b]thiazol-7-yl)-1-methyl-1-carbapen-2-em-3-carboxylate.

To a solution of 276 mg of (3S,4R)-1-(allyloxycarbonyl)(triphenylphosphoranylidene)methyl-3-((1R)-1-t-butyldimethylsilyloxyethyl)-4-[(1R)-1-(imidazo[5,1-b]thiazol-7-yl-1-carbonyl)ethyl]-azetidine-2-one in 8 ml of xylene was added 8 mg of hydroquinone, and the mixture was heated to 125° C. After cooling, the reaction mixture was purified by column chromatography on silica gel (hexane:ethyl acetate=1:1–1:3) to give 145 mg of allyl (1S,5R,6S)-6-((1R)-1-t-butyldimethylsilyloxyethyl)-2-(imidazo[5,1-b]thiazol-7-yl)-1-methyl-1-carbapen-2-em-3-carboxylate.

NMR (CDCl$_3$) δ: 0.10(6H, m), 0.90(9H, s), 1.20(3H, d, J=7.2 Hz), 1.32(3H, d, J=6.2 Hz) 3.25(1H, dd, J$_1$=6.9 Hz, J$_2$=2.6 Hz), 3.9–4.3(3H, m), 4.8(2H, m), 5.3–5.4(2H, m), 6.0(1H, m), 7.03(1H, d, J=4.3 Hz), 7.50(1H, d, J=4.3 Hz), 8.10(1H, s).

c) Allyl (1S,5R,6S)-6-((1R)-1-hydroxyethyl)-2-(imidazo[5,1-b]thiazol-7-yl)-1-methyl-1-carbapen-2-em-3-carboxylate To a solution of 460 mg of allyl (1S,5R,6S)-6-((1R)-1-t-butyldimethylsilyloxyethyl)-2-(imidazo[5,1-b]thiazol-7-yl)-1-methyl-1-carbapen-2-em-3-carboxylate in 14 ml of THF were added 860 μl and 3.76 ml of a 1 M tetra-n-butylammonium fluoride in THF, and the reaction was stirred at room temperature for 2 days. The reaction mixture was diluted with 120 ml of ethy acetate, washed with 30 ml of semi-saturated aqueous saline, and then with 30 ml of a mixed solution of semi-saturated aqueous saline and a saturated aqueous sodium hydrogen carbonate solution (1:1), dried over anhydrous magnesium sulfate, and the solvent was removed under reduced pressure. The residue thus obtained was purified by column chromatography on silica gel (dichloromethane:methanol=97:3–95:5) to give 286 mg of allyl (1S,5R,6S)-6-((1R)-1-hydroxyethyl)-2-(imidazo[5,1-b]thiazol-7-yl)-1-methyl-1-carbapen-2-em-3-carboxylate.

NMR (CDCl$_3$) δ: 1.21(3H, d, J=7.2 Hz), 1.39(3H, d, J=6.3 Hz), 3.30(1H, dd, J$_1$=6.9 Hz, J$_2$=2.5 Hz), 4.0(1H, m), 4.2–4.4(2H, m), 4.83(2H, m), 5.2–5.5(2H, m), 6.0(1H, m), 7.04(1H, d, J=4.3 Hz), 7.53(1H, d, J=4.3 Hz), 8.12(1H, s).

d) Potassium (1S,5R,6S)-6-((1R)-1-hydroxyethyl)-2-(imidazo[5,1-b]thiazol-7-yl)-1-methyl-1-carbapen-2-em-3-carboxylate To a solution of 117 mg of allyl (1S,5R,6S)-6-((1R)-1-hydroxyethyl)-2-(imidazo[5,1-b]thiazol-7-yl)-1-methyl-1-carbapen-2-em-3-carboxylate in a mixed solvent of 2.5 ml of dichloromethane and 2.5 ml of ethy acetate were added 8.1 mg of triphenylphosphine, 56.5 mg of potassium 2-ethylhexanoate, and 11.8 mg of tetrakis (triphenylphosphine)palladium (0), and the mixture was stirred under the atmosphere of argon at room temperature for 20 minutes. After confirming the exhaustion of the starting materials, the reaction mixture was diluted with 10 ml of ethyl acetate, extracted three or four times with water, and the aqueous layer was concentrated under reduced pressure. The concentrate was purified by column chromatography on COSMOSEAL 40C18-PREP to give the title compound in a yield of 55 mg.

NMR ($D_2O$) δ (HOD=4.80 ppm): 1.13(3H, d, J=7.2 Hz), 1.34(3H, d, J=6.3 Hz), 3.37(1H, dd, $J_1$=6.5 Hz, $J_2$=2 Hz), 3.53(1H, m), 4.17(1H, dd, $J_1$=8.6 Hz, $J_2$=2 Hz), 4.26(1H, m), 7.17(1H, d, J=4.1 Hz), 7.69(1H, d, J=4.1 Hz), 8.26(1H, s).

Example 79

(1S,5R,6S)-6-((1R)-1-hydroxyethyl)-2-(6-methylimidazo[5,1-b]thiazol-7-yl)-1-methyl-1-carbapen-2-em-3-carboxylate (inner salt)

To a solution of 77 mg of allyl (1S,5R,6S)-6-((1R)-1-hydroxyethyl)-2-(imidazo[5,1-b]thiazol-7-yl)-1-methyl-carbapen-2-em-3-carboxylate in dichloromethane was added dropwise 37 mg of trifluoromethanesulfonic acid under ice-cooling. After confirming the exhaustion of the starting materials, the solvent was removed under reduced pressure. The residue was triturated with 2.4 ml of dichloromethane and 2.4 ml of ethyl acetate, followed by about 1 ml of acetonitrile to form a homogeneous solution, to which 5.2 mg of triphenylphosphine and 36.5 mg of potassium 2-ethylhexanoate was added, followed by tetrakis (triphenylphosphine)palladium (0) for further 40 minute stirring at room temperature. The reaction mixture was diluted with 10 ml of dichloromethane, and extracted twice with 20 ml of water. The aqueous layer was concentrated, and the residue was purified by column chromatography on DIAION HP-20 (water—water:acetone=10:1) and on COSMOSEAL 40C18-PREP (water:acetonitrile=95:5–90:10) in this sequence to give 5.8 mg of the title compound.

NMR ($D_2O$) δ (HOD=4.80 ppm): 1.09(3H, d, J=7.4 Hz), 1.31(3H, d, J=6.5 Hz), 2.58(1H, m), 3.5–3.7(2H, m), 3.96 (3H, s), 4.30(1H, m), 4.45(1H, dd, $J_1$=10.2 Hz, $J_2$=3.0 Hz), 7.53(1H, d, J=4.2 Hz), 7.92(1H, d, J=4.2 Hz), 9.31(1H, s).

Example 80

Sodium (5R,6S)-2-(7-chloroimidazo[5,1-b]thiazol-2-yl)-6-((1R)-1-hydroxyethyl)-1-carbapen-2-em-3-carboxylate a) 4-nitrobenzyl (5R,6S)-2-(7-chloroimidazo[5,1-b]thiazol-2-yl)-6-((1R)-1-hydroxyethyl)-1-carbapen-2-em-3-carboxylate In the same manner as in Example 5-a), 4-nitrobenzyl (5R,6S)-2-(7-chloroimidazo[5,1-b]thiazol-2-yl)-6-((1R)-1-hydroxyethyl)-1-carbapen-2-em-3-carboxylate was obtained as a yellow powder in a yield of 907 mg from 887 mg of 4-nitrobenzyl (3R,5R,6S)-6-((1R)-1-hydroxyethyl)-2-oxo-1-carbapen-2-em-3-carboxylate and 1.254 g of 7-chloro-2-(tri-n-butylstannyl)imidazo[5,1-b]thiazole.

NMR (DMSO-$d_6$) δ: 1.17(3H, d, J=6.3 Hz), 3.40–3.50 (2H, m), 3.52(1H, dd, $J_1$=6.1 Hz, $J_2$=3.1 Hz), 3.97–4.05(1H, m), 4.25(1H, dt, $J_1$=10.3 Hz, $J_2$=2.8 Hz), 5.17(1H, d, J=4.9 Hz), 5.42(1H, d, J=13.7 Hz), 5.54(1H, d, J=13.7 Hz), 7.76(2H, d, J=8.5 Hz), 8.22(1H, s), 8.25(2H, d, J=8.5 Hz), 8.36(1H, s). MS (TSP): 489 ($M^+$+H).

b) Sodium (5R,6S)-2-(7-chloroimidazo[5,1-b]thiazol-2-yl)-6-((1R)-1-hydroxyethyl)-1-carbapen-2-em-3-carboxylate In the same manner as in Example 134-d) except that purification was carried out on CHP-20P (2% THF in water), 113 mg of the title compound was obtained from 245 mg of (5R,6S)-2-(7-chloroimidazo[5,1-b]thiazol-2-yl)-6-((1R)-1-hydroxyethyl)-1-carbapen-2-em-3-carboxylate.

NMR ($D_2O$) δ (HOD=4.80 ppm): 1.30(1H, d, J=6.3 Hz), 3.21–3.25(2H, m), 3.51(1H, dd, $J_1$=5.9 Hz, $J_2$=2.9 Hz), 4.20–4.26(2H, m), 7.71(1H, s), 8.00(1H, s).

Example 81

(5R,6S)-2-(5-carbamoylimidazo[5,1-b]thiazol-2-yl)-6-((1R)-1-hydroxyethyl)-1-carbapen-2-em-3-carboxylic Acid a) 4-nitrobenzyl (5R,6S)-2-(5-carbamoylimidazo[5,1-b]thiazol-2-yl)-6-((1R)-1-hydroxyethyl)-1-carbapen-2-em-3-carboxylate In the same manner as in Example 5-a), 108 mg of 4-nitrobenzyl (5R,6S)-2-(5-carbamoylimidazo[5,1-b]thiazol-2-yl)-6-((1R)-1-hydroxyethyl)-1-carbapen-2-em-3-carboxylate was obtained from 170 mg of 4-nitrobenzyl (3R,5R,6S)-6-((1R)-1-hydroxyethyl)-2-oxo-1-carbapenam-3-carboxylate and 267 mg of 5-carbamoyl-2-(tri-n-butylstannyl)imidazo[5,1-b]thiazole.

NMR (DMSO-$d_6$) δ: 1.17(3H, d, J=6.3 Hz), 3.53(3H, m), 4.03(1H, m), 4.27(1H, m), 5.15(1H, d, J=5.0 Hz), 5.42(1H, d, J=13.8 Hz), 5.54(1H, d, J=13.8 Hz), 7.23(1H, s), 7.53(1H, br.s), 7.76(2H, d, J=8.7 Hz), 7.83(1H, br.s), 8.24(2H, d, J=8.7 Hz), 8.63(1H, s).

b) (5R,6S)-2-(5-carbamoylimidazo[5,1-b]thiazol-2-yl)-6-((1R)-1-hydroxyethyl)-1-carbapen-2-em-3-carboxylic Acid In the same manner as in Example 5-b), 34.7 mg of the title compound was obtained from 105 mg of 4-nitrobenzyl (5R,6S)-2-(5-carbamoylimidazo[5,1-b]thiazol-2-yl)-6-((1R)-1-hydroxyethyl)-1-carbapen-2-em-3-carboxylate.

NMR ($D_2O$) δ (HOD=4.80 ppm): 1.33(3H, d, J=6.1 Hz), 3.28(2H, m), 3.53(1H, m), 4.28(2H, m), 7.10(1H, s), 8.00 (1H, s).

Example 82

Pivaloyloxymethyl (5R,6S)-2-(5-carbamoylimidazo[5,1-b]thiazol-2-yl)-6-((1R)-1-hydroxyethyl)-1-carbapen-2-em-3-carboxylate In the same manner as in Example 19, 12.2 mg of the title compound was obtained from 35.8 mg of (5R,6S)-2-(5-carbamoylimidazo[5,1-b]thiazol-2-yl)-6-((1R)-1-hydroxyethyl)-1-carbapen-2-em-3-carboxylic acid.

NMR ($CDCl_3$) δ: 1.24(9H, s), 1.37(3H, d, J=6.3 Hz), 3.33(1H, dd, $J_1$=6.3 Hz, $J_2$=2.8 Hz), 3.46(2H, m), 4.30(2H, m), 5.60(1H, br.s), 5.91(1H, d, J=5.5 Hz), 6.03(1H, d, J=5.5 Hz), 6.98(1H, br.s), 7.13(1H, s), 8.56(1H, s).

Example 83

(1S,5R,6S)-2-(5-formyl-6-methylimidazo[5,1-b]thiazolium-2-yl)-6-((1R)-1-hydroxyethyl)-1-methyl-1-carbapen-2-em-3-carboxylate (inner salt)

To a suspension of 33 mg of 4-nitrobenzyl (1S,5R,6S)-2-(5-formylimidazo[5,1-b]thiazol-2-yl)-6-((1R)-1-hydroxyethyl)-1-methyl-1-carbapen-2-em-3-carboxylate in 1 ml of dichloromethane was added 0.017 ml of methyl trifluoromethanesulfonate under ice-cooling. The mixture was stirred for 5 hours, and concentrated under reduced pressure. The residual concentrate was dissolved in 2 ml of THF and 2 ml of 1/15 M sodium phosphate buffer (pH 6.6), and 47 mg of 10% Pd-C was added therto. The reactor was purged with hydrogen, and the reaction mixture was stirred at room temperature for 2 hours. The catalyst was collected by filtration on Celite, and washed with water. The filtrate was washed with ethyl acetate, and the aqueous layer was purified by column chromatography on DIAION HP-20 (20% methanol in water) and on COSMOSEAL 40C18-PREP (water:methanol=10:1) to give 2.5 mg of the title compound.

NMR (D$_2$O) δ (HOD=4.80 ppm): 1.27(3H, d, J=6.9 Hz), 1.32(3H, d, J=6.3 Hz), 3.57(1H, m), 3.64(1H, m). 4.07(3H, s), 4.29(1H, m), 4.35(lH, m), 7.52(1H, s), 8.09(1H, s), 9.12(1H, s).

Example 84

Pivaloyloxymethyl (1S,5R,6S)-6-((1R)-1-hydroxyethyl)-2-(imidazo[5,1-b]thiazol-7-yl)-1-methyl-1-carbapen-2-em-3-carboxylate To a solution of 27 mg of sodium (1S,5R,6S)-6-((1R)-1-hydroxyethyl)-2-(imidazo[5,1-b]thiazol-7-yl)-1-methyl-1-carbapen-2-em-3-carboxylate in 0.5 ml of DMF was added 4.0 mg of sodium hydrogen carbonate, and the mixture was cooled to −30° C. under the atmosphere of argon. Pivaloyloxymethyl iodide (30 mg) was added, and the reaction mixture was stirred at −20—−30° C. for 1 hour. The reaction mixture was diluted with 20 ml of ethyl acetate and 10 ml of semi-saturated aqueous saline, and the mixture was stirred and separated. The organic layer was washed with semi-saturated aqueous saline, dried over anhydrous magnesium sulfate, and the solvent was concentrated under reduced pressure to a volume of about 1 ml. It was purified by column chromatography on silica gel (ethyl acetate-ethyl acetate:methanol=97:3), and the solvent was concentrated under reduced pressure to a volume of about 0.5 ml and added dropwise to isopropyl ether. The resulting precipitate was collected by filtration, and desiccated under reduced pressure to give 17 mg of the title compound.

NMR (CDCl$_3$) δ: 1.23(9H, s), 1.24(3H, d, J=7.9 Hz), 1.38(3H, d, J=6.3 Hz), 3.29(1H, dd, J$_1$=6.6 Hz, J$_2$=2.5 Hz), 3.98(1H, m), 4.2–4.4(2H, m), 5.96(1H, d, J=5.5 Hz), 6.05 (1H, d, J=5.5 Hz), 7.02(1H, d, J=4.2 Hz), 7.54(1H, d, J=4.2 Hz), 8.12(1H, s).

Example 85

Pivaloyloxymethyl (1S,5R,6S)-6-((1R)-1-hydroxyethyl)-2-(7-hydroxymethylimidazo[5,1-b]thiazol-2-yl)-1-methyl-1-carbapen-2-em-3-carboxylate In the same manner as in Example 19, 7.5 mg of the title compound was obtained from 58.5 mg of (1S,5R,6S)-6-((1R)-1-hydroxyethyl)-2-(7-hydroxymethylimidazo[5,1-b]thiazol-2-yl)-1-methyl-1-carbapen-2-em-3-carboxylic acid.

NMR (CDCl$_3$) δ: 1.14(9H, s), 1.20(3H, d, J=7.4 Hz), 1.29(3H, d, J=6.2 Hz), 3.25(1H, dd, J$_1$=6.6 Hz, J$_2$=2.7 Hz), 3.25–3.40(1H, m), 4.18–4.28(2H, m), 4.71(2H, s), 5.81(1H, d, J=5.6 Hz), 5.91(1H, d, J=5.6 Hz), 6.64(1H, s), 7.95(1H, s), 8.25(1H, s).

Example 86

(5R,6S)-2-(7-chloro-6-methylimidazo[5,1-b]thiazolium-2-yl)-6-((1R)-1-hydroxyethyl)-1-carbapen-2-em-3-carboxylate (inner salt)

In the same manner as in Example 4-a) except that 98 mg of 4-nitrobenzyl (5R,6S)-2-(7-chloroimidazo[5,1-b]thiazol-2-yl)-6-((1R)-1-hydroxyethyl)-1-carbapen-2-em-3-carboxylate and a mixed solvent of dichloromethane and DMF (1:1), the crude 4-nitrobenzyl (5R,6S)-2-(7-chloro-6-methylimidazo[5,1-b]thiazolium-2-yl)-6-((1R)-1-hydroxyethyl)-1-carbapen-2-em-3-carboxylate iodide was obtained as a yellowish brown oil in a yield of 99 mg.

In the same manner as in Example 4-b) except that a 61.0 mg portion of the crude product was used in the reaction, and purification was carried out with CHP-20P (10% methanol in water), the title compound was obtained in a yield of 7.5 mg as a pale yellow flocculate.

NMR (D$_2$O) δ (HOD=4.80 ppm): 1.30(3H, d, J=6.3 Hz), 3.30–3.45(2H, m), 3.56(1H, dd, J$_1$=6.1 Hz, J$_2$=3.0 Hz), 4.00(3H, s), 4.22–4.35(2H, m), 7.97(1H, s), 8.44(0.2H, s, partially exchanged with D$_2$O). MS (FAB$^+$): 370(M$^+$+3), 368(M$^+$+1).

Example 87

Pivaloyloxymethyl (5R,6S)-2-(7-chloroimidazo[5,1-b]thiazol-2-yl)-6-((1R)-1-hydroxyethyl)-1-carbapen-2-em-3-carboxylate In the same manner as in Example 135, the title compound was obtained in a yield of 41 mg as a yellow powder from 58 mg of sodium (5R,6S)-2-(7-chloroimidazo[5,1-b]thiazol-2-yl)-6-((1R)-1-hydroxyethyl)-1-carbapen-2-em-3-carboxylate.

NMR (CDCl$_3$) δ: 1.22(9H, s), 1.36(3H, d, J=6.3 Hz), 3.25–3.35(3H, m), 4.22–4.37(2H, m), 5.90(1H, d, J=5.6 Hz), 6.01(1H, d, J=5.6 Hz), 7.92(1H, s), 8.18(1H, s). MS (FAB$^+$): 470(M$^+$+3), 468(M$^+$+1).

Example 88

(5R,6S)-2-(6-carbamoylmethylimidazo[5,1-b]thiazolium-2-yl)-6-((1R)-1-hydroxyethyl)-1-carbapen-2-em-3-carboxylate (inner salt)

a) 4-nitrobenzyl (5R,6S)-2-(6-carbamoylmethylimidazo[5,1-b]thiazolium-2-yl)-6-((1R)-1-hydroxyethyl)-1-carbapen-2-em-3-carboxylate To a suspension of 69 mg of 4-nitrobenzyl (5R,6S)-6-((1R)-1-hydroxyethyl)-2-(imidazo[5,1-b]thiazol-2-yl)-1-carbapen-2-em-3-carboxylate in 2 ml of acetone was added 281 mg of iodoacetamide, and the mixture was stirred at room temperature for 25 hours. The reaction mixture was concentrated under reduced pressure to dryness. The residue was triturated with 3 ml of ethyl acetate, and the insolubles were collected by filtration to give 4-nitrobenzyl (5R,6S)-2-(6-carbamoylmethylimidazo[5,1-b]thiazolium-2-yl)-6-((1R)-1-hydroxyethyl)-1-carbapen-2-em-3-carboxylate iodide.

NMR (DMSO-d$_6$) δ: 1.18(3H, d, J=6.1 Hz), 3.45(3H, m), 4.03(1H, m), 4.32(1H, m), 5.17(2H, s), 5.45(1H, d, J=13.8 Hz), 5.55(1H, d, J=13.8 Hz), 7.08(1H, br.s), 7.63(1H, br.s), 7.75(2H, d, J=8.5 Hz), 7.83(1H, s), 8.25(2H, d, J=8.5 Hz), 8.60(1H, s), 9.55(1H, s).

b) (5R,6S)-2-(6-carbamoylmethylimidazo[5,1-b]thiazolium-2-yl)-6-((1R)-1-hydroxyethyl)-1-carbapen-2-em-3-carboxylate (inner salt)

In the same manner as in Example 4-b), the title compound was obtained in a yield of 11.2 mg from the whole amount of 4-nitrobenzyl (5R,6S)-2-(6-carbamoylmethylimidazo[5,1-b]thiazolium-2-yl)-6-((1R)-1-hydroxyethyl)-1-carbapen-2-em-3-carboxylate.

NMR (D$_2$O) δ (HOD=4.80 ppm): 1.30(3H, d, J=6.5 Hz), 3.32(2H, m), 3.54(1H, dd, J$_1$=5.6 Hz, J$_2$=2.8 Hz), 4.26(2H, m), 5.24(2H, s), 7.53(1H, s), 7.94(1H, s).

Example 89

Sodium (1S,5R,6S)-2-(5,7-dimethylimidazo[5,1-b]thiazol-2-yl)-6-((1R)-1-hydroxyethyl)-1-methyl-1-carbapen-2-em-3-carboxylate a) 4-nitrobenzyl (1S,5R,6S)-2-(5,7-dimethylimidazo[5,1-b]thiazol-2-yl)-6-((1R)-1-hydroxyethyl)-1-methyl-1-carbapen-2-em-3-carboxylate In the same manner as in example 5-a), 4-nitrobenzyl (1S,5R,6S)-2-(5,7-dimethylimidazo[5,1-b]thiazol-2-yl)-6-((1R)-1-hydroxyethyl)-1-methyl-1-carbapen-2-em-3-carboxylate was obtained in a yield of 365 mg as a dark yellow powder from 544 mg of 4-nitrobenzyl (1R,3R,5R, 6S)-6-((1R)-1-hydroxyethyl)-1-methyl-2-oxo-1-carbapen-2-em-3-carboxylate and 728 mg of 5,7-dimethyl-2-(tri-n-butylstannyl)imidazo[5,1-b]thiazole.

NMR (DMSO-$d_6$) δ: 1.18(3H, d, J=6.6 Hz), 1.21(3H, d, J=7.8 Hz), 2.14(3H, s), 2.45(3H, s), 3.34–3.41(1H, m), 3.65–3.77(1H, m), 3.97–4.05(1H, m), 4.30(1H, dd, $J_1$=9.5 Hz, $J_2$=2.6 Hz), 5.15(1H, d, J=5.0 Hz), 5.37(1H, d, J=13.8 Hz), 5.50(1H, d, J=13.8 Hz), 7.72(2H, d, J=8.8 Hz), 8.21 (1H, s), 8.22(2H, d, J=8.8 Hz). MS (TSP): 497($M^+$+H).

b) Sodium (1S,5R,6S)-2-(5,7-dimethylimidazo[5,1-b]thiazol-2-yl)-6-((1R)-1-hydroxyethyl)-1-methyl-1-carbapen-2-em-3-carboxylate In the same manner as in Example 134-d) except that 224 mg of 4-nitrobenzyl (1S,5R,6S)-2-(5,7-dimethylimidazo[5,1-b]thiazol-2-yl)-6-((1R)-1-hydroxyethyl)-1-methyl-1-carbapen-2-em-3-carboxylate and 224 mg of 10% palladium on carbon were used, and that purification was carried out on HP-20 (20% methanol in water) and on COSMOSEAL 40C18-PREP (10% methanol in water), the title compound was obtained in a yield of 103 mg.

NMR ($D_2O$) δ (HOD=4.80 ppm): 1.24(3H, d, J=6.9 Hz), 1.31(3H, d, J=6.6 Hz), 2.28(3H, s), 2.65(3H, s), 3.50–3.65 (2H, m), 4.24–4.35(2H, m), 7.79(1H, s). MS (TSP): 384 ($M^+$+Na), 362 ($M^+$+H).

Example 90

Sodium (1S,5R,6S)-2-(7-formylaminomethyl imidazo[5,1-b]thiazol-2-yl)-6-((1R)-1-hydroxyethyl)-1-methyl-1-carbapen-2-em-3-carboxylate a) 4-nitrobenzyl (1S,5R,6S)-2-(7-formylaminomethyl imidazo[5,1-b]thiazol-2-yl)-6-((1R)-1-hydroxyethyl)-1-methyl-1-carbapen-2-em-3-carboxylate In the same manner as in Example 5-a), 4-nitrobenzyl (1S,5R,6S)-2-(7-formylaminomethyl imidazo[5,1-b]thiazol-2-yl)-6-((1R)-1-hydroxyethyl)-1-methyl-1-carbapen-2-em-3-carboxylate was obtained in a yield of 0.46 g from 0.36 g of 4-nitrobenzyl (1R,3R,5R,6S)-6-((1R)-1-hydroxyethyl)-1-methyl-2-oxo-1-carbapenam-3-carboxylate and 0.47 g of 7-formylaminomethyl-2-(tri-n-butylstannyl)imidazo[5,1-b]thiazole.

NMR ($CDCl_3$) δ: 1.27(3H, d, J=7.4 Hz), 1.38(3H, d, J=6.3 Hz), 3.34(1H, dd, J=2.8, 6.6 Hz), 3.45(1H, m), 4.25(1H, m), 4.45(1H, dd, J=2.8, 9.4 Hz), 4.49(2H, s), 5.29(1H, d, J=13.5 Hz), 5.50(1H, d, J=13.5 Hz), 7.66(2H, d, J=8.5 Hz), 8.00 (1H, s), 8, 19(1H, s), 8.22(2H, d, J=8.5 Hz), 8.30(1H, s).

b) Sodium (1S,5R,6S)-2-(7-formylaminomethyl imidazo[5,1-b]thiazol-2-yl)-6-((1R)-1-hydroxyethyl)-1-methyl-1-carbapen-2-em-3-carboxylate In the same manner as in Example 134-d), the title compound was obtained in a yield of 58 mg from 0.27 g of 4-nitrobenzyl (1S,5R,6S)-2-(7-formylaminomethyl imidazo [5,1-b]thiazole2-yl)-6-((1R-)-1-hydroxyethyl)-1-methyl-1-carbapen-2-em-3-carboxylate.

NMR ($D_2O$) δ (HOD=4.80 ppm): 1.22(3H, d, J=7.1 Hz), 1.31((3H, d, J=6.3 Hz), 3.45–3.60(2H, m), 4.20–4.30(2H, m), 4.43(2H, s), 7.84(1H, s), 8.05(1H, s), 8.16(1H, s).

Example 91

Acetoxymethyl (5R,6S)-6-((1R)-1-hydroxyethyl)-2-(imidazo[5,1-b]thiazol-3-yl)-1-carbapen-2-em-3-carboxylate To a solution-of 60.2 mg of sodium (5R,6S)-6-((1R)-1-hydroxyethyl)-2-(imidazo[5,1-b]thiazol-3-yl)-1-carbapen-2-em-3-carboxylate in 1.4 ml of DMF was added 67.7 mg of acetoxymethyl bromide under the atmosphere of argon at a temperature of −30° C., and the mixture was stirred for 3 hours during which the temperature was raised up to −10° C. The reaction mixture was diluted twice with 20 ml of ethy acetate, and washed twice with 10 ml of semi-saturated aqueous saline. The organic layer was dried over anhydrous magnesium sulfate, filtered, and concentrated under reduced pressure to a volume of 2 ml. The residue thus obtained was purified by column chromatography on silica gel (dichloromethane:methanol=15:1) and Sephadex LH-20 (dichloromethane:methanol=1:1) in this sequence to give 22.1 mg of the title compound.

NMR ($CDCl_3$) δ: 1.39(3H, d, J=6.3 Hz), 2.10(3H, s), 3.32–3.40(3H, m), 4.25–4.34(1H, m), 4.37–4.45(1H, m), 5.78(1H, d, J=5.6 Hz), 5.86(1H, d, J=5.6 Hz), 7.13(2H, s), 7.79(1H, s). MS (TSP): 392 ($M^+$+H).

Example 92

1-(acetoxy)ethyl (5R,6S)-2-(imidazo[5,1-b]thiazol-3-yl)-6-((1R)-1-hydroxyethyl)-1-carbapen-2-em-3-carboxylate (diastereomer mixture)

In the same manner as in Example 91, the title compound was obtained in a yield of 21.2 mg from 56.4 mg of sodium (5R,6S)-6-((1R)-1-hydroxyethyl)-2-(imidazo[5,1-b]thiazol-3-yl)-1-carbapen-2-em-3-carboxylate and 70.6 mg of 1-(acetoxy)ethyl iodide.

NMR ($CDCl_3$) δ: 1.35–1.48(6H, m), 2.05–2.10(3H, m), 3.30–3.41(3H, m), 4.23–4.32(1H, m), 4.36–4.45(1H, m), 6.85–6.92(1H, m), 7.08, 7.10(total 1H, s each), 7.12(1H, s), 7.83, 7.84(total 1H, s each). MS (TSP): 406 ($M^+$+H).

Example 93

(1-methylcyclohexan-1-yl)carbonyloxymethyl (5R,6S)-6-((1R)-1-hydroxyethyl)-2-(imidazo[5,1-b]thiazol-3-yl)-1-carbapen-2-em-3-carboxylate In the same manner as in Example 91, the title compound was obtained in a yield of 55.5 mg from 62.5 mg of sodium (5R,6S)-6-((1R)-1-hydroxyethyl)-2-(imidazo[5,1-b]thiazol-3-yl)-1-carbapen-2-em-3-carboxylate and 69.8 mg of (1-methylcyclohexan-1-yl)carbonyloxymethyl iodide.

NMR ($CDCl_3$) δ: 1.15–1.25(6H, m), 1.36(3H, s), 1.37 (3H, d, J=6.3 Hz), 1.40–1.56(3H, m), 1.93–2.06(2H, m), 3.31–3.29(3H, m), 4.25–4.33(1H, m), 4.37–4.45(1H, m), 5.82(1H, d, J=5.5 Hz), 5.87(1H, d, J=5.5 Hz), 7.12(1H, s), 7.14(1H, s), 7.82(1H, s). MS (TSP): 474 ($M^+$+H).

Example 94

1-(ethoxycarbonyloxy)ethyl (5R,6S)-6-((1R)-1-hydroxyethyl)-2-(imidazo[5,1-b]thiazol-3-yl)-1-carbapen-2-em-3-carboxylate (diastereomer mixture)

In the same manner as in Example 91, the title compound was obtained in a yield of 28.4 mg from 60.0 mg of sodium (5R,6S)-6-((1R)-1-hydroxyethyl)-2-(imidazo[5,1-b]thiazol-3-yl)-1-carbapen-2-em-3-carboxylate and 85.9 mg of 1-(ethoxycarbonyloxy)ethyl iodide.

NMR ($CDCl_3$) δ: 1.21–1.36(6H, m), 1.40–1.46(3H, m), 3.24–3.32(3H, m), 4.12–4.28(3H, m), 4.30–4.39(1H, m), 6.71–6.47(1H, m), 7.05(2H, s), 7.75(1H, s). MS (TSP): 436 ($M^+$+H).

Example 95

1-(isopropoxycarbonyloxy)ethyl (5R,6S)-6-((1R)-1-hydroxyethyl)-2-(imidazo[5,1-b]thiazol-3-yl)-1-carbapen-2-em-3-carboxylate (diastereomer mixture)

To a solution of 48 mg of sodium (5R,6S)-6-((1R)-1-hydroxyethyl)-2-(imidazo[5,1-b]thiazol-3-yl)-1-carbapen- 2-em-3-carboxylate in 1 ml of DMF was added 73 mg of 1-(isopropoxycarbonyloxy)ethyl iodide under the atmosphere of argon at −20° C., and the mixture was stirred for 3 hours during which the temperature was raised up to −10° C. The reaction mixture was extracted twice with 20 ml of ethyl acetate, and washed twice with 10 ml of semi-saturated aqueous saline. The organic layer was dried over anhydrous magnesium sulfate, filtered and concentrated under reduced pressure to a volume of 2 ml. The residue thus obtained was purified by column chromatography on silica gel (chloroform:methanol=9:1) and on Sephadex LH-20 (dichloromethane:methanol=1:1) in this sequence to give the title compound in a yield of 22 mg.

NMR (CDCl$_3$) δ: 1.28–1.47(12 Hz, m), 3.24–3.42(3H, m), 4.21–4.47(2H, m), 6.67–6.88(1H, m). 7.10(1H, s), 7.13 (1H, s), 7.85(1H, s). MS (TSP): 450 (M$^+$+H).

Example 96

1-(cyclohexyloxycarbonyloxy)ethyl (5R,6S)-6-((1R)-1-hydroxyethyl)-2-(imidazo[5,1-b]thiazol-3-yl)-1-carbapen-2-em-3-carboxylate (diastereomer mixture)

In the same manner as in Example 95, the title compound was obtained in a yield of 45 mg from 48 mg of sodium (5R,6S)-6-((1R)-1-hydroxyethyl)-2-(imidazo[5,1-b]thiazol-3-yl)-1-carbapen-2-em-3-carboxylate and 63 mg of 1-(cyclohexyloxycarbonyloxy)ethyl iodide.

NMR (CDCl$_3$) δ: 1.20–1.67(12H, m), 1.68–1.84(2H, m), 1.86–2.20(2H, m), 3.24–3.45(3H, m), 4.22–4.48(2H, m), 4.57–4.71(1H, m), 6.77–6.88(1H, m), 7.11, 7.12(total 1H, s each), 7.14(1H, s), 7.84, 7.85(total 1H, s each). MS (TSP): 490 (M$^+$+H).

Example 97

Cyclohexyloxycarbonyloxy methyl (5R,6S)-6-((1R)-1-hydroxyethyl)-2-(imidazo[5,1-b]thiazol-3-yl)-1-carbapen-2-em-3-carboxylate In the same manner as in Example 91, the title compound was obtained in a yield of 39.5 mg from 61.7 mg of sodium (5R,6S)-6-((1R)-1-hydroxyethyl)-2-(imidazo[5,1-b]thiazol-3-yl)-1-carbapen-2-em-3-carboxylate and 69.8 mg of cyclohexyloxycarbonyloxymethyl iodide.

NMR (CDCl$_3$) δ: 1.23–1.98(10H, m), 1.38(3H, d, J=6.2 Hz), 3.33–3.42(3H, m), 4.26–4.36(1H, m), 4.36–4.46(1H, m), 4.00–4.70(1H, m), 5.80(1H, d, J=5.7 Hz), 5.88(1H, d, J=5.7 Hz), 7.13(1H, s), 7.18(1H, s), 7.83(1H, s). MS (TSP): 476 (M$^+$+H).

Example 98

3-phthalidyl (5R,6S)-6-((1R)-1-hydroxyethyl)-2-(imidazo[5,1-b]thiazol-3-yl)-1-carbapen-2-em-3-carboxylate (diastereomer mixture)

In the same manner as in Example 95, the title compound was obtained in a yield of 24 mg from 42 mg of sodium (5R,6S)-6-((1R)-1-hydroxyethyl)-2-(imidazo[5,1-b]thiazol-3-yl)-1-carbapen-2-em-3-carboxylate and 39 mg of 3-phthalidyl bromide.

NMR (CDCl$_3$) δ: 1.36, 1.37(total 3H, d each, J=6.3 Hz), 3.13–3.45(3H, m), 4.21–4.50(2H, m), 6.98, 6.99(total 1H, s each), 7.10, 7.25(total 1H, s each), 7.40(1H, s), 7.80, 7.87 (total 1H, s each), 7.35–7.91(4H, m). MS (TSP): 452 (M$^+$+H).

Example 99

(5-methyl-2-oxo-1,3-dioxolen-4-yl)methyl (5R,6S)-6-((1R)-1-hydroxyethyl)-2-(imidazo[5,1-b]thiazol-3-yl)-1-carbapen-2-em-3-carboxylate In the same manner as in Example 91, the title compound was obtained in a yield of 15.9 mg from 65.3 mg of sodium (5R,6S)-6-((1R)-1-hydroxyethyl)-2-(imidazo[5,1-b]thiazol-3-yl)-1-carbapen-2-em-3-carboxylate and 65.8 mg of (5-methyl-2-oxo-1,3-dioxolen-4-yl)methyl bromide.

NMR (CDCl$_3$) δ: 1.39(3H, d, J=6.3 Hz), 2.78(3H, s), 3.35–3.40(3H, m), 4.29–4.34(1H, m), 4.38–4.46(1H, m), 4.90(1H, s), 4.91(1H, s), 7.03(1H, s), 7.12(1H, s), 7.73(1H, s). MS (TSP): 476 (M$^+$+H).

Example 100

Pivaloyloxymethyl (1S,5R,6S)-2-(7-formylaminomethyl imidazo[5,1-b]thiazol-2-yl)-6-((1R)-1-hydroxyethyl)-1-methyl-1-carbapen-2-em-3-carboxylate To a solution of 33 mg of sodium (1S,5R,6S)-2-(7-formylaminomethyl imidazo[5,1-b]thiazol-2-yl)-6-((1R)-1-hydroxyethyl)-1-methyl-1-carbapen-2-em-3-carboxylate in 0.8 ml of DMF was added 29 mg of pivaloyloxymethyl iodide at −30° C., and the mixture was stirred for 1 hour during which the temperature was raised up to room temperature. The reaction mixture was diluted with 30 ml of dichloromethane, washed with semi-saturated aqueous saline, and dried over anhydrous magnesium sulfate. The solvent was removed under reduced pressure, and the residue thus obtained was purified by column chromatography on silica gel (ethyl acetate:methanol=4:1) to give the title compound in a yield of 29 mg.

NMR (CDCl$_3$) δ: 1.20(9H, s), 1.24(3H, d, J=7.2 Hz), 1.34(3H, d, J=6.2 Hz), 3.31(1H, dd, J=2.8, 6.5 Hz), 3.41(1H, m), 3.49(2H, s), 4.25–4.35(2H, m), 4.45–4.60(2H, m), 5.86 (1H, d, J=5.6 Hz), 5.98(1H, d, J=5.6 Hz), 6.72(1H, br.s s), 8.00(1H, s), 8.26(1H, s), 8.34(1H, s).

Example 101

Sodium (5R,6S)-2-(7-formylaminomethyl imidazo [5,1-b]thiazol-3-yl)-6-((1R)-1-hydroxyethyl)-1-carbapen-2-em-3-carboxylate a) 4-nitrobenzyl (5R,6S)-2-(7-formylaminomethyl imidazo [5,1-b]thiazol-3-yl)-6-((1R)-1-hydroxyethyl)-1-carbapen-2-em-3-carboxylate In the same manner as in Example 5-a), 4-nitrobenzyl (5R,6S)-2-(7-formylaminomethyl imidazo[5,1-b]thiazol-3-yl)-6-((1R)-1-hydroxyethyl)-1-carbapen-2-em-3-carboxylate was obtained in a yield of 0.70 g from 0.42 g of 4-nitrobenzyl (3R,5R,6S)-6-((1R)-1-hydroxyethyl)-2-oxo-1-carbapenam-3-carboxylate and 0.47 g of 7-formylaminomethyl-3-(tri-n-butylstannyl)imidazo[5,1-b] thiazole.

NMR (DMSO-d$_6$) δ: 1.17(3H, d, J=6.0 Hz), 3.15–3.30 (2H, m), 3.50–3.62(1H, m), 3.95–4.05(1H, m), 4.25–4.33 (3H, m), 5.28(1H, d, J=13.5 Hz), 5.33(1H, d, J=13.5 Hz), 7.37(1H, s), 7.52(2H, d, J=8.3 Hz), 7.96(1H, s), 8.14(1H, s), 8.17(2H, d, J=8.3 Hz).

b) Sodium (5R,6S)-2-(7-formylaminomethyl imidazo[5,1-b] thiazol-3-yl)-6-((1R)-1-hydroxyethyl)-1-carbapen-2-em-3-carboxylate In the same manner as in Example 134-d), the title compound was obtained in a yield of 27 mg from 0.55 g of 4-nitrobenzyl (5R,6S)-2-(7-formylaminomethylimidazo[5,1-b]thiazol-3-yl)-6-((1R)-1-hydroxyethyl)-1-carbapen-2-em-3-carboxylate.

NMR (D$_2$O) δ (HOD=4.80 ppm): 1.32(3H, d, J=6.3 Hz), 3.20(1H, dd, J=2.9, 5.9 Hz), 3.40–3.48(1H, m), 3.58(1H, dd, J=2.9, 5.9 Hz), 4.23–4.30(1H, m), 4.32–4.41(1H, m), 4.50 (2H, s), 7.05(1H, s), 7.94(1H, s), 8.17(1H, s).

Example 102

Pivaloyloxymethyl (5R,6S)-2-(7-formylaminomethylimidazo[5,1-b]thiazol-3-yl)-6-((1R)-1-hydroxyethyl)-1-carbapen-2-em-3-carboxylate In the same manner as in Example 50, the title compound was obtained in a yield of 24 mg from 45 mg of sodium (5R,6S)-2-(7-formylaminomethylimidazo[5,1-b]thiazol-3-yl)-6-((1R)-1-hydroxyethyl)-1-carbapen-2-em-3-carboxylate.

NMR (D$_2$O) δ (HOD=4.80 ppm): 1.20(9H, s), 1.35(3H, d, J=6.2 Hz), 3.29–3.40(3H, m), 4.22–4.32(1H, m), 4.35–4.44 (1H, m), 4.50(2H, d, J=5.6 Hz), 5.73(1H, d, J=5.6 Hz), 5.83(1H, d, J=5.6 Hz), 6.85(1H, t, J=5.6 Hz), 7.06(1H, s), 7.72(1H, s), 8.22(1H, s).

Example 103

(5R,6S)-2-(7-carbamoylimidazo[5,1-b]thiazol-3-yl)-6-((1R)-1-hydroxyethyl)-1-carbapen-2-em-3-carboxylic Acid a) 4-nitrobenzyl (5R,6S)-2-(7-carbamoylimidazo[5,1-b]thiazol-3-yl)-6-((1R)-1-hydroxyethyl)-1-carbapen-2-em-3-carboxylate In the same manner as in Example 5-a), 124 mg of 4-nitrobenzyl (5R,6S)-2-(7-carbamoylimidazo[5,1-b]thiazol-3-yl)-6-((1R)-1-hydroxyethyl)-1-carbapen-2-em-3-carboxylate was obtained from 255 mg of 4-nitrobenzyl (3R,5R,6S)-6-((1R)-1-hydroxyethyl)-2-oxo-1-carbapenam-3-carboxylate and 401 mg of 7-carbamoyl-3-(-tri-n-butylstannyl)imidazo[5,1-b]thiazole.

NMR (CDCl$_3$) δ: 1.41(3H, d, J=6.1 Hz), 3.39(3H, m), 4.32(1H, m), 4.46(1H, m), 5.21(1H, d, J=13.0 Hz), 5.37(1H, d, J=13.0 Hz), 7.17(1H, s), 7.47(2H, d, J=8.7 Hz), 7.56(1H, s), 8.19(2H, d, J=8.7 Hz).

b) (5R,6S)-2-(7-carbamoylimidazo[5,1-b]thiazol-3-yl)-6-((1R)-1-hydroxyethyl)-1-carbapen-2-em-3-carboxylic Acid In the same manner as in Example 5-b), the title compound was obtained in a yield of 42.3 mg from 124 mg of 4-nitrobenzyl (5R,6S)-2-(7-carbamoylimidazo[5,1-b]thiazol-3-yl)-6-((1R)-1-hydroxyethyl)-1-carbapen-2-em-3-carboxylate.

NMR (D$_2$O) δ (HOD=4.80 ppm): 1.33(3H, d, J=6.5 Hz), 3.23(1H, dd, J$_1$=17.0 Hz, J$_2$=9.9 Hz), 3.48(1H, dd, J$_1$=17.0 Hz, J$_2$=8.5 Hz), 3.60(1H, m), 4.29(1H, m), 4.40(1H, m), 7.21(1H, s), 7.87(1H, s).

Example 104

Pivaloyloxymethyl (5R,6S)-2-(7-carbamoylimidazo [5,1-b]thiazol-3-yl)-6-((1R)-1-hydroxyethyl)-1-carbapen-2-em-3-carboxylate In the same manner as in Example 19, the title compound was obtained in a yield of 14.1 mg from 44.6 mg of (5R,6S)-2-(7-carbamoylimidazo[5,1-b]thiazol-3-yl)-6-((1R)-1-hydroxyethyl)-1-carbapen-2-em-3-carboxylic acid.

NMR (CDCl$_3$) δ: 1.19(9H, s), 1.37(3H, d, J=6.3 Hz), 3.38(3H, m), 4.29(1H, m), 4.43(1H, m), 5.71(1H, br.s), 5.77(1H, d, J=5.5 Hz), 5.88(1H, d, J=5.5 Hz), 6.91(1H, br.s), 7.21(1H, s), 7.71(1H, s).

Example 105

(1S,5R,6S)-6-((1R)-1-hydroxyethyl)-1-methyl-2-( 5,6,7-trimethylimidazo[5,1-b]thiazolium-2-yl)-1-carbapen-2-em-3-carboxylate (inner salt)

a) 4-nitrobenzyl (1S,5R,6S)-6-((1R)-1-hydroxyethyl)-1-methyl-2-(5,6,7-trimethylimidazo[5,1-b]thiazolium-2-yl)-1-carbapen-2-em-3-carboxylate Iodide In the same manner as in Example 4-a), 121.3 mg of 4-nitrobenzyl (1S,5R,6S)-6-((1R)-1-hydroxyethyl)-1-methyl-2-(5,6,7-trimethylimidazo[5,1-b]thiazolium-2-yl)-1-carbapen-2-em-3-carboxylate was obtained as a yellowish orange powder from 99.3 mg of 4-nitrobenzyl (1S,5R,6S)-2-(5,7-dimethylimidazo[5,1-b]thiazol-2-yl)-6-((1R)-1-hydroxyethyl)-1-methyl-1-carbapen-2-em-3-carboxylate and 1.0 ml of methyl iodide.

NMR (DMSO-d$_6$) δ: 1.18(3H, d, J=6.3 Hz), 1.23(3H, d, J=7.2 Hz), 2.44(3H, s), 2.83(3H, s), 3.48(1H, dd, J$_1$=5.9 Hz, J$_2$=2.9 Hz), 3.73–3.84(1H, m), 3.80(3H, s), 4.02–4.09(1H, m), 4.39(1H, dd, J$_1$=10.1 Hz, J$_2$=2.9 Hz), 5.19(1H, d, J=5.2 Hz), 5.40(1H, d, J=13.8 Hz), 5.52(1H, d, J=13.8 Hz), 7.73(2H, d, J=8.8 Hz), 8.24(2H, d, J=8.8 Hz), 8.59(1H, s). MS (TSP): 511 (M$^+$).

b) (1S,5R,6S)-6-((1R)-1-hydroxyethyl)-1-methyl-2-(5,6,7-trimethylimidazo[5,1-b]-thiazolium-2-yl)-1-carbapen-2-em-3-carboxylate (inner salt)

In the same manner as in Example 4-b) except that 115 mg of 4-nitrobenzyl (1S,5R,6S)-6-((1R)-1-hydroxyethyl)-1-methyl-2-(5,6,7-trimethylimidazo[5,1-b]thiazolium-2-yl)-1-carbapen-2-em-3-carboxylate iodide was used and that purification was carried out on CHP-20P (20–30% methanol in water) and on COSMOSEAL 40C18-PREP (20% methanol in water), the title compound was obtained in a yield of 9.1 mg as a milk-white flocculate.

NMR (D$_2$O) δ (HOD=4.80 ppm): 1.26(3H, d, J=7.1 Hz), i.31(3H, d, J=6.5 Hz), 2.39(3H, s), 2.76(3H, s), 3.55(1H, dd, J$_1$=6.2 Hz, J$_2$=2.8 Hz), 3.57–3.67(1H, m), 3.79(3H, s), 4.28(1H, quintet, J=6.2 Hz), 4.34(1H, dd, J$_1$=9.3 Hz, J$_2$=2.8 Hz), 7.92(1H, s). MS (TSP): 376 (M$^+$+H).

Example 106

Sodium (5R,6S)-6-((1R)-1-hydroxyethyl)-2-(7-hydroxymethylimidazo[5,1-b]thiazol-3-yl)-1-carbapen-2-em-3-carboxylate a) 4-nitrobenzyl (5R,6S)-2-(7-t-butyldimethylsilyloxymethylimidazo[5,1-b]thiazol-3-yl)-6-((1R)-1-hydroxyethyl)-1-carbapen-2-em-3-carboxylate In the same manner as in Example 5-a), 4-nitrobenzyl (5R,6S)-2-(7-t-butyldimethylsilyloxymethylimidazo[5,1-b]thiazol-3-yl)-6-((1R)-1-hydroxyethyl)-1-carbapen-2-em-3-carboxylate was obtained in a yield of 1.53 g from 994.3 mg of 4-nitrobenzyl (3R,5R,6S)-6-((1R)-1-hydroxyethyl)-2-oxo-1-carbapenam-3-carboxylate and 1.76 g of 7-t-butyldimethylsilyloxymethyl-3-(tri-n-butylstannyl)imidazo [5,1-b]thiazole.

NMR (CDCl$_3$) δ: 0.14(6H, s), 0.96(9H, s), 1.37(3H, d, J=6.3 Hz), 2.48(1H, br.s, s), 3.33–3.40(3H, m), 4.26–4.33 (1H, m), 4.39–4.47(1H, m), 4.83(2H, s), 5.19(1H, d, J=13.5 Hz), 5.33(1H, d, J=13.5 Hz), 7.02(1H, s), 7.39(2H, d, J=8.9 Hz), 7.74(1H, s), 8.14(2H, d, J=8.9 Hz). MS (TSP): 599 (M$^+$).

b) 4-nitrobenzyl (5R,6S)-6-((1R)-1-hydroxyethyl)-2-(7-hydroxymethylimidazo[5,1-b]thiazol-3-yl)-1-carbapen-2-em-3-carboxylate To a solution of 848.8 mg of 848.8 mg of 4-nitrobenzyl (5R,6S)-2-(7-t-butyldimethylsilyloxymethylimidazo[5,1-b]thiazol-3-yl)-6-((1R)-1-hydroxyethyl)-1-carbapen-2-em-3-carboxylate in 20 ml of THF was added 1.22 ml of acetic acid and 7.1 ml of a 1 M solution of tetra-n-butylammonium fluoride in THF, and the mixture was stirred at room temperature for 2.5 hours. After neutralizing the mixture with a saturated aqueous sodium hydrogen carbonate solution, it was extracted two times with ethyl acetate, washed with semi-saturated aqueous saline, and dried over anhydrous magnesium sulfate, and the solvent was removed under reduced pressure. The residue thus obtained was purified by column chromatography on silica gel (ethyl acetate:methanol=9:1) to give 324.3 mg of 4-nitrobenzyl (5R,6S)-6-((1R)-1-hydroxyethyl)-2-(7-hydroxymethylimidazo[5,1-b]thiazol-3-yl)-1-carbapen-2-em-3-carboxylate.

NMR (CDCl$_3$) δ: 1.29(3H, d, J=6.3 Hz), 3.40–3.48(31H, m), 4.18–4.28(1H, m), 4.32–4.40(1H, m), 4.15(2H, s), 5.13(2H, d, J=13.9 Hz), 5.28(2H, d, J=13.9 Hz), 6.98(1H, s), 7.35(2H, d, J=8.7 Hz), 7.12(1H, s), 8.10(2H, d, J=8.7 Hz). MS (TSP): 485 (M$^+$+H).

c) Sodium (5R,6S)-6-((1R)-1-hydroxyethyl)-2-(7-hydroxymethylimidazo[5,1-b]thiazol-3-yl)-1-carbapen-2-em-3-carboxylate In the same manner as in Example 134-d ), the title compound was obtained in a yield of 57.7 mg from 157.0 mg of 4-nitrobenzyl (5R,6S)-6-((1R)-1-hydroxyethyl)-2-(7-hydroxymethylimidazo[5,1-b]thiazol-3-yl)-1-carbapen-2-em-3-carboxylate.

NMR (D$_2$O) δ (HOD=4.80 ppm): 1.32(3H, d, J=6.4 Hz), 3.10–3.27(1H, m), 3.41–3.50(1H, m), 3.57–3.61(1H, m), 4.20–4.40(2H, m), 4.76(2H, s), 7.23(1H, s), 8.26(1H, s).

Example 107

Sodium (1S,5R,6S)-2-(7-formylimidazo[5,1-b]thiazol-2-yl)-6-((1R)-1-hydroxyethyl)-1-methyl-1-carbapen-2-em-3-carboxylate a) 4-nitrobenzyl (1S,5R,6S)-2-(7-formylimidazo[5,1-b]thiazol-2-yl)-6-((1R)-1-hydroxyethyl)-1-methyl-1-carbapen-2-em-3-carboxylate To a solution of 183.0 mg of 4-nitrobenzyl (1S,5R,6S)-6-((1R)-1-hydroxyethyl)-2-(7-hydroxymethylimidazo[5,1-b]thiazol-2-yl)-1-methyl-1-carbapen-2-em-3-carboxylate in 15 ml of dichloromethane 15 ml was added 596.7 mg of manganese dioxide, and the mixture was stirred at room temperature for 38 hours. The catalyst was removed by filtration on Celite, and the filtrate was removed under reduced pressure. The residue thus obtained was purified by column chromatography on silica gel (ethyl acetate:methanol=9:1) to give 127 mg of 127 mg of 4-nitrobenzyl (1S,5R,6S)-2-(7-formylimidazo[5,1-b]thiazol-2-yl)-6-((1R)-1-hydroxyethyl)-1-methyl-1-carbapen-2-em-3-carboxylate.

NMR (CDCl$_3$) δ: 1.24(3H, d, J=7.2 Hz), 1.32(3H, d, J=6.3 Hz), 3.34(1H, dd, J$_1$=6.4 Hz, J$_2$=2.7 Hz), 3.41–4.50(1H, m), 4.21–4.32(1H, m), 4.37(1H, dd, J$_1$=9.6 Hz, J$_2$=2.7 Hz), 5.20(1H, d, J=13.7 Hz), 5.45(1H, d, J=13.7 Hz), 7.59(2H, d, J=8.4 Hz), 8.02(1H, s), 8.14(2H, d, J=8.4 Hz), 8.42(1H, s), 9.83(1H, s).

b) Sodium (1S,5R,6S)-2-(7-formylimidazo[5,1-b]thiazol-2-yl)-6-((1R)-1-hydroxyethyl)-1-methyl-1-carbapen-2-em-3-carboxylate In the same manner as in Example 134-d), the title compound was obtained in a yield of 56.7 mg from 127.0 mg of 4-nitrobenzyl (1S,5R,6S)-2-(7-formylimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.19(3H, d, J=6.6 Hz), 1.32(3H, d, J=5.9 Hz), 3.46–3.60(2H, m), 4.21–4.34(2H, m), 7.94(1H, s), 8.12(1H, s), 9.41(1H, s).

Example 108

Pivaloyloxymethyl (1S,5R,6S)-2-(7-formylimidazo[5,1-b]thiazol-2-yl)-6-((1R)-1-hydroxyethyl)-1-methyl-1-carbapen-2-em-3-carboxylate In the same manner as in Example 135, the title compound was obtained in a yield of 26.0 mg from 31.4 mg of sodium (1S,5R,6S)-2-(7-formylimidazo[5,1-b]thiazol-2-yl)-6-((1R)-1-hydroxyethyl)-1-methyl-1-carbapen-2-em-3-carboxylate.

NMR (CDCl$_3$) δ: 1.19(9H, s), 1.33(3H, d, J=7.2 Hz), 1.36(3H, d, J=6.3 Hz), 3.35–3.40(1H, m), 3.49–3.56(1H, m), 4.23–4.27(1H, m), 4.41(1H, dd, J$_1$=9.2 Hz, J$_2$=2.8 Hz), 5.87(1H, d, J=5.7 Hz), 5.99(1H, d, J=5.7 Hz), 8.11(1H, s), 8.51(1H, s), 9.91(1H, s).

Example 109

(1S,5R,6S)-2-(7-carbamoylimidazo[5,1-b]thiazol-2-yl)-6-((1R)-1-hydroxyethyl)-1-methyl-1-carbapen-2-em-3-carboxylic Acid a) 4-nitrobenzyl (1S,5R,6S)-2-(7-carbamoylimidazo[5,1-b]thiazol-2-yl)-6-((1R)-1-hydroxy-thyl)-1-methyl-1-carbapen-2-em-3-carboxylate In the same manner as in Example 5-a), 4-nitrobenzyl (1S,5R,6S)-2-(7-carbamoylimidazo[5,1-b]thiazol-2-yl)-6-((1R)-1-hydroxyethyl)-1-methyl-1-carbapen-2-em-3-carboxylate was obtained in a yield of 109 mg from 215 mg of 4-nitrobenzyl (1R,3R,5R,6S)-6-((1R)-1-hydroxyethyl)-1-methyl-2-oxo-1-carbapenam-3-carboxylate and 324 mg of 7-carbamoyl-2-(tri-n-butylstannyl)imidazo[5,1-b]thiazole.

NMR (CDCl$_3$) δ: 1.30(3H, d, J=7.4 Hz), 1.40(3H, d, J=6.3 Hz), 3.38(1H, dd, J$_1$=6.6 Hz, J$_2$=2.8 Hz), 3.50(1H, m), 4.32(1H, m), 4.41(1H, dd, J$_1$=9.7 Hz, J$_2$=2.8 Hz), 5.27(1H, d, J=13.5 Hz), 5.52(1H, d, J=13.5 Hz), 5.53(1H, br.s), 6.78(1H, br.s), 7.67(2H, d, J=8.9 Hz), 7.95(1H, s), 8.24(2H, d, J=8.9 Hz), 8.50(1H, s).

b) (1S,5R,6S)-2-(7-carbamoylimidazo[5,1-b]thiazol-2-yl)-6-((1R)-1-hydroxyethyl)-1-methyl-1-carbapen-2-em-3-carboxylic Acid In the same manner as in Example 5-b) と同様にして, the title compound was obtained in a yield of 73.8 mg from 123 mg of 4-nitrobenzyl (1S,5R,6S)-2-(7-carbamoylimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.22(3H, d, J=7.1 Hz), 1.33(3H, d, J=6.4 Hz), 3.53(2H, m), 4.30(2H, m), 7.92(1H, s), 8.05(1H, s).

Example 110

Pivaloyloxymethyl (1S,5R,6S)-2-(7-carbamoylimidazo[5,1-b]thiazol- 2-yl)-6-((1R)-1-hydroxyethyl)-1-inethyl-1-carbapen-2-em-3-carboxylate In the same manner as in Example 19, the title compound was obtained in a yield of 31.5 mg from 35.2 mg of (1S,5R,6S)-2-(7-carbamoylimidazo[5,1-b]thiazol-2-yl)-6-((1R)-1-hydroxyethyl)-1-methyl-1-carbapen-2-em-3-carboxylic acid.

NMR (CDCl$_3$) δ: 1.20(9H, s), 1.28(3H, d, J=7.4 Hz), 1.37(3H, d, J=6.2 Hz), 3.35(1H, dd, J$_1$=6.8 Hz, J$_2$=2.7 Hz), 3.50(1H, m), 4.28(1H, m), 4.41(1H, dd, $J_1$=9.9 Hz, $J_2$=2.7 Hz), 5.58(1H, br.s), 5.87(1H, d, J=5.6 Hz), 5.98(1H, d, J=5.6 Hz), 6.92(1H, br.s), 8.01(1H, s), 8.51(1H, s).

Example 111

Sodium (1S,5R,6S)-6-((1R)-1-hydroxyethyl)-2-(7-methoxymethylimidazo[5,1-b]thiazol-2-yl)-1-methyl-1-carbapen-2-em-3-carboxylate a) 4-nitrobenzyl (1S,5R,6S)-6-((1R)-1-hydroxyethyl)-2-(7-methoxymethylimidazo[5,1-b]thiazol-2-yl)-1-methyl-1-carbapen-2-em-3-carboxylate In the same manner as in Example 5-a), 4-nitrobenzyl (1S,5R,6S)-6-((1R)-1-hydroxyethyl)-2-(7-methoxymethylimidazo[5,1-b]thiazol-2-yl)-1-methyl-carbapen-2-em-3-carboxylate was obtained in a yield of 550 mg from 730 mg of (1R,3R,5R,6S)-6-((1R)-1-hydroxyethyl)-1-methyl-2-oxo-1-carbapenam-3-carboxylate and 1.010 g of 7-methoxymethyl-2-(tri-n-butylstannyl)imidazo[5,1-b]thiazole.

NMR (CDCl$_3$) δ: 1.28(3H, d, J=7.3 Hz), 1.37(3H, d, J=6.1 Hz), 3.35(3H, s), 3.3–3.5(1H, m), 3.55(1H, m), 4.27(1H, m), 4.37(1H, dd, $J_1$=9.5 Hz, $J_2$=2.3 Hz), 4.60(2H, s),5.27(1H, d, J=13.7 Hz), 5.50(1H, d, J=13.7 Hz), 7.65(2H, d, J=8.7 Hz), 8.18(1H, m), 8.20(2H, d, J=8.7 Hz), 8.30(1H, s).

b) Sodium (1S,5R,6S)-6-((1R)-1-hydroxyethyl)-2-(7-methoxymethylimidazo[5,1-b]thiazol-2-yl)-1-methyl-1-carbapen-2-em-3-carboxylate To a solution of 550 mg of 4-nitrobenzyl (1S,5R,6S)-6-((1R)-1-hydroxyethyl)-2-(7-methoxyniethylimidazo[5,1-b]thiazol- 2-yl)-1-methyl-1-carbapen-2-em-3-carlboxylate in 30 ml of THF and 30 ml of a 1/15 M phosphate buffer (pH 6.8) was added 660 mg of 10% Pd-C, and the mixture was stirred under the atmosphere of hydrogen at room temperature for 1 hour. After filtration through Celite, the catalyst was washed with a mixture of THF:water (1:1). The combined filtrates were adjusted to pH 6.7 with a saturated aqueous sodium hydrogen carbonate solution, washed with 30 ml of ethyl acetate, and concentrated under reduced pressure. The residue thus obtained was purified by column chromatography on DIAION HP-20, and lyophilized to give 220 mg of a powder product. A 120 mg portion of the product was purified by column chromatography on COSMOSEAL 40C18-PREP to give the title compound in a yield of 58 mg.

NMR (D$_2$O) δ (HOD=4.80 ppm) 1.22(3H, d, J=7.1 Hz), 1.31(3H, d, J=6.3 Hz), 3.36(3H, s), 3.50(1H, dd, $J_1$=6.1 Hz, $J_2$=2.6 Hz), 3.54(1H, m), 4.26(1H, m), 4.29(1H, dd, $J_1$=9.3 Hz, $J_2$=2.5 Hz), 4.49(2H, s), 7.84(1H, s), 8.13(1H, s).

Example 112

Pivaloyloxymethyl (1S,5R,6S)-6-((1R)-1-hydroxyethyl)-2-(7-methoxymethylimidazo[5,1-b]thiazol-2-yl)-1-methyl-1-carbapen-2-em-3-carboxylate To a solution of 40 mg of sodium (1S,5R,6S)-6-((1R)-1-hydroxyethyl)-2-(7-methoxymethylimidazo[5,1-b]thiazol-2-yl)-1-methyl-1-carbapen-2-em-3-carboxylate in 0.6 ml of DMF was added 4.2 mg of sodium hydrogen carbonate, and the mixture was cooled to −30° C. under the atmosphere of argon. Pivaloyloxymethyl iodide (34 mg) was added, and the mixture was stirred for 1 hour, diluted with 30 ml of ethyl acetate, and washed with 20 ml of saturated aqueous saline and 20 ml of semi-saturated squeous saline. The organic layer was dried over anhydrous magnesium sulfate, and concentrated under reduced pressure to a volume of about 1 ml. The concentrate was purified by column chromatography on silica gel (chloroform:methanol=95:5) to give the title compound was obtained in a yield of 18.4 mg.

NMR (CDCl$_3$) δ: 1.21(9H, s), 1.28(3H, d, J=7.2 Hz), 1.36(3H, d, J=6.3 Hz), 3.32(1H, dd, $J_1$=6.8 Hz, $J_2$=2.8 Hz), 3.44(3H, s), 3.4–3.5(1H, m), 4.27(1H, m), 4.34(1H, dd, $J_1$=9.7 Hz, $J_2$=2.8 Hz), 4.58(2H, s), 5.88(1H, d, J=5.7 Hz), 5.93(1H, d, J=5.7 Hz), 8.02(1H, s), 8.33(1H, s).

Example 113

Sodium (5R,6S)-6-((1R)-1-hydroxyethyl)-2-(7-methoxyinethylimidazo[5,1-b]thiazol-3-yl)-1-carbapen-2-em-3-carboxylate a) 4-nitrobenzyl (5R,6S)-6-((1R)-1-hydroxyethyl)-2-(7-methoxymethylimidazo[5,1-b]thiazol-3-yl)-1-carbapen-2-em-3-carboxylate In the same manner as in Example 5-a), 4-nitrobenzyl (5R,6S)-6-((1R)-1-hydroxyethyl)-2-(7-methoxyimethylimidazo[5,1-b]thiazol-3-yl)-1-carbapen-2-em-3-carboxylate was obtained in a yield of 450 mg from 697 mg of 4-nitrobenzyl (3R,5R,6S)-6-((1R)-1-hydroxyethyl)-2-oxo-1-carbapenam-3-carboxylate and 896 mg of 7-methoxymethyl-3-(tri-n-butylstannyl)imidazo[5,1-b]thiazole.

b) Sodium (5R,6S)-6-((1R)-1-hydroxyethyl)-2-(7-methoxymethylimidazo[5,1-b]thiazol-3-yl)-carbapen-2-em-3-carboxylate In the same manner as in Example 134-d), the title compound was obtained in a yield of 30 mg from 4-nitrobenzyl (5R,6S)-6-((1R)-1-hydroxyethyl)-2-(7-methoxymethylimidazo[5,1-b]thiazol-3-yl)-carbapen-2-em-3-carboxylate.

NMR (D$_2$O) δ (HOD=4.80 ppm): 1.31(3H, d, J=6.3 Hz), 3.33(2H, m), 3.39(3H, s), 3.59(1H, dd, $J_1$=5.8 Hz, $J_2$=2.3 Hz), 4.2–4.4(2H, m), 4.60(2H, s), 7.13(1H, s), 8.04(1H, s).

Example 114

Pivaloyloxymethyl (5R,6S)-6-((1R)-1-hydroxyethyl)-2-(7-methoxymethylimidazo[5,1-b]-thiazol-3-yl)-1-carbapen-2-em-3-carboxylate In the same manner as in Example 135, the title compound was obtained in a yield of 10 mg from 28 mg of sodium (5R,6S)-6-((1R)-1-hydroxyethyl)-2-(7-methoxymethylimidazo[5,1-b]thiazol-3-yl)-1-carbapen-2-em-3-carboxylate.

NMR (CDCl$_3$) δ: 1.19(9H, s), 1.37(3H, d, J=6.3 Hz), 3.3–3.4(2H, m), 3.43(3H, s), 4.27(1H, s), 4.40(1H, m), 5.78(1H, d, J=5.5 Hz), 5.88(1H, d, J=5.5 Hz), 7.14(1H, s), 7.78(1H, s).

Example 115

Pivaloyloxymethyl (5R,6S)-6-((1R)-1-hydroxyethyl)-2-(7-hydroxymethylimidazo[5,1-b]thiazol-3-yl)-1-carbapen-2-em-3-carboxylate In the same manner as in Example 135, the title compound was obtained in a yield of 9.0 mg from 39.5 mg of sodium (5R,6S)-6-((1R)-1-hydroxyethyl)-2-(7-hydroxymethylimidazo[5,1-b]thiazol-3-yl)-1-carbapen-2-em-3-carboxylate.

NMR (CDCl$_3$) δ: 1.20(3H, d, J=5.8 Hz), 3.68–3.80(3H, m), 4.90–5.05(2H, m), 5.72(1H, d, J=6.0 Hz), 5.88(1H, d, J=6.0 Hz), 6.30–6.42(2H, m), 7.70(1H, s), 9.60(1H, s).

Example 116

(1S,5R,6S)-2-(7-cyanoimidazo[5,1-b]thiazol-2-yl)-6-((1R)-1-hydroxyethyl)-1-methyl-1-carbapen-2-em-3-carboxylic Acid a) 4-nitrobenzyl (1S,5R,6S)-2-(7-cyanoimidazo[5,1-b]thiazol-2-yl)-6-((1R)-1-hydroxyethyl)-1-methyl-1-carbapen-2-em-3-carboxylate In the same manner as in Example 5-a), 4-nitrobenzyl (1S,5R,6S)-2-(7-cyanoimidazo[5,1-b]thiazol-2-yl)-6-((1R)-1-hydroxyethyl)-1-methyl-1-carbapen-2-em-3-carboxylate was obtained in a yield of 253 mg from 362 mg of 4-nitrobenzyl (1R,3R,5R,6S)-6-((1R)-1-hydroxyethyl)-1-methyl-2-oxo-1-carbapenam-3-carboxylate and 526 mg of 7-cyano-2-(tri-n-butylstannyl)imidazo[5,1-b]thiazole.

NMR (CDCl$_3$) δ: 1.32(3H, d, J=7.2 Hz), 1.40(3H, d, J=6.3 Hz), 3.49(1H, dd, J$_1$=6.4 Hz, J$_2$=2.8 Hz), 3.50(1H, m), 4.32(1H, m), 4.42(1H, dd, J$_1$=9.8 Hz, J$_2$=2.8 Hz), 5.29(1H, d, J=13.7 Hz), 5.53(1H, d, J=13.7 Hz), 7.68(2H, d, J=8.9 Hz), 8.01(1H, s), 8.25(2H, d, J=8.9 Hz), 8.37(1H, s).

b) (1S,5R,6S)-2-(7-cyanoimidazo[5,1-b]thiazol-2-yl)-6-((1R)-1-hydroxyethyl)-1-methyl-1-carbapen-2-em-3-carboxylic Acid In the same manner as in Example 5-b), the title compound was obtained in a yield of 62.1 mg from 4-nitrobenzyl (1S,5R,6S)-2-(7-cyanoimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.23(3H, d, J=7.1 Hz), 1.32(3H, d, J=6.2 Hz), 3.51(1H, m), 3.59(1H, m), 4.29(2H, m), 8.00(1H, s), 8.16(1H, s).

Example 117

Pivaloyloxymethyl (1S,5R,6S)-2-(7-cyanoimidazo [5,1-b]thiazol-2-yl)-6-((1R)-1-hydroxyethyl)-1-methyl-1-carbapen-2-em-3-carboxylate In the same manner as in Example 19, the title compound was obtained in a yield of 34.3 mg from 36.7 mg of (1S,5R,6S)-2-(7-cyanoimidazo[5,1-b]thiazol-2-yl)-6-((1R)-1-hydroxyethyl)-1-methyl-1-carbapen-2-em-3-carboxylic acid.

NMR (CDCl$_3$) δ: 1.21(9H, s), 1.30(3H, d, J=7.2 Hz), 1.37(3H, d, J=6.3 Hz), 3.37(1H, dd, J$_1$=6.5 Hz, J$_2$=3.0 Hz), .3.50(1H, m), 4.30(1H, m), 4.41(1H, dd, J$_1$=9.9 Hz, J$_2$=3.0 Hz), 5.87(1H, d, J=5.6 Hz), 5.99(1H, d, J=5.6 Hz), 8.06(1H, s), 8.37(1H, s).

Example 118

(1S,5R,6S)-2-(7-ethylimidazo[5,1-b]thiazol-2-yl)-6-((1R)-1-hydroxyethyl)-1-methyl-1-carbapen-2-em-3-carboxylic Acid a) 4-nitrobenzyl (1S,5R,6S)-2-(7-ethylimidazo[5,1-b]thiazol-2-yl)-6-((1R)-1-hydroxyethyl)-1-methyl-1-carbapen-2-em-3-carboxylate In the same manner as in Example 5-a), 4-nitrobenzyl (1S,5R,6S)-2-(7-ethylimidazo[5,1-b]thiazol-2-yl)-6-((1R)-1-hydroxyethyl)-1-methyl-1-carbapen-2-em-3-carboxylate in a yield of 258 mg was obtained from 362 mg of 4-nitrobenzyl (1R,3R,5R,6S)-6-((1R)-1-hydroxyethyl)-1-methyl-2-oxo-1-carbapenam-3-carboxylate and 529 mg of 7-ethyl-2-(tri-n-butylstannyl)imidazo[5,1-b]thiazole.

NMR (CDCl$_3$) δ: 1.32(6H, m), 1.40(3H, d, J=6.2 Hz), 2.75(2H, q, J=7.6 Hz), 3.36(1H, dd, J$_1$=6.5 Hz, J$_2$=2.8 Hz), 3.46(1H, m), 4.33(2H, m), 5.28(1H, d, J=13.7 Hz), 5.52(1H, d, J=13.7 Hz), 7.68(2H, d, J=8.6 Hz), 7.94(1H, s), 8.24(2H, d, J=8.6 Hz), 8.26(1H, s).

b) (1S,5R,6S)-2-(7-ethylimidazo[5,1-b]thiazol-2-yl)-6-((1R)-1-hydroxyethyl)-1-methyl-1-carbapen-2-em-3-carboxylic Acid In the same manner as in Example 5-b) except that purification was carried out by column chromatography on DIAION HP-20 (10% methanol in water–40% methanol in water) and on COSMOSEAL 40C18PREP (water:methanol=5:1), the title compound was obtained in a yield of 31.7 mg from 164 mg of 4-nitrobenzyl (1S,5R,6S)-2-(7-ethylimidazo[5,1-b]thiazol-2-yl)-6-((1R)-1-hydroxyethyl)-1-methyl-1-carbapen-2-em-3-carboxylate.

NMR (D$_2$O) δ (HOD=4.80 ppm): 1.30(9H, m), 2.82(2H, q, J=7.7 Hz), 3.56(1H, dd, J$_1$=6.0 Hz, J$_2$=3.0 Hz), 3.61(1H, m), 4.28(1H, m), 4.34(1H, dd, J$_1$=9.4 Hz, J$_2$=3.0 Hz), 8.02(1H, s), 8.86(1H, s).

Example 119

Pivaloyloxymethyl (1S,5R,6S)-2-(7-ethylimidazo[5,1-b]thiazol-2-yl)-6-((1R)-1-hydroxyethyl)-1-methyl-1-carbapen-2-em-3-carboxylate In the same manner as in Example 19, the title compound was obtained in a yield of 15.8 mg from 45.3 mg of (1S,5R,6S)-2-(7-ethylimidazo[5,1-b]thiazol-2-yl)-6-((1R)-1-hydroxyethyl)-1-methyl-1-carbapen-2-em-3-carboxylic acid.

NMR (CDCl$_3$) δ: 1.21(9H, s), 1.29(3H, d, J=7.2 Hz), 1.32(3H, t, J=7.6 Hz), 1.37(3H, d, J=6.2 Hz), 2.75(2H, q, J=7.6 Hz), 3.32(1H, dd, J$_1$=6.0 Hz, J$_2$=2.8 Hz), 3.44(1H, m), 4.31(2H, m), 5.88(1H, d, J=5.6 Hz), 5.98(1H, d, J=5.6 Hz), 7.97(1H, s), 8.26(1H, s).

Example 120

(5R,6S)-2-(5-carbamoylimidazo[5,1-b]thiazol-3-yl)-6-((1R)-1-hydroxyethyl-1-carbapen-2-em-3-carboxylic Acid a) 4-nitrobenzyl (5R,6S)-2-(5-carbamoylimidazo[5,1-b]thiazol-3-yl)-6-((1R)-1-hydroxyethyl)-1-carbapen-2-em-3-carboxylate In the same manner as in Example 5-a), 4-nitrobenzyl (5R,6S)-2-(5-carbamoylimidazo[5,1-b]thiazol-3-yl)-6-((1R)-1-hydroxyethyl)-1-carbapen-2-em-3-carboxylate was obtained in a yield of 27.8 mg from 239 mg of 4-nitrobenzyl (3R,5R,6S)-6-((1R)-1-hydroxyethyl)-2-oxo-1-carbapenam-3-carboxylate and 376 mg of 5-carbamoyl-3-(tri-n-butylstannyl)imidazo[5,1-b]thiazole.

NMR (CD$_3$OD) δ: 1.31(3H, d, J=6.3 Hz), 3.1–3.7(3H, m), 4.1–4.4(2H, m), 4.9–5.2(2H, m), 7.30(2H, m), 8.1(2H, m).

b) (5R,6S)-2-(5-carbamoylimidazo[5,1-b]thiazol-3-yl)-6-((1R)-1-hydroxyethyl)-1-carbapen-2-em-3-carboxylic Acid In the same manner as in Example 5-b), the title compound was obtained in a yield of 16.9 mg from 33.2 mg of 4-nitrobenzyl (5R,6S)-2-(5-carbamoylimidazo[5,1-b]thiazol-3-yl)-6-((1R)-1-hydroxyethyl)-1-carbapen-2-em-3-carboxylate.

NMR (D$_2$O) δ (HOD=4.80 ppm): 1.33(3H, d, J=6.3 Hz), 3.15(1H, dd, J$_1$=17.6 Hz, J$_2$=9.9 Hz), 3.27(1H, dd, J$_1$=17.7 Hz, J$_2$=8.5 Hz), 3.53(1H, m), 4.30(2H, m), 7.19(1H, s), 7.21(1H, Example 121

(5R,6S)-2-(7-ethylimidazo[5,1-b]thiazol-2-yl)-6-((1R)-1-hydroxyethyl)-1-carbapen-2-em-3-carboxylic Acid a) 4-nitrobenzyl (5R,6S)-2-(7-ethylimidazo[5,1-b]thiazol-2-yl)-6-((1R)-1-hydroxyethyl)-1-carbapen-2-em-3-carboxylate In the same manner as in Example 5-a), 4-nitrobenzyl (5R,6S)-2-(7-ethylimidazo[5,1-b]thiazol-2-yl)-6-((1R)-1-hydroxyethyl)-1-carbapen-2-em-3-carboxylate was obtained in a yield of 203 mg from 348 mg of 4-nitrobenzyl (3R,5R,6S)-6-((1R)-1-hydroxyethyl)-2-oxo-1-carbapenam-3-carboxylate and 529 mg of 7-ethyl-2-(-tri-n-butylstannyl) imidazo[5,1-b]thiazole.

NMR (CDCl$_3$) δ: 1.31(3H, t, J=7.5 Hz), 1.39(3H, d, J=6.3 Hz), 2.74(2H, q, J=7.5 Hz), 3.32(3H, m), 4.32(2H, m), 5.30(1H, d, J=13.7 Hz), 5.54(1H, d, J=13.7 Hz), 7.68(2H, d, J=8.4 Hz), 7.93(1H, s), 8.15(1H, s), 8.23(2H, d, J=8.4 Hz).

b) (5R,6S)-2-(7-ethylimidazo[5,1-b]thiazol-2-yl)-6-((1R)-1-hydroxyethyl)-1-carbapen-2-em-3-carboxylic Acid In the same manner as in Example 5-b), the title compound was obtained in a yield of 49.1 mg from 203 mg of 4-nitrobenzyl (5R,6S)-2-(7-ethylimidazo[5,1-b]thiazol-2-yl)-6-((1R)-1-hydroxyethyl)-1-carbapen-2-em-3-carboxylate.

NMR (D$_2$O) δ (HOD=4.80 ppm): 1.31(6H, m), 2.76(2H, q, J=7.5 Hz), 3.31(2H, m), 3.54(1H, m), 4.28(2H, m), 7.79(1H, s), 8.58(1H, s).

Example 122

Pivaloyloxymethyl (5R,6S)-2-(7-ethylimidazo[5,1-b]thiazol-2-yl)-6-((1R)-1-hydroxyethyl)-1-carbapen-2-em-3-carboxylate In the same manner as in Example 19, the title compound was obtained in a yield of 23.3 mg from 43.0 mg of (5R,6S)-2-(7-ethylimidazo[5,1-b]thiazol-2-yl)-6-((1R)-1-hydroxyethyl)-1-carbapen-2-em-3-carboxylic acid.

NMR (CDCl$_3$) δ: 1.23(9H, s), 1.32(3H, t, J=7.6 Hz), 1.36(3H, d, J=6.3 Hz), 2.74(2H, q, J=7.6 Hz), 3.29(3H, m), 4.28(2H, m), 5.91(1H, d, J=5.6 Hz), 6.00(1H, d, J=5.6 Hz), 7.96(1H, s), 8.20(1H, s).

Example 123

(5R,6S)-2-(7-ethylimidazo[5,1-b]thiazol-3-yl)-6-((1R)-1-hydroxyethyl)-1-carbapen-2-em-3-carboxylic Acid a) 4-nitrobenzyl (5R,6S)-2-(7-ethylimidazo[5,1-b]thiazol-3-yl)-6-((1R)-1-hydroxyethyl)-1-carbapen-2-em-3-carboxylate In the same manner as in Example 5-a), the title compound was obtained in a yield of 765 mg from 627 mg of 4-nitrobenzyl (3R,5R,6S)-6-((1R)-1-hydroxyethyl)-2-oxo-1-carbapenam-3-carboxylate and 882 mg of 7-ethyl-3-(tri-n-butylstannyl)imidazo[5,1-b]thiazole.

NMR (CDCl$_3$) δ: 1.30(3H, t), 1.38(3H, d), 2.72(2H, q), 3.25–3.45(3H, m), 4.32(1H, m), 4.33(1H, m), 5.28(2H, ABq), 7.00(1H, s), 7.42(2H, d), 7.67(1H, s), 8.17(2H, d).

b) (5R,6S)-2-(7-ethylimidazo[5,1-b]thiazol-3-yl)-6-((1R)-1-hydroxyethyl)-1-carbapen-2-em-3-carboxylic Acid In the same manner as in Example 5-b), the title compound was obtained in a yield of 86.6 mg from 203 mg of 4-nitrobenzyl (5R,6S)-2-(7-ethylimidazo[5,1-b]thiazol-3-yl)-6-((1R)-1-hydroxyethyl)-1-carbapen-2-em-3-carboxylate.

NMR (D$_2$O) δ (HOD=4.80 ppm): 1.31(6H, m), 2.80(2H, q, J=7.7 Hz), 3.21(1H, dd, J$_1$=17.3 Hz, J$_2$=10.1 Hz), 3.45 (1H, dd, J$_1$=17.3 Hz, J$_2$=8.9 Hz), 3.59(1H, m), 4.29(1H, m), 4.38(1H, m), 7.25(1H, s), 8.33(1H, s).

Example 124

Pivaloyloxymethyl (5R,6S)-2-(7-ethylimidazo[5,1-b]thiazol-3-yl)-6-((1R)-1-hydroxyethyl)-1-carbapen-2-em-3-carboxylate In the same manner as in Example 19, the title compound was obtained in a yield of 29.1 mg from 41.6 mg of (5R,6S)-2-(7-ethylimidazo[5,1-b]thiazol-3-yl)-6-((1R)-1-hydroxyethyl)-1-carbapen-2-em-3-carboxylic acid.

NMR (CDCl$_3$) δ: 1.19(9H, s), 1.32(3H, t, J=7.6 Hz), 1.37(3H, d, J=6.3 Hz), 2.75(2H, q, J=7.6 Hz), 3.35(3H, m), 4.28(1H, m), 4.40(1H, m), 5.78(1H, d, J=5.5 Hz), 5.88(1H, d, J=5.5 Hz), 7.08(1H, s), 7.72(1H, s).

Example 125

(5R,6S)-2-(7-cyanoimidazo[5,1-b]thiazol-2-yl)-6-((1R)-1-hydroxyethyl)-1-carbapen-2-em-3-carboxylic Acid a) 4-nitrobenzyl (5R,6S)-2-(7-cyanoimidazo[5,1-b]thiazol-2-yl)-6-((1R)-1-hydroxyethyl)-1-carbapen-2-em-3-carboxylate In the same manner as in Example 5-a), 4-nitrobenzyl (5R,6S)-2-(7-cyanoimidazo[5,1-b]thiazol-2-yl)-6-((1R)-1-hydroxyethyl)-1-carbapen-2-em-3-carboxylate was obtained in a yield of 200 mg from 276 mg of 4-nitrobenzyl (3R,5R,6S)-6-((1R)-1-hydroxyethyl)-2-oxo-1-carbapenam-3-carboxylate and 417 mg of 7-cyano-2-(tri-n-butylstannyl)imidazo[5,1-b]thiazole.

NMR(DMSO-d$_6$) δ: 1.17(3H, d, J=6.3 Hz), 3.47(2H, m), 3.54(1H, dd, J$_1$=6.0 Hz, J$_2$=3.0 Hz), 4.01(1H, m), 4.27(1H, m), 5.17(1H, d, J=5.0 Hz), 5.43(1H, d, J=13.7 Hz), 5.56(1H, d, J=13.7 Hz), 7.76(2H, d, J=8.5 Hz), 8.25(2H, d, J=8.5 Hz), 8.43(1H, s), 8.51(1H, s).

b) (5R,6S)-2-(7-cyanoimidazo[5,1-b]thiazol-2-yl)-6-((1R)-1-hydroxyethyl)-1-carbapen-2-em-3-carboxylic Acid In the same manner as in Example 5-b), the title compound was obtained in a yield of 53.8 mg from 4-nitrobenzyl (5R,6S)-2-(7-cyanoimidazo[5,1-b]thiazol-2-yl)-6-((1R)-1-hydroxyethyl)-1-carbapen-2-em-3-carboxylate.

NMR (D$_2$O) δ (HOD=4.80 ppm): 1.31(3H, d, J=6.4 Hz), 3.27(3H, m), 3.51(1H, dd, J$_1$=5.8 Hz, J$_2$=2.8 Hz), 4.26(2H, m), 7.82(1H, s), 8.13(1H, s).

Example 126

Pivaloyloxymethyl (5R,6S)-2-(7-cyanoimidazo[5,1-b]thiazol-2-yl)-6-((1R)-1-hydroxyethyl)-1-carbapen-2-em-3-carboxylate In the same manner as in Example 19, the title compound was obtained in a yield of 18.5 mg from 41.2 mg of (5R,6S)-2-(7-cyanoimidazo[5,1-b]thiazol-2-yl)-6-((1R)-1-hydroxyethyl)-1-carbapen-2-em-3-carboxylic acid.

NMR (CDCl$_3$) δ: 1.23(9H, s), 1.37(3H, d, J=6.3 Hz), 3.34(3H, m), 4.32(2H, m), 5.90(1H, d, J=5.6 Hz), 6.02(1H, d, J=5.6 Hz), 8.03(1H, s), 8.29(1H, s).

Example 127

(1S,5R,6S)-2-(7-ethyl-6-methylimidazo[5,1-b]thiazolium-2-yl)-6-((1R)-1-hydroxyethyl)-1-methyl-1-carbapen-2-em-3-carboxylate (inner salt)

a) 4-nitrobenzyl (1S,5R,6S)-2-(7-ethyl-6-methylimidazo[5,1-b]thiazolium-2-yl)-6-((1R)-1-hydroxyethyl)-1-methyl-1-carbapen-2-em-3-carboxylate Iodide In the same manner as in Example 4-a), 4-nitrobenzyl (1S,5R,6S)-2-(7-ethyl-6-methylimidazo[5,1-b]thiazolium-2-yl)-6-((1R)-1-hydroxyethyl)-1-methyl-1-carbapen-2-em-3-carboxylate iodide was obtained from 97.7 mg of 4-nitrobenzyl (1S,5R,6S)-2-(7-ethylimidazo[5,1-b]thiazol-2-yl)-6-((1R)-1-hydroxyethyl)-1-methyl-1-carbapen-2-em-3-carboxylate NMR (DMSO-d$_6$) δ: 1.18(3H, d, J=6.3 Hz), 1.22(3H, d, J=7.4 Hz), 1.29(3H, t, J=7.6 Hz), 2.88(2H, t, J=7.6 Hz), 3.49(1H, dd, J$_1$=5.7 Hz, J$_2$=3.1 Hz), 3.73(1H, m), 3.98(3H, s), 4.04(1H, m), 4.39(1H, dd, J$_1$=10.1 Hz), J$_2$=3.1 Hz), 5.18(1H, d, J=4.4 Hz), 5.40(1H, d, J=13.9 Hz), 5.53(1H, d, J=13.9 Hz), 7.73(2H, d, J=8.7 Hz), 8.23(2H, d, J=8.7 Hz), 8.61(1H, s), 9.51(1H, s).

b) (1S,5R,6S)-2-(7-ethyl-6-methylimidazo[5,1-b]thiazolium-2-yl)-6-((1R)-1-hydroxyethyl)-1-methyl-1-carbapen-2-em-3-carboxylate (inner salt)

In the same manner as in Example 4-b), the title compound was obtained in a yield of 50.6 mg from the whole amount of 4-nitrobenzyl (1S,5R,6S)-2-(7-ethyl-6-methylimidazo[5,1-b]thiazolium-2-yl)-6-((1R)-1-hydroxyethyl)-1-methyl-1-carbapen-2-em-3-carboxylate iodide obtained above.

NMR (D$_2$O) δ (HOD=4.80 ppm): 1.22(3H, d, J=6.9 Hz), 1.33(6H, m), 2.82(2H, q, J=7.4 Hz), 3.55(2H, m), 3.94(3H, s), 4.27(2H, m), 8.02(1H, s), 9.05(1H, s).

Example 128

(5R,6S)-2-(5,7-dimethylimidazo[5,1-b]thiazol-2-yl)-6-((1R)-1-hydroxyethyl)-1-carbapen-2-em-3-carboxylic Acid a) 4-nitrobenzyl (5R,6S)-2-(5,7-dimethylimidazo[5,1-b]thiazol-2-yl)-6-((1R)-1-hydroxyethyl)-1-carbapen-2-em-3-carboxylate In the same manner as in Example 5-a), 4-nitrobenzyl (5R,6S)-2-(5,7-dimethylimidazo[5,1-b]thiazol-2-yl)-6-((1R)-1-hydroxyethyl)-1-carbapen-2-em-3-carboxylate was obtained from 560 mg of 4-nitrobenzyl (3R,5R,6S)-6-((1R)-1-hydroxyethyl)-2-oxo-1-carbapenam-3-carboxylate and 852 mg of 5,7-dimethyl-2-(tri-n-butylstannyl)imidazo[5,1-b]thiazole.

NMR (DMSO-d6) δ: 1.17(3H, d, J=6.3 Hz), 2.14(3H, s), 2.46(3H, s), 3.3–3.5(3H, m), 4.01(1H, m), 4.24(1H, m), 5.16(1H, d, J=5.0 Hz), 5.40(1H, d, J=14.0 Hz), 5.52(1H, d, J=14.0 Hz), 7.75(2H, d, J=8.3 Hz), 8.15(1H, s), 8.24(2H, d, J=8.3 Hz).

b) (5R,6S)-2-(5,7-dimethylimidazo[5,1-b]thiazol-2-yl)-6-((1R)-1-hydroxyethyl)-1-carbapen-2-em-3-carboxylic Acid In the same manner as in Example 5-b), the title compound was obtained in a yield of 105.2 mg from 269 mg of 4-nitrobenzyl (5R,6S)-2-(5,7-dimethylimidazo[5,1-b]thiazol-2-yl)-6-((1R)-1-hydroxyethyl)-1-carbapen-2-em-3-carboxylate.

NMR (D$_2$O) δ (HOD=4.80 ppm): 1.32(3H, d, J=6.2 Hz), 2.33(3H, s), 2.70(3H, s), 3.30(2H, m), 3.55(1H, m), 4.30 (2H, m), 7.71(1H, s).

Example 129

Pivaloyloxymethyl (5R,6S)-2-(5,7-dimethylimidazo[5,1-b]thiazol-2-yl)-6-((1R)-1-hydroxyethyl)-1-carbapen-2-em-3-carboxylate In the same manner as in Example 19, the title compound was obtained in a yield of 40.3 mg from 99.4 mg of (5R,6S)-2-(5,7-dimethylimidazo[5,1-b]thiazol-2-yl)-6-((1R)-1-hydroxyethyl)-1-carbapen-2-em-3-carboxylic acid.

NMR (CDCl$_3$) δ: 1.23(9H, s), 1.37(3H, d, J=6.3 Hz), 2.28(3H, s), 2.57(3H, s), 3.28(3H, m), 4.27(2H, m), 5.90 (1H, d, J=5.6 Hz), 6.01(1H, d, J=5.6 Hz), 8.02(1H, s).

Example 130

(5R,6S)-2-(7-formylimidazo[5,1-b]thiazol-3-yl)-6-((1R)-1-hydroxyethyl)-1-carbapen-2-em-3-carboxylic Acid a) 4-nitrobenzyl (5R,6S)-2-(7-formylimidazo[5,1-b]thiazol-3-yl)-6-((1R)-1-hydroxyethyl)-1-carbapen-2-em-3-carboxylate To a solution 428 mg of 4-nitrobenzyl (5R,6S)-6-((1R)-1-hydroxyethyl)-2-(7-hydroxymethylimidazo[5,1-b]thiazol-3-yl)-1-carbapen-2-em-3-carboxylate in 30 ml of dichloromethane was added 1.03 g of manganese dioxide, and the mixture was stirred at room temperature for 18 hours. The catalyst was removed by filtration, and the filtrate was concentrated under reduced pressure. The residue thus obtained was washed with diethyl ether to give 202.8 mg of 4-nitrobenzyl (5R,6S)-2-(7-formylimidazo[5,1-b]thiazol-3-yl)-6-((1R)-1-hydroxyethyl)-1-carbapen-2-em-3-carboxylate.

NMR (CDCl$_3$) δ: 1.32(3H, d, J=6.4 Hz), 3.30–3.40(4H, m), 4.21–4.36(1H, m), 4.42(1H, dt, J$_1$=9.6 Hz, J$_2$=3.0 Hz), 5.14(1H, d, J=13.5 Hz), 5.29(1H, d, J=13.5 Hz), 7.40(2H, d, J=8.8 Hz), 7.72(1H, s), 8.09(2H, d, J=8.8 Hz), 9.79(1H, s). MS (TSP): 483 (M$^+$+H).

b) (5R,6S)-2-(7-formylimidazo[5,1-b]thiazol-3-yl)-6-((1R)-1-hydroxyethyl)-1-carbapen-2-em-3-carboxylic Acid In the same manner as in Example 5-b), the title compound was obtained in a yield of 45.1 mg from 142.1 mg of 4-nitrobenzyl (5R,6S)-2-(7-formylimidazo[5,1-b]thiazol-3-yl)-6-((1R)-1-hydroxyethyl)-1-carbapen-2-em-3-carboxylate.

NMR (D$_2$O) δ (HOD=4.80 ppm): 1.27(3H, d, J=6.2 Hz), 3.19–3.28(1H, m), 3.43–3.53(1H, m), 3.59–3.62(1H, m), 4.25–4.32(1H, m), 4.36–4.44(1H, m), 7.34(1H, s), 7.99(1H, s), 9.58(1H, s).

Example 131

Pivaloyloxymethyl (5R,6S)-2-(7-formylimidazo[5,1-b]thiazol-3-yl)-6-((1R)-1-hydroxyethyl)-1-carbapen-2-em-3-carboxylate In the same manner as in Example 19, the title compound was obtained in a yield of 8.2 mg from 31.4 mg of (5R,6S)-6-((1R)-1-hydroxyethyl)-2-(7-formylimidazo[5,1-b]thiazol-3-yl)-1-methyl-1-carbapen-2-em-3-carboxylic acid and 0.016 mg of pivaloyloxymethyl iodide.

NMR (CDCl$_3$) δ: 1.19(9H, s), 1.38(3H, d, J=6.3 Hz), 2.33(1H, br.s, s), 3.37–3.41(3H, m), 4.28–4.34(1H, m), 4.42–4.50(1H, m), 5.77(1H, d, J=5.5 Hz), 5.88(1H, d, J=5.5 Hz), 7.27(1H, s), 7.84(1H, s).

Example 132

(5R,6S)-2-(7-ethyl-6-methylimidazo[5,1-b]-thiazolium-3-yl)-6-((1R)-1-hydroxyethyl)-1-carbapen-2-em-3-carboxylate (inner salt)

In the same manner as in Example 14, the title compound was obtained in a yield of 2.2 mg from 73.9 mg of 4-nitrobenzyl (5R,6S)-2-(7-ethylimidazo[5,1-b]-thiazol-3-yl)-6-((1R)-1-hydroxyethyl)-1-carbapen-2-em-3-carboxylate.

NMR (D$_2$O) δ (HOD=4.80 ppm): 1.32(3H, d, J=6.4 Hz), 1.40(3H, t, J=7.4 Hz), 2.90(2H, q, J=7.4 Hz), 3.24(1H, dd, J$_1$=17.1 Hz, J$_2$=9.8 Hz), 3.45(1H, dd, J$_1$=17.1 Hz, J$_2$=8.7 Hz), 3.60(1H, m), 3.96(3H, s), 4.29(1H, m), 4.39(1H, m), 7.44(1H, s), 8.84(1H, s).

Example 133

(5R,6S)-6-((1R)-1-hydroxyethyl)-2-(5,6,7-trimethylimidazo[5,1-b]thiazolium-2-yl)-1-carbapen-2-em-3-carboxylate (inner salt)

a) 4-nitrobenzyl (5R,6S)-6-((1R)-1-hydroxyethyl)-2-(5,6,7-trimethylimidazo[5,1-b]thiazolium-2-yl)-1-carbapen-2-em-3-carboxylate Iodide In the same manner as in Example 4-a) except that the reaction was carried out for 4 days, 4-nitrobenzyl (5R,6S)-

6-((1R)-1-hydroxyethyl)-2-(5,6,7-trimethylimidazo[5,1-b]thiazolium-2-yl)-1-carbapen-2-em-3-carboxylate iodide was obtained from 86.1 mg of 4-nitrobenzyl (5R,6S)-2-(5,7-dimethylimidazo[5,1-b]-thiazol-2-yl)-6-((1R)-1-hydroxyethyl)-1-carbapen-2-em-3-carboxylate iodide.

NMR(DMSO-$d_6$) δ: 1.17(3H, d, J=6.5 Hz), 2.44(3H, s), 2.84(3H, s), 3.50(2H, m), 3.60(1H, m), 3.80(3H, s), 4.04 (1H, m), 4.33(1H, m), 5.20(1H, br.s), 5.44(1H, d, J=13.6 Hz), 5.56(1H, d, J=13.6 Hz), 7.76(2H, d, J=8.4 Hz), 8.26 (2H, d, J=8.4 Hz), 8.55(1H, s).

b) (5R,6S)-6-((1R)-1-hydroxyethyl)-2-(5,6,7-trimethylimidazo[5,1-b]thiazolium-2-yl)-1-carbapen-2-em-3-carboxylate (inner salt)

In the same manner as in Example 4-b), the title compound was obtained in a yield of 19.8 mg from the whole amount of 4-nitrobenzyl (5R,6S)-6-((1R)-1-hydroxyethyl)-2-(5,6,7-methylimidazo[5,1-b]thiazolium-2-yl)-1-carbapen-2-em-3-carboxylate. NMR ($D_2O$) δ (HOD=4.80 ppm): 1.28 (3H, d, J=6.4 Hz), 2.34(3H, s), 2.73(3H, s), 3.25(2H, m), 3.46(1H, m), 3.76(3H, s), 4.22(2H, m), 7.73(1H, s).

Example 134

Sodium (1S,5R,6S)-2-(7-acetylimidazo[5,1-b]thiazol-2-yl)-6-((1R)-1-hydroxyethyl)-1-methyl-1-carbapen-2-em-3-carboxylate a) 4-nitrobenzyl (1S,5R,6S)-2-[7-(1-t-butyldimethylsilyloxy)ethylimidazo[5,1-b]thiazol-2-yl]-6-((1R)-1-hydroxyethyl)-1-methyl-1-carbapen-2-em-3-carboxylate (Diastereoisomer mixture of about 1:1)

In the same manner as in Example 5-a), 4-nitrobenzy (1S,5R,6S)-2-[7-(1-t-butyldimethylsilyloxy)ethylimidazo [5,1-b]thiazol-2-yl]-6-((1R)-1-hydroxyethyl)-1-methyl-1-carbapen-2-em-3-carboxylate (diastereoisomer mixture of about 1:1) was obtained in a yield of 332 mg from 575 mg of 4-nitrobenzyl (1R,3R,5R,6S)-6-((1R)-1-hydroxyethyl)-1-methyl-2-oxo-1-carbapenam-3-carboxylate and 1.09 g of 7-(1-t-butyldimethylsilyloxy)ethyl-2-(tri-n-butylstannyl) imidazo[5,1-b]thiazole(racemic mixture).

NMR (CDCl$_3$) δ: 0.09(1.5H, s), 0.11(1.5H, s), 0.13(3H, s), 0.95(4.5H, s), 0.96(4.5H, s), 1.30(3H, d, J=7.2 Hz), 1.39(3H, d, J=6.3 Hz), 1.50(3H, m), 3.36(1H, dd, J$_1$=6.5 Hz, J$_2$=2.7 Hz), 3.45(1H, m), 4.34(2H, m), 5.09(1H, m), 5.26 (1H, d, J=13.7 Hz), 5.51(1H, d, J=13.7 Hz), 7.67(2H, d, J=8.8 Hz), 7.93(1H, s), 8.23(2H, d, J=8.8 Hz), 8.32(0.5H, s), 8.32(0.5H, s).

b) 4-nitrobenzyl (1S,5R,6S)-6-((1R)-1-hydroxyethyl)-2-[7-(1-hydroxy)ethylimidazo[5,1-b]thiazol-2-yl]-1-methyl-1-carbapen-2-em-3-carboxylate (Diastereoisomer mixture of about 1:1)

To a solution of 332 mg of 4-nitrobenzyl (1S,5R,6S)-2-[7-(1-t-butyldimethylsilyloxy)ethylimidazo[5,1-b]thiazol-2-yl]-6-((1R)-1-hydroxyethyl)-1--methyl-1-carbapen-2-em-3-carboxylate (diastereoisomer mixture of about 1:1) in 3 ml of DMF and 1 ml of NMP was added 180 mg of ammonium hydrogen dif luoride, and the mixture was stirred at room temperature for 16 hours. The reaction mixture was diluted with 50 ml of ethyl acetate and 50 ml of aqueous saline, and adjusted to pH 8 with a sodium hydrogen carbonate solution to pH 8. The organic layer was separated, and the aqueous layer was further extracted with ethyl acetate. The combined organic layer was washed twice with aqueous saline, dried over anhydrous magnesium sulfate, and the solvent was removed under reduced pressure. The residue thus obtained was purified by column chromatography on silica gel (dichloromethane:methanol=20:1) to give 80.5 mg of 4-nitrobenzyl (1S,5R,6S)-6-((1R)-1-hydroxyethyl)-2-[7-(1-hydroxy)ethylimidazo[5,1-b]thiazol-2-yl]-1-methyl-1-carbapen-2-em-3-carboxylate (diastereoisomer mixture of about 1:1).

NMR (CDCl$_3$) δ: 1.30(3H, d, J=7.2 Hz), 1.40(3H, d, J=6.3 Hz), 1.61(3H, d, J=6.5 Hz), 3.36(1H, dd, J$_1$=6.3 Hz, J$_2$=2.6 Hz), 3.46(1H, m), 4.34(2H, m), 5.07(1H, q, J=6.5 Hz), 5.27(1H, d, J=13.7 Hz), 5.52(1H, d, J=13.7 Hz), 7.68(2H, d, J=8.6 Hz), 7.96(1H, s), 6.24(2H, d, J=8.6 Hz), 8.32(1H, s).

c) 4-nitrobenzyl (1S,5R,6S)-2-(7-acetylimidazo[5,1-b]thiazol-2-yl)-6-((1R)-1-hydroxyethyl)-1-methyl-1-carbapen-2-em-3-carboxylate In the same manner as in Example 74-a), 4-nitrobenzyl (1S,5R,6S)-2-(7-acetylimidazo[5,1-b]thiazol-2-yl)-6-((1R)-1-hydroxyethyl)-1-methyl-1-carbapen-2-em-3-carboxylate was obtained from 197 mg of 4-nitrobenzyl (1S,5R,6S)-6-((1R)-1-hydroxyethyl)-2-[7-(1-hydroxy)ethylimidazo[5,1-b]thiazol-2-yl]-1-methyl-1-carbapen-2-em-3-carboxylate (diastereoisomer mixture of about 1:1).

NMR (CDCl$_3$) δ: 1.31(3H, d, J=7.4 Hz), 1.40(3H, d, J=6.2 Hz), 2.61(3H, s), 3.40(1H, dd, J$_1$=6.6 Hz, J$_2$=2.9 Hz), 3.52(1H, m), 4.32(1H, m), 4.42(1H, dd, J$_1$=9.7 Hz, J$_2$=2.9 Hz), 5.27(1H, d, J=13.5 Hz), 5.52(1H, d, J=13.5 Hz), 7.67(2H, d, J=8.5 Hz), 8.01(1H, s), 8.22(2H, d, J=8.5 Hz), 8.50(1H, s).

d) Sodium (1S,5R,6S)-2-(7-acetylimidazo[5,1-b]thiazol-2-yl)-6-((1R)-1-hydroxyethyl)-1-methyl-1-carbapen-2-em-3-carboxylate To a solution of 98.2 mg of 4-nitrobenzyl (1S,5R,6S)-2-(7-acetylimidazo[5,1-b]thiazol-2-yl)-6-((1R)-1-hydroxyethyl)-1-methyl-1-carbapen-2-em-3-carboxylate in 5.8 ml of THF and 5.8 ml of 1/15 M sodium phosphate buffer (pH 6.6) was added 98 mg of 10% Pd-C. The reactor was purged with hydrogen, and the reaction mixture was stirred at room temperature for 2 hours. The catalyst was removed by filtration through Celite, and washed with water. The filtrate was adjusted to pH 6.5 with an aqueous sodium hydrogen carbonate solution, washed with ethyl acetate, and the aqueous layer was purified by column chromatography on DIAION HP-20 (20% methanol in water) to give 38.1 mg of the title compound.

NMR (D$_2$O) δ (HOD=4.80 ppm): 1.20(3H, d, J=7.2 Hz), 1.33(3H, d, J=6.4 Hz), 2.45(3H, s), 3.50(1H, dd, J$_1$=6.1 Hz, J$_2$=2.5 Hz), 3.57(1H, m), 4.28(1H, m), 4.33(1H, dd, J$_1$=9.3 Hz, J$_2$=2.5 Hz), 7.92(1H, s), 8.05(1H, s).

Example 135

Pivaloyloxymethyl (1S,5R,6S)-2-(7-acetylimidazo [5,1-b]thiazol-2-yl)-6-((1R)-1-hydroxyethyl)-1-methyl-1-carbapen-2-em-3-carboxylate To a solution of 38.1 mg of sodium (1S,5R,6S)-2-(7-acetylimidazo[5,1-b]thiazol-2-yl)-6-((1R)-1-hydroxyethyl)-1-methyl-1-carbapen-2-em-3-carboxylate in 3 ml of DMF was added 0.021 ml of pivaloyloxymethyl iodide under the atmosphere of argon at −30° C., and the mixture was stirred for 1.5 hours. The reaction mixture was diluted with 20 ml of ethyl acetate and washed with 20 ml of semi-saturated aqueous saline. The organic layer was dried over anhydrous magnesium sulfate, filtered, and concentrated under reduced pressure to a volume of 3 ml. The residue thus obtained was purified by column chromatography on silica gel (dichloromethane:methanol=20:1) and on Sephadex LH-20 (chloroform:methanol=1:1) in this sequence to give 35.8 mg of the title compound.

NMR (CDCl$_3$) δ: 1.20(9H, s), 1.29(311, d, J=7.3 Hz), 1.37(3H, d, J=6.3 Hz), 2.62(3H, s), 3.36(1H, dd, J$_1$=6.5 Hz, J$_2$=2.9 Hz), 3.50(1H, m), 4.30(1H, m), 4.40(1H, dd, J$_1$=9.7 Hz, J$_2$=2.9 Hz), 5.87(1H, d, J=5.6 Hz), 5.99(1H, d, J=5.6 Hz), 8.05(1H, s), 8.51(1H, s).

Example 136

(5R,6S)-2-(7-acetylimidazo[5,1-b]thiazol-3-yl)-6-((1R)-1-hydroxyethyl)-1-carbapen-2-em-3-carboxylic Acid a) 4-nitrobenzyl (5R,6S)-2-[7-(1-t-butyldimethylsilyloxy) ethylimidazo[5,1-b]thiazol-3-yl]-6-((1R)-1-hydroxyethyl)-1-carbapen-2-em-3-carboxylate (Diastereoisomer mixture of about 1:1)

In the same manner as in Example 5-a), 4-nitrobenzyl (5R,6S)-2-[7-(1-t-butyldimethylsilyloxy)ethylimidazo[5,1-b]-thiazol-3-yl]-6-((1R)-1-hydroxyethyl)-1-carbapen-2-em-3-carboxylate (diastereoisomer mixture of about 1:1) was obtained in a yield of 1.26 g from 4-nitrobenzyl (3R,5R,6S)-6-((1R)-1-hydroxyethyl)-2-oxo-1-carbapenam-3-carboxylate and 3.00 g of 7-(1-t-butyldimethylsilyloxy) ethyl-3-(-tri-n-butylstannyl)imidazo[5,1-b]thiazole (racemic mixture).

NMR (CDCl$_3$) δ: 0.10(3H, s), 0.13(3H, s), 0.96(9H, s), 1.39(3H, d, J=6.3 Hz), 1.47(1.5H, d, J=6.2 Hz), 1.49(1.5H, d, J=6.2 Hz), 3.36(3H, m), 4.31(1H, m), 4.42(1H, m), 5.08(1H, q, J=6.2 Hz), 5.23(1H, d, J=13.5 Hz), 5.37(1H, d, J=13.5 Hz), 7.04(0.5H, s), 7.05(0.5H, s), 7.43(1H, d, J=8.2 Hz), 7.45(1H, d, J=8.2 Hz), 7.66(1H, s), 8.18(2H, d, J=8.2 Hz).

b) 4-nitrobenzyl (5R,6S)-6-((1R)-1-hydroxyethyl)-2-[7-(1-hydroxy)ethylimidazo[5,1-b]thiazol-3-yl]-1-carbapen-2-em-3-carboxylate (Diastereoisomer mixture of about 1:1)

In the same manner as in Example 134-b) except that the reaction was carried out for 4 days, 4-nitrobenzyl (5R,6S)-6-((1R)-1-hydroxyethyl)-2-[7-(1-hydroxy)ethylimidazo[5,1-b]-thiazol-3-yl]-1-carbapen-2-em-3-carboxylate (diastereoisomer mixture of about 1:1) was obtained in a yield of 245 mg from 1.03 g of 4-nitrobenzyl (5R,6S)-2-[7-(1-t-butyldimethylsilyloxy)ethylimidazo[5,1-b]thiazol-3-yl]-6-((1R)-1-hydroxyethyl)-1-carbapen-2-em-3-carboxylate (diastereoisomer mixture of about 1:1).

NMR (CDCl$_3$) δ: 1.41(3H, d, J=6.3 Hz), 1.59(3H, d, J=6.3 Hz), 3.36(3H, m), 4.32(1H, m), 4.43(1H, m), 5.03(1H, q, J=6.3 Hz), 5.21(1H, d, J=13.5 Hz), 5.36(1H, d, J=13.5 Hz), 7.03(1H, s), 7.44(2H, d, J=8.8 Hz), 7.67(1H, s), 8.18(2H, d, J=8.8 Hz).

c) 4-nitrobenzyl (5R,6S)-2-(7-acetylimidazo[5,1-b]thiazol-3-yl)-6-((1R)-1-hydroxyethyl)-1-carbapen-2-em-3-carboxylate In the same manner as in Example 74-a), 4-nitrobenzyl (5R,6S)-2-(7-acetylimidazo[5,1-b]thiazol-3-yl)-6-((1R)-1-hydroxyethyl)-1-carbapen-2-em-3-carboxylate was obtained in a yield of 58.6 mg from 262 mg of 4-nitrobenzyl (5R,6S)-6-((1R)-1-hydroxyethyl)-2-[7-(1-hydroxy)ethylimidazo[5,1-b]thiazol-3-yl]-1-carbapen-2-em-3-carboxylate (diastereoisomer mixture of about 1:1).

NMR (CDCl$_3$) δ: 1.40(3H, d, J=6.3 Hz), 2.57(3H, s), 3.41(3H, m), 4.33(1H, m), 4.48(1H, m), 5.20(1H, d, J=13.4 Hz), 5.36(1H, d, J=13.4 Hz), 7.23(1H, s), 7.46(2H, d, J=8.8 Hz), 7.79(1H, s), 8.16(2H, d, J=8.8 Hz).

d) (5R,6S)-2-(7-acetylimidazo[5,1-b]thiazol-3-yl)-6-((1R)-1-hydroxyethyl)-1-carbapen-2-em-3-carboxylic Acid In the same manner as in Example 5-b), the title compound was obtained in a yield of 6.6 mg from 58.6 mg of 4-nitrobenzyl (5R,6S)-2-(7-acetylimidazo[5,1-b]thiazol-3-yl)-6-((1R)-1-hydroxyethyl)-1-carbapen-2-em-3-carboxylate.

NMR (D$_2$O) δ (HOD=4.80 ppm): 1.32(3H, d, J=6.3 Hz), 2.56(3H, s), 3.25(1H, m), 3.48(1H, m), 3.61(1H, m), 4.29 (1H, m), 4.40(1H, m), 7.31(1H, s), 7.96(1H, s).

Example 137

(1S,5R,6S)-6-((1R)-1-hydroxyethyl)-2-(7-methoxyiminomethylimidazo[5,1-b]thiazol-2-yl)-1-methyl-1-carbapen-2-em-3-carboxylate (geometrical isomer derived from a raw material which is a high polar oxime isomer)

a) 4-nitrobenzyl (1S,5R,6S)-6-((1R)-1-hydroxyethyl)-2-(7-methoxyiminomethylimidazo[5,1-b]thiazol-2-yl)-1-methyl-1-carbapen-2-em-3-carboxylate (geometrical isomer derived from a raw material which is a high polar oxime isomer)

In the same manner as in Example 5-a), 4-nitrobenzyl (1S,5R,6S)-6-((1R)-1-hydroxyethyl)-2-(7-methoxyiminomethylimidazo[5,1-b]thiazol-2-yl)-1-methyl-1-carbapen-2-em-3-carboxylate (geometrical isomer derived from a raw material which is a high polar oxime isomer) was obtained in a yield of 275 mg from 362 mg of 4-nitrobenzyl (1R,3R,5R,6S)-6-((1R)-1-hydroxyethyl)-1-methyl-2-oxo-1-carbapenam-3-carboxylate and 564 mg of 7-methoxyiminomethyl-2-(tri-n-butyls-tannyl)imidazo[5,1-b]thiazole(geometrical isomer derived from a raw material which is a high polar oxime isomer) described in Preparation 14.

NMR (CDCl$_3$) δ: 1.30(3H, d, J=7.4 Hz), 1.39(3H, d, J=6.2 Hz), 3.38(1H, dd, J$_1$=6.3 Hz, J$_2$=2.8 Hz), 3.50(1H, m), 4.00(3H, s), 4.33(1H, m), 4.40(1H, dd, J$_1$=9.6 Hz, J$_2$=2.8 Hz), 5.26(1H, d, J=13.7 Hz), 5.52(1H, d, J=13.7 Hz), 7.46(1H, s), 7.66(2H, d, J=8.8 Hz), 7.96(1H, s), 8.21(2H, d, J=8.8 Hz), 8.33(1H, s).

b) (1S,5R,6S)-6-((1R)-1-hydroxyethyl)-2-(7-methoxyiminomethylimidazo[5,1-b]thiazol-2-yl)-1-methyl-1-carbapen-2-em-3-carboxylate (geometrical isomer derived from a raw material which is a high polar oxime isomer)

In the same manner as in Example 5-b), the title compound was obtained in a yield of 14.7 mg from 225 mg of 4-nitrobenzyl (1S,5R,6S)-6-((1R)-1-hydroxyethyl)-2-(7-methoxyiminomethylimidazo[5,1-b]thiazol-2-yl)-1-methyl-1-carbapen-2-em-3-carboxylate (geometrical isomer derived from a raw material which is a high polar oxime isomer).

NMR (D$_2$O) δ (HOD=4.80 ppm): 1.19(3H, d, J=7.0 Hz), 1.32(3H, d, J=6.5 Hz), 3.47(2H, m), 3.88(3H, s), 4.28(2H, m), 7.23(1H, s), 7.80(1H, s), 8.13(1H, s).

Example 138

(1S,5R,6S)-6-((1R)-1-hydroxyethyl)-1-methyl-2-[7-(N-methylcarbamoyl)imidazo[5,1-b]thiazol-2-yl]-1-carbapen-2-em-3-carboxylic Acid a) 4-nitrobenzyl (1S,5R,6S)-6-((1R)-1-hydroxyethyl)-1-methyl-2-[7-(N-methylcarbamoyl)imidazo[5,1-b]thiazol-2-yl]-1-carbapen-2-em-3-carboxylate In the same manner as in Example 5-a), 4-nitrobenzyl (1S,5R,6S)-6-((1R)-1-hydroxyethyl)-1-methyl-2-[7-(N-methylcarbamoyl)imidazo[5,1-b]thiazol-2-yl]-1-carbapen-2-em-3-carboxylate was obtained in a yield of 201 mg from 205 mg of (1R,3R,5R,6S)-6-((1R)-1-hydroxyethyl)-1-methyl-2-oxo-1-carbapenam-3-carboxylate and 299 mg of 7-(N-methylcarbamoyl)-2-(tri-n-butylstannyl)imidazo[5,1-b]thiazole.

NMR (CDCl$_3$) δ: 1.30(3H, d, J=7.3 Hz), 1.40(3H, d, J=6.2 Hz), 1.72(1H, m), 3.01(3H, d, J=5.0 Hz), 3.38–3.41(1H, m), 3.45–3.54(1H, m), 4.28–4.37(1H, m), 4.40–4.45(1H, m), 5.27(1H, d, J=13.7 Hz), 5.51(1H, d, J=13.7 Hz), 7.66(2H, d, J=8.9 Hz), 7.92(1H, s), 8.23(2H, d, J=8.9 Hz), 8.48(1H, s).
MS (APCI): 526 (M$^+$+H).

b) (1S,5R,6S)-6-((1R)-1-hydroxyethyl)-1-methyl-2-[7-(N-methylcarbamoyl)imidazo[5,1-b]thiazol-2-yl]-1-carbapen-2-em-3-carboxylic Acid In the same manner as in Example 5-b), the title compound was obtained in a yield of 61 mg from 116.2 mg of 4-nitrobenzyl (1S,5R,6S)-6-((1R)-1-hydroxyethyl)-1-methyl-2-[7-(N-methylcarbamoyl)imidazo[5,1-b]thiazol-2-yl]-1-carbapen-2-em-3-carboxylate.

NMR ($D_2O$) δ (HOD=4.80 ppm): 1.22(3H, d, J=6.9 Hz), 1.31(3H, d, J=6.0 Hz), 2.91(3H, s), 3.48–3.61(2H, m), 4.23–4.32(2H, m), 7.92(1H, s), 8.04(1H, s).

Example 139

Pivaloyloxymethyl (1S,5R,6S)-6-((1R)-1-hydroxyethyl)-1-methyl-2-[7-(N-methylcarbamoyl)imidazo[5,1-b]-thiazol-2-yl]-1-carbapen-2-em-3-carboxylate In the same manner as in Example 19, the title compound was obtained in a yield of 23.0 mg from 41.8 mg of (1S,5R,6S)-6-((1R)-1-hydroxyethyl)-1-methyl-2-[7-(N-methylcarbamoyl)imidazo[5,1-b]thiazol-2-yl]-1-carbapen-2-em-3-carboxylate and 0.023 ml of pivaloyloxymethyl iodide.

NMR ($CDCl_3$) δ: 1.17(9H, s), 1.28(3H, d, J=7.4 Hz), 1.37(3H, d, J=6.3 Hz), 2.26–2.29(1H, m), 3.01(3H, d, J=5.0 Hz), 3.32–3.38(1H, m), 3.45–3.54(1H, m), 4.26–4.33(1H, s), 4.38–4.41(1H, m), 5.87(1H, d, J=5.6 Hz), 5.99(1H, d, J=5.6 Hz), 6.88–6.93(1H, m), 7.97(1H, s), 8.51(1H, s). MS (TSP): 505 ($M^+$+H).

Example 140

Sodium (1S,5R,6S)-2-[7-(N,N-dimethylcarbamoyl)imidazo[5,1-b]thiazol-2-yl]-6-((1R)-1-hydroxyethyl)-1-methyl-1-carbapen-2-em-3-carboxylate A solution of 725 mg of 4-nitrobenzyl (1R,3R,5R,6S)-6-((1R)-1-hydroxyethyl)-1-methyl-2-oxo-1-carbapenam-3-carboxylate in 6 ml of anhydrous acetonitrile was cooled to −25° C. under the atmosphere of argon. To the solution was added diisopropylethylamine (520 mg) followed by 636 mg of anhydrous trifluoromethanesulfonic acid, and the mixture was stirred for 30–40 minutes, then diluted with 50 ml of ethyl acetate and 20 ml of semi-saturated aqueous saline, stirred and separated. The organic layer was washed with a mixture of 15 ml of semi-saturated aqueous saline and 2 ml of 1 N hydrochloric acid and with a mixture of 15 ml of semi-saturated aqueous saline and 1 ml of a saturated sodium hydrogen carbonate solution, stirred, dried over anhydrous magnesium sulfate, and the solvent was removed under reduced pressure. After concentrating the solvent to a volume of about 1 ml, it was diluted with 6 ml of NMP, and the mixture was concentrated again. To the concentrate were added a solution of a mixture of 7-(N,N-dimethylcarbamoyl)-2-(-tri-n-butylstannyl)imidazothiazole and 7-(N,N-dimethylcarbamoyl)-3-(tri-n-butylstannyl)imidazo-thiazole (ca 1:1) described in Preparation 22 in 3 ml of NMP, followed by 55 mg of tris(dibynzylideneacetone)dipalladium (0), 56 mg of tri-2-furylphosphine, and 560 mg of sufficiently desiccated zinc chloride, and the mixture was stirred under the atmosphere of argon at room temperature for 1 hour and at 55° C. for further 2 hours. The reaction mixture was diluted with 100 ml of ethyl acetate, washed with 50 ml of water and three or four times with 50 ml of semi-saturated aqueous saline, and dried over anhydrous magnesium sulfate, and the solvent was removed under reduced pressure. The residue thus obtained was purified by column chromatography on silica gel (dichloromethane:methanol=98:2–95:5) to give 699 mg of a mixture of 4-nitrobenzyl (1S,5R,6S)-2-[7-(N,N-dimethylcarbamoyl)imidazo[5,1-b]thiazol-2-yl]-6-((1R)-1-hydroxyethyl)-1-methyl-1-carbapen-2-em-3-carboxylate and 4-nitrobenzyl (1S,5R,6S)-2-[7-(N,N-dimethylcarbamoyl)imidazo[5,1-b]thiazol-3-yl]-6-((1R)-1-hydroxyethyl)-1-methyl-1-carbapen-2-em-3-carboxylate (ca. 1:1).

To a solution of the mixture in 28.5 ml of THF and 28.5 ml of a 1/15 M phosphate buffer (pH 6.8) was added 600 mg of 10% Pd-C, and the reactor was purged with hydrogen.

The reaction mixture was stirred vigorously at room temperature for 2 hours and filtered through Celite, and the Celite was washed with 50 ml of a THF/water (1:1). The combined filtrate was washed with 80 ml of ethyl acetate, and the solvent was concentrated under reduced pressure. The residue thus obtained was purified by desalting by column chromatography on DIAION HP-20 (water—water:acetonitrile=9:1), then by separation by preparative column chromatography on COSMOSEAL 5C18-MS (20× 250 mm) (acetonitrile:water=1:1), and the first fractions among those containing two primary components were collected, concentrated under reduced pressure, and lyophilized to give the title compound in a yield of 156 mg.

NMR ($D_2O$) δ (HOD=4.80 ppm): 1.21(3H, d, J=7.1 Hz), 1.32(3H, d, J=6.3 Hz), 2.9–3.7(7H, m), 3.49(1H, dd, $J_1$=6.3 Hz, $J_2$=2.5 Hz), 4.27(2H, m), 7.89(1H, s), 8.01(1H, s).

Example 141

Pivaloyloxymethyl (1S,5R,6S)-2-[7-(N,N-dimethylcarbamoyl)imidazo[5,1-b]thiazol-2-yl]-6-((1R)-1-hydroxyethyl)-1-methyl-1-carbapen-2-em-3-carboxylate To a solution of 50 mg of sodium (1R,5R,6S)-2-[7-(N,N-dimethylcarbamoyl)imidazo[5,1-b]thiazol-2-yl]-6-((1R)-1-hydroxyethyl)-1-methyl-carbapen-2-em-3-carboxylate in 0.7 ml of DMF was added 5.0 mg of sodium hydrogen carbonate, and the mixture was cooled to −30° C. under the atmosphere of argon. The reaction mixture was added with 43 mg of pivaloyloxymethyl iodide, stirred for 1 hour, extracted with 20 ml of ethyl acetate, and the organic layer was washed with 12 ml of semi-saturated aqueous saline, dried over anhydrous magnesium sulfate, and concentrated under reduced pressure to a volume of about 1 ml. The residue thus obtained was purified by column chromatography on silica gel (dichloromethane:methanol=95:5) to give 55 mg of the title compound.

NMR ($CDCl_3$) δ: 1.18(9H, s), 1.26(3H, d, J=7.3 Hz), 1.35(3H, d, J=6.3 Hz), 3.0–3.8(6H, m), 3.32(1H, dd, $J_1$=7.1 Hz, $J_2$=2.8 Hz), 3.46(1H, m), 4.23(1H, m), 4.37(1H, dd, $J_1$=9.8 Hz, $J_2$=2.8 Hz), 5.85(1H, d, J=5.6 Hz), 5.96(1H, d, J=5.6 Hz), 8.00(1H, s), 8.50(1H, s).

Example 142

Sodium (1S,5R,6S)-2-[7-(N,N-dimethylcarbamoyl)imidazo[5,1-b]thiazol-3-yl]-6-((1R)-1-hydroxyethyl)-1-methyl-1-carbapen-2-em-3-carboxylate In the preparative chromatography in Example 140, the second fractions among those containing two primary components were collected, concentrated under reduced pressure, and lyophilized to give the title compound in a yield of 154 mg.

NMR (CDCl$_3$) δ: 1.14(3H, d, J=7.1 Hz), 1.31(3H, d, J=6.4 Hz), 3.0–3.7(8H, m), 4.3(1H, m), 4.41(1H, dd, J$_1$=9.9 Hz, J$_2$=3.0 Hz), 7.25(1H, s), 8.01(1H, s).

Example 143

Pivaloyloxymethyl (1S,5R,6S)-2-[7-(N,N-dimethylcarbamoyl)imidazo[5,1-b]thiazol-3-yl]-6-((1R)-1-hydroxyethyl)-1-methyl-1-carbapen-2-em-3-carboxylate To a solution of 50 mg of sodium (1S,5R,6S)-2-[7-(N,N-dimethylcarbamoyl)imidazo[5,1-b]thiazol-3-yl]-6-((1R)-1-hydroxyethyl)-1-methyl-1-carbapen-2-em-3-carboxylate in 0.7 ml of DMF was added 5.0 mg of sodium hydrogen carbonate, and the mixture was cooled to −30° C. under the atmosphere of argon. After addition of 43 mg of pivaloyloxymethyl iodide, the mixture was stirred for 1 hour, extracted with 20 ml of ethyl acetate, and the organic layer was washed with 12 ml of semi-saturated aqueous saline, dried over anhydrous magnesium sulfate, and concentrated under reduced pressure to a volume of about 1 ml. The residue thus obtained was purified by column chromatography on silica gel (dichloromethane:methanol=95:5) to give 48 mg of the title compound.

NMR (CDCl$_3$) δ: 1.14(9H, s), 1.12(3H, d, J=7.6 Hz), 1.34(3H, d, J=6.2 Hz), 3.0–3.8(6H, m), 3.42(1H, dd, J$_1$=6.5 Hz, J$_2$=3.2 Hz), 3.6(1H, m), 4.28(1H, m), 4.48(1H, dd, J$_1$=10.4 Hz, J$_2$=3.2 Hz), 5.70(1H, d, J=5.6 Hz), 5.83(1H, d, J=5.6 Hz), 7.18(1H, s), 7.74(1H, s).

Example 144

(5R,6S)-2-(7-cyanoimidazo[5,1-b]thiazol-3-yl)-6-((1R)-1-hydroxyethyl)-1-carbapen-2-em-3-carboxylic Acid a) 4-nitrobenzyl (5R,6S)-2-(7-cyanoimidazo[5,1-b]thiazol-3-yl)-6-((1R)-1-hydroxyethyl)-1-carbapen-2-em-3-carboxylate In the same manner as in Example 5-a), 4-nitrobenzyl (5R,6S)-2-(7-cyanoimidazo[5,1-b]thiazol-3-yl)-6-((1R)-1-hydroxyethyl)-1-carbapen-2-em-3-carboxylate was obtained in a yield of 29.7 mg from 46 mg of 4-nitrobenzyl (3R,5R,6S)-6-((1R)-1-hydroxyethyl)-2-oxo-1-carbapenam-3-carboxylate and 69.6 mg of 7-cyano-3-(tri-n-butylstannyl)imidazo[5,1-b]thiazole.

NMR (CDCl$_3$) δ: 1.41(3H, d, J=6.3 Hz), 3.39(3H, m), 4.33(1H, m), 4.47(1H, m), 5.23(1H, d, J=13.3 Hz), 5.39(1H, d, J=13.3 Hz), 7.18(1H, s), 7.54(2H, d, J=8.4 Hz), 7.69(1H, s), 8.22(2H, d, J=8.4 Hz).

b) (5R,6S)-2-(7-cyanoimidazo[5,1-b]thiazol-3-yl)-6-((1R)-1-hydroxyethyl)-1-carbapen-2-em-3-carboxylic Acid In the same manner as in Example 5-b), the title compound was obtained in a yield of 35.4 mg from 124 mg of 4-nitrobenzyl (5R,6S)-2-(7-cyanoimidazo[5,1-b]thiazol-3-yl)-6-((1R)-1-hydroxyethyl)-1-carbapen-2-em-3-carboxylate.

NMR (D$_2$O) δ (HOD=4.80 ppm): 1.32(3H, d, J=6.4 Hz), 3.23(1H, dd, J$_1$=17.3 Hz, J$_2$=9.9 Hz), 3.46(1H, dd, J$_1$=17.3 Hz, J$_2$=8.3 Hz), 3.60(1H, dd, J$_1$=6.0 Hz, J$_2$=2.9 Hz), 4.28 (1H, m), 4.39(1H, m), 7.27(1H, s), 7.98(1H, s).

Example 145

Pivaloyloxymethyl (5R,6S)-2-(7-cyanoimidazo[5,1-b]thiazol-3-yl)-6-((1R)-1-hydroxyethyl)-1-carbapen-2-em-3-carboxylate In the same manner as in Example 19, the title compound was obtained in a yield of 23.2 mg from 31.1 mg of (5R,6S)-2-(7-cyanoimidazo[5,1-b]thiazol-3-yl)-6-((1R)-1-hydroxyethyl)-1-carbapen-2-em-3-carboxylic acid.

NMR (CDCl$_3$) δ: 1.20(9H, s), 1.38(3H, d, J=6.3 Hz), 3.38(3H, m), 4.30(1H, m), 4.4(1H, m), 5.76(1H, d, J=5.6 Hz), 5.88(1H, d, J=5.6 Hz), 7.20(1H, s), 7.76(1H, s).

Example 146

(5R,6S)-6-((1R)-1-hydroxyethyl)-2-[7-(N-methylcarbamoyl)imidazo[5,1-b]thiazol-2-yl]-1-carbapen-2-em-3-carboxylic Acid a) 4-nitrobenzyl (5R,6S)-6-((1R)-1-hydroxyethyl)-2-[7-(N-methylcarbamoyl)imidazo[5,1-b]thiazol-2-yl]-1-carbapen-2-em-3-carboxylate In the same manner as in Example 5-a), 4-nitrobenzyl (5R,6S)-6-((1R)-1-hydroxyethyl)-2-[7-(N-methylcarbamoyl)imidazo[5,1-b]thiazol-2-yl]-1-carbapen-2-em-3-carboxylate was obtained in a yield of 217.6 mg from 264.3 mg of 4-nitrobenzyl (3R,5R,6S)-6-((1R)-1-hydroxyethyl)-2-oxo-1-carbapenam-3-carboxylate and 379.2 mg of 7-(N-methylcarbamoyl)-2-(tri-n-butylstannyl)imidazo[5,1-b]thiazole.

NMR (CDCl$_3$) δ: 1.41(3H, d, J=6.3 Hz), 3.01(3H, d, J=5.0 Hz), 3.32–3.40(3H, m), 4.30–4.40(3H, m), 5.32(1H, d, J=13.8 Hz), 5.54(1H, d, J=13.8 Hz), 6.86(1H, br.s, s), 7.69(2H, d, J=8.4 Hz), 7.92(1H, s), 8.25(2H, d, J=8.4 Hz), 8.49(1H, s). MS (TSP): 512 (M$^+$+H).

b) (5R,6S)-6-((1R)-1-hydroxyethyl)-2-[7-(N-methylcarbamoyl)imidazo[5,1-b]-thiazol-2-yl]-1-carbapen-2-em-3-carboxylic Acid In the same manner as in Example 5-b), the title compound was obtained in a yield of 61 mg from 116.2 mg of 4-nitrobenzyl (5R,6S)-6-((1R)-1-hydroxyethyl)-2-[7-(N-methylcarbamoyl)imidazo[5,1-b]thiazol-2-yl]-1-carbapen-2-em-3-carboxylate.

NMR (D$_2$O) δ (HOD=4.80 ppm): 1.30(3H, d, J=6.5 Hz), 2.90(3H, s), 3.15–3.21(2H, m), 3.42–3.48(1H, m), 4.18–4.30(2H, m), 7.65(1H, s), 7.93(1H, s).

Example 147

Pivaloyloxymethyl (5R,6S)-6-((1R)-1-hydroxyethyl)-2-[7-(N-methylcarbamoyl)imidazo[5,1-b]thiazol-2-yl]-1-carbapen-2-em-3-carboxylate In the same manner as in Example 19, the title compound was obtained in a yield of 23.0 mg from 41.8 mg of (5R,6S)-6-((1R)-1-hydroxyethyl)-2-[7-(N-methylcarbamoyl)imidazo[5,1-b]thiazol-2-yl]-1-carbapen-2-em-3-carboxylate and 0.023 ml of pivaloyloxymethyl iodide.

NMR (CDCl$_3$) δ: 1.22(9H, s), 1.37(3H, d, J=6.3 Hz), 1.18(1H, br.s, s), 3.01(3H, d, J=5.1 Hz), 3.29–3.37(3H, m), 4.26–4.38(2H, m), 5.90(1H, d, J=5.6 Hz), 6.01(1H, d, J=5.6 Hz), 6.89(1H, br.s, s), 7.95(1H, s), 8.58(1H, s). MS (FAB$^+$): 491 (M$^+$+H).

Example 148

Sodium (1S,5R,6S)-6-((1R)-1-hydroxyethyl)-2-(7-methoxyiminomethylimidazo[5,1-b]thiazol-2-yl)-1-methyl-1-carbapen-2-em-3-carboxylate (geometrical isomer derived from a raw material which is a low polar oxime isomer)

a) 4-nitrobenzyl (1S,5R,6S)-6-((1R)-1-hydroxyethyl)-2-(7-methoxyiminomethylimidazo[5,1-b]thiazol-2-yl)-1-methyl-1-carbapen-2-em-3-carboxylate (geometrical isomer derived from a raw material which is a low polar oxime isomer)

In the same manner as in Example 5-a), 4-nitrobenzyl (1S,5R,6S)-6-((1R)-1-hydroxyethyl)-2-(7-methoxyiminomethylimidazo[5,1-b]-thiazol-2-yl)-1-methyl-1-carbapen-2-em-3-carboxylate (geometrical isomer derived from a raw material which is a low polar oxime isomer) was obtained in a yield of 252 mg from 452 mg of 4-nitrobenzyl (1R,3R,5R,6S)-6-((1R)-1-hydroxyethyl)-1-methyl-2-oxo-1-carbapenam-3-carboxylate and 704 mg of 7-methoxyiminomethyl-2-(tri-n-butylstannyl)imidazo[5,1-b]thiazole described in Preparation 15 (geometrical isomer derived from a raw material which is a low polar oxime isomer).

NMR (CDCl$_3$) δ: 1.32(3H, d, J=7.2 Hz), 1.39(3H, d, J=6.1 Hz), 3.38(1H, dd, J$_1$=6.4 Hz, J$_2$=2.8 Hz), 3.52(1H, m), 3.96(3H, s), 4.33(1H, m), 4.40(1H, dd, J$_1$=9.6 Hz, J$_2$=2.8 Hz), 5.28(1H, d, J=13.7 Hz), 5.53(1H, d, J=13.7 Hz), 7.67(2H, d, J=8.2 Hz), 8.03(1H, s), 8.22(1H, s), 8.23(2H, d, J=8.2 Hz), 8.44(1H, s).

b) Sodium (1S,5R,6S)-6-((1R)-1-hydroxyethyl)-2-(7-methoxyiminomethylimidazo[5,1-b]thiazol-2-yl)-1-methyl-1-carbapen-2-em-3-carboxylate (geometrical isomer derived from a raw material which is a low polar oxime isomer)

In the same manner as in Example 134-d), the title compound was obtained in a yield of 90.8 mg from 252 mg of 4-nitrobenzyl (1S,5R,6S)-6-((1R)-1-hydroxyethyl)-2-(7-methoxyiminomethylimidazo[5,1-b]-thiazol-2-yl)-1-methyl-1-carbapen-2-em-3-carboxylate (geometrical isomer derived from a raw material which is a low polar oxime isomer).

NMR (D$_2$O) δ (HOD=4.80 ppm): 1.22(3H, d, J=6.9 Hz), 1.33(3H, d, J=6.3 Hz), 3.53(2H, m), 3.93(3H, s), 4.30(2H, m), 7.85(1H, s), 8.05(2H, 2s).

Example 149

Pivaloyloxynethyl (1S,5R,6S)-6-((1R)-1-hydroxyethyl)-2-(7-methoxyiminomethylimidazo[5,1-b]thiazol-2-yl)-1-methyl-1-carbapen-2-em-3-carboxylate (geometrical isomer derived from a raw material which is a low polar oxime isomer)

In the same manner as in Example 135, the title compound was obtained in a yield of 96.2 mg from 105 mg of sodium (1S,5R,6S)-6-((1R)-1-hydroxyethyl)-2-(7-methoxyiminomethylimidazo[5,1-b]thiazol-2-yl)-1-methyl-1-carbapen-2-em-3-carboxylate (geometrical isomer derived from a raw material which is a low polar oxime isomer).

NMR (CDCl$_3$) δ: 1.20(9H, s), 1.30(3H, d, J=7.2 Hz), 1.37(3H, d, J=6.2 Hz), 3.34(1H, dd, J$_1$=6.3 Hz, J$_2$=2.7 Hz), 3.49(1H, m), 3.97(3H, s), 4.30(1H, m), 4.37(1H, dd, J$_1$=9.8 Hz, J$_2$=2.7 Hz), 5.88(1H, d, J=5.6 Hz), 6.00(1H, d, J=5.6 Hz), 8.07(1H, s), 8.23(1H, s), 8.44(1H, s).

The structures of the compounds in Examples above are illustrated below.

In this connection, * represents the linkage with the position 2 on the carbapenam ring, and POM represents a pivaloyloxymethyl group.

| | $R^1$ | $R^2$ | $R^3$ | $R^4$ | $R^5$ | $R^6$ | R |
|---|---|---|---|---|---|---|---|
| 1.2 | CH$_3$ | * | H | H | H | — | H |
| 3 | CH$_3$ | * | H | H | H | — | POM |
| 4 | CH$_3$ | * | H | H | H | CH$_3$ | — |
| 5 | CH$_3$ | H | * | H | H | — | H |
| 6 | CH$_3$ | H | * | H | H | — | POM |
| 7 | CH$_3$ | H | * | H | H | CH$_3$ | — |
| 8 | H | * | H | H | H | — | H |
| 9 | CH$_3$ | * | CH$_3$ | H | H | — | H |
| 10 | CH$_3$ | * | CH$_3$ | H | H | — | POM |
| 11 | CH$_3$ | * | CH$_3$ | H | H | CH$_3$ | — |
| 12 | H | H | * | H | H | — | H |
| 13 | H | H | * | H | H | — | POM |
| 14 | H | H | * | H | H | CH$_3$ | — |
| 15 | H | * | H | H | H | CH$_3$ | — |
| 16 | CH$_3$ | * | H | H | H | CH$_2$CONH$_2$ | — |
| 17 | CH$_3$ | * | H | CH$_3$ | H | — | H |
| 18 | CH$_3$ | * | H | CH$_3$ | H | CH$_3$ | — |
| 19 | CH$_3$ | * | H | CH$_3$ | H | — | POM |
| 20 | CH$_3$ | * | H | H | Cl | — | H |
| 21 | CH$_3$ | CH$_3$ | * | H | H | — | H |
| 22 | H | CH$_3$ | * | H | H | — | H |
| 23 | CH$_3$ | * | H | H | Cl | CH$_3$ | — |
| 24 | H | * | H | H | H | — | POM |
| 25 | H | * | H | CH$_3$ | H | — | H |
| 26 | H | * | H | CH$_3$ | H | — | POM |
| 27 | CH$_3$ | * | H | H | CH$_3$ | — | Na |
| 28 | CH$_3$ | * | H | H | CH$_3$ | — | POM |
| 29 | CH$_3$ | * | H | H | CH$_3$ | CH$_3$ | — |
| 30 | H | * | H | CH$_3$ | H | CH$_3$ | — |
| 31 | CH$_3$ | * | H | CH$_2$NHCHO | H | — | H |
| 32 | CH$_3$ | * | H | CH$_2$NHCHO | H | — | POM |
| 33 | CH$_3$ | * | H | CH$_2$NHCHO | H | CH$_3$ | — |
| 34 | CH$_3$ | * | H | CH$_2$OH | H | — | H |
| 35 | CH$_3$ | * | H | CH$_2$OH | H | — | POM |
| 36 | CH$_3$ | * | CH$_2$OH | H | H | — | H |
| 37 | CH$_3$ | H | * | H | CH$_3$ | — | H |
| 38 | H | * | H | H | CH$_3$ | — | Na |
| 39 | H | * | H | H | CH$_3$ | — | POM |

-continued

| | $R^1$ | $R^2$ | $R^3$ | $R^4$ | $R^5$ | $R^6$ | R |
|---|---|---|---|---|---|---|---|
| 40 | CH₃ | H | * | H | CH₃ | — | POM |
| 41 | CH₃ | * | H | CH₂OH | H | CH₃ | — |
| 42 | H | * | H | H | CH₃ | CH₃ | — |
| 43 | H | H | * | H | CH₃ | — | H |
| 44 | H | H | * | H | CH₃ | — | POM |
| 45 | H | H | * | H | CH₃ | CH₃ | — |
| 46 | H | * | CH₃ | H | H | — | H |
| 47 | H | * | CH₃ | H | H | — | POM |
| 48 | CH₃ | H | H | * | H | — | K |
| 49 | CH₃ | * | H | H | CH₂NHCHO | CH | — |
| 50 | CH₃ | H | H | * | H | — | POM |
| 51 | CH₃ | * | CH₃ | H | H | CH₃ | |
| 52 | CH₃ | * | H | H | H | — | CH₂OC(O)CH₃ |
| 53 | CH₃ | * | H | H | H | — | CH(CH₃)OC(O)CH₃ |
| 54 | CH₃ | * | H | H | H | — | CH₂OC(O)-(1-methylcyclohexyl) |
| 55 | CH₃ | * | H | H | H | — | CH(CH₃)OC(O)OCH₂CH₃ |
| 56 | CH₃ | * | H | H | H | — | CH(CH₃)OC(O)OCH(CH₃)₂ |
| 57 | CH₃ | * | H | H | H | — | CH(CH₃)OC(O)O-cyclohexyl |
| 58 | CH₃ | * | H | H | H | — | CH₂OC(O)O-cyclohexyl |
| 59 | CH₃ | * | H | H | H | — | 3-methyl-phthalide-3-yl |
| 60 | CH₃ | * | H | H | H | — | (4-ethyl-5-methyl-1,3-dioxol-2-one-yl) |
| 61 | CH₃ | * | H | H | H | — | CH(CH₃)OC(O)OCH₂-cyclohexyl |
| 62 | CH₃ | * | H | H | H | — | CH(CH₃)OC(O)O-(2-methylcyclohexyl) |
| 63 | CH₃ | * | H | H | H | — | CH₂OC(O)O-cyclopentyl |

-continued

| | $R^1$ | $R^2$ | $R^3$ | $R^4$ | $R^5$ | $R^6$ | R |
|---|---|---|---|---|---|---|---|
| 64 | CH₃ | * | H | H | H | — | 3-propylidenephthalide structure |
| 65 | CH₃ | * | H | H | H | — | menthyl-type cyclohexane structure |
| 66 | CH₃ | * | H | H | H | — | menthyl-type cyclohexane structure |
| 67 | CH₃ | * | H | H | H | — | CH(CH₃)OC(O)O—phenyl |
| 68 | CH₃ | * | H | H | H | — | CH₂OC(O)O—phenyl |
| 69 | CH₃ | * | H | H | H | — | CH(CH₂CH₃)OC(O)O—cyclohexyl |
| 70 | CH₃ | * | H | CONH₂ | H | — | H |
| 71 | CH₃ | * | H | CONH₂ | H | — | POM |
| 72 | H | H | H | * | H | — | K |
| 73 | H | H | H | * | H | — | POM |
| 74 | CH₃ | * | H | CHO | H | — | H |
| 75 | CH₃ | * | H | CHO | H | — | POM |
| 76 | CH₃ | * | H | H | CH₂OH | — | H |
| 77 | CH₃ | * | H | H | CH₂OH | CH₃ | — |
| 78 | CH₃ | H | H | H | * | — | K |
| 79 | CH₃ | H | H | H | * | CH₃ | — |
| 80 | H | * | H | H | Cl | — | Na |
| 81 | H | * | H | CONH₂ | H | — | H |
| 82 | H | * | H | CONH₂ | *H | — | POM |
| 83 | CH₃ | * | H | CHO | H | CH₃ | — |
| 84 | CH₃ | H | H | H | * | * | POM |
| 85 | CH₃ | * | H | H | CH₂OH | — | POM |
| 86 | H | * | H | H | Cl | CH₃ | — |
| 87 | H | * | H | H | Cl | — | POM |
| 88 | H | * | H | H | H | CH₂CONH₂ | — |
| 89 | CH₃ | * | H | CH₃ | CH₃ | — | Na |
| 90 | CH₃ | * | H | H | CH₂NHCHO | — | Na |
| 91 | H | H | * | H | H | — | CH₂OC(O)CH₃ |
| 92 | H | H | * | H | H | — | CH(CH₃)OC(O)CH₃ |
| 93 | H | H | * | H | H | — | CH₂OC(O)—(1-methylcyclohexyl) |

|     | R¹ | R² | R³ | R⁴ | R⁵ | R⁶ | R |
| --- | --- | --- | --- | --- | --- | --- | --- |
| 94 | H | H | * | H | H | — | CH(CH₃)OC(C)OCH₂CH₃ |
| 95 | H | H | * | H | H | — | CH(CH₃)OC(O)OCH(CH₃)₂ |
| 96 | H | H | * | H | H | — | CH(CH₃)OC(O)O-cyclohexyl |
| 97 | H | H | * | H | H | — | CH₂OC(O)O-cyclohexyl |
| 98 | H | H | * | H | H | — | 3-methyl-isobenzofuran-1(3H)-one |
| 99 | H | H | * | H | H | — | (4-ethyl-5-methyl-1,3-dioxol-2-one)yl |
| 100 | CH₃ | * | H | H | CH₂NHCHO | — | POM |
| 101 | H | H | * | H | CH₂NHCHO | — | Na |
| 102 | H | H | * | H | CH₂NHCHO | — | POM |
| 103 | H | H | * | H | CONH₂ | — | H |
| 104 | H | H | * | H | CONH₂ | — | POM |
| 105 | CH₃ | * | H | CH₃ | CH₃ | CH₃ | — |
| 106 | H | H | * | H | CH₂OH | — | Na |
| 107 | CH₃ | * | H | H | CHO | — | N |
| 108 | CH₃ | * | H | H | CHO | — | POM |
| 109 | CH₃ | * | H | H | CONH₂ | — | H |
| 110 | CH₃ | * | H | H | CONH₂ | — | POM |
| 111 | CH₃ | * | H | H | CH₂OCH₃ | — | Na |
| 112 | CH₃ | * | H | H | CH₂OCH₃ | — | POM |
| 113 | H | H | * | H | CH₂OCH₃ | — | Na |
| 114 | H | H | * | H | CH₂OCH₃ | — | POM |
| 115 | H | H | * | H | CH₂OH | — | POM |
| 116 | CH₃ | * | H | H | CN | — | H |
| 117 | CH₃ | * | H | H | CN | — | POM |
| 118 | CH₃ | * | H | H | CH₂CH₃ | — | H |
| 119 | CH₃ | * | H | H | CH₂CH₃ | — | POM |
| 120 | H | H | * | CONH₂ | H | — | H |
| 121 | H | * | H | H | CH₂CH₃ | — | H |
| 122 | H | * | H | H | CH₂CH₃ | — | POM |
| 123 | H | H | * | H | CH₂CH₃ | — | H |
| 124 | H | H | * | H | CH₂CH₃ | — | POM |
| 125 | H | * | H | H | CN | — | H |
| 126 | H | * | H | H | CN | — | POM |
| 127 | CH₃ | * | H | H | CH₂CH₃ | CH₃ | — |
| 128 | H | * | H | CH₃ | CH₃ | — | H |
| 129 | H | * | H | CH₃ | CH₃ | — | POM |
| 130 | H | H | * | H | CHO | — | H |
| 131 | H | H | * | H | CHO | — | POM |
| 132 | H | H | * | H | CH₂CH₃ | CH₃ | — |
| 133 | H | * | H | CH₃ | CH₃ | CH₃ | — |
| 134 | CH₃ | * | H | H | C(O)CH₃ | — | Na |
| 135 | CH₃ | * | H | H | C(O)CH₃ | — | POM |
| 136 | H | H | * | H | C(O)CH₃ | — | H |
| 137 | CH₃ | * | H | H | CH=NOCH₃ | — | H |
| 138 | CH₃ | * | H | H | C(O)NHCH₃ | — | H |
| 139 | CH₃ | * | H | H | C(O)NHCH₃ | — | POM |
| 140 | CH₃ | * | H | H | C(O)N(CH₃)₂ | — | Na |
| 141 | CH₃ | * | H | H | C(O)N(CH₃)₂ | — | POM |
| 142 | CH₃ | H | * | H | C(O)N(CH₃)₂ | — | Na |

-continued

|  | R¹ | R² | R³ | R⁴ | R⁵ | R⁶ | R |
|---|---|---|---|---|---|---|---|
| 143 | CH₃ | H | * | H | C(O)N(CH₃)₂ | — | POM |
| 144 | H | H | * | H | CN | — | H |
| 145 | H | H | * | H | CN | — | POM |
| 146 | H | * | H | H | C(O)NHCH₃ | — | H |
| 147 | H | * | H | H | C(O)NHCH₃ | — | POM |
| 148 | CH₃ | * | H | H | CH=NOCH₃ | — | Na |
| 149 | CH₃ | * | H | H | CH=NOCH | — | POM |

Preparation Example 1
Injection

The compound of Example 1 is aseptically dispensed in a vial in an amount of 1000 mg (titer).

Preparation Example 2
Capsule

| Compound of Example 3 | 250 parts (titer) |
|---|---|
| Lactose | 60 parts (titer) |
| Magnesium stearate | 5 parts (titer) |

The components were mixed homogeneously and filled into a capsule in an amount of 250 mg (titer)/capsule.

Preparation Example 3
Soft Capsule for Rectal Dosage

| Olive oil | 160 parts (titer) |
|---|---|
| Polyoxyethylene lauryl ether | 10 parts (titer) |
| Sodium hexamethanoate | 5 parts (titer) |

The compound of Example 3 in an amount of 25 parts (titer) was added to and mixed with the base consisting of the components, and filled into a soft capsule for rectal dosage in an amount of 250 mg(titer)/capsule.

Test 1
Anti-microbial Activities

The minimum inhibiting concentrations (MIC, $\mu$Mg/ml) of the compounds according to the present invention to various pathogenic bacteria was measured in accordance with the method described in CHEMOTHERAPY, vol. 16, No. 1, 99, 1968. The culture medium for measurement was Sensitivity Disk agar-N+5% Horse blood, and the amount of inoculants was $10^6$ CFU/ml.

The results are shown in the following table.

| Organism | Example 1 | Example 4 | Example 8 | Compound A | Compound B |
|---|---|---|---|---|---|
| S. aureus 209P JC-1 | <0.025 | <0.025 | <0.025 | <0.025 | <0.025 |
| S. aureus M126* | 3.13 | 3.13 | 6.25 | 25 | 6.25 |
| S. epidermidis ATCC14990 | <0.025 | <0.025 | 0.05 | <0.025 | 0.05 |
| E. hirae ATCC8043 | 0.39 | 0.78 | 0.78 | 0.78 | 1.56 |
| E. faecalis W-73 | 0.20 | 0.10 | 0.39 | 0.78 | 3.13 |
| S. pneumoniae PRC9** | 0.10 | 0.05 | 0.20 | 0.20 | 0.39 |
| B. catarrhalis W-0506 | <0.025 | <0.025 | <0.025 | <0.025 | <0.025 |
| H. influenzae PRC2 | <0.025 | 0.05 | 0.05 | 0.78 | 0.10 |
| H. influenzae PRC44 | 0.39 | 0.39 | 0.78 | 12.5 | 0.78 |
| E. coli NIHJ JC-2 | 0.10 | <0.025 | 0.10 | 0.10 | 0.05 |
| K. pneumoniae PCI602 | 0.10 | 0.05 | 0.05 | 0.20 | 0.10 |
| P. vulgaris GN7919 | 0.05 | 0.10 | 0.10 | 0.10 | 0.10 |
| C. freundii GN346 | 1.56 | 0.10 | 0.20 | 0.20 | 0.10 |

In the table,

*: methicillin-hyper resistant strain (MRSA);

**: penicillin-hyper resistant strain (PRSP);

Compound A: imipenem;

Compound B: (1R,5S,6S)-6-((1R)-1-hydroxyethyl)-1-methyl-2-[(3S,5S)-5-(6-methylimidazo[5,1-b]thiazolium-2-yl)methylpyrrolidin-3-yl]thiocarbapen-2-em-3-carboxylic acid iodide.

As is apparent from the above described test results, the compounds according to the present invention have strong anti-microbial activities against MRSA, PRSP, enterococci, influenza as well as various pathogenic bacteria including β-lactamase producing bacteria.

Test 2
Stability Against DHP-I

The stabilities of the compounds according to the present invention against porcine and mouse renal dehydropeptidases were measured by the following method.

(1) Preparation of DHP-1 from kidney acetone powders of various animals

Kidney acetone powder, Porcine Type II(Sigma; Lot. 33H7225; 1.5 g) was suspended in a 50 mM Tris.HCl buffer (pH 7.0) containing 20% butanol, and the mixture was stirred at 5° C. for 48 hours. Dialysis (Cellulose tube 30/32; Viskase Sales Corp) was conducted with a 50 mM Tris.HCl buffer (pH 7.0) in order to remove butanol to a level of no smell of butanol. The dialysate was centrifuged at 10000×g (KUBOTA 6800) for 20 minutes to give a supernatant as a partly purified DHP-I, which was divided into portions and stored at −80° C. Also, a partly purified DHP-I was prepared from 1.5 g of Mouse (Lot. 23F8105), and stored in the same manner as above.

(2) Measurement of stabilities to various DHP-I's

The compounds according to the present invention as a basic pharmaceutical was diluted with sterile purified water to prepare a solution having a titer of 2000 μg/ml. The solution of the compound according to the present invention having a titer of 2000 μg/ml was added to the partly purified DHP-I's of the above described animals so as to have a final concentration of 100 μg (titer)/ml. As a blank, 50 mM Tris.HCl buffer (pH 7.0) was used in place of the partly purified DHP-I's of the animals. After reaction at 37° C. for 3 hours, a portion of the reaction mixture was taken out, diluted with the same amount of methanol to stop the reaction by cooling in ice. The reaction mixture was filtered through SUNPLEP LCR13-LH, MILLIPORE), and subjected to HPLC (column: CAPCELL PACK C18 SG120, SHISEIDO; UV detector; mobile phase: acetonitrile—10 mM aqueous acetic acid solution) to measure the residual amount (%) of the partly purified DHP-I according to the following equation.

$$\text{Residual amount (\%)} = \frac{\text{Sample peak area}}{\text{Blank peak area}} \times 100$$

The residual amounts (%) of the compounds according to the present invention after 3 hours are shown below.

| DHP-I | Example 1 | Example 4 | Example 8 | Compound A | Compound C |
|---|---|---|---|---|---|
| Porcine | 87 | 100 | 60 | 0.6 | 72 |
| Mouse | <2.9 | 94 | <0.2 | 24 | 18 |

In the table, Compound A: imipenem;

Compound B: meropenem.

It is understood from the above table that the compounds according to the present invention have high stabilities to the porcine renal DHP-I, and the carbapenei derivatives represented by the general formula (II) have high stabilities to both of the porcine and mouse renal DHP-I.

Test 3

Oral Absorption Ability Test

The compound of Example 3 was orally administered to mice (ICR, male, n=3) in an amount of 0.5 mg (based on the weight of the compound of Example 1 from which the compound of Example 3 is derived)/0.2 ml/mouse as a 0.5% methylcellulose suspension, and then cilastatin was immediately administered subcutaneously in the same amount (because of the instability of the compound of Example 1 to mouse DHP-I, cilastatin as an inhibitor of DHP-I was used in combination). As a result, the compound of Example 1 was excreted in urine in an amount of 36% of the dose by 8 hours after administration.

Test 4

Acute Toxicity Test

The compound of Example 1 was administered intravenously to mice (ICR, male, n =3) in an amount of 2000 mg/kg. As a result, all of the animals were survived.

What is claimed is:

1. A compound represented by the formula (I), or a pharmaceutically acceptable salt thereof:

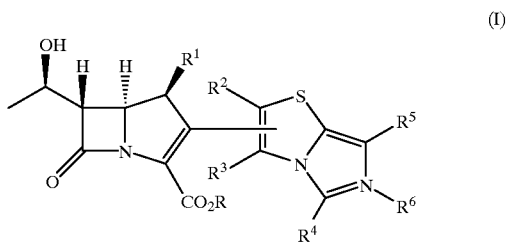

(I)

wherein $R^1$ represents a hydrogen or methyl, $R^2$, $R^3$, $R^4$, and $R^5$, either one of which represents the bond to the 2-position on the carbapenem ring, and the other three of which-may be the same or different, respectively represent hydrogen, halogen, nitro, cyano, lower alkyl, in which one or more hydrogen atoms on the alkyl group may be substituted by groups selected from the group consisting of halogen, nitro, cyano, lower cycloalkyl, lower alkylthlio, lower alkoxy, hydroxy, amino, N-lower alkylamino, formyl, lower alkylcarbonyl, aryl carbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, and aryl, lower cycloalkyl, in ewhich one or more hydrogen atoms on the cycloalkyl group may be substituted by groups selected from the group consisting of lower alkyl, halogen, nitro, cyano, lower alkylthio, lower alkoxy, hydroxy, amino, N-lower alkylamino, formyl, lower alkylcarbonyl, aryl carbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylanmino)sulfonyl, (N-lower alkylamino)sulfonylamino, aminosulfonylamino, (N,N-di-lower alkylamino)sulfonylamino, and aryl, lower alkylthio, $C_{2-4}$ alkenyl, in which one or more hydrogen atoms on the alkenyl group may be substituted by groups selected from the group consisting of lower alkyl, halogen, nitro, cyano, lower cycloalkyl, lower alkylthio, lower alkoxy, hydroxy, amino, N-lower alkylamino, formyl, lower alkylcarbonlyl, aryl carbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino) sulfonyl, (N-lower alkylamino)sulfonylamino, aminosulfonylamino, (N,N-di-lower alkylamino) sulfonylamino, and aryl, formyl, lower alkylcarbonyl, lower alkoxycarbonyl, lower alkylsulfonyl, lower arylsulfonyl,
aminosulfonyl,
aryl carbonyl,
aryl, in which one or more hydrogen atoms on the aryl group may be substituted by groups selected from the group consisting of lower alkyl, halogen, nitro, cyano, lower cycloalkyl, lower alkylthio, lower alkoxy, hydroxy, amino, N-lower alkylamino, formyl, lower alkylcarbonyl, aryl carbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, and (N,N-di-lower alkylamino)sulfonylamino,
carbamoyl,
N-lower alkylcarbamoyl,
N,N-di-lower alkylaminocarbonyl,
lower alkoxyiminomethyl, or
hydroxyiminomethyl, $R^6$ is not present or represents
lower alkyl, in which one or more hydrogen atoms on the alkyl group may be substituted by groups selected from the group consisting of halogen, nitro, cyano, lower cycloalkyl, lower alkylthio, lower alkoxy, hydroxy, amino, N-lower alkylamino, formyl, lower alkylcarbonyl, aryl carbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, and aryl,
lower cycloalkyl, in which one or more hydrogen atoms on the cycloalkyl group may be substituted by groups selected from the group consisting of lower alkyl, halogen, nitro, cyano, lower alkylthio, lower alkoxy, hydroxy, amino, N-lower alkylamino, formyl, lower alkylcarbonyl, aryl carbonyl, carboxyl, lower alkoxycarbonyl, formylamino, lower alkylcarbonylamino, carbamoyl, N-lower alkylcarbamoyl, N,N-di-lower alkcylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, and aryl, or
$C_{2-4}$ alkenyl, in which one or more hydrogen atoms on the alkenyl group may be substituted by groups selected from the group consisting of lower alkyl, halogen, nitro, cyano, lower cycloalkyl, lower alkylthio, lower alkoyy, hydroxy, amino, N-lower alkylamino, formyl, lower alkylcarbonyl, aryl carbonyl, carboxyl, lower alkoxycarbonyl, formylamino, lower alkylcarbonyl amino, carbamoyl, N-lower alkylcarbaioyl, N,N-di-lower alkylaminocarbonyl, aminosulfonyl, (N-lower alkylamino)sulfonyl, (N,N-di-lower alkylamino) sulfonyl, (N-lower alkylamino)sulfonylamino, aminosulfonylamino, (N,N-di-lower alkylamino) sulfonylamino, and aryl, and R is not present, or represents hydrogen or a group which may be metabolically hydrolyzed in the body,
provided that when $R^6$ is not present, R represents hydrogen or group may be metabolically hydrolyzed in the body, and when $R^6$ is present, R is not present and the compound forms an inner salt.

2. A compound according to claim 1, wherein $R^6$ is not present, and R represents hydrogen or a group may be metabolically hydrolyzed in the body.

3. A compound according to claim 2, wherein $R^1$ represents hydrogen or methyl,
$R^2$, $R^3$, $R^4$, and $R^5$, except the one which represents the bond to the 2-position on the carbapenem ring, which may be the same or different, and respectively represent
hydrogen,
halogen,
cyano,
lower alkyl, in which one or more hydrogen atoms on the alkyl group may be substituted by groups selected from the group consisting of halogen, nitro, cyano, lower cycloalkyl, lower alkylthio, lower alkoxy, hydroxy, amino, N-lower alkylamino, formyl, lower alkylcarbonyl, aryl carbonyl, carboxyl, lower allkoxycarbonyl, formylamino, lower alkylcarbonylamino, carbamoyl, N-lower alkylcarbamoyl, N,N-di-lower, alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, and aryl,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl.

4. A compound according to claim 3, wherein the lower alkyl is unsubstituted or substituted by lower alkoxy, hydroxy, or formylamino.

5. A compound according to any one of claims 2–4, wherein R represents
lower alkylcarbonyloxy lower alkyl,
lower cycloalkylcarbonyloxy lower alkyl,
lower alkyloxycarbonyloxy lower alkyl,
lower cycloalkyloxycarbonyloxy lower alkyl,
lower cycloalkylmethoxycarbonyloxy lower alkyl,
aryloxycarbonyloxy lower alkyl,
2-oxo-5-lower alkyl-1,3-dioxolene-4-ylmethyl,
3-phthalidyl of which the aromatic ring may be substituted by lower alkyl, halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino) sulfonyl, (N,N-di-lower alkylamino) sulfonyl, (N-lower alkylamino) sulfonylamino, aminosulfonylamino, (N,N-di-lower alkylamino) sulfonylamino, or aryl, or
2-(3-phthalidylidene)ethyl of which the aromatic ring may be substituted by lower alkyl, halogen, nitro, cyano, lower cycloalkyl, lower alkylthio, lower alkoxy, hydroxy, amino, N-lower alkylamino, formyl, lower alkylcarbonyl, arylcarbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino) sulfonyl, (N,N-di-lower alkylamino) sulfonyl, (N-lower alkylamino) sulfonylamino, aminosulfonylamino, (N,N-di-lower alkylamino) sulfonylamino, or aryl.

6. A compound according to claim 2, wherein $R^1$ represents methyl, $R^2$ represents the bond to the 2-position on the carbapenem ring, and $R^3$, $R^4$, and $R^5$, which may be the same or different, respectively represent
hydrogen,
halogen,
cyano,
lower alkyl, in which one or more hydrogen atoms on the alkyl may be substituted by lower alkoxy, hydroxy, or formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl.

7. A compound according to claim 2, wherein $R^1$ represents hydrogen, $R^2$ represents the bond to the 2-position on the carbapenem ring, and $R^3$, $R^4$, and $R^5$, which may be the same or different, respectively represent
hydrogen,
halogen,
cyano,
lower alkyl, in which one or more hydrogen atoms on the alkyl may be substituted by lower alkoxy, hydroxy, or formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl.

8. A compound according to claim 2, wherein $R^1$ represents methyl, $R^3$ represents the bond to the 2-position on the carbapenem ring, and $R^2$, $R^4$, and $R^5$, which may be the same or different, respectively represent
hydrogen,
halogen,
cyano,
lower alkyl, in which one or more hydrogen atoms on the alkyl may be substututed by lower alkoxy, hydroxy, or formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl.

9. A compound according to claim 2, wherein $R^1$ represents hydrogen, $R^3$ represents the bond to the 2-position on the carbapenem ring, and $R^2$, $R^4$, and $R^5$, which may be the same or different, respectively represent
hydrogen,
halogen,
cyano,
lower alkyl, in which one or more hydrogen atoms on the alkyl may be substituted by lower alkoxy, hydroxy, or formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl.

10. A compound according to claim 2, wherein $R^1$ represents hydrogen or methyl, $R^4$ represents the bond to the 2-position on the carbapenem ring, and $R^2$, $R^3$, and $R^5$, which may be the same or different, respectively represent
hydrogen,
halogen,
cyano,
lower alkyl, in which one or more hydrogen atoms may be substituted by lower alkoxy, hydroxy, or formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl.

11. A compound according to claim 2, wherein $R^1$ represents hydrogen or methyl, $R^5$ represents the bond to the 2-position on the carbapenem ring, and $R^2$, $R^3$, and $R^4$, which may be the same or different, respectively represent
hydrogen,
halogen,
cyano,
lower alkyl, in which one or more hydrogen atoms may be substituted by lower alkoxy, hydroxy, or formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl.

12. A compound according to claim 1, wherein $R^6$ is present, R is not present, and the compound forms an inner salt.

13. A compound according to claim 12, wherein $R^1$ represents hydrogen or methyl, and $R^2$, $R^3$, $R^4$, $R^5$, and $R^6$, except the one representing the bond to the 2-position on the carbapenem ring, which may be the same or different, respectively represent hydrogen,
halogen,
cyano,
lower alkyl, in which one or more hydrogen atoms on the alkyl may be substituted by a group selected from the group consisting of halogen, nitro, cyano, lower cycloalkyl, lower alkylthio, lower alkoxy, hydroxy, amino, N-lower alkylamino, formyl, lower alkylcarbonyl, aryl carbonyl, carboxyl, lower alkoxycarbonyl, formylamino, lower alkylcarbonylamino, carbamoyl, N-lower alkylcarbamoyl, N,N-di-lower alkylaminocarbonyl, aminosulfonyl, (N-lower alkylamino)sulfonyl, (N,N-di-lower alkylamino)sulfonyl, (N-lower alkylamino)sulfonylamino, aminosulfonylamino, (N,N-di-lower alkylamino)sulfonylamino, and aryl,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl.

14. A compound according to claim 13, wherein $R^2$, $R^3$, $R^4$, and $R^5$, except the one representing the bond to the 2-position on the carbapenem ring, represent hydrogen,
halogen,
cyano,
lower alkyl, in which one or more hydrogen atoms on the alkyl may be substituted by a group selected from the group consisting of lower alkoxy, hydroxy, and formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl, and
$R^6$ represents lower alkyl which may be substituted by a group selected from the group consisting of lower alkoxy, hydroxy, formylamino, and carbamoyl.

15. A compound according to claim 12, wherein $R^1$ represents methyl, $R^2$ represents the bond to the 2-position on the carbapenem ring, $R^3$, $R^4$, and $R^5$, which may be the same or different, respectively represent hydrogen,
halogen,
cyano,
lower alkyl, in which one or more hydrogen atoms on the alkyl may be substituted by a group selected from the group consisting of lower alkoxy, hydroxy, and formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl, and
$R^6$ represents lower alkyl which may be substituted by a group selected from the group consisting of lower alkoxy, hydroxy, formylamino, and carbamoyl.

16. A compound according to claim 12, wherein $R^1$ represents hydrogen, $R^2$ represents the bond to the 2-position on the carbapenem ring, $R^3$, $R^4$, and $R^5$, which may be the same or different, respectively represent hydrogen,
halogen,
cyano,
lower alkyl, in which one or more hydrogen atoms on the alkyl may be substituted by a group selected from the group consisting of lower alkoxy, hydroxy, and formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl, and
$R^6$ represents lower alkyl which may be substituted by a group selected from the group consisting of lower alkoxy, hydroxy, formylamino, and carbamoyl.

17. A compound according to claim 12, wherein $R^1$ represents methyl, $R^3$ represents the bond to the 2-position on the carbapenem ring, $R^2$, $R^4$ and $R^5$, which may be the same or different, respectively represent hydrogen,
halogen,
cyano,
lower alkyl, in which one or more hydrogen atoms may be substituted by a group selected from the group consisting of lower alkoxy, hydroxy, and formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl, and
$R^6$ represents lower alkyl which may be substituted by a group selected from the group consisting of lower alkoxy, hydroxy, formylamino, and carbamoyl.

18. A compound according to claim 12, wherein $R^1$ represents hydrogen, $R^3$ represents the bond to the 2-position on the carbapenem ring, $R^2$, $R^4$, and $R^5$, which may be the same or different, respectively represent
hydrogen,
halogen,
cyano,
lower alkyl, in which one or more hydrogen atoms on the alkyl may be substituted by a group selected from the group consisting of lower alkoxy, hydroxy, and formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl, and
$R^6$ represents lower alkyl which may be substituted by a group selected from the group consisting of lower alkoxy, hydroxy, formylamino, and carbamoyl.

19. A compound according to claim 12, wherein $R^1$ represents hydrogen or methyl,
$R^4$ represents the bond to the 2-position on the carbapenem ring,
$R^2$, $R^3$, and $R^5$, which may be the same or different, respectively represent
hydrogen,
halogen,
cyano,
lower alkyl, in which one or more hydrogen atoms on the alkyl may be substituted by a group selected from the group consisting of lower alkoxy, hydroxy, and formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl, and
$R^6$ represents lower alkyl which may be substituted by a group selected from the group consisting of lower alkoxy, hydroxy, formylamino, and carbamoyl.

20. A compound according to claim 12, wherein $R^1$ represents hydrogen or methyl,
$R^5$ represents the bond to the 2-position on the carbapenem ring,
$R^2$, $R^3$, and $R^4$, which may be the same or different, respectively represent
hydrogen,
halogen,
cyano,
lower alkyl, in which one or more hydrogen atoms on the alkyl may be substituted by a group selected from the group consisting of lower alkoxy, hydroxy, and formylamino,
formyl,
lower alkylcarbonyl,
lower alkoxycarbonyl,
aminosulfonyl,
carbamoyl,
N-lower alkylcarbamoyl,
N,N-di-lower alkylaminocarbonyl,
lower alkoxyiminomethyl, or
hydroxyiminomethyl, and
$R^6$ represents lower alkyl which may be substituted by a group selected from the group consisting of lower alkoxy, hydroxy, formylamino, and carbamoyl.

21. A compound according to claim 1, wherein $R^2$ or $R^3$ represents the bond to the 2-position on the carbapenem ring.

22. A compound according to claim 1, wherein $R^6$ represents alkyl having one or two carbon atoms which may be substituted by carbamoyl, fluorine, or hydroxy.

23. A compound according to claim 1, wherein $R^2$ represents the bond to the 2-position on the carbapenem ring, all of $R^3$, $R^4$, and $R^5$ represent hydrogen, or both $R^3$ and $R^4$ represent hydrogen, and $R^5$ represents a group selected from the group consisting of lower alkyl which may be substituted by formylamino or lower alkoxy, chlorine, formyl, lower alkylcarbonyl, cyano, carbamoyl, N-lower alkylcarbamoyl, and N,N-di-lower alkylaminocarbonyl.

24. A compound according to claim 1, wherein $R^2$ represents the bond to the 2-position on the carbapenem ring, $R^3$ represents methyl.

25. A compound according to claim 1, wherein $R^3$ represents the bond to the 2-position on the carbapenem ring, both $R^2$ and $R^4$ represent hydrogen, and $R^5$ represents hydrogen or cyano.

26. A pharmaceutical composition comprising the compound according to claim 1, and a pharmacologically acceptable carrier.

27. A method for treating bacterial infectious diseases, comprising administering the compound according to any one of claims 1–4 or 6–25 to an animal including humans.

28. A pharmaceutical composition comprising the compound according to claim 5, and a pharmacologically acceptable carrier.

29. A method for treating bacterial infectious diseases, comprising administering the compound according to claim 5 to an animal including humans.

* * * * *